US008815522B2

(12) United States Patent
Sasisekharan et al.

(10) Patent No.: US 8,815,522 B2
(45) Date of Patent: Aug. 26, 2014

(54) DECOY INFLUENZA THERAPIES

(75) Inventors: Ram Sasisekharan, Bedford, MA (US); Karthik Viswanathan, Arlington, MA (US); Aarthi Chandrasekaran, Sunnyvale, CA (US); Rahul Raman, Waltham, MA (US); Aravind Srinivasan, Cambridge, MA (US); S. Raguram, Hillsborough, NJ (US); Viswanathan Sasisekharan, Bedford, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 55 days.

(21) Appl. No.: 12/348,265

(22) Filed: Jan. 2, 2009

(65) Prior Publication Data

US 2010/0004195 A1 Jan. 7, 2010

Related U.S. Application Data

(60) Provisional application No. 61/018,783, filed on Jan. 3, 2008.

(51) Int. Cl.

| | |
|---|---|
| ***G01N 33/53*** | (2006.01) |
| ***A61K 31/702*** | (2006.01) |
| ***A61K 31/715*** | (2006.01) |
| ***C07H 3/06*** | (2006.01) |

(52) U.S. Cl.
USPC .............. 435/7.2; 514/61; 514/54; 536/123.1

(58) Field of Classification Search
USPC ...................... 435/7.2; 514/61, 54; 536/123.1
See application file for complete search history.

(56) References Cited

U.S. PATENT DOCUMENTS

| | | | |
|---|---|---|---|
| 4,270,537 | A | 6/1981 | Romaine |
| 4,596,556 | A | 6/1986 | Morrow et al. |
| 4,790,824 | A | 12/1988 | Morrow et al. |
| 4,886,499 | A | 12/1989 | Cirelli et al. |
| 4,940,460 | A | 7/1990 | Casey, I. et al. |
| 4,941,880 | A | 7/1990 | Burns |
| 5,015,235 | A | 5/1991 | Crossman |
| 5,064,413 | A | 11/1991 | McKinnon et al. |
| 5,141,496 | A | 8/1992 | Dalto et al. |
| 5,190,521 | A | 3/1993 | Hubbard et al. |
| 5,312,335 | A | 5/1994 | McKinnon et al. |

(Continued)

FOREIGN PATENT DOCUMENTS

| | | |
|---|---|---|
| JP | 2002284798 A * | 10/2002 |
| WO | WO-9713537 A1 | 4/1997 |

(Continued)

OTHER PUBLICATIONS

English translation of JP 2002-284798 A, Keio Gijuku Otsuka Pharmaceutical Co. Ltd. (KGO), 2002.*

(Continued)

*Primary Examiner* — Rosanne Kosson
(74) *Attorney, Agent, or Firm* — Choate, Hall & Stewart, LLP; Brenda Herschbach Jarrell; Paul A. Nuzzi

(57) ABSTRACT

The present invention provides umbrella-topology glycan decoys. The present invention provides systems and methods treating influenza infection utilizing inventive umbrella-topology glycan decoys. The present invention provides methods for identifying novel umbrella-topology glycan decoys.

36 Claims, 61 Drawing Sheets

(56) References Cited

U.S. PATENT DOCUMENTS

| | | | |
|---|---|---|---|
| 5,328,483 A | 7/1994 | Jacoby | |
| 5,334,144 A | 8/1994 | Alchas et al. | |
| 5,339,163 A | 8/1994 | Homma et al. | |
| 5,383,851 A | 1/1995 | McKinnon, Jr. et al. | |
| 5,417,662 A | 5/1995 | Hjertman et al. | |
| 5,466,220 A | 11/1995 | Brenneman | |
| 5,480,381 A | 1/1996 | Weston | |
| 5,503,627 A | 4/1996 | McKinnon et al. | |
| 5,520,639 A | 5/1996 | Peterson et al. | |
| 5,527,288 A | 6/1996 | Gross et al. | |
| 5,569,189 A | 10/1996 | Parsons | |
| 5,599,302 A | 2/1997 | Lilley et al. | |
| 5,649,912 A | 7/1997 | Peterson | |
| 5,704,911 A | 1/1998 | Parsons | |
| 5,893,397 A | 4/1999 | Peterson et al. | |
| 5,993,412 A | 11/1999 | Deily et al. | |
| 2007/0184065 A1 | 8/2007 | Holgersson | |
| 2007/0243629 A1 | 10/2007 | Angstrom et al. | |

FOREIGN PATENT DOCUMENTS

| | | |
|---|---|---|
| WO | WO-9737705 A1 | 10/1997 |
| WO | WO-9934850 A1 | 7/1999 |
| WO | WO 2005037187 A2 | 4/2005 |
| WO | WO 2007132335 A2 | 11/2007 |
| WO | WO 2007132355 A2 | 11/2007 |
| WO | WO-2008/073161 A2 | 6/2008 |
| WO | WO 2008073161 A2 | 6/2008 |

OTHER PUBLICATIONS

Chandrasekaran, et al., "Glycan topology determines human adaptation of avian H5N1 virus hemagglutinin" *Nat. Biotech.*, 26:107-113, 2008.

Colas et al., "The impact of two-hybrid and related methods on biotechnology " *Trends Biotech*, 16:355, 1998.

Connor et al., "Receptor specificity in human, avian, and equine H2 and H3 influenza virus isolates" *Virology*, 205:17, 1994.

Eisen et al., "Binding of the Influenza A virus to cell-surface receptors: Structures of five hemagglutinin sialyloligosaccharide complexes determined by X-ray crystallography" *Virology*, 232:19, 1997.

Fields et al., "The two-hybrid system: an assay for protein-protein interactions" *Trends in Genetics*, 10:286, 1994.

Gamblin et al., "The structure and receptor binding properties of the 1918 influenza hemagglutinin" *Science*, 303:1838, 2004.

Ha et al., "X-ray structures of H5 avian and H9 swine influenza virus hemagglutinins bound to avian and human receptor analogs" *Proc. Natl. Acad. Sci., USA*, 98:11181, 2001.

Ha et al., "X-ray structure of the hemagglutinin of a potential H3 avian progenitor of the 1968 Hong Kong pandemic influenza virus" *Virology*, 309:209, 2003.

International Search Report for PCT/US09/030056, mailed on May 19, 2009.

Kelm et al., "Use of sialic acid analogues to define functional groups involved in binding to the influenza virus hemagglutinin." *Eur. J. Biochem.*, 205:146, 1992.

Kumari et al., "Receptor binding specificity of recent human H3N2 influenza viruses" *Virol.J.*, 4:42, 2007.

Matrosovich et al., "Human and avian influenza viruses target different cell types in cultures of human airway epithelium" *Proc. Natl. Acad. Sci., USA*, 101:4620, 2004.

Mostow et al., "Application of the single radial diffusion test for assay of antibody to influenza type A viruses" *J. Clin. Microbiol.*, 2:531, 1975.

Rogers and Paulson, "Receptor determinants of human and animal influenza virus isolates: differences in receptor specificity of the H3 hemagglutinin based on species of origin" *Virology*, 127:361, 1983.

Rogers et al., "Single amino acid substitutions in influenza haemagglutinin change receptor binding specificity" *Nature*, 304:76, 1983.

Russell et al., "Avian and human receptor binding by hemagglutinins of influenza A viruses" *Glycoconj. J.*, 23:85, 2006.

Russell et al., "H1 and H7 influenza haemagglutinin structures extend a structural classification of haemagglutinin" *Virology*, 325:287, 2004.

Sauter et al., "Binding of influenza virus hemagglutinin to analogs of its cell-surface receptor, sialic acid: analysis by proton nuclear magnetic resonance spectroscopy and X-ray crystallography" *Biochemistry*, 31:9609, 1992.

Schild et al., Single-radial-hemolysis: a new method for the assay of antibody to influenza haemagglutinin. Applications for diagnosis and seroepidemiologic surveillance of influenza *Bull. World Health Organ.*, 52:43-50, 1975.

Schild et al., "A single-radial-immunodiffusion technique for the assay of influenza haemagglutinin antigen. Proposals for an assay method for the haemagglutinin content of influenza vaccines" *Bull. World Health Organ.*, 52: 223-31, 1975.

Skehel and Wiley, "Receptor binding and membrane fusion in virus entry: the influenza hemagglutinin" *Ann. Rev. Biochem.*, 69:531, 2000.

Stevens et al., "Structure and Receptor Specificity of the Hemagglutinin from an H5N1 Influenza Virus" *Science*, 312:404, 2006.

Stevens et al., "Glycan microarray technologies: tools to survey host specificity of influenza viruses" *Nat. Rev. Microbiol.*, 4:857, 2006.

Stevens et al., "Structure of the uncleaved human H1 hemagglutinin from the extinct 1918 influenza virus" *Science*, 303:1866, 2004.

Tumpey et al., "A Two-Amino Acid Change in the Hemagglutinin of the 1918 Influenza Virus Abolishes Transmission" *Science*, 315:655, 2007.

Tumpey et al., "Characterization of the reconstructed 1918 Spanish influenza pandemic virus" *Science*, 310:77, 2005.

Written Opinion for PCT/US09/030056, mailed on May 19, 2009.

Yamada et al., "Haemagglutinin mutations responsible for the binding of H5N1 influenza A viruses to human-type receptors" *Nature*, 444:378, 2006.

Hungarian Intellectual Property Office Written Opinion for Application No. SG 201004504 dated May 15, 2012.

Hungarian Intellectual Property Office Search Report for Application No. SG 201004504 date of completion May 11, 2012.

Stevens J. et al., Glycan microarray analysis of the hemagglutinins from modern and pandemic influenza viruses reveals different receptor specificities. Journal of Molecularl Biology, Feb. 3, 2006, 355(5): 1143-1155.

Kumari K. et al., Receptor binding specificity of recent human H3N2 influenza viruses. Virology Journal, May 9, 2007, 4 (1):42 (12 pages).

Supplementary European Search Report for EP 09700461.8 dated Feb. 22, 2012.

Stevens et al., "Structure and receptor specificity of the hemagglutinin from an H5N1 influenza virus," *Science*, vol. 312, No. 5772, Apr. 1, 2006, pp. 404-410.

Viswanathan et al., "Glycans as receptors for influenza pathogenesis," *Glycoconjugate Journal*, vol. 27, No. 6, Aug. 1, 2010, pp. 561-570.

Kumari et al., "Receptor binding specificity of recent human H3N2 influenza viruses," *Virology Journal*, vol. 4, No. 1, May 9, 2007, p. 42.

Hungarian Intellectual Property Office Written Opinion for Application No. SG 201004504-5 dated Feb. 28, 2013.

Stevens J. et al., Glycan microarray analysis of the hemagglutinins from modern and pandemic influenza viruses reveals different receptor specificities. Journal of Molecular Biology 355(5): 1143-1155 (2006).

Kumari K. et al., Receptor binding specificity of recent human H3N2 influenza viruses. Virology Journal, 4 (1):42 (2007).

* cited by examiner

FIG. 1

| FIG. 1A |
| --- |
| FIG. 1B |
| FIG. 1C |

```
          97                                                         139              153                                     183
H1_Av     ENGTCYPGEFIDYEELREQLSSISSFEKFEIFPKASSWPNHETTKGVTAACSYS-GASSFYRNLLWITKKG-TS-YPKLSKSYTNNKGKEVLVLWGVHHPPSVSEQQSLYQNAD
H1_Hu1    ENGTCYPGDFIDYEELREQLSSVSSFEKFEIFPKTSSWPNHETTKGVTAACSYA-GASSFYRNLLWLTKKG-SS-YPKLSKSYVNNKGKEVLVLWGVHHPPTGTDQQSLYQNAD
H1_Hu2    ENGTCYPGYFADYEELREQLSSVSSFERFEIFPKESSWPNHTVT-GVSASCSHN-GKSSFYRNLLWLTGKN-GL-YPNLSKSYVNNKEKEVLVLWGVHHPPNIGDQRALYHTEN
H2_Av     ANGLCYPGSFNDYEELKHLLTSVTHFEKVKILPR-DQWTQHTTTGG-SRACAVS-GNPSFFRNMVWLTEKG-SN-YPIAKRSYNNTSGKQMLVIWGIHHPNDDTEQRTLYQNVG
H2_Hu     RDGLCYPGSFNDYEELKHLLSSVKHFEKVKILPK-DRWTQHTTTGG-SRACAVS-GNPSFFRNMVWLTEKG-SN-YPVAKGSYNNTSGEQMLIIWGVHHPNDEKEQRTLYQNVG
H3_Av     FS-NCYPYDIPDYASLRSLVASSGTLEFITEG---FTW-TGVTQNGGSSACKRG-PANGFFSRLNWLTKS--ESAYPVLNVTMPNNDNFDKLYIWGVHHPSTNQEQTDLYVQAS
H3_Hu1    FS-NCYPYDVPDYASLRSLVASSGTLEFITEG---FTW-TGVTQNGGSNACKRG-PGSGFFSRLNWLTKS--GSTYPVLNVTMPNNDNFDKLYIWGIHHPSTNQEQTSLYVQAS
H3_Hu2    YS-NCYPYDVPDYASLRSLVASSGTLEFNNES---FNW-AGVTQNGTSSACKRR-SNKSFFSRLNWLTHL--KYKYPALNVTMPNNEKFDKLYIWGVHHPVTDSDQISLYAQAS
H4_Av     VD-TCYPFDVPDYQSLRSILANNGKFEFIAEE---FQW-NTVKQNGKSGACKRA-NVNDFFNRLNWLTKSN-GDAYPLQNLTKVNNGDYARLYIWGVHHPSTDTEQTDLYKNNP
H5_Av1    VNDLCYPGDFNDYEELKHLLSRINHFEKIQIIPK-SSWSSHEASLGVSSACPYQ-GKSSFFRNVVWLIKKN-ST-YPTIKRSYNNTNQEDLLVLWGIHHPNDAAEQTKLYQNPT
H5_Av2    ANDLCYPGDFNDYEELKHLLSRINHFEKIQIIPK-NSWSSHEASLGVSSACPYQ-GKSSFFRNVVWLIKKN-NA-YPTIKRSYNNTNQEDLLVLWGIHHPNDAAEQTRLYQNPT
H6_Av     QNGICYPGTLNEIEELKALIGSGERIERFEMFPK-STWSGVNTNNGVTRACPDN-SGSSFYRNLLWITKTNSAA-YPVIKGTYNNTGNQPILYFWGVHHPPDTNAQNNLYGSGD
H7_Av     SD-VCYPGKFVNEEALRQILRESGGINKETMG---FTY-SGIRTNGATSTCRRS-G-SSFYAEMKWLLSNTDNAAFPQMTKSYKNTRKDPALIIWGIHHSGSTTEQTKLYGSGN
H8_Av     PEGMCYPGSVENLEELRFVFSSAASYKRIRLFDY-SRWN--VTRSGTSKACNASTGGQSFYRSINWLTKKKPDT-YDFNEGAYVNNEDGDIIFLWGIHHPPDTKEQTTLYKNAN
H9_Av     VNGTCYPGNVENLEELRTLFSSASSYQRIQIFPD-TIWN--VTYTGTSKACS-----GSFYRSMRWLTQK-SGS-YPVQDAQYTNNREKSILFVWGIHHPPTDTAQTNLYINTD
H10_Av    IA-YCYPGATVNEEALRQKIMESGGIDKISTG---FTYGSSINSAGTTRSCMRS-GGNSFYAELKWLVSKNKGQNFPQTANTYRNTDSAEHLIIWGIHHPSSTQEKNDLYGTQS
H11_Av    TNGICYPGTLENEEELRLKFSGVLEFSKFEAFTS-NGWGAVNSGAGVTAACKFG-SSNSFFRNMIWLIH-QSGT-YPVIRRTFNNTKGRDVLVVWGVHHPATLKEHQDLYKKDS
H12_Av    MEGVCYPGSIENQEELRSLFSSIKKYERVKMFDF-TKWN--VTYTGTSRACNNTSNRGSFYRSMRWLTLK-SGQ-FPVQTDEYKNTRDSDILFTWAIHHPPTSAEQVQLYKNPD
H13_Av    PHGLCYPGELNNNGELRHLFSGIRSFSRTELIPP-TSWGEVLD--GATSACRDDKGTNSFYRNLVWFVK-KNNR-YPVISKTYNNTTGRDVLVLWGIHHPVSVEETKTLYVNSD
H14_Av    VD-TCYPFDVPDYQSLRSILASSGSLEFIAEQ---FTW-NGVKVDGSSSACLRG-GRNSFFSRLNWLTKET-NGNYGPINVTKENTGSYVRLYLWGVHHPSSDNEQTDLYKVAT
H15_Av    SD-ICYPGKFTNEEALRQIIRESGGIDKEPMG---FRY-SGIKTDGATSACKRT-V-SSFYSEMKWLLSSKANQVFPQLNQTYRNNRKEPALIVWGVHHSSSLDEQNKLYGAGN
H16_Av    PNKLCFPGELDNNGELRHLFSGVNSFSRTELISP-NKWGDILD--GVTASCRDN-GASSFYRNLVWIVKNKNGK-YPVIKGDYNNTTGRDVLVLWGIHHPDTETTAINLYASKN
```

FIG. 1A

```
H1_Av   AYVSVGSSKYNRRFAPEIAARPEVRGQAGRMNYYWTLLDQGDTITFEATGNLIAPWYAFALNKGSD--------SGIITS-DAPVH-NCDTRCQTPHGALNSSLPFQNVHPIT
H1_Hu1  AYVSVGSSKYNRRFTPEIAARPKVRDQAGRMNYYWTLLEPGDTITFEATGNLIAPWYAFALNRGSG--------SGIITS-DAPVH-DCNTKCQTPHGAINSSLPFQNIHPVT
H1_Hu2  AYVSVVSSHYSRRFTPEIAKRPKVRDQEGRINYYWTLLEPGDTIIFEANGNLIAPWYAFALSRGFG--------SGIITS-NAPMD-ECDAKCQTPQGAINSSLPFQNVHPVT
H2_Av   TYVSVGTSTLNKRSIPEIATRPKVNGQGGRMEFSWTLLETWDVINFESTGNLIAPEYGFKISKRGS--------SGIMKT-EKTLE-NCETKCQTPLGAINTTLPFHNIHPLT
H2_Hu   TYVSVGTSTLNKRSTPDIATRPKVNGLGSRMEFSWTLLDMWDTINFESTGNLIAPEYGFKISKRGS--------SGIMKT-EGTLE-NCETKCQTPLGAINTTLPFHNVHPLT
H3_Av   GRVTVSTRRSQQTIIPNIGSRPWVRGQPGRISIYWTIVKPGDVLVINSNGNLIAPRGYFKMRTG---------KSSIMRS-DAPID-TCISECITPNGSIPNDKPFQNVNKIT
H3_Hu1  GRVTVSTRRSQQTIIPNIGSRPWVRGLSSRISIYWTIVKPGDVLVINSNGNLIAPRGYFKMRTG---------KSSIMRS-DAPID-TCISECITPNGSIPNDKPFQNVNKIT
H3_Hu2  GRITVSTKRSQQTVIPNIGYRPRVRDISSRISIYWTIVKPGDILLINSTGNLIAPRGYFKIRSG---------KSSIMRS-DAPIG-KCNSECITPNGSIPNDKPFQNVNRIT
H4_Av   GRVTVSTKTSQTSVVPNIGSRPWVRGQSGRISFYWTIVDPGDIIVFNTIGNLIAPRGHYKLNSQK--------KSTILNT-AVPIG-SCVSKCHTDRGSITTTKPFQNISRIS
H5_Av1  TYISVGTSTLNQRLVPRIATRSKVNGQSGRMEFFWTILKPNDAINFESNGNFIAPEYAYKIVKKGD--------STIMKS-ELEYG-NCNTKCQTPMGAINSSMPFHNIHPLT
H5_Av2  TYISVGTSTLNQRLVPKIATRSKVNGQNGRMEFFWTILKPNDAINFESNGNFIAPEYAYKIVKKGD--------SAIMKS-ELEYG-NCNTKCQTPMGAINSSMPFHNIHPLT
H6_Av   RYVRMGTESMNFAKGPEISARPVVNGQRGRIDYYWSVLKPGETLNVESNGNLIAPWYAYKFVSTNSK-------GAVFKS-NLPIE-NCDATCQTIAGVLRTNKTFQNVSPLW
H7_Av   KLITVESSNYQQSFVPSPGARPKVDGQSGRIDFHWLMLNPNDTITFSFNGAFIAPDRASFLR----------GKSMGIQS-GVQVDDNCEGDCYHSGGTIISNLPFQNINSRA
H8_Av   TLSSVTTNTINRSFQPNIGPRPLVRGQQGRMDYYWGILKRGETLKIRTNGNLIAPEFGYLLKGESY--------GRIIQNEDIPIG-NCNTKCQTYAGAINSSKPFQNASRHY
H9_Av   TTTSVTTEDLNRIFKPVIGPRPLVNGLQGRINYYWSVLKPGQTLRVRSNGNLIAPWYGHVLSGGSH--------GRILKT-DLNSG-NCVVQCQTEKGGLNSTLPFHNISKYA
H10_Av  LSISVGSSTYQNNFVPVVGARPQVNGQSGRIDFHWTMVQPGDNITFSHNGGLIAPSRVSKLK----------GRGLGIQS-GASVDNDCESKCFWKGGSINTKLPFQNLSPRT
H11_Av  SYVAVDSESYNRRFTPEISTRPKVNGQAGRMTFYWTIVKPGEAITFESNGAFLAPRYAFELVSLGN--------GKLFRS-DLNIE-SCSTKCQSEIGGINTNRSFHNVHRNT
H12_Av  TLSSVTTDEINRSFKPNIGPRPLVRGQQGRMDYYWAVLKPGQTVKIQTNGNLIAPEYGHLITGKSH--------GRILKN-NLPVG-QCVTECQLNEGVMNTSKPFQNTSKHY
H13_Av  PYTLVSTKSWSEKYKLETGVRPGYNGQRSWMKIYWSLLHPGEMITFESNGGLLAPRYGYIIEEYGK--------GRIFQS-RIRMS-KCNTKCQTSVGGINTNRIFQNIDKNA
H14_Av  GRVTVSTRSDQISIVPNIGSRPRVRNQSGRISIYWTLVNPGDSIIFNSIGNLIAPRGHYKISKST--------KSTVLKS-DKRIG-SCTSPCLTDKGSIQSDKPFQNVSRIA
H15_Av  KLITVGSSKYQQSFSPSPGDRPKVNGQAGRIDFHWMLLDPGDTVTFTFNGAFIAPDRATFLRSNAPSGVEYNGKSLGIQS-DAQIDESCEGECFYSGGTINSPLPFQNIDSWA
H16_Av  PYTLVSTKEWSKRYELEIGTRIG-DGQRSWMKLYWHLMRPGERIMFESNGGLIAPRYGYIIEKYGT--------GRIFQS-GVRMA-KCNTKCQTSLGGINTNKTFQNIERNA
```

FIG. 1B

```
                              324      333
H1_Av   IGECPKYVKSTKLRMATGLRNVPSIQ----SRGLFGAIAGFIEGGWTGMIDGWYGYHHQNEQGSGYAADQKSTQNAIDGITSKVNSVIEKMNTQFTAVGKEFNNLERRIENLN
H1_Hu1  IGECPKYVRSTKLRMATGLRNIPSIQ----SRGLFGAIAGFIEGGWTGMIDGWYGYHHQNEQGSGYAADQKSTQNAIDGITNKVNSVIEKMNTQFTAVGKEFNNLERRIENLN
H1_Hu2  IGECPKYVRSAKLRMVTGLRNIPSIQ----SRGLFGAIAGFIEGGWTGMVDGWYGYHHQNEQGSGYAADQKSTQNAINGITNKVNSVIEKMNTQFTAVGKEFNKLERRMENLN
H2_Av   IGECPKYVKSDRLVLATGLRNVPQIE----SRGLFGAIAGFIEGGWQGHVDGWYGYHHSNDQGSGYAADKESTQKAIDGITNKVNSVIEKMNTQFEAVGKEFNNLERRLENLN
H2_Hu   IGECPKYVKSEKLVLATGLRNVPQIE----SRGLFGAIAGFIEGGWQGMIDGWYGYHHSNDQGSGYAADKESTQKAFDGITNKVNSVIEKMNTQFEAVGKEFSNLERRLENLN
H3_Av   YGACPKYVKQNTLKLATGMRNVPGK----QTRGLFGAIAGFIENGWEGMIDGWYGFRHQNSEGTGQAADLKSTQAAIDQINRKLNRVIEKTNEKFHQIEKEFSEVEGRIQDLE
H3_Hu1  YGACPKYVKQNTLKLATGMRNVPEK----QTRGLFGAIAGFIENGWEGMIDGWYGFRHQNSEGTGQAADLKSTQAAIDQINGKLNRVIEKTNEKFHQIEKEFSEVEGRIQDLE
H3_Hu2  YGACPRYVKQNTLKLATGMRNVPEK----QTRGIFGAIAGFIENGWEGMVDGWYGFRHQNSEGTGQAADLKSTQAAINQINGKLNRLIGKTNEKFHQIEKEFSEVEGRIQDLE
H4_Av   IGDCPKYVKQGSLKLATGMRNIPEK----ATRGLFGAIAGFIENGWQGLIDGWYGFRHQNAEGTGTAADLKSTQAAIDQINGKLNRLIEKTNEKYHQIEKEFEQVEGRIQDLE
H5_Av1  IGECPKYVKSNRLVLATGLRNSPQRERRRKKRGLFGAIAGFIEGGWQGMVDGWYGYHHSNEQGSGYAADKESTQKAIDGVTNKVNSIIDKMNTQFEAVGREFNNLERRIENLN
H5_Av2  IGECPKYVKSNRLVLATGLRNSPQRERRRKKRGLFGAIAGFIEGGWQGMVDGWYGYHHSNEQGSGYAADKESTQKAIDGVTNKVNSIIDKMNTQFEAVGREFNNLERRIENLN
H6_Av   IGKCPKYVKSESLRLATGLRNVPQIA----TRGLFGAIAGFIEGGWTGLVDGWYGYHHENSQGSGYAADRESTQKAIDGITNKVNSIIDKMNTQFEAVDHEFSNLERRIDNMN
H7_Av   VGKCPRYVKQESLMLATGMKNVPEIP---KGRGLFGAIAGFIENGWEGLIDGWYGFRHQNAQGEGTAADYKSTQSAIDQITGKLNRLIEKTNQQFELIDNEFTEVEKQIGNVI
H8_Av   MGECPKYVKKASLRLAVGLRNTPSVE----PRGLFGAIAGFIEGGWSGMIDGWYGFHHSNSEGTGMAADQKSTQEAIDKITNKVNNIVDKMNREFEVVNHEFSEVEKRINMIN
H9_Av   FGICPKYVRVKSLKLAVGLRNVPARS----NRGLFGAIAGFIEGGWPGLVAGWYGFQHSNDQGVGMAADRDSTQRAIDKITSKVNNIVDKMNKQYEIIDHEFSEVETRLNMIN
H10_Av  VGQCPKYVNKKSLLLATGMRNVPEVV---QGRGLFGAIAGFIENGWEGMVDGWYGFRHQNAQGTGQAADYKSTQAAIDQITGKLNRLIEKTNTEFESIESEFSEIEHQIGNVI
H11_Av  IGDCPKYVNVKSLKLATGLRNVPAIA----TRGLFGAIAGFIEGGWPGLINGWYGFQHRNEEGTGIAADKESTQKAIDQITSKVNNIVDRMNTNFESVQHEFSEIEERINQLS
H12_Av  IGKCPKYIPSGSLKLAIGLRNVPQVQ----NRGLFGAIAGFIEGGWPGLVAGWYGFQHQNAEGTGMAADRDSTQKAIDNMQNKLNNVIDKMNKQFEVVNHEFSEVESRINMIN
H13_Av  LGDCPKYIKSGQLKLATGLRNVPAIS----NRGLLGAIAGFIEGGWPGLINGWYGFQHQNEQGTGIAADKESTQKAIDQITTKINNIIDKMNGNYDSIRGEFNQVEKRINMLA
H14_Av  IGNCPKYVKQGSLMLATGMRNIPGK----QAKGLFGAIAGFIENGWQGLIDGWYGFRHQNAEGTGTAADLKSTQAAIDQINGKLNRLIEKTNEKYHQIEKEFEQVEGRIQDLE
H15_Av  VGRCPRYVKQSSLPLALGHKNVPEKI---HTRGLFGAIAGFIENGWEGLIDGWYGFRHQNAQGQGTAADYKSTQAAIDQITGKLNRLIEKTNTQFELIDNEFTEVEQQIGNVI
H16_Av  LGDCPKYIKSGQLKLATGLRNVPSVG----ERGLFGAIAGFIEGGWPGLINGWYGFQHQNEQGTGIAADKASTQKAIDEITTKINNIIEKMNGNYDSIRGEFNQVEKRINMLA
```

```
                   98                                       136                  153
H1 Subtype          :                                        :                    :
ADA76   SYIIETSNSENGTCYPGEFIDYEELREQLSSISSFEKFEIFPKASSWPNHETTKGVTAACSYSGASSFYRNLLWITKKGTSY
ASI30   SYIVETSNSDNGTCYPGDFIDYEELREQLSSVSSFEKFEIFPKTSSWPNHETTRGVTAACPYAGASSFYRNLLWLVKKGNSY
APR34   SYIVETPNSENGICYPGDFIDYEELREQLSSVSSFERFEIFPKESSWPNHNTNG-VTAACSHEGKSSFYRNLLWLTEKEGSY
ASC18   SYIVETSNSENGTCYPGDFIDYEELREQLSSVSSFEKFEIFPKTSSWPNHETTKGVTAACSYAGASSFYRNLLWLTKKGSSY
AT91    SYIAETPNPENGTCYPGYFADYEELREQLSSVSSFERFEIFPKESSWPNHTVTKGVTTSCSHNGKSSFYRNLLWLTKKNGLY
ANY18   SYIVETSNSENGTCYPGDFIDYEELREQLSSVSSFEKFEIFPKTSSWPNHETTKGVTAACSYAGASSFYRNLLWLTKKGSSY

H3 Subtype
ADU63   DLFVERSNAFS-NCYPYDIPDYASLRSLVASSGTLEFITEG----FTWTGVTQNGGSSACKRGPANGFFSRLNWLTKSESAY
AAI68   DLFVERSKAFS-NCYPYDVPDYASLRSLVASSG---TLEFITEGFTWTG-VTQNGGSNACKRGPGSGFFSRLNWLTKSGSTY
AM99    DLFVERSKAYS-NCYPYDVPDYASLRSLVASSGTLEFNNES----FNWTGVAONGTSSSCKRRSIKSFFSRLNWLHOLKYRY

H5 Subtype
ADS97   SYIVEKDNPVNGLCYPENFNDYEELKHLLSSTNHFEKIRIIPR-SSWSNHDASSGVSSACPYNGRSSFFRNVVWLIKKNNAY
Viet04  SYIVEKANPVNDLCYPGDFNDYEELKHLLSRINHFEKIQIIPK-SSWSSHEASLGVSSACPYQGKSSFFRNVVWLIKKNSTY
```

```
                                   183    190                              222 226
H1 Subtype                           :      :                                :   :
ADA76   PKLSKSYTNNKGKEVLVLWGVHHPPSVSEQQSLYQNADAYVSVGSSKYNRRFAPEIAARPEVRGQAGRMNYYWTLLDQGDTI
ASI30   PKLSKSYVNNKGKEVLVLWGVHHPPTSTDQQSLYQNADAYVSVGSSKYDRRFTPEIAARPKVRSQAGRMNYYWTLLEPGDTI
APR34   PKLKNSYVNKKGKEVLVLWGIHHPPNSKEQQNLYQNENAYVSVVTSNYNRRFTPEIAERPNVRDQAGRMNYYWTLLKPGDTI
ASC18   PKLSKSYVNNKGKEVLVLWGVHHPPTGIDQQSLYQNADAYVSVGSSKYNRRFTPEIAARPKVRDQAGRMNYYWTLLEPGDTI
AT91    PNVSKSYVNNKEKEVLVLWGVHHPSNISDQRAIYHTENAYVSVVSSHYSRRFTPEIAKRPKVRDQEGRINYYWTLLEPGDTI
ANY18   PKLSKSYVNNKGKEVLVLWGVHHPPTGTDQQSLYQNADAYVSVGSSKYNRRFTPEIAARPKVRDQAGRMNYYWTLLEPGDTI

H3 Subtype
ADU63   PVLNVTMPNNDNFDKLYIWGVHHPSTNQEQTNLYVQASGRVTVSTRRSQQTIIPNIGSRPWVRGQPGRISIYWTIVKPGDVL
AAI68   PVLNVTMPNNDNFDKLYIWGIHHPSTNQEQTSLYVQASGRVTVSTRRSQQTIIPNIGSRPWVRGLSSRISIYWTIVKPGDVL
AM99    PALNVTMPNNDKFDKLYIWGVHHPSTDSDQTSLYTQASGRVTVSTKRSQQTVIPNIGSRPWVRGISSRISIYWTIVKPGDIL

H5 Subtype
ADS97   PTIKRSYNNTNQEDLLILWGIHHPNDAAEQTKLYQNPTTYVSVGTSTLNQRSVPEIATRPKVNGQSGRMEFFWTILKPNDAI
Viet04  PTIKRSYNNTNQEDLLYLWGIHHPNDAAEQTKLYQNPTTYISVGTSTLNQRLVPRIATRSKVNGQSGRMEFFWTILKPNDAI
```

| FIG. 3A |
|---|
| FIG. 3B |

FIG. 3A

```
                97                                        139            153                                     183
H1_Av    ENGTCYPGEFIDYEELREQLSSISSFEKFEIFPKASSWPNHETTKGVTAACSYS-GASSFYRNLLWITKKG-TS-YPKLSKSYTNNKGKEVLVLWGVHHPPSVSEQQSLYQNAD
H1_Hu1   ENGTCYPGDFIDYEELREQLSSVSSFEKFEIFPKTSSWPNHETTKGVTAACSYA-GASSFYRNLLWLTKKG-SS-YPKLSKSYVNNKGKEVLVLWGVHHPPTGTDQQSLYQNAD
H1_Hu2   ENGTCYPGYFADYEELREQLSSVSSFERFEIFPKESSWPNHTVT-GVSASCSHN-GKSSFYRNLLWLTGKN-GL-YPNLSKSYVNNKEKEVLVLWGVHHPPNIGDQRALYHTEN
H2_Av    ANGLCYPGSFNDYEELKHLLTSVTHFEKVKILPR-DQWTQHTTTGG-SRACAVS-GNPSFFRNMVWLTEKG-SN-YPIAKRSYNNTSGKQMLVIWGIHHPNDDTEQRTLYQNVG
H2_Hu    RDGLCYPGSFNDYEELKHLLSSVKHFEKVKILPK-DRWTQHTTTGG-SRACAVS-GNPSFFRNMVWLTEKG-SN-YPVAKGSYNNTSGEQMLIIWGVHHPNDEKEQRTLYQNVG
H3_Av    FS-NCYPYDIPDYASLRSLVASSGTLEFITEG---FTW-TGVTQNGGSSACKRG-PANGFFSRLNWLTKS--ESAYPVLNVTMPNNDNFDKLYIWGVHHPSTNQEQTDLYVQAS
H3_Hu1   FS-NCYPYDVPDYASLRSLVASSGTLEFITEG---FTW-TGVTQNGGSNACKRG-PGSGFFSRLNWLTKS--GSTYPVLNVTMPNNDNFDKLYIWGIHHPSTNQEQTSLYVQAS
H3_Hu2   YS-NCYPYDVPDYASLRSLVASSGTLEFNNES---FNW-AGVTQNGTSSACKRR-SNKSFFSRLNWLTHL--KYKYPALNVTMPNNEKFDKLYIWGVHHPVTDSDQISLYAQAS
H4_Av    VD-TCYPFDVPDYQSLRSILANNGKFEFIAEE---FQW-NTVKQNGKSGACKRA-NVNDFFNRLNWLTKSN-GDAYPLQNLTKVNNGDYARLYIWGVHHPSTDTEQTDLYKNNP
H5_Av1   VNDLCYPGDFNDYEELKHLLSRINHFEKIQIIPK-SSWSSHEASLGVSSACPYQ-GKSSFFRNVVWLIKKN-ST-YPTIKRSYNNTNQEDLLVLWGIHHPNDAAEQTKLYQNPT
H5_Av2   ANDLCYPGDFNDYEELKHLLSRINHFEKIQIIPK-NSWSSHEASLGVSSACPYQ-GKSSFFRNVVWLIKKN-NA-YPTIKRSYNNTNQEDLLVLWGIHHPNDAAEQTRLYQNPT
H6_Av    QNGICYPGTLNEIEELKALIGSGERIERFEMFPK-STWSGVNTNNGVTRACPDN-SGSSFYRNLLWITKTNSAA-YPVIKGTYNNTGNQPILYFWGVHHPPDTNAQNNLYGSGD
H7_Av    SD-VCYPGKFVNEEALRQILRESGGINKETMG---FTY-SGIRTNGATSTCRRS-G-SSFYAEMKWLLSNTDNAAFPQMTKSYKNTRKDPALIIWGIHHSGSTTEQTKLYGSGN
H8_Av    PEGMCYPGSVENLEELRFVFSSAASYKRIRLFDY-SRWN--VTRSGTSKACNASTGGQSFYRSINWLTKKKPDT-YDFNEGAYVNNEDGDIIFLWGIHHPPDTKEQTTLYKNAN
H9_Av    VNGTCYPGNVENLEELRTLFSSASSYQRIQIFPD-TIWN--VTYTGTSKACS-----GSFYRSMRWLTQK-SGS-YPVQDAQYTNNREKSILFVWGIHHPPTDTAQTNLYINTD
H10_Av   IA-YCYPGATVNEEALRQKIMESGGIDKISTG---FTYGSSINSAGTTRSCMRS-GGNSFYAELKWLVSKNKGQNFPQTANTYRNTDSAEHLIIWGIHHPSSTQEKNDLYGTQS
H11_Av   TNGICYPGTLENEEELRLKFSGVLEFSKFEAFTS-NGWGAVNSGAGVTAACKFG-SSNSFFRNMIWLIH-QSGT-YPVIRRTFNNTKGRDVLVVWGVHHPATLKEHQDLYKKDS
H12_Av   MEGVCYPGSIENQEELRSLFSSIKKYERVKMFDF-TKWN--VTYTGTSRACNNTSNRGSFYRSMRWLTLK-SGQ-FPVQTDEYKNTRDSDILFTWAIHHPPTSAEQVQLYKNPD
H13_Av   PHGLCYPGELNNNGELRHLFSGIRSFSRTELIPP-TSWGEVLD--GATSACRDDKGTNSFYRNLVWFVK-KNNR-YPVISKTYNNTTGRDVLVLWGIHHPVSVEETKTLYVNSD
H14_Av   VD-TCYPFDVPDYQSLRSILASSGSLEFIAEQ---FTW-NGVKVDGSSSACLRG-GRNSFFSRLNWLTKET-NGNYGPINVTKENTGSYVRLYLWGVHHPSSDNEQTDLYKVAT
H15_Av   SD-ICYPGKFTNEEALRQIIRESGGIDKEPMG---FRY-SGIKTDGATSACKRT-V-SSFYSEMKWLLSSKANQVFPQLNQTYRNNRKEPALIVWGVHHSSSLDEQNKLYGAGN
H16_Av   PNKLCFPGELDNNGELRHLFSGVNSFSRTELISP-NKWGDILD--GVTASCRDN-GASSFYRNLVWIVKNKNGK-YPVIKGDYNNTTGRDVLVLWGIHHPDTETTAINLYASKN
```

Figure 3B:
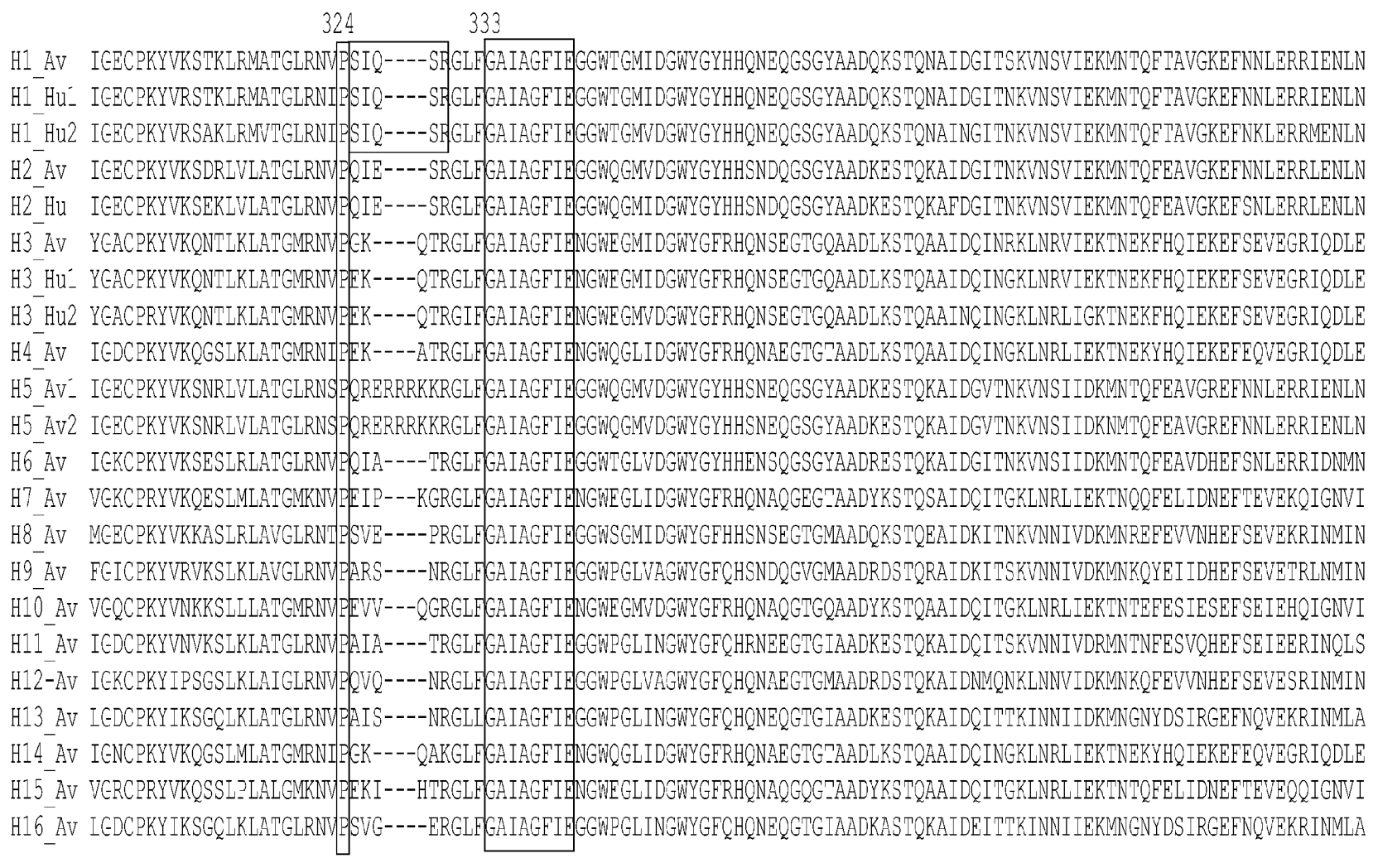

```
                               324      333
H1_Av   IGECPKYVKSTKLRMATGLRNVPSIQ----SRGLFGAIAGFIEGGWTGMIDGWYGYHHQNEQGSGYAADQKSTQNAIDGITSKVNSVIEKMNTQFTAVGKEFNNLERRIENLN
H1_Hu1  IGECPKYVRSTKLRMATGLRNIPSIQ----SRGLFGAIAGFIEGGWTGMIDGWYGYHHQNEQGSGYAADQKSTQNAIDGITNKVNSVIEKMNTQFTAVGKEFNNLERRIENLN
H1_Hu2  IGECPKYVRSAKLRMVTGLRNIPSIQ----SRGLFGAIAGFIEGGWTGMVDGWYGYHHQNEQGSGYAADQKSTQNAINGITNKVNSVIEKMNTQFTAVGKEFNKLERRMENLN
H2_Av   IGECPKYVKSDRLVLATGLRNVPQIE----SRGLFGAIAGFIEGGWQGMVDGWYGYHHSNDQGSGYAADKESTQKAIDGITNKVNSVIEKMNTQFEAVGKEFNNLERRLENLN
H2_Hu   IGECPKYVKSEKLVLATGLRNVPQIE----SRGLFGAIAGFIEGGWQGMIDGWYGYHHSNDQGSGYAADKESTQKAFDGITNKVNSVIEKMNTQFEAVGKEFSNLERRLENLN
H3_Av   YGACPKYVKQNTLKLATGMRNVPGK----QTRGLFGAIAGFIENGWEGMIDGWYGFRHQNSEGTGQAADLKSTQAAIDQINRKLNRVIEKTNEKFHQIEKEFSEVEGRIQDLE
H3_Hu1  YGACPKYVKQNTLKLATGMRNVPEK----QTRGLFGAIAGFIENGWEGMIDGWYGFRHQNSEGTGQAADLKSTQAAIDQINGKLNRVIEKTNEKFHQIEKEFSEVEGRIQDLE
H3_Hu2  YGACPRYVKQNTLKLATGMRNVPEK----QTRGIFGAIAGFIENGWEGMVDGWYGFRHQNSEGTGQAADLKSTQAAINQINGKLNRLIGKTNEKFHQIEKEFSEVEGRIQDLE
H4_Av   IGDCPKYVKQGSLKLATGMRNIPEK----ATRGLFGAIAGFIENGWQGLIDGWYGFRHQNAEGTGTAADLKSTQAAIDQINGKLNRLIEKTNEKYHQIEKEFEQVEGRIQDLE
H5_Av1  IGECPKYVKSNRLVLATGLRNSPQRERRRKKRGLFGAIAGFIEGGWQGMVDGWYGYHHSNEQGSGYAADKESTQKAIDGVTNKVNSIIDKMNTQFEAVGREFNNLERRIENLN
H5_Av2  IGECPKYVKSNRLVLATGLRNSPQRERRRKKRGLFGAIAGFIEGGWQGMVDGWYGYHHSNEQGSGYAADKESTQKAIDGVTNKVNSIIDKNMTQFEAVGREFNNLERRIENLN
H6_Av   IGKCPKYVKSESLRLATGLRNVPQIA----TRGLFGAIAGFIEGGWTGLVDGWYGYHHENSQGSGYAADRESTQKAIDGITNKVNSIIDKMNTQFEAVDHEFSNLERRIDNMN
H7_Av   VGKCPRYVKQESLMLATGMKNVPEIP---KGRGLFGAIAGFIENGWEGLIDGWYGFRHQNAQGEGTAADYKSTQSAIDQITGKLNRLIEKTNQQFELIDNEFTEVEKQIGNVI
H8_Av   MGECPKYVKKASLRLAVGLRNTPSVE----PRGLFGAIAGFIEGGWSGMIDGWYGFHHSNSEGTGMAADQKSTQEAIDKITNKVNNIVDKMNREFEVVNHEFSEVEKRINMIN
H9_Av   FGICPKYVRVKSLKLAVGLRNVPARS----NRGLFGAIAGFIEGGWPGLVAGWYGFQHSNDQGVGMAADRDSTQRAIDKITSKVNNIVDKMNKQYEIIDHEFSEVETRLNMIN
H10_Av  VGQCPKYVNKKSLLLATGMRNVPEVV---QGRGLFGAIAGFIENGWEGMVDGWYGFRHQNAQGTGQAADYKSTQAAIDQITGKLNRLIEKTNTEFESIESEFSEIEHQIGNVI
H11_Av  IGDCPKYVNVKSLKLATGLRNVPAIA----TRGLFGAIAGFIEGGWPGLINGWYGFQHRNEEGTGIAADKESTQKAIDQITSKVNNIVDRMNTNFESVQHEFSEIEERINQLS
H12-Av  IGKCPKYIPSGSLKLAIGLRNVPQVQ----NRGLFGAIAGFIEGGWPGLVAGWYGFQHQNAEGTGMAADRDSTQKAIDNMQNKLNNVIDKMNKQFEVVNHEFSEVESRINMIN
H13_Av  IGDCPKYIKSGQLKLATGLRNVPAIS----NRGLIGAIAGFIEGGWPGLINGWYGFQHQNEQGTGIAADKESTQKAIDQITTKINNIIDKMNGNYDSIRGEFNQVEKRINMLA
H14_Av  IGNCPKYVKQGSLMLATGMRNIPGK----QAKGLFGAIAGFIENGWQGLIDGWYGFRHQNAEGTGTAADLKSTQAAIDQINGKLNRLIEKTNEKYHQIEKEFEQVEGRIQDLE
H15_Av  VGRCPRYVKQSSLPLALGMKNVPEKI---HTRGLFGAIAGFIENGWEGLIDGWYGFRHQNAQGQGTAADYKSTQAAIDQITGKLNRLIEKTNTQFELIDNEFTEVEQQIGNVI
H16_Av  IGDCPKYIKSGQLKLATGLRNVPSVG----ERGLFGAIAGFIEGGWPGLINGWYGFQHQNEQGTGIAADKASTQKAIDEITTKINNIIEKMNGNYDSIRGEFNQVEKRINMLA
```

| FIG. 4A |
|---|
| FIG. 4B |

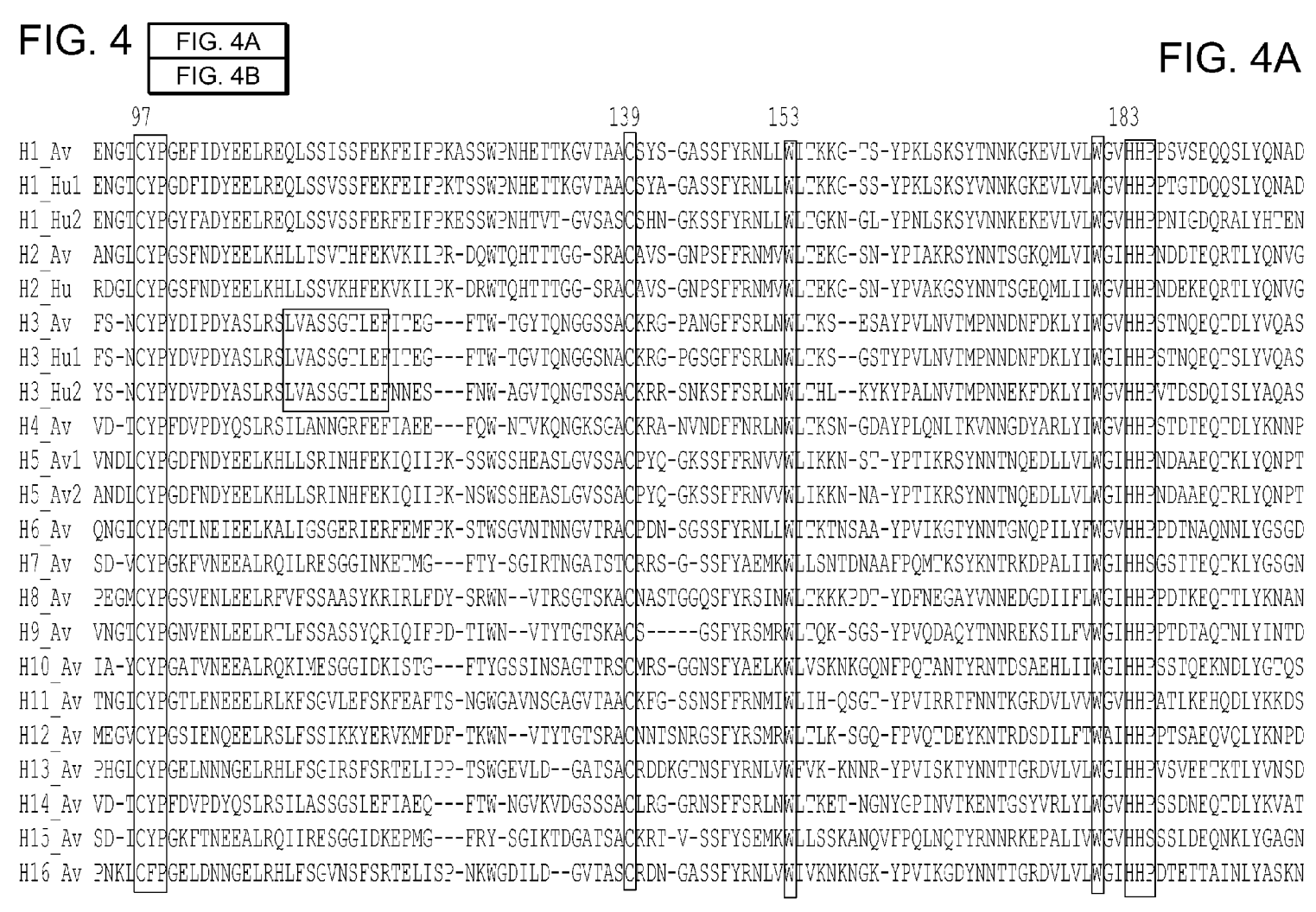

FIG. 4A

```
                 97                                          139            153                                     183
H1_Av    ENGTCYPGEFIDYEELREQLSSISSFEKFEIFPKASSWPNHETTKGVTAACSYS-GASSFYRNLLWITKKG-TS-YPKLSKSYTNNKGKEVLVLWGVHHPPSVSEQQSLYQNAD
H1_Hu1   ENGTCYPGDFIDYEELREQLSSVSSFEKFEIFPKTSSWPNHETTKGVTAACSYA-GASSFYRNLLWLTKKG-SS-YPKLSKSYVNNKGKEVLVLWGVHHPPTGTDQQSLYQNAD
H1_Hu2   ENGTCYPGYFADYEELREQLSSVSSFERFEIFPKESSWPNHTVT-GVSASCSHN-GKSSFYRNLLWLTGKN-GL-YPNLSKSYVNNKEKEVLVLWGVHHPPNIGDQRALYHTEN
H2_Av    ANGLCYPGSFNDYEELKHLLTSVTHFEKVKILPR-DQWTQHTTTGG-SRACAVS-GNPSFFRNMVWLTEKG-SN-YPIAKRSYNNTSGKQMLVIWGIHHPNDDTEQRTLYQNVG
H2_Hu    RDGLCYPGSFNDYEELKHLLSSVKHFEKVKILPK-DRWTQHTTTGG-SRACAVS-GNPSFFRNMVWLTEKG-SN-YPVAKGSYNNTSGEQMLIIWGVHHPNDEKEQRTLYQNVG
H3_Av    FS-NCYPYDIPDYASLRSLVASSGTLEFITEG---FTW-TGYTQNGGSSACKRG-PANGFFSRLNWLTKS--ESAYPVLNVTMPNNDNFDKLYIWGVHHPSTNQEQTDLYVQAS
H3_Hu1   FS-NCYPYDVPDYASLRSLVASSGTLEFITEG---FTW-TGVTQNGGSNACKRG-PGSGFFSRLNWLTKS--GSTYPVLNVTMPNNDNFDKLYIWGIHHPSTNQEQTSLYVQAS
H3_Hu2   YS-NCYPYDVPDYASLRSLVASSGTLEFNNES---FNW-AGVTQNGTSSACKRR-SNKSFFSRLNWLTHL--KYKYPALNVTMPNNEKFDKLYIWGVHHPVTDSDQISLYAQAS
H4_Av    VD-TCYPFDVPDYQSLRSILANNGRFEFIAEE---FQW-NTVKQNGKSGACKRA-NVNDFFNRLNWLTKSN-GDAYPLQNLTKVNNGDYARLYIWGVHHPSTDTEQTDLYKNNP
H5_Av1   VNDLCYPGDFNDYEELKHLLSRINHFEKIQIIPK-SSWSSHEASLGVSSACPYQ-GKSSFFRNVVWLIKKN-ST-YPTIKRSYNNTNQEDLLVLWGIHHPNDAAEQTKLYQNPT
H5_Av2   ANDLCYPGDFNDYEELKHLLSRINHFEKIQIIPK-NSWSSHEASLGVSSACPYQ-GKSSFFRNVVWLIKKN-NA-YPTIKRSYNNTNQEDLLVLWGIHHPNDAAEQTRLYQNPT
H6_Av    QNGICYPGTLNEIEELKALIGSGERIERFEMFPK-STWSGVNTNNGVTRACPDN-SGSSFYRNLLWITKTNSAA-YPVIKGTYNNTGNQPILYFWGVHHPPDTNAQNNLYGSGD
H7_Av    SD-VCYPGKFVNEEALRQILRESGGINKETMG---FTY-SGIRTNGATSTCRRS-G-SSFYAEMKWLLSNTDNAAFPQMTKSYKNTRKDPALIIWGIHHSGSTTEQTKLYGSGN
H8_Av    PEGMCYPGSVENLEELRFVFSSAASYKRIRLFDY-SRWN--VTRSGTSKACNASTGGQSFYRSINWLTKKKPDT-YDFNEGAYVNNEDGDIIFLWGIHHPPDTKEQTTLYKNAN
H9_Av    VNGTCYPGNVENLEELRTLFSSASSYQRIQIFPD-TIWN--VTYTGTSKACS-----GSFYRSMRWLTQK-SGS-YPVQDAQYTNNREKSILFVWGIHHPPTDTAQTNLYINTD
H10_Av   IA-YCYPGATVNEEALRQKIMESGGIDKISTG---FTYGSSINSAGTTRSCMRS-GGNSFYAELKWLVSKNKGQNFPQTANTYRNTDSAEHLIIWGIHHPSSTQEKNDLYGTQS
H11_Av   TNGICYPGTLENEEELRLKFSGVLEFSKFEAFTS-NGWGAVNSGAGVTAACKFG-SSNSFFRNMIWLIH-QSGT-YPVIRRTFNNTKGRDVLVVWGVHHPATLKEHQDLYKKDS
H12_Av   MEGVCYPGSIENQEELRSLFSSIKKYERVKMFDF-TKWN--VTYTGTSRACNNTSNRGSFYRSMRWLTLK-SGQ-FPVQTDEYKNTRDSDILFTWAIHHPPTSAEQVQLYKNPD
H13_Av   PHGLCYPGELNNNGELRHLFSGIRSFSRTELIPP-TSWGEVLD--GATSACRDDKGTNSFYRNLVWFVK-KNNR-YPVISKTYNNTTGRDVLVLWGIHHPVSVEETKTLYVNSD
H14_Av   VD-TCYPFDVPDYQSLRSILASSGSLEFIAEQ---FTW-NGVKVDGSSSACLRG-GRNSFFSRLNWLTKET-NGNYGPINVTKENTGSYVRLYLWGVHHPSSDNEQTDLYKVAT
H15_Av   SD-ICYPGKFTNEEALRQIIRESGGIDKEPMG---FRY-SGIKTDGATSACKRT-V-SSFYSEMKWLLSSKANQVFPQLNQTYRNNRKEPALIVWGVHHSSSLDEQNKLYGAGN
H16_Av   PNKLCFPGELDNNGELRHLFSGVNSFSRTELISP-NKWGDILD--GVTASCRDN-GASSFYRNLVWIVKNKNGK-YPVIKGDYNNTTGRDVLVLWGIHHPDTETTAINLYASKN
```

```
                                         324         333
H1_Av   IGECPKYVKSTKLRMATGLRNVPSIQ----SRGLFGAIAGFIEGGWTGMIDGWYGYHHQNEQGSGYAADQKSTQNAIDGITSKVNSVIEKMNTQFTAVGKEFNNLERRIENLN
H1_Hu1  IGECPKYVRSTKLRMATGLRNIPSIQ----SRGLFGAIAGFIEGGWTGMIDGWYGYHHQNEQGSGYAADQKSTQNAIDGITNKVNSVIEKMNTQFTAVGKEFNNLERRIENLN
H1_Hu2  IGECPKYVRSAKLRMVTGLRNIPSIQ----SRGLFGAIAGFIEGGWTGMVDGWYGYHHQNEQGSGYAADQKSTQNAINGITNKVNSVIEKMNTQFTAVGKEFNKLERRMENLN
H2_Av   IGECPKYVKSDRLVLATGLRNVPQIE----SRGLFGAIAGFIEGGWQGMVDGWYGYHHSNDQGSGYAADKESTQKAIDGITNKVNSVIEKMNTQFEAVGKEFNNLERRLENLN
H2_Hu   IGECPKYVKSEKLVLATGLRNVPQIE----SRGLFGAIAGFIEGGWQGMIDGWYGYHHSNDQGSGYAADKESTQKAFDGITNKVNSVIEWMNTQFEAVGKEFSNLERRLENLN
H3_Av   YGACPKYVKQNTLKLATGMRNVPGK----QTRGLFGAIAGFIENGWEGMIDGWYGFRHQNSEGTGQAADLKSTQAAIDQINRKLNRVIEKTNEKFHQIEKEFSEVEGRIQDLE
H3_Hu1  YGACPKYVKQNTLKLATGMRNVPEK----QTRGLFGAIAGFIENGWEGMIDGWYGFRHQNSEGTGQAADLKSTQAAIDQINGKLNRVIEKTNEKFHQIEKEFSEVEGRIQDLE
H3_Hu2  YGACPRYVKQNTLKLATGMRNVPEK----QTRGIFGAIAGFIENGWEGMVDGWYGFRHQNSEGTGQAADLKSTQAAINQINGKLNRLIGKTNEKFHQIEKEFSEVEGRIQDLE
H4_Av   IGDCPKYVKQGSLKLATGMRNIPEK----ATRGLFGAIAGFIENGWQGLIDGWYGFRHQNAEGTGTAADLKSTQAAIDQINGKLNRLIEKTNEKYHQIEKEFEQVEGRIQDLE
H5_Av1  IGECPKYVKSNRLVLATGLRNSPQRERRRKKRGLFGAIAGFIEGGWQGMVDGWYGYHHSNEQGSGYAADKESTQKAIDGVTNKVNSIIDKMNTQFEAVGREFNNLERRIENLN
H5_Av2  IGECPKYVKSNRLVLATGLRNSPQRERRRKKRGLFGAIAGFIEGGWQGMVDGWYGYHHSNEQGSGYAADKESTQKAIDGVTNKVNSIIDKMNTQFEAVGREFNNLERRIENLN
H6_Av   IGKCPKYVKSESLRLATGLRNVPQIA----TRGLFGAIAGFIEGGWTGLVDGWYGYHHENSQGSGYAADRESTQKAIDGITNKVNSIIDKMNTQFEAVDHEFSNLERRIDNMN
H7_Av    VGKCPRYVKQESLMLATGMKNVPEIP---KGRGLFGAIAGFIENGWEGLIDGWYGFRHQNAQGEGTAADYKSTQSAIDQITGKLNRLIEKTNQQFELIDNEFTEVEKQIGNVI
H8_Av   MGECPKYVKKASLRLAVGLRNTPSVE----PRGLFGAIAGFIEGGWSGMIDGWYGFHHSNSEGTGMAADQKSTQEAIDKITNKVNNIVDKMNREFEYVNHEFSEVEKRINMIN
H9_Av   FGICPKYVRVKSLKLAVGLRNVPARS----NRGLFGAIAGFIEGGWPGLVAGWYGFQHSNDQGVGMAADRDSTQRAIDKITSKVNNIVDKMNKQYEIIDHEFSEVETRLNMIN
H10_Av  VGQCPKYVNKKSLLLATGMRNVPEVV---QGRGLFGAIAGFIENGWEGMVDGWYGFRHQNAQGTGQAADYKSTQAAIDQITGKLNRLIEKTNTEFESIESEFSEIEHQIGNVI
H11_Av  IGDCPKYVNVKSLKLATGLRNVPAIA----TRGLFGAIAGFIEGGWPGLINGWYGFQHRNEEGTGIAADKESTQKAIDQITSKVNNIVDRMNTNFESVQHEFSEIEERINQLS
H12_Av  IGKCPKYIPSGSLKLAIGLRNVPQVQ----NRGLFGAIAGFIEGGWPGLVAGWYGFQHQNAEGTGMAADRDSTQKAIDNMQNKLNNVIDKMNKQFEYVNHEFSEVESRINMIN
H13_Av  LGDCPKYIKSGQLKLATGLRNVPAIS----NRGLLGAIAGFIEGGWPGLINGWYGFQHQNEQGTGIAADKESTQKAIDQITTKINNIIDKMNGNYDSIRGEFNQVEKRINMLA
H14_Av  IGNCPKYVKQGSLMLATGMRNIPGK----QAKGLFGAIAGFIENGWQGLIDGWYGFRHQNAEGTGTAADLKSTQAAIDQINGKLNRLIEKTNEKYHQIEKEFEQVEGRIQDLE
H15_Av  VGRCPRYVKQSSLPLALGMKNVPEKI---HTRGLFGAIAGFIENGWEGLIDGWYGFRHQNAQGQGTAADYKSTQAAIDQITGKLNRLIEKTNTQFELIDNEFTEVEQQIGNVI
H16_Av  LGDCPKYIKSGQLKLATGLRNVPSVG----ERGLFGAIAGFIEGGWPGLINGWYGFQHQNEQGTGIAADKASTQKAIDEITTKINNIIEKMNGNYDSIRGEFNQVEKRINMLA
```

| FIG. 5A-1 |
|---|
| FIG. 5A-2 |

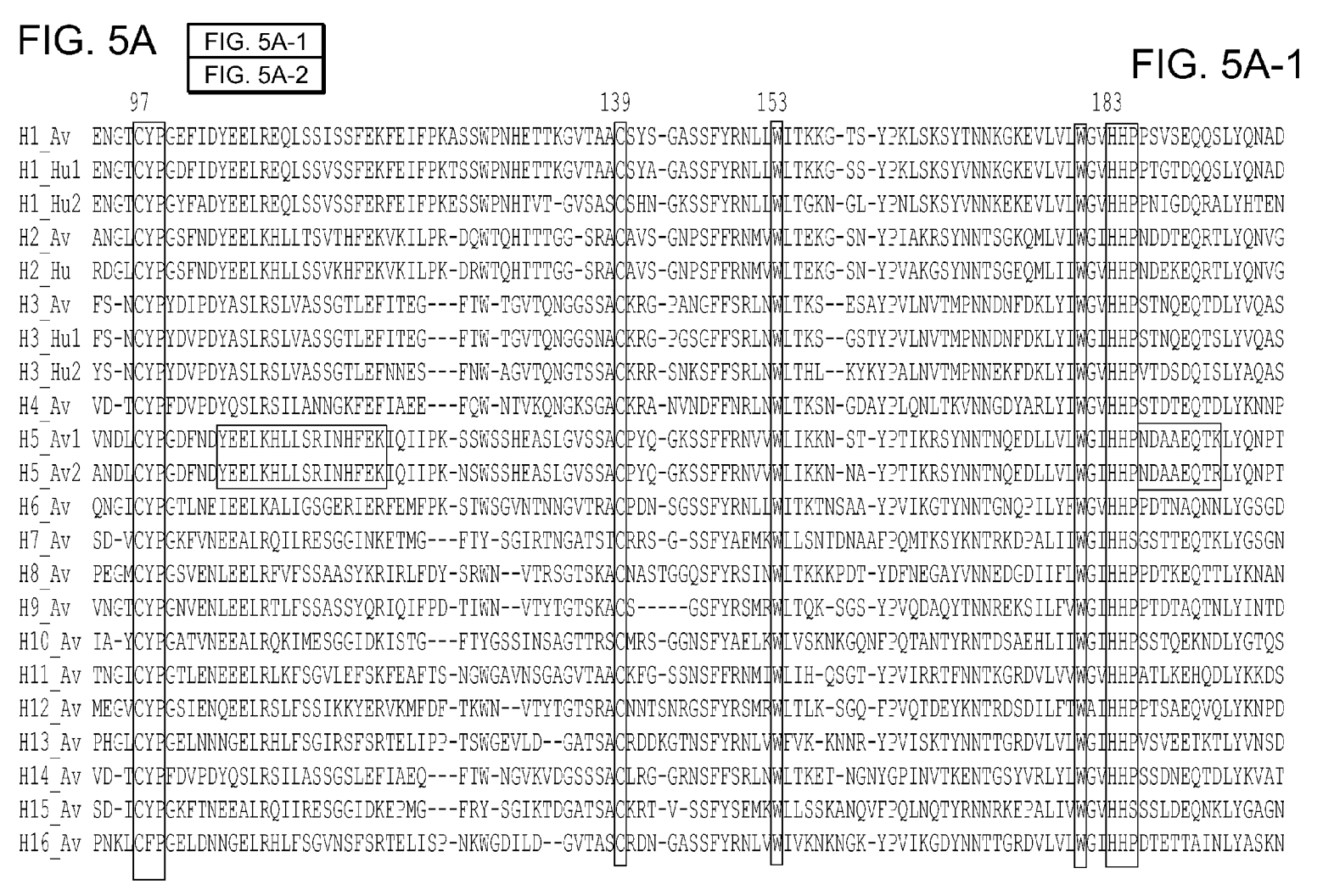

FIG. 5A-1

```
              97                                          139            153                                183
H1_Av   ENGTCYPGEFIDYEELREQLSSISSFEKFEIFPKASSWPNHETTKGVTAACSYS-GASSFYRNLLWITKKG-TS-YPKLSKSYTNNKGKEVLVLWGVHHPPSVSEQQSLYQNAD
H1_Hu1  ENGTCYPGDFIDYEELREQLSSVSSFEKFEIFPKTSSWPNHETTKGVTAACSYA-GASSFYRNLLWLTKKG-SS-YPKLSKSYVNNKGKEVLVLWGVHHPPTGTDQQSLYQNAD
H1_Hu2  ENGTCYPGYFADYEELREQLSSVSSFERFEIFPKESSWPNHTVT-GVSASCSHN-GKSSFYRNLLWLTGKN-GL-YPNLSKSYVNNKEKEVLVLWGVHHPPNIGDQRALYHTEN
H2_Av   ANGLCYPGSFNDYEELKHLLTSVTHFEKVKILPR-DQWTQHTTTGG-SRACAVS-GNPSFFRNMVWLTEKG-SN-YPIAKRSYNNTSGKQMLVIWGIHHPNDDTEQRTLYQNVG
H2_Hu   RDGLCYPGSFNDYEELKHLLSSVKHFEKVKILPK-DRWTQHTTTGG-SRACAVS-GNPSFFRNMVWLTEKG-SN-YPVAKGSYNNTSGEQMLIIWGVHHPNDEKEQRTLYQNVG
H3_Av   FS-NCYPYDIPDYASLRSLVASSGTLEFITEG---FTW-TGVTQNGGSSACKRG-PANGFFSRLNWLTKS--ESAYPVLNVTMPNNDNFDKLYIWGVHHPSTNQEQTDLYVQAS
H3_Hu1  FS-NCYPYDVPDYASLRSLVASSGTLEFITEG---FTW-TGVTQNGGSNACKRG-PGSGFFSRLNWLTKS--GSTYPVLNVTMPNNDNFDKLYIWGIHHPSTNQEQTSLYVQAS
H3_Hu2  YS-NCYPYDVPDYASLRSLVASSGTLEFNNES---FNW-AGVTQNGTSSACKRR-SNKSFFSRLNWLTHL--KYKYPALNVTMPNNEKFDKLYIWGVHHPVTDSDQISLYAQAS
H4_Av   VD-TCYPFDVPDYQSLRSILANNGKFEFIAEE---FQW-NTVKQNGKSGACKRA-NVNDFFNRLNWLTKSN-GDAYPLQNLTKVNNGDYARLYIWGVHHPSTDTEQTDLYKNNP
H5_Av1  VNDLCYPGDFNDYEELKHLLSRINHFEKIQIIPK-SSWSSHEASLGVSSACPYQ-GKSSFFRNVVWLIKKN-ST-YPTIKRSYNNTNQEDLLVLWGIHHPNDAAEQTKLYQNPT
H5_Av2  ANDLCYPGDFNDYEELKHLLSRINHFEKIQIIPK-NSWSSHEASLGVSSACPYQ-GKSSFFRNVVWLIKKN-NA-YPTIKRSYNNTNQEDLLVLWGIHHPNDAAEQTRLYQNPT
H6_Av   QNGICYPGTLNEIEELKALIGSGERIERFEMFPK-STWSGVNTNNGVTRACPDN-SGSSFYRNLLWITKTNSAA-YPVIKGTYNNTGNQPILYFWGVHHPPDTNAQNNLYGSGD
H7_Av   SD-VCYPGKFVNEEALRQILRESGGINKETMG---FTY-SGIRTNGATSTCRRS-G-SSFYAEMKWLLSNTDNAAFPQMTKSYKNTRKDPALIIWGIHHSGSTTEQTKLYGSGN
H8_Av   PEGMCYPGSVENLEELRFVFSSAASYKRIRLFDY-SRWN--VTRSGTSKACNASTGGQSFYRSINWLTKKKPDT-YDFNEGAYVNNEDGDIIFLWGIHHPPDTKEQTTLYKNAN
H9_Av   VNGTCYPGNVENLEELRTLFSSASSYQRIQIFPD-TIWN--VTYTGTSKACS-----GSFYRSMRWLTQK-SGS-YPVQDAQYTNNREKSILFVWGIHHPPTDTAQTNLYINTD
H10_Av  IA-YCYPGATVNEEALRQKIMESGGIDKISTG---FTYGSSINSAGTTRSCMRS-GGNSFYAELKWLVSKNKGQNFPQTANTYRNTDSAEHLIIWGIHHPSSTQEKNDLYGTQS
H11_Av  TNGICYPGTLENEEELRLKFSGVLEFSKFEAFTS-NGWGAVNSGAGVTAACKFG-SSNSFFRNMIWLIH-QSGT-YPVIRRTFNNTKGRDVLVVWGVHHPATLKEHQDLYKKDS
H12_Av  MEGVCYPGSIENQEELRSLFSSIKKYERVKMFDF-TKWN--VTYTGTSRACNNTSNRGSFYRSMRWLTLK-SGQ-FPVQTDEYKNTRDSDILFTWAIHHPPTSAEQVQLYKNPD
H13_Av  PHGLCYPGELNNNGELRHLFSGIRSFSRTELIPP-TSWGEVLD--GATSACRDDKGTNSFYRNLVWFVK-KNNR-YPVISKTYNNTTGRDVLVLWGIHHPVSVEETKTLYVNSD
H14_Av  VD-TCYPFDVPDYQSLRSILASSGSLEFIAEQ---FTW-NGVKVDGSSSACLRG-GRNSFFSRLNWLTKET-NGNYGPINVTKENTGSYVRLYLWGVHHPSSDNEQTDLYKVAT
H15_Av  SD-ICYPGKFTNEEALRQIIRESGGIDKEPMG---FRY-SGIKTDGATSACKRT-V-SSFYSEMKWLLSSKANQVFPQLNQTYRNNRKEPALIVWGVHHSSSLDEQNKLYGAGN
H16_Av  PNKLCFPGELDNNGELRHLFSGVNSFSRTELISP-NKWGDILD--GVTASCRDN-GASSFYRNLVWIVKNKNGK-YPVIKGDYNNTTGRDVLVLWGIHHPDTETTAINLYASKN
```

```
                                      324       333
H1_Av   IGECPKYVKSTKLRMATGLRNVPSIQ----SRGLFGAIAGFIEGGWTGMIDGWYGYHHQNEQGSGYAADQKSTQNAIDGITSKVNSVIEKMNTQFTAVGKEFNNLERRIENLN
H1_Hu1  IGECPKYVRSTKLRMATGLRNIPSIQ----SRGLFGAIAGFIEGGWTGMIDGWYGYHHQNEQGSGYAADQKSTQNAIDGITNKVNSVIEKMNTQFTAVGKEFNNLERRIENLN
H1_Hu2  IGECPKYVRSAKLRMVTGLRNIPSIQ----SRGLFGAIAGFIEGGWTGMVDGWYGYHHQNEQGSGYAADQKSTQNAINGITNKVNSVIEKMNTQFTAVGKEFNKLERRMENLN
H2_Av   IGECPKYVKSDRLVLATGLRNVPQIE----SRGLFGAIAGFIEGGWQGMVDGWYGYHHSNDQGSGYAADKESTQKAIDGITNKVNSVIEKMNTQFEAVGKEFNNLERRLENLN
H2_Hu   IGECPKYVKSEKLVLATGLRNVPQIE----SRGLFGAIAGFIEGGWQGMIDGWYGYHHSNDQGSGYAADKESTQKAFDGITNKVNSVIEKMNTQFEAVGKEFSNLERRLENLN
H3_Av   YGACPKYVKQNTLKLATGMRNVPGK----QTRGLFGAIAGFIENGWEGMIDGWYGFRHQNSEGTGQAADLKSTQAAIDQINRKLNRVIEKTNEKFHQIEKEFSEVEGRIQDLE
H3_Hu1  YGACPKYVKQNTLKLATGMRNVPEK----QTRGLFGAIAGFIENGWEGMIDGWYGFRHQNSEGTGQAADLKSTQAAIDQINGKLNRVIEKTNEKFHQIEKEFSEVEGRIQDLE
H3_Hu2  YGACPRYVKQNTLKLATGMRNVPEK----QTRGIFGAIAGFIENGWEGMVDGWYGFRHQNSEGTGQAADLKSTQAAINQINGKLNRLIGKTNEKFHQIEKEFSEVEGRIQDLE
H4_Av   IGDCPKYVKQGSLKLATGMRNIPEK----ATRGLFGAIAGFIENGWQGLIDGWYGFRHQNAEGTGTAADLKSTQAAIDQINGKLNRLIEKTNEKYHQIEKEFEQVEGRIQDLE
H5_Av1  IGECPKYVKSNRLVLATGLRNSPQRERRRKKRGLFGAIAGFIEGGWQGMVDGWYGYHHSNEQGSGYAADKESTQKAIDGVTNKVNSIIDKMNTQFEAVGREFNNLERRIENLN
H5_Av2  IGECPKYVKSNRLVLATGLRNSPQRERRRKKRGLFGAIAGFIEGGWQGMVDGWYGYHHSNEQGSGYAADKESTQKAIDGVTNKVNSIIDKMNTQFEAVGREFNNLERRIENLN
H6_Av   IGKCPKYVKSESLRLATGLRNVPQIA----TRGLFGAIAGFIEGGWTGLVDGWYGYHHENSQGSGYAADRESTQKAIDGITNKVNSIIDKMNTQFEAVDHEFSNLERRIDNMN
H7_Av   VGKCPRYVKQESLMLATGMKNVPEIP---KGRGLFGAIAGFIENGWEGLIDGWYGFRHQNAQGEGTAADYKSTQSAIDQITGKLNRLIEKTNQQFELIDNEFTEVEKQIGNVI
H8_Av   MGECPKYVKKASLRLAVGLRNTPSVE----PRGLFGAIAGFIEGGWSGMIDGWYGFHHSNSEGTGMAADQKSTQEAIDKITNKVNNIVDKMNREFEVVNHEFSEVEKRINMIN
H9_Av   FGICPKYVRVKSLKLAVGLRNVPARS----NRGLFGAIAGFIEGGWPGLVAGWYGFQHSNDQGVGMAADRDSTQRAIDKITSKVNNIVDKMNKQYEIIDHEFSEVETRLNMIN
H10_Av  VGQCPKYVNKKSLLLATGMRNVPEVV---QGRGLFGAIAGFIENGWEGMVDGWYGFRHQNAQGTGQAADYKSTQAAIDQITGKLNRLIEKTNTEFESIESEFSEIEHQIGNVI
H11_Av  IGDCPKYVNVKSLKLATGLRNVPAIA----TRGLFGAIAGFIEGGWPGLINGWYGFQHRNEEGTGIAADKESTQKAIDQITSKVNNIVDRMNTNFESVQHEFSEIEERINQLS
H12_Av  IGKCPKYIPSGSLKLAIGLRNVPQVQ----NRGLFGAIAGFIEGGWPGLVAGWYGFQHQNAEGTGMAADRDSTQKAIDNMQNKLNNVIDKMNKQFEVVNHEFSEVESRINMIN
H13_Av  LGDCPKYIKSGQLKLATGLRNVPAIS----NRGLLGAIAGFIEGGWPGLINGWYGFQHQNEQGTGIAADKESTQKAIDQITTKINNIIDKMNGNYDSIRGEFNQVEKRINMLA
H14_Av  IGNCPKYVKQGSLMLATGMRNIPGK----QAKGLFGAIAGFIENGWQGLIDGWYGFRHQNAEGTGTAADLKSTQAAIDQINGKLNRLIEKTNEKYHQIEKEFEQVEGRIQDLE
H15_Av  VGRCPRYVKQSSLPLALGMKNVPEKI---HTRGLFGAIAGFIENGWEGLIDGWYGFRHQNAQGQGTAADYKSTQAAIDQITGKLNRLIEKTNTQFELIDNEFTEVEQQIGNVI
H16_Av  LGDCPKYIKSGQLKLATGLRNVPSVG----ERGLFGAIAGFIEGGWPGLINGWYGFQHQNEQGTGIAADKASTQKAIDEITTKINNIIEKMNGNYDSIRGEFNQVEKRINMLA
```

FIG. 5A-2

```
Positions from 1 till 60
consensus  MEKIVLLLAIVSLVKSDQICIGYHANNSTEQVDTIMEKNVTVTHAQDILEKTHNGKLCDL
AAL59142   ............................................................
AAZ29963   .......F....................................................
ABA70758   .......F....................................................
ABB87042   ..R..IA...I.I..G.............K.....................E......S.
ABD14810   ............................................................
ABD46740   ----........................................................
ABD85144   -------F....................................................
ABE97569   ............................................................

Positions from 61 till 120
consensus  DGVKPLILRDCSVAGWLLGNPMCDEFINVPEWSYIVEKANPANDLCYPGDFNDYEELKEL
AAL59142   .......................................S.D..................
AAZ29963   .........................................V..................
ABA70758   .........................................V..................
ABB87042   K..R....K.................L...........D..I.G................
ABD14810   ........K........................................I..........
ABD46740   ..........................L...........I..........N..........
ABD85144   ..........................L...........I..........N..........
ABE97569   .................................................N..........
```

FIG. 5B-1

```
Positions from 121 till 180
consensus    L S R I N H F E K I Q E E P K S S W S D H E A S S G V S S A C P Y Q G K S S F F R N V V W L I K K N S A Y P T I K R S Y
AAL59142     . . . . . . . . . . . . . . . . . . . N . . . . . . . . . . . . . H . . . . . . . . . . . . . . . . . . . . . . . . . .
AAZ29963     . . . . . . . . . . . . . . . . . . . S . . . . L . . . . . . . . . . . . . . . . . . . . . . . . . . T . . . . . . . .
ABA70758     . . . . . . . . . . . . . . . . . . . S . . . . L . . . . . . . . . . . P . . . . . . . . . . . . . . T . . . . . . . .
ABB87042     M . S T . . . . . . . . . . R . . . . N . D . . . . . . . . . . . N . R . . . . . . . . . . . . . . N . . . . . . . T .
ABD14810     . . . . . . . . . . . . . . . . . . . . . . . . . . . . . . . . . . . . . . . . . . . . . . . . . . . . . . . . . I . .
ABD46740     . . . . . . . . . . . . . . . . . . . . . . . . . . . . . . . . . . . R . . . . . . . . . . . . . D N . . . . . . . . .
ABD85144     . . . . . . . . . . . . . . . . . . . . . . . . . . . . . . . . . . . R . . . . . . . . . . . . . D N . . . . . . . . .
ABE97569     . . . . . . . . . . . . . . . . . . . . . . . . . . . . . . . . . L . . . . . . . . . . . . . . . . . . . . . . . . . .

Positions from 181 till 240
consensus    N N T N Q K D L L V L W G E H H P N D A A E Q T K L Y Q N P T T Y E S V G T S T L N Q R L V P K I A T R S K V N G Q S G
AAL59142     . . . . . . . . . . . . . . . . . . . . . . . . . . . . . . . . . . . . . . . . . . . . . . . . . . . . . . . . . . . .
AAZ29963     . . . . . . . . . . . . . . . . . . . . . . . . . . . . . . . . . . . . . . . . . . . . . . . R . . . . . . . . . . . .
ABA70758     . . . . . . . . V . . . . . . . . . . . . . . . . . . . . . . . . . . . . . . . . . . . . . . R . . . . . . . . . . . .
ABB87042     . . . . I . . . . L . . . . . . . . . . . . . . . . . . . S N . . V . . . . . . . . . . S I . E . . . . . P . . . . . .
ABD14810     . . . . . . . . . . . . . . . . . . . . . . . . R . . . . . . . . . . . . . . . . . . . . . . . . . . . . . . . . . . .
ABD46740     . . . . . . . . . . . . . . . . . . . . . . . . R . . . . . . . . . . . . . . . . . . . . . . . . . . . . . . . . . . .
ABD85144     . . . . . . . . . . . . . . . . . . . . . . . . R . . . . . . . . . . . . . . . . . . . . . . . . . . . . . . . . . . .
ABE97569     . . . . . . . . . . . . . . . . . . . . . . . . R . . . . . . . . . . . . . . . . . . . . . . . . . . . . . . . . . . .
```

FIG. 5B-2

```
Positions from 241 till 300
consensus  R M E F F W T I L K P N D A I N F E S N G N F I A P E Y A Y K I V K K G D S T I M K S B L E Y G N C N T K C Q T P M G A
AAL59142   . . . . . . . . . . . . . . . . . . . . . . . . . . . . . . . . . . . . . . A . . . . . . . . . . . . . . . . . . . . .
AAZ29963   . . . . . . . . . . . . . . . . . . . . . . . . . . . . . . . . . . . . . . . . . . . . . . . . . . . . . . . . . . . .
ABA70758   . . . . . . . . . . . . . . . . . . . . . . . . . . . . . . . . . . . . . . . . . . . . . . . . . . . . . . . . . . . .
ABB87042   . . . . . . . . . . . . . . . S . . . . . . . . . . . . . . . . . . . . . . A . . . . . . . . . . . D . . . . . . V . .
ABD14810   . . . . . . . . . . . . . . V . . . . . . . . . . . . . . . . . . . . . . . . . . . . . . . . . D . . . . . . . . . . .
ABD46740   . . . . . . . . . . . . . . . . . . . . . . . . . . . N . . . . . . . . . . . . . . . . . . . . . . . . . . . . . I . .
ABD85144   . . . . . . . . . . S . . . . . . . . . . . . . . . . N . . . . . . . . . . . . . . . . . . . . . . . . . . . . . I . .
ABE97569   . . . . . . . . . . . . . . . . . . . . . . . . . . . . . . . . . . . . . . A . . . . . . . . . . . . . . . . . . . . .

Positions from 301 till 360
consensus  I N S S M P F H N I H P L T I G E C P K Y V K S N R L V L A T G L R N S P Q R E R R R K K R G L F G A I A G F I E G G W
AAL59142   . . . . . . . . . . . . . . . . . . . . . . . . . . . . . . . . . . . T . . . . G . . . . . . . . . . . . . . . . . . .
AAZ29963   . . . . . . . . . . . . . . . . . . . . . . . . . . . . . . . . . . . . . . . . . . . . . . . . . . . . . . . . . . . .
ABA70758   . . . . . . . . . . . . . . . . . . . . . . . . . . . . . . . . . . . . . . . . K . . . . . . . . . . . . . . . . . . .
ABB87042   . . . . . . . . . V . . . . . . . . . . . . . . D K . . . . . . . . . V . . . . - - - - T . . . . . . . . . . . . . . .
ABD14810   . . . . . . . . . . . . . . . . . . . . . . . . . . . . . . . . . . . . . . . . - . . . . . . . . . . . . . . . . . . .
ABD46740   . . . . . . . . . . . . . . . . . . . . . . . . . . . . . . . . . . . . . . G . . . . . . . . . . . . . . . . . . . . .
ABD85144   . . . . . . . . . . . . . . . . . . . . . . . . . . . . . . . . . . . . . . G . . . . . . . . . . . . . . . . . . . . .
ABE97569   . . . . . . . . . . . . . . . . . . . . . . . . . . . . . . . . . . . . . . . . . . . . . . . . . . . . . . . . . . . .
```

FIG. 5B-3

```
Positions from 361 till 420
consensus   Q G M V D G W Y G Y H H S N E Q G S G Y A A D K E S T Q K A I D G V T N K V N S - - D K M N T Q F E A V G R E F N N I E
AAL59142    . . . . . . . . . . . . . . . . . . . . . . . . . . . . . . . . . . . . . . . . . . . . . . . . . . . . . . . . . K . .
AAZ29963    . . . . . . . . . . . . . . . . . . . . . . . . . . . . . . . . . . . . . . . . . . . . . . . . . . . . . . . . . . . .
ABA70758    . . . . . . . . . . . . . . K . . . . . . . . . . . . . . . . . . . . . . . . . . . . . . . . . . . . . . . . . . . . .
ABB87042    . . . . . . . . . . . . . . . . . . . . . . . . . . . . . . . . . I . . . . . . . . . . . . . . . . T . . K . . . . . .
ABD14810    . . . . . . . . . . . . . . . . . . . . . . . . . . . . . . . . . . . . . . . . . . . . . . . . . . . . . . . . . . . .
ABD46740    . . . . . . . . . . . . . . . . . . . . . . . . . . . . . . . . . . . . . . . . . . . . . . . . . . . . . . . . . . . .
ABD85144    . . . . . . . . . . . . . . . . . . . . . . . . . . . . . . . . . . . . . . . . . . . . . . . . . . . . . . . . . . . .
ABE97569    . . . . . . . . . . . . . . . . . . . . . . . . . . . . . . . . . . . . . . . . . . . . . . . . . . . . . . . . . . . .

Positions from 421 till 480
consensus   R R I E N I N K K M E D G F I D V W T Y N A E L L V L M E N E R T L D F H D S N V K N L Y D K V R I Q L R D N A K E I G
AAL59142    . . . . . . . . . . . . . . . . . . . . . . . . . . . . . . . . . . . . . . . . . . . . . . . . . . . . . . . . . . . .
AAZ29963    . . . . . . . . . . . . . . . . . . . . . . . . . . . . . . . . . . . . . . . . . . . . . . . . . . . . . . . . . . . .
ABA70758    . . . . . . . . . . . . . . . . . . . . . . . . . . . . . . . . . . . . . . . . . . . . . . . . . . . . . . . . . . . .
ABB87042    . . . . . . . . . . . . . . . . . . . . . . . . . . . . . . . . . . . . . . . . . . . . . . . . . . . . . . . . . . . .
ABD14810    . . . . . . . . . . . . . . . . . . . . . . . . . . . . . . . . . . . . . . . . . . . . . . . . . . . . . . . . . . . .
ABD46740    . . . . . . . . . . . . . . . . . . . . . . . . . . . . . . . . . . . . . . . . . . . . . . . . . . . . . . . . . . . .
ABD85144    . . . . . . . . . . . . . . . . . . . . . . . . . . . . . . . . . . . . . . . . . . . . . . . . . . . . . . . . . . . .
ABE97569    . . . . . . . . . . . . . . . . . . . . . . . . . . . . . . . . . . . . . . . . . . . . . . . . . . . . . . . . . . . .
```

FIG. 5B-4

Positions from 481 till 540

| | |
|---|---|
| consensus | N G C F E F Y H K C D N E C M E S V R N G T Y D Y P Q Y S E E A R I K R B B I S G V K L E S I G T Y Q I L S I Y S T V A |
| AAL59142 | . . . . . . . . . . . . . . . . . . K . . . . . . . . . . . . . . . N . . . . . . . . . . . M . . . . . . . . . . . . . |
| AAZ29963 | . . . . . . . . . . . . . . . . . . . . . . . . . . . . . . . . . . . . . . . . . . . . . . . . I . . . . . . . . . . . |
| ABA70758 | . . . . . . . . . . . . . . . . . . . . . . . . . . . . . . . . . . . . . . . . . . . . . . . . I . . . . . . . . . . . |
| ABB87042 | . . . . . . . . . . . . . . . . . . . . . . . . . . . . . . . S . . N . . . . D . . . . . . M . . . . . . . . . . . . . |
| ABD14810 | . . . . . . . . . . . . . . . . . . . . . . . . . . . . . . . . . . . . . . . . . . . . . . . . . . . . . . . . . . . . |
| ABD46740 | . . . . . . . . R . . . . . . . . . . . . . . . . . . . . . . . . . . . . . . . . . . . . . . . . . . . . . . . . . . |
| ABD85144 | . . . . . . . . R . . . . . . . . . . . . . . . . . . . . . . . . . . . . . . . . . . . . . . . . . . . . . . . . . . |
| ABE97569 | . . . . . . . . . . . . . . . . . I . . . . . N . . . . . . . . . . . . . . . . . . . . . . . . I . . . . . . . . . . . |

Positions from 541 till 568

| | |
|---|---|
| consensus | S S L A L A I M V A G L S L W M C S N G S L Q C R I C I |
| AAL59142 | . . . . . . . . . . . . . . . . . . . . . . . . . . . . |
| AAZ29963 | . . . . . . . . . . . . . . . . - - - - - - - - - - - - |
| ABA70758 | . . . . . . . . . . . . . . . . . . . . . . . . . . . . |
| ABB87042 | . . . . . . . . . . . . . F . . . . . . . . . . . . . . |
| ABD14810 | . . . . . . . . . . . . . . . . . . . . . . . . . . . . |
| ABD46740 | . . . . . . . . . . . . . . . . . . . . - - - - - - - - |
| ABD85144 | . . . . . . . . . . . . F . . . . . . . . V T M - - - - |
| ABE97569 | . . . . . . . . M . . . . - - - - - - - - - - - - - - - |

FIG. 5B-5

*AAL59142*: 568 Avian 4 (HA) H5N1 Hong Kong 2000 Influenza A virus (A/Goose/Hong Kong/385.3.2000(H5N1))

*AAZ29963*: 556 Avian 4 (HA) H5N1 Thailand 2004 Influenza A virus (A/Ostrich/Samut Prakan/Thailand/CU-19/04(H5N1))

*ABA70758*: 568 Avian 4 (HA) H5N1 Belgium 2004 Influenza A virus (A/crested eagle/Belgium/01/2004(H5N1))

*ABB87042*: 564 Avian 4 (HA) H5N2 Canada 1976/08/12 Influenza A virus (A/mallard duck/ALB/57/1976(H5N2))

*ABD14810*: 567 Avian 4 (HA) H5N1 China 2004 Influenza A virus (A/duck/Guanxi/13/2004(H5N1))

*ABD46740*: 566 Avian 4 (HA) H5N1 Nigeria 2006/01/17 Influenza A virus (A/chicken/Nigeria/641/2006(H5N1))

*ABD85144*: 557 Avian 4 (HA) H5N1 Egypt 2006 Influenza A virus (A/chicken/Egypt/960N3-004/2006(H5N1))

*ABE97569*: 553 Avian 4 (HA) H5N1 Indonesia 2004 Influenza A virus (A/turkey/Kedaton/BPPV3/2004(H5N1))

FIG. 5B-6

Conformational sampling of α2–3 linkage

| | |
|---|---|
| *Cone*-like | 100% |
| *Umbrella*-like | 0% |

FIG. 7E

Conformational sampling of α2–6 linkage

| | *Umbrella*-like (%) : *Cone*-like (%) |
|---|---|
| ω = - 60° | 60 : 20 |
| ω = + 60° | 10 : 40 |
| ω = 180° | 30 : 30 |

FIG. 7F

α2–3 and α2–6 motif in Cone topology

- Typical of short oligosaccharide or oligosaccharide branch attached to a Core Structure

- Short branch of N-linked Core

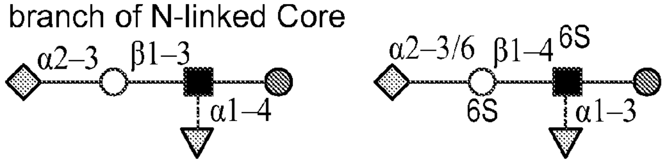

- Short branch of O-linked Core

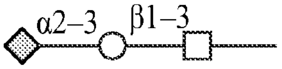

- The Cone topology can also be adopted by longer α2–3 and α2–6 oligosaccharide branch attached to Core Structure

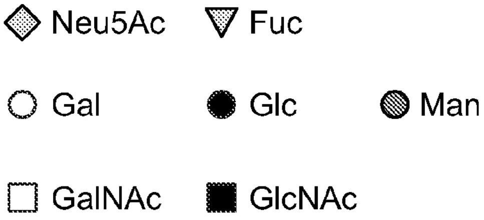

Dotted Gray lines, 4S and 6S indicate potential sites for fucosylation and sulfation modifications

FIG. 8

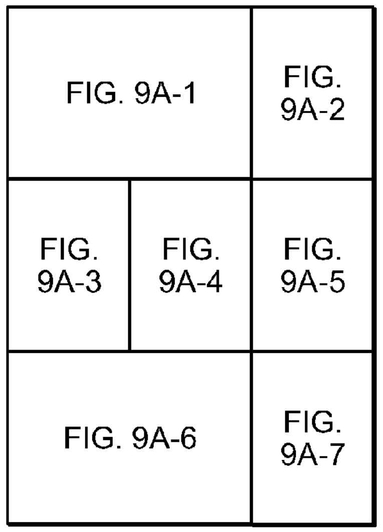
FIG. 9A
Key: GlcNAc GalNAc Gal Glc Neu5Ac Fucose Terminal HexNAc
**Long α2–6 *umbrella*-like topology glycan decoys**
N-linked glycans:
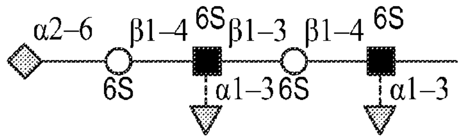
*α2–6 Type 2 extension branch attached to trimannosyl core*
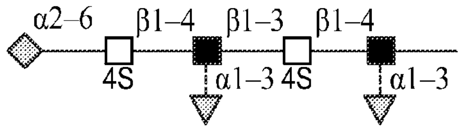
*α2–6 LacDiNAc extension branch attached to trimannosyl core*
FIG. 9A-1

**Long α2–6 *umbrella*-like topology glycans that are not decoys**

N-linked glycans:

*α2–6 linkage on GlcNAc of Type 1/Type 2 extension*

**Long α2–6 *umbrella*-like topology glycan decoys**
O-linked glycans:
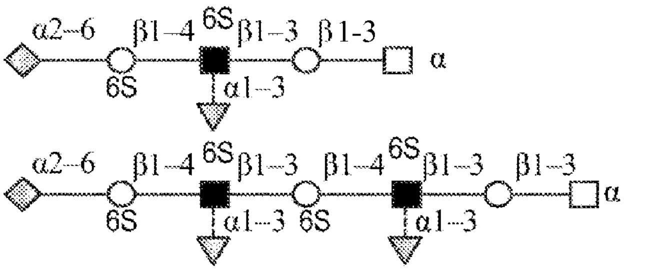
*α2–6 Type 2 extension branch in a Core 1 type structure*
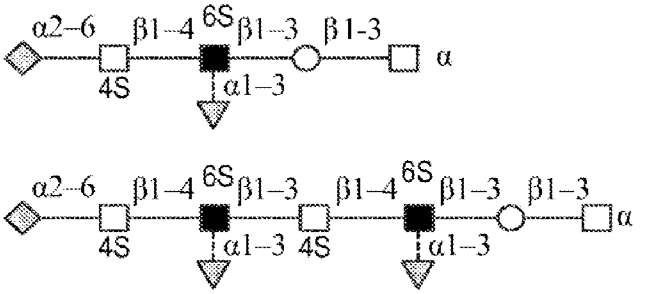
*α2–6 LacDiNAc extension branch in a Core 1 type structure*
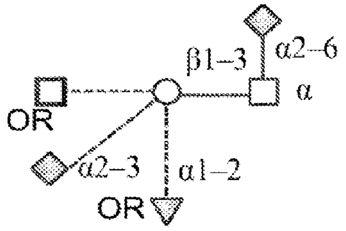
*α2–6 attached to core GalNAc in Core 1 type structure*
FIG. 9A-3

**Long α2–6 *umbrella*-like topology glycan decoys**
O-linked glycans:
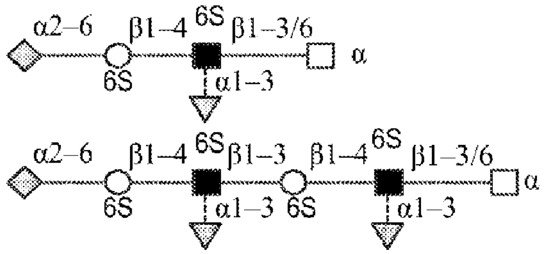
*α2–6 Type 2 extension branch in a Core 2 or 3 or 4 type structure*
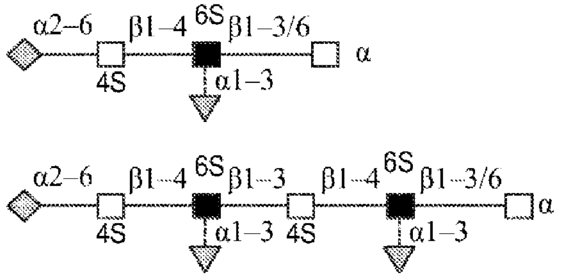
*α2–6 LacDiNAc extension branch in a Core 2 or 3 or 4 type structure*
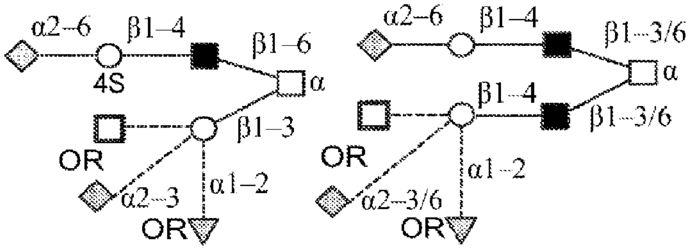
*α2–6 attached to branched Core 2 and Core 4 structures*
FIG. 9A-4

Long α2-6 *umbrella*-like topology glycans that are not decoys

O-linked glycans:

| | |
|---|---|
| <br>*α2-6 on GlcNAc of Type 1/Type 2 extension on Core 1 type structure* | <br>*α2-6 on GlcNAc of Type 1/Type 2 extension on Core 2 or 3 or 4 type structure* |

**Long α2–6 *umbrella*-like topology glycan decoys**
Glycolipids:
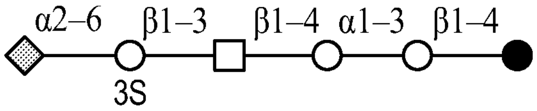
*Glucosylceramide Core Isoglobo type*
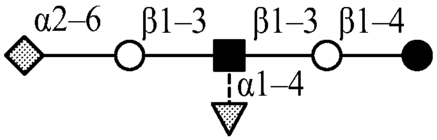
*Glucosylceramide Core Lacto type*
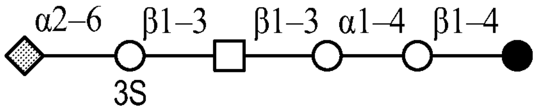
*Glucosylceramide Core Globo type*
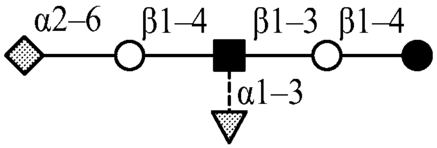
*Glucosylceramide Core Neolacto type*
FIG. 9A-6

Long α2-6 *umbrella*-like topology glycans that are not decoys

Glycolipids:

*Glucosylceramide Core Ganglio type*

*Glucosylceramide Core Globo type*

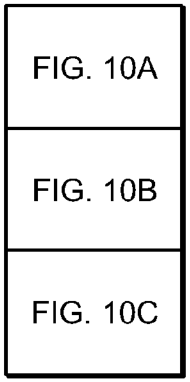
FIG. 10
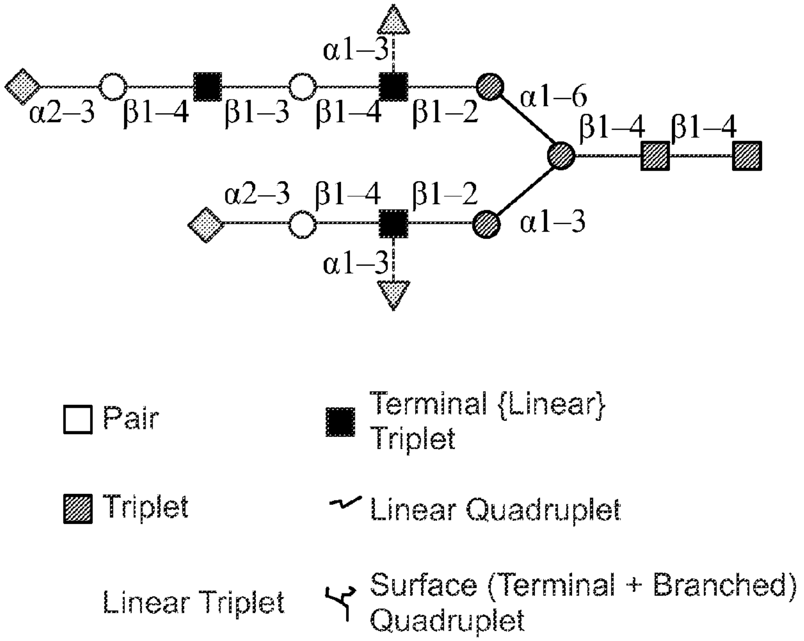
| Influenza HA | α2–3 Type | α2–6 Type |
|---|---|---|
| *A/Duck/Alberta/35/76 (Avian H1N1)* | 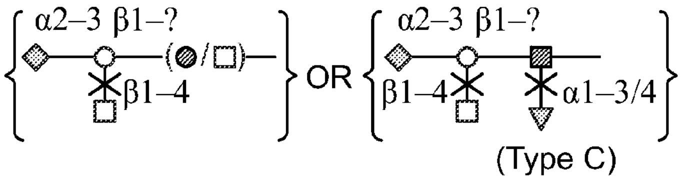  | No |
FIG. 10A

| | | |
|---|---|---|
| *A/Duck/Ukraine/1/63 (Avian H3N8)* | 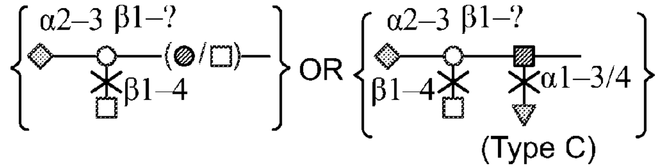 (Type C) | No |
| *A/Duck/Singapore/3/97 (Avian H5N3)* | 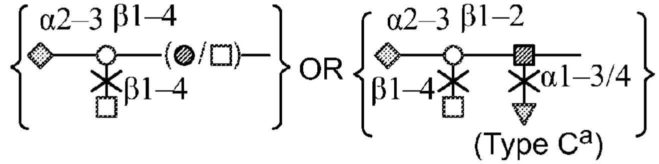 (Type C[a]) | No |
| *A/Vietnam/1203/04 (H5N1*)* | 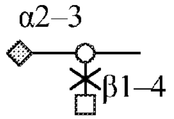 (Type A) | 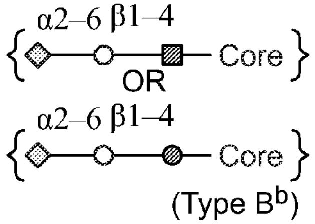 (Type B[b]) |
| *A/Vietnam/1203/04 (H5N1*) Gln226Leu/Gly228Ser double mutant* | 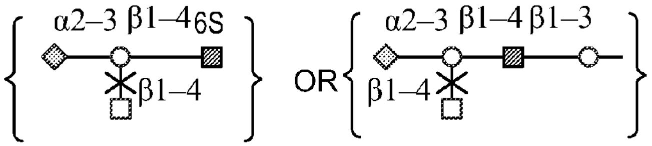 (Type B) | 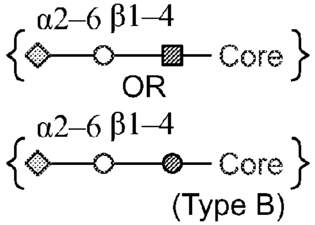 (Type B) |
| *A/South Carolina/11/18 (Human H1N1)* | No | 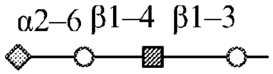 (Type A[c]) |
FIG. 10B Lectin staining of upper respiratory tissue sections.

ConA/Jacalin
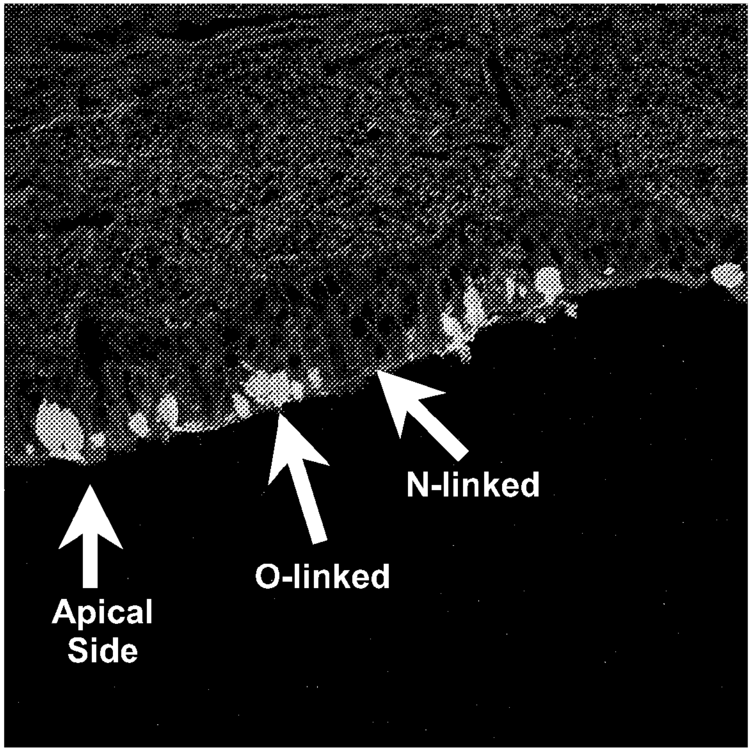
➢ Red = N-linked ➢ Green = O-linked
SNA/Jacalin
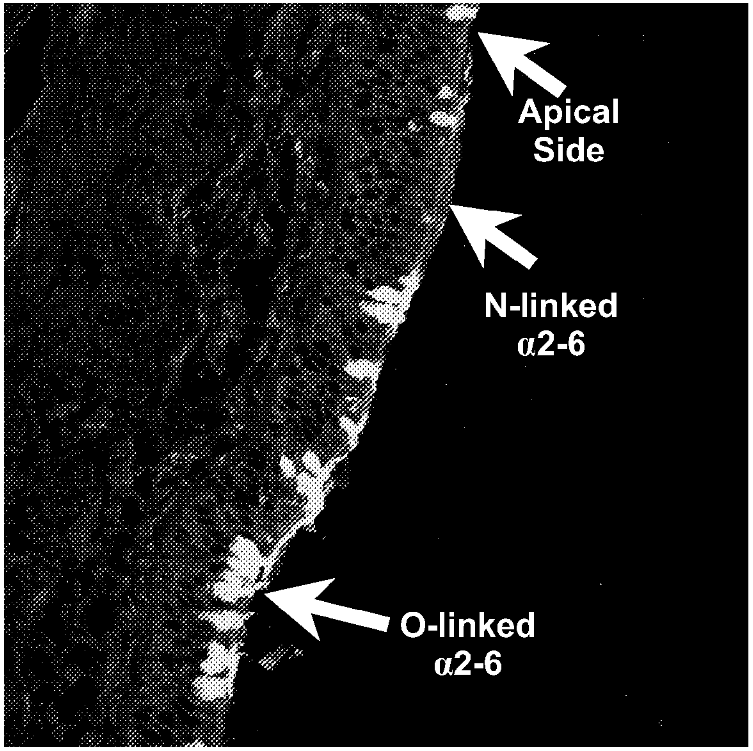
➢ Red = N-linked α2-6 ➢ Yellow = O-linked α2-6
FIG. 12B

- Variation around trisaccharide motif
  (Neu5Acα2-3Galβ1-3/4GlcNAc-) critically governs binding.
  The following motif present as a part of short and long
  α2-3 in biological and synthetic glycans would provide ideal
  target for avian viruses H5N1 A/Vietnam/1203/04 virus

| FIG. 16A |
|----------|
| FIG. 16B |

| | 190 | 192 | 193 | 222 | 225 | 226 |
|---|---|---|---|---|---|---|
| SC18 | D | Q | S | K | D | Q |
| NY18 | D | Q | S | K | G | Q |
| AV18 | E | Q | S | K | G | Q |
| ASI30 | D | Q | S | K | G | Q |
| APR34 | E | Q | N | K | D | Q |

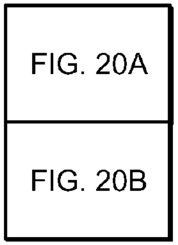

FIG. 20

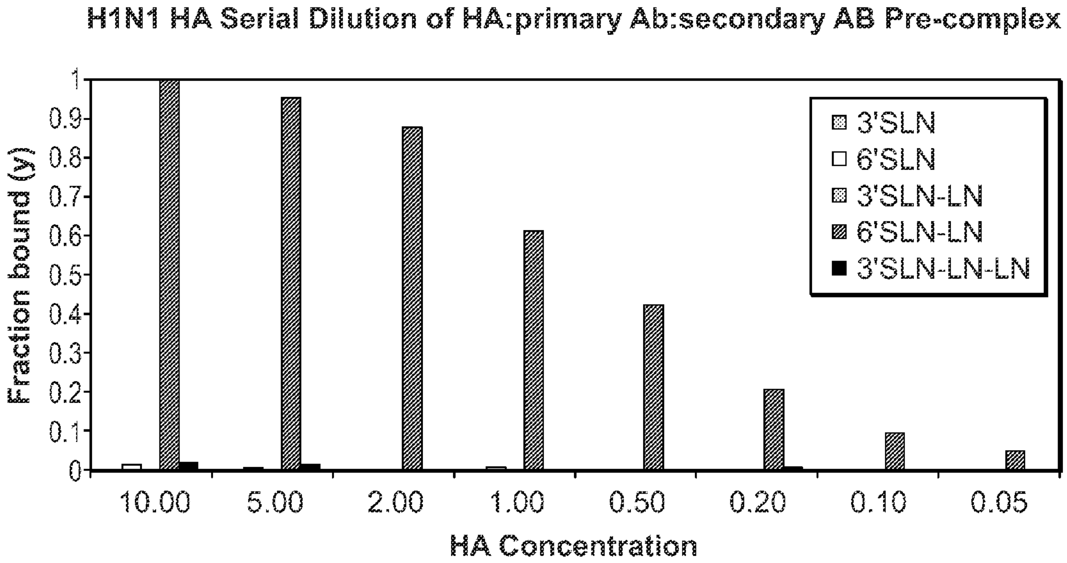

FIG. 20A

Protein concentration [Protein] converted to molar using $$\frac{\text{Concentration } [\mu g/ml] * 10^{-3}}{200000 \text{ ( ~ trimeric HA Mwt)}}$$

Relationship used to fit:

$y = L^n/ (L^n + Kd)$ $log_{10}(y/(1-y)) = n*log_{10}([protein]) - log_{10}(Kd)$ y = fractional saturation of glycan ligands in array (assume glycan is in excess of precomplex)

L = [Protein]

Slope (n) = Hill coefficient (measure of cooperativity)

Kd – apparent dissociation constant

| | | |
|---|---|---|
| A/Vietnam/1203/04 *(Avian H5N1)* Arg216Glu, Ser221 Pro double mutant | 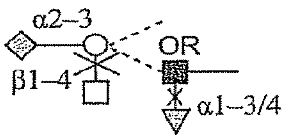  (Type C) | No |

[1] Border line high binder; [2] Sulfated GlcNAc[6/S]/Gal[6S] high binders [3]; Border line high) binders to a2-6 Type B. Only sulfated GlcNAc[6S]/Gal[6S] are high binders; [4] Binds to several non-sialylated glycans; [5] Border line high to α2-3 sialylated glycans; [6] Few border line high binders to sulfated GlcNAc on Neu5Acα3Galβ3/4GlcNAc; [7] High binders are Neu5Acα6Galβ4GlcNAcβ3Gal & !GlcNAcα6Man; Others are borderline high.

Keys: GlcNAc; GalNAc; Gal; Man; Fuc; Neu5Ac;

The data from glycan microarray screening of H1, H3 and H5 subtypes were obtained from the Consortium for Functional Glycomics (CFG) web site – http://www.functionalglycomics.org/glycomics/publicdata/primaryscreen.jsp. The details of the data mining analysis including the description of features and classifiers are provided in Suppl Figure 5. The rule induction classification method was used to generate the following classifiers (or rules) that govern the binding of HA to α2-3/6 sialylated glycans. Classifiers for α2-3 sialylated glycan binding – Type A: Neu5Acα3Gal & !GalNAcβ4Gal, Type B: Neu5Acα3Galβ4GlcNAc & !GalNAcβ4Gal & {GlcNAcβ3Gal or GlcNAc[6S]}, Type C: Neu5Acα3Galβ & !GalNAcβ4Gal & !Fucα3/4GlcNAc. Classifiers for α2-6 sialylated glycan binding – Type A: Neu5Acα6Galβ4GlcNAcb?Man, Type B: Neu5Acα6Galβ4GlcNAc & !GlcNAcb?Man. These complex rules are graphically represented in the table for clarity. The rules are provided as a logical combination of features among high affinity binders that enhance binding and features among weak and non-binders that are detrimental to binding (shown after the '!' symbol in the text description and as a red linkage with a 'x' sign in the graphical representation). The presence of mannose in the α2-6 classifiers arises from the single 6'-sialyl lactosamine containing biantennary N-linked glycan on the glycan array.

FIG. 24

| Influenza Strain | α2–3 Type[a] | | α2–6 Type[b] | |
|---|---|---|---|---|
| A/Duck/Alberta/35/76 *(Avian H1N1)* | 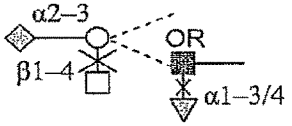 | (Type C) |  | (Type A[1]) |
| A/Duck/Alberta/35/76 *(Avian H1N1)* Glu190Asp/Gly225 Asp double mutant | No | |  | (Type B) |
| A/South Carolina/1/18 *(Human H1N1)* | No | | 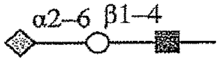 | (A or B) |
| A/New York/1/18 *(Human H1N1)* | 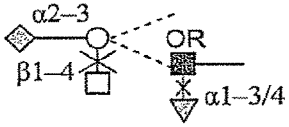 | (Type C[2]) |  | (Type B[3]) |
| A/Texas/36/91 *(Human H1N1)* | 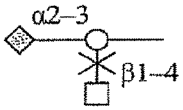 | (Type A[5]) | 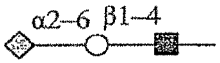 | (A or B) |
| A/New York/1/18 *(Human H1N1)* Asp 190Glu mutant[4] | 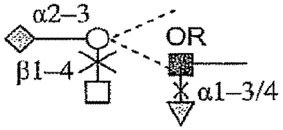 | (Type C[5]) | 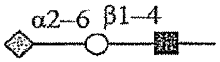 | (A or B) |
FIG. 25B

| Abbreviation (P | Virus strain | Glycan (with assigned coordinates) |
|---|---|---|
| ASI30_H1_23 (1R | A/Swine/Iowa/30 (H1N1) | Neu5Ac |
| ASI30_H1_26 (1R | A/Swine/Iowa/30 (H1N1) | Neu5Acα6Galβ4GlcNAcβ3Galβ4Glc |
| APR34_H1_23 (1] | A/Puerto Rico/8/34 (H1N1) | Neu5Acα3Galβ4GlcNAc |
| APR34_H1_26 (1RVZ) | A/Puerto Rico/8/34 (H1N1) | Neu5Acα6Galβ4GlcNAc |
| ADU63_H3_23 (1MQM) | A/Duck/Ukraine/1/63 (H3N8) | Neu5Acα3Gal |
| ADU63_H3_26 (1MQN) | A/Duck/Ukraine/1/63 (H3N8) | Neu5Acα6Gal |
| AAI68_H3_23 (1HGG) | A/Aichi/2/68 (H3N2) | Neu5Acα3Galβ4Glc |
| ADS97_H5_23 (1JSN) | A/Duck/Singapore/3/97 (H5N3) | Neu5Acα3Galβ3GlcNAc |
| ADS97_H5_26(1JSO) | A/Duck/Singapore/3/97 (H5N3) | Neu5Ac |
| Viet04_H5 (2FK0) | A/Vietnam/1203/2004 (H5N1) | |

The HA-α2-6 sialylated glycan complexes were generated by superimposition of the CA trace of the HA1 subunit of ADU63_H3 and ADS97_H5 and Viet04_H5 on ASI30_H1_26 and APR34_H1_26 (H1). Although the structural complexes of the human A/Aichi/2/68 (H3N2) with α2- 6 sialylated glycans are published[17], their coordinates were not available in the Protein Data Bank. The SARF2 (http://123d.ncifcrf.gov/sarf2.html) program was used to obtain the structural alignment of the different HA1 subunits for superimposition.

FIG. 25C

DECOY INFLUENZA THERAPIES

CROSS-REFERENCE TO RELATED APPLICATIONS

The present application claims priority to U.S. Provisional patent application Ser. No. 61/018,783, filed Jan. 3, 2008, the entire contents of which are incorporated herein by reference.

GOVERNMENT SUPPORT

This invention was made with United States government support awarded by the National Institute of General Medical Sciences (glue grant contract number U54 GM62116) and by the National Institutes of Health (contract number GM57073). The United States Government has certain rights in the invention.

BACKGROUND OF THE INVENTION

Influenza has a long history of pandemics, epidemics, resurgences and outbreaks. Avian influenza, including the H5N1 strain, is a highly contagious and potentially fatal pathogen, but it currently has only a limited ability to infect humans. However, avian flu viruses have historically observed to accumulate mutations that alter its host specificity and allow it to readily infect humans. In fact, two of the major flu pandemics of the last century originated from avian flu viruses that changed their genetic makeup to allow for human infection.

Influenza remains a significant challenge to medical systems. Furthermore, there is a significant concern that the current H5N1, H7N7, H9N2 and H2N2 avian influenza strains might accumulate mutations that alter their host specificity and allow them to readily infect humans. There remains a need for improved systems and reagents for decreasing and treating influenza in humans, including influenza epidemics and pandemics.

SUMMARY OF THE INVENTION

The present invention provides systems for identifying agents useful as influenza therapeutics, as well as such agents, compositions containing them, and methods of employing them. Among other things, the invention provides agents that mimic umbrella-topology glycans, and/or that compete with influenza hemagglutinin polypeptides for interaction with umbrella-topology glycans.

BRIEF DESCRIPTION OF THE DRAWING

FIG. 1: Alignment of exemplary sequences of wild type HA. Sequences were obtained from the NCBI influenza virus sequence database (http://www.ncbi.nlm.nih.gov/genomes/FLU/FLU.html). H1_Av (SEQ ID NO. 1); H1_Hul (SEQ ID NO. 2); H1_Hu2 (SEQ ID NO. 3); H2_Av (SEQ ID NO. 4); H2_Hu (SEQ ID NO. 5); H3_Av (SEQ ID NO. 6); H3_Hu1 (SEQ ID NO. 7); H3_Hu2 (SEQ ID NO. 8); H4_Av (SEQ ID NO. 9); H5_Av1 (SEQ ID NO. 10); H5_Av2 (SEQ ID NO. 11); H6_Av (SEQ ID NO. 12); H7_Av (SEQ ID NO. 13); H8_Av (SEQ ID NO. 14); H9_Av (SEQ ID NO. 15); H10_Av (SEQ ID NO. 16); H11_Av (SEQ ID NO. 17); H12_Av (SEQ ID NO. 18); H13_Av (SEQ ID NO. 19); H14_Av (SEQ ID NO. 20); H15_Av (SEQ ID NO. 21); and H16_Av (SEQ ID NO. 22).

FIG. 3: Sequence alignment illustrating conserved subsequences characteristic of H1 HA. H1_Av (SEQ ID NO. 1); H1_Hu1 (SEQ ID NO. 2); H1_Hu2 (SEQ ID NO. 3); H2_Av (SEQ ID NO. 4); H2_Hu (SEQ ID NO. 5); H3_Av (SEQ ID NO. 6); H3_Hu1 (SEQ ID NO. 7); H3_Hu2 (SEQ ID NO. 8); H4_Av (SEQ ID NO. 9); H5_Av1 (SEQ ID NO. 10); H5_Av2 (SEQ ID NO. 11); H6_Av (SEQ ID NO. 12); H7_Av (SEQ ID NO. 13); H8_Av (SEQ ID NO. 14); H9_Av (SEQ ID NO. 15); H10_Av (SEQ ID NO. 16); H11_Av (SEQ ID NO. 17); H12_Av (SEQ ID NO. 18); H13_Av (SEQ ID NO. 19); H14_Av (SEQ ID NO. 20); H15_Av (SEQ ID NO. 21); and H16_Av (SEQ ID NO. 22).

FIG. 4: Sequence alignment illustrating conserved subsequences characteristic of H3 HA. H1_Av (SEQ ID NO. 1); H1_Hu1 (SEQ ID NO. 2); H1_Hu2 (SEQ ID NO. 3); H2_Av (SEQ ID NO. 4); H2_Hu (SEQ ID NO. 5); H3_Av (SEQ ID NO. 6); H3_Hu1 (SEQ ID NO. 7); H3_Hu2 (SEQ ID NO. 8); H4_Av (SEQ ID NO. 9); H5_Av1 (SEQ ID NO. 10); H5_Av2 (SEQ ID NO. 11); H6_Av (SEQ ID NO. 12); H7_Av (SEQ ID NO. 13); H8_Av (SEQ ID NO. 14); H9_Av (SEQ ID NO. 15); H10_Av (SEQ ID NO. 16); H11_Av (SEQ ID NO. 17); H12_Av (SEQ ID NO. 18); H13_Av (SEQ ID NO. 19); H14_Av (SEQ ID NO. 20); H15_Av (SEQ ID NO. 21); and H16_Av (SEQ ID NO. 22).

FIG. 8. Exemplary cone topologies. This Figure illustrates certain exemplary (but not exhaustive) glycan structures that adopt cone topologies.

$$y = \frac{[HA]^n}{[HA]^n + K_d'}$$

which upon linearization becomes:

$$\log\left(\frac{y}{1-y}\right) = n * \log([HA]) - \log(K_d')$$

where y—fractional saturation of the glycan binding sites in the HA units; [HA]—concentration of HA (in M); n—cooperativity factor; $K_d'$—apparent binding constant for the multivalent HA-glycan interactions. The value of y is calculated by normalizing the binding signals to the saturating binding signal which represent 100% occupancy on all HA units. n and $K_d'$ were calculated based on the linearized Hill model. Typically n≥1 indicates positive cooperativity where binding of one HA unit enhances the binding of the other in the precomplex. On the other hand n≤1 indicates negative cooperativity where binding of one HA unit in the precomplex has a negative effect on binding of other subunits. The apparent binding constant $K_d'$ is used mainly for quantifying relative binding affinities of different HAs to different glycans and hence its absolute value should be taken in the context of comparing the affinities. An assumption in the above model is that the glycans in each well of the plate are in excess of HA. To satisfy this assumption, binding signals for HA concentration range from 0.05 μg/ml to 5 μg/ml were used to calculate n and $K_d'$. All efficiently human-adapted H1 and H3 HAs bind with high affinity to long α2-6 glycans (6'SLN-LN). Human-adapted SC18 and TX91 H1N1 viruses transmit efficiently in the ferret model. Human-adapted Mos99 H3N2 virus is a vaccine strain. Although HA from NY18 (a single Asp225Gly mutant of SC18, a virus that transmits inefficiently) shows comparable α2-6 binding to the other efficiently human-adapted HAs at high concentration, it has a dramatically lower long α2-6 binding affinity. Conversely, HA from AV18 (Asp 190Glu/Asp225Gly double mutant of SC18, a virus that does not transmit) shows a reverse trend of high binding affinity to α2-3.

Figure 22:
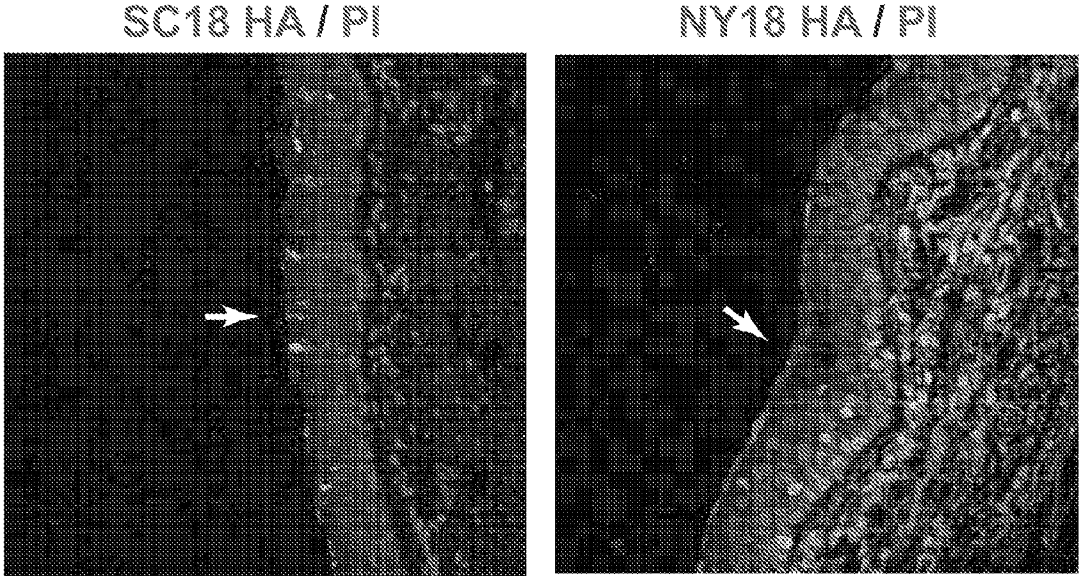

FIG. 22: Binding of SC18 and NY18 HA to human tracheal sections. The apical side of the tracheal epithelia is indicated by white arrow in all the sections. The binding pattern of SC18 HA is localized around specific regions on the apical side. NY18 HA shows well-distributed apical binding pattern (HA in green against PI in red). NY18 HA shows significant staining on the inner regions of the epithelia which express α2-3 glycans, as determined by MAL-II staining patterns.

Figure 23:
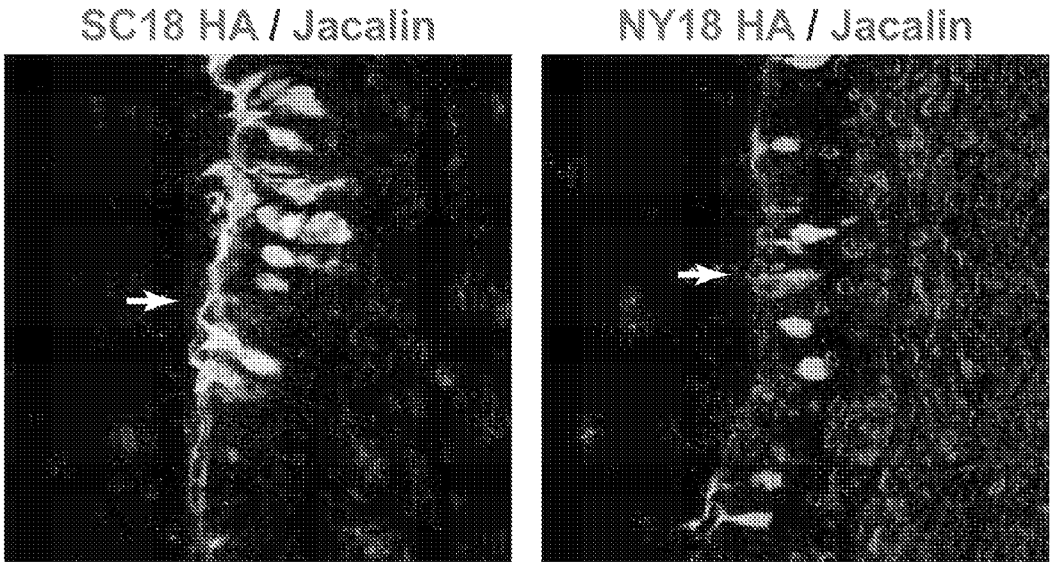

FIG. 23: Human tracheal co-staining of SC18 and NY18 HA with Jacalin. The apical side of tracheal epithelia is indicated by white arrow in all the sections. Distinct apical binding patterns of SC18 and NY18 (FIG. 22) are further elaborated by co-staining the HAs (red) with Jacalin (green), a marker for goblet cells. Representative regions of the apical side are enlarged for clarity. The significant co-stain of SC18 HA with Jacalin (yellow) indicates that SC18 HA predominantly binds to goblet cells on the apical side of the epithelia. Binding patterns of NY18 HA have minimal overlap with that of Jacalin, indicating that it does not bind to goblet cells on the apical side of tracheal tissue.

FIG. 24: Crystal structures of HA-glycan complexs. The HA-α2-6 sialylated glycan complexes were generated by superimposition of the CA trace of the HA1 subunit of ADU63_H3 and ADS97_H5 and Viet04_H5 on ASI30_H1__26 and APR34_H1__26 (H1).

Figure 25A:
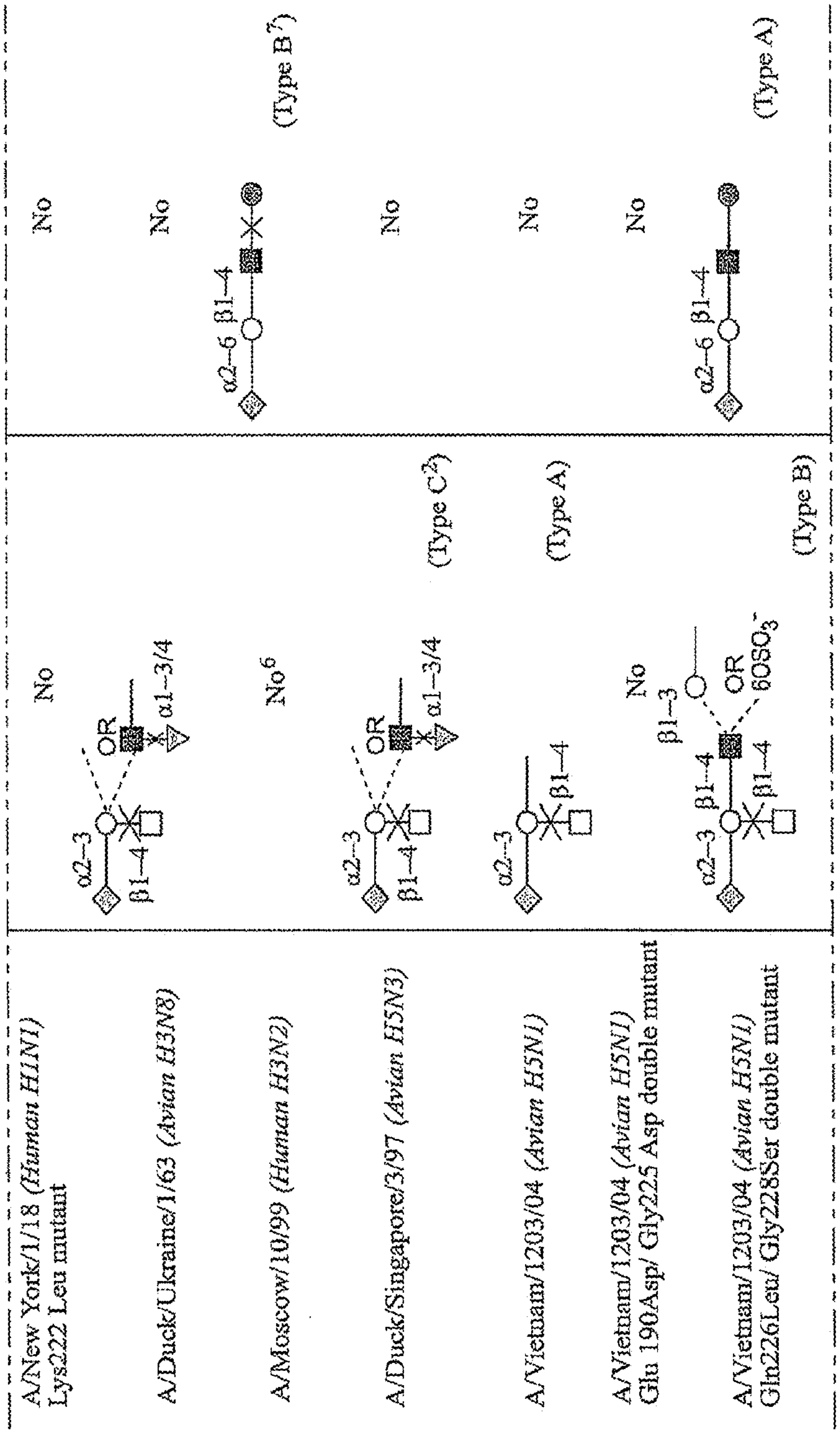

FIG. 25: Glycan receptor specificity of HAs based on classifier rules. Data from glycan microarray screening of H1, H3 and H5 subtypes. The details of the data mining analysis including the description of features and classifiers are provided.

DESCRIPTION OF HA SEQUENCE ELEMENTS

HA Sequence Element 1

HA Sequence Element 1 is a sequence element corresponding approximately to residues 97-185 (where residue positions are assigned using H3 HA as reference) of many HA proteins found in natural influenza isolates. This sequence element has the basic structure:

C (Y/F) P $X_1$ C $X_2$ W $X_3$ W $X_4$ H H P (SEQ ID NO. 34), wherein:

$X_1$ is approximately 30 to approximately 45 amino acids long;

$X_2$ is approximately 5 to approximately 20 amino acids long;

$X_3$ is approximately 25 to approximately 30 amino acids long; and $X_4$ is approximately 2 amino acids long.

In some embodiments, $X_1$ is about 35 to about 45, or about 35 to about 43, or about 35, about 36, about 37, about 38, about 39, about 40, about 41, about 42, or about 43 amino acids long. In some embodiments, $X_2$ is about 9 to about 15, or about 9 to about 14, or about 9, about 10, about 11, about 12, about 13, or about 14 amino acids long. In some embodiments, $X_3$ is about 26 to about 28, or about 26, about 27, or about 28 amino acids long. In some embodiments, $X_4$ has the sequence (G/A) (I/V). In some embodiments, $X_4$ has the sequence GI; in some embodiments, $X_4$ has the sequence GV; in some embodiments, $X_4$ has the sequence AI; in some embodiments, $X_4$ has the sequence AV. In some embodiments, HA Sequence Element 1 comprises a disulfide bond. In some embodiments, this disulfide bond bridges residues corresponding to positions 97 and 139 (based on the canonical H3 numbering system utilized herein).

In some embodiments, and particularly in H1 polypeptides, $X_1$ is about 43 amino acids long, and/or $X_2$ is about 13 amino acids long, and/or $X_3$ is about 26 amino acids long.

In some embodiments, and particularly in H1 polypeptides, HA Sequence Element 1 has the structure:

C Y P $X_{1A}$ T (A/T) (A/S) C $X_2$ W $X_3$ W $X_4$ H H P (SEQ ID NO. 44), wherein:

$X_{1A}$ is approximately 27 to approximately 42, or approximately 32 to approximately 42, or approximately 32 to approximately 40, or approximately 26 to approximately 41, or approximately 31 to approximately 41, or approximately 31 to approximately 39, or approximately 31, approximately 32, approximately 33, approximately 34, approximately 35, approximately 36, approximately 37, approximately 38, approximately 39, or approximately 40 amino acids long, and $X_2$-$X_4$ are as above.

In some embodiments, and particularly in H1 polypeptides, HA Sequence Element 1 has the structure:

C Y P $X_{1A}$ T (A/T) (A/S) C $X_2$ W (I/L) (T/V) $X_{3A}$ W $X_4$ H H P (SEQ ID NO. 45), wherein:

$X_{1A}$ is approximately 27 to approximately 42, or approximately 32 to approximately 42, or approximately 32 to approximately 40, or approximately 32, approximately 33, approximately 34, approximately 35, approximately 36, approximately 37, approximately 38, approximately 39, or approximately 40 amino acids long, $X_{3A}$ is approximately 23 to approximately 28, or approximately 24 to approximately 26, or approximately 24, approximately 25, or approximately 26 amino acids long, and $X_2$ and $X_4$ are as above.

Figures 2, 9A:
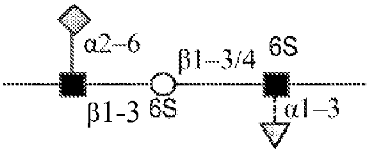
FIG. 2: Sequence alignment of HA glycan binding domain. Gray: conserved amino acids involved in binding to sialic acid. Red: particular amino acids involved in binding to Neu5Acα2-3/6Gal motifs. Yellow: amino acids that influence positioning of Q226 (137, 138) and E190 (186, 228). Green: amino acids involved in binding to other monosaccharides (or modifications) attached to Neu5Acα2-3/6Gal motif. The sequence for ASI30, APR34, ADU63, ADS97 and Viet04 were obtained from their respective crystal structures. The other sequences were obtained from SwissProt (http://us.expasy.org). Abbreviations: ADA76 (SEQ ID NO. 23), A/duck/Alberta/35/76 (H1N1); ASI30 (SEQ ID NO. 24), A/Swine/Iowa/30 (H1N1); APR34 (SEQ ID NO. 25), A/Puerto Rico/8/34 (H1N1); ASC18 (SEQ ID NO. 26), A/South Carolina/1/18 (H1N1), AT91 (SEQ ID NO. 27), A/Texas/36/91 (H1N1); ANY18 (SEQ ID NO. 28), A/New York/1/18 (H1N1); ADU63 (SEQ ID NO. 29), A/Duck/Ukraine/1/63 (H3N8); AAI68 (SEQ ID NO. 30), A/Aichi/2/68 (H3N2); AM99 (SEQ ID NO. 31), A/Moscow/10/99 (H3N2); ADS97 (SEQ ID NO. 32), A/Duck/Singapore/3/97 (H5N3); Viet04 (SEQ ID NO. 33), A/Vietnam/1203/2004 (H5N1).
Figure 9A:
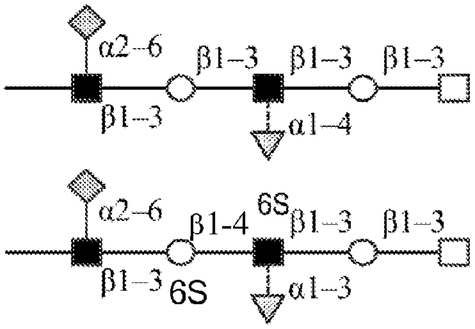
FIG. 9. Exemplary umbrella topologies. (A) Certain exemplary (but not exhaustive) N- and O-linked glycan structures that can adopt umbrella topologies. (B) Certain exemplary (but not exhaustive) O-linked glycan structures that can adopt umbrella topologies.

In some embodiments, and particularly in H1 polypeptides, HA Sequence Element 1 includes the sequence:

Q L S S I S S F E K (SEQ ID NO. 46), typically within $X_1$, (including within $X_{1A}$) and especially beginning about residue 12 of $X_1$ (as illustrated, for example, in FIGS. 1-3).

In some embodiments, and particularly in H3 polypeptides, $X_1$ is about 39 amino acids long, and/or $X_2$ is about 13 amino acids long, and/or $X_3$ is about 26 amino acids long.

In some embodiments, and particularly in H3 polypeptides, HA Sequence Element 1 has the structure:

C Y P $X_{1A}$ S (S/N) (A/S) C $X_2$ W $X_3$ W $X_4$ H H P (SEQ ID NO. 47), wherein:

$X_{1A}$ is approximately 27 to approximately 42, or approximately 32 to approximately 42, or approximately 32 to approximately 40, or approximately 23 to approximately 38, or approximately 28 to approximately 38, or approximately 28 to approximately 36, or approximately 28, approximately 29, approximately 30, approximately 31, approximately 32, approximately 33, approximately 34, approximately 35, approximately 36, approximately 37, approximately 38, approximately 39, or approximately 40 amino acids long, and $X_2$-$X_4$ are as above.

In some embodiments, and particularly in H3 polypeptides, HA Sequence Element 1 has the structure:

C Y P $X_{1A}$ S (S/N) (A/S) C $X_2$ W L (T/H) $X_{3A}$ W $X_4$ H H P (SEQ ID NO. 48), wherein:

$X_{1A}$ is approximately 27 to approximately 42, or approximately 32 to approximately 42, or approximately 32 to approximately 40, or approximately 32, approximately 33, approximately 34, approximately 35, approximately 36, approximately 37, approximately 38, approximately 39, or approximately 40 amino acids long, $X_{3A}$ is approximately 23 to approximately 28, or approximately 24 to approximately 26, or approximately 24, approximately 25, or approximately 26 amino acids long, and $X_2$ and $X_4$ are as above.

In some embodiments, and particularly in H3 polypeptides, HA Sequence Element 1 includes the sequence:

(L/I) (V/I) A S S G T L E F (SEQ ID NO. 49), typically within $X_1$ (including within $X_{1A}$), and especially beginning about residue 12 of $X_1$ (as illustrated, for example, in FIGS. 1, 2 and 4).

In some embodiments, and particularly in H5 polypeptides, $X_1$ is about 42 amino acids long, and/or $X_2$ is about 13 amino acids long, and/or $X_3$ is about 26 amino acids long.

In some embodiments, and particularly in H5 polypeptides, HA Sequence Element 1 has the structure:

C Y P $X_{1A}$ S S A C $X_2$ W $X_3$ W $X_4$ H H P (SEQ ID NO. 50), wherein:

$X_{1A}$ is approximately 27 to approximately 42, or approximately 32 to approximately 42, or approximately 32 to approximately 40, or approximately 23 to approximately 38, or approximately 28 to approximately 38, or approximately 28 to approximately 36, or approximately 28, approximately 29, approximately 30, approximately 31, approximately 32, approximately 33, approximately 34, approximately 35, approximately 36, approximately 37, approximately 38, approximately 39, or approximately 40 amino acids long, and $X_2$-$X_4$ are as.

In some embodiments, and particularly in H5 polypeptides, HA Sequence Element 1 has the structure:

C Y P $X_{1A}$ S S A C $X_2$W L I $X_{3A}$ W $X_4$H H P (SEQ ID NO. 51), wherein:

$X_{1A}$ is approximately 27 to approximately 42, or approximately 32 to approximately 42, or approximately 32 to approximately 40, or approximately 32, approximately 33, approximately 34, approximately 35, approximately 36, approximately 37, approximately 38, approximately 39, or approximately 40 amino acids long, and $X_{3A}$ is approximately 23 to approximately 28, or approximately 24 to approximately 26, or approximately 24, approximately 25, or approximately 26 amino acids long, and $X_2$ and $X_4$ are as above.

In some embodiments, and particularly in H5 polypeptides, HA Sequence Element 1 is extended (i.e., at a position corresponding to residues 186-193) by the sequence:

N D A A E X X (K/R) (SEQ ID NO. 52)

Figure 5:
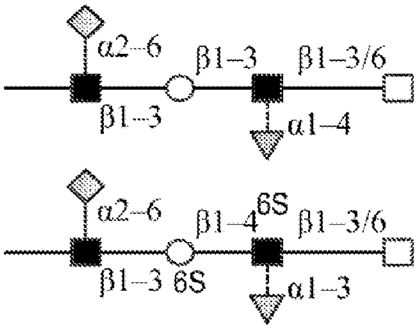
Figure 9A:
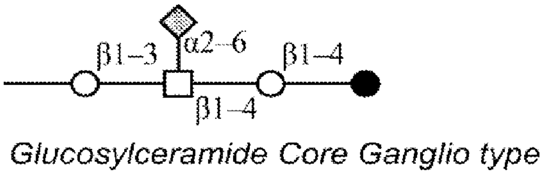

In some embodiments, and particularly in H5 polypeptides, HA Sequence Element 1 includes the sequence:

Y E E L K H L X S X X N H F E K (SEQ ID NO. 53), typically within $X_1$, and especially beginning about residue 6 of $X_1$ (as illustrated, for example, in FIGS. 1, 2, and 5).

HA Sequence Element 2

HA Sequence Element 2 is a sequence element corresponding approximately to residues 324-340 (again using a numbering system based on H3 HA) of many HA proteins found in natural influenza isolates. This sequence element has the basic structure:

G A I A G F I E (SEQ ID NO. 54)

In some embodiments, HA Sequence Element 2 has the sequence:

P $X_1$G A I A G F I E (SEQ ID NO. 55), wherein:

$X_1$ is approximately 4 to approximately 14 amino acids long, or about 8 to approximately 12 amino acids long, or about 12, approximately 11, approximately 10, approximately 9, or approximately 8 amino acids long. In some embodiments, this sequence element provides the HA0 cleavage site, allowing production of HA1 and HA2.

In some embodiments, and particularly in H1 polypeptides, HA Sequence Element 2 has the structure:

P S (I/V) Q S R $X_{1A}$ G A I A G F I E (SEQ ID NO. 56), wherein:

$X_{1A}$ is approximately 3 amino acids long; in some embodiments, $X_{1A}$ is G (L/I) F.

In some embodiments, and particularly in H3 polypeptides, HA Sequence Element 2 has the structure:

P X K X T R $X_{1A}$ G A I A G F I E (SEQ ID NO. 57), wherein:

$X_{1A}$ is approximately 3 amino acids long; in some embodiments, $X_{1A}$ is G (L/I) F.

In some embodiments, and particularly in H5 polypeptides, HA Sequence Element 2 has the structure:

P Q R X X X R X X R $X_{1A}$ G A I A G F I E (SEQ ID NO. 58), wherein:

$X_{1A}$ is approximately 3 amino acids long; in some embodiments, $X_{1A}$ is G (L/I) F.

Definitions

Affinity: As is known in the art, "affinity" is a measure of the tightness with a particular ligand (e.g., an HA polypeptide) binds to its partner (e.g., an HA receptor). Affinities can be measured in different ways.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Characteristic portion: As used herein, the phrase a "characteristic portion" of a protein or polypeptide is one that contains a continuous stretch of amino acids, or a collection of continuous stretches of amino acids, that together are characteristic of a protein or polypeptide. Each such continuous stretch generally will contain at least two amino acids. Furthermore, those of ordinary skill in the art will appreciate that typically at least 5, 10, 15, 20 or more amino acids are required to be characteristic of a protein. In general, a characteristic portion is one that, in addition to the sequence identity specified above, shares at least one functional characteristic with the relevant intact protein.

Characteristic sequence: A "characteristic sequence" is a sequence that is found in all members of a family of polypeptides or nucleic acids, and therefore can be used by those of ordinary skill in the art to define members of the family.

Figure 5B:
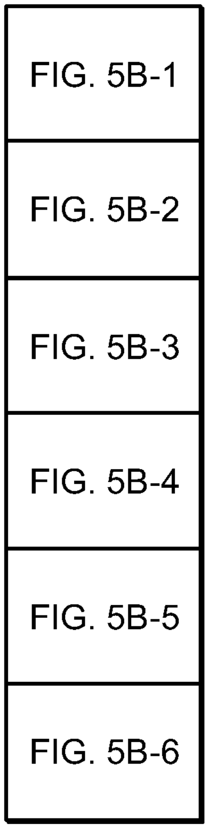
FIG. 5: Sequence alignment illustrating conserved subsequences characteristic of H5 HA. 5A1-A2: H1_Av (SEQ ID NO. 1); H1_Hu1 (SEQ ID NO. 2); H1_Hu2 (SEQ ID NO. 3); H2_Av (SEQ ID NO. 4); H2_Hu (SEQ ID NO. 5); H3_Av (SEQ ID NO. 6); H3_Hul (SEQ ID NO. 7); H3_Hu2 (SEQ ID NO. 8); H4_Av (SEQ ID NO. 9); H5_Av1 (SEQ ID NO. 10); H5_Av2 (SEQ ID NO. 11); H6_Av (SEQ ID NO. 12); H7_Av (SEQ ID NO. 13); H8_Av (SEQ ID NO. 14); H9_Av (SEQ ID NO. 15); H10_Av (SEQ ID NO. 16); H11_Av (SEQ ID NO. 17); H12_Av (SEQ ID NO. 18); H13_Av (SEQ ID NO. 19); H14_Av (SEQ ID NO. 20); H15_Av (SEQ ID NO. 21); and H16_Av (SEQ ID NO. 22). 5B1-B6: Consensus (SEQ ID NO. 34); AAL59142 (SEQ ID NO. 35); AAZ29963 (SEQ ID NO. 36); ABA70758 (SEQ ID NO. 37); ABB87042 (SEQ ID NO. 38); ABD14810 (SEQ ID NO. 39); ABD46740 (SEQ ID NO. 40); ABD85144 (SEQ ID NO. 41); and ABE97569 (SEQ ID NO. 42).
Figures 6, 6A:
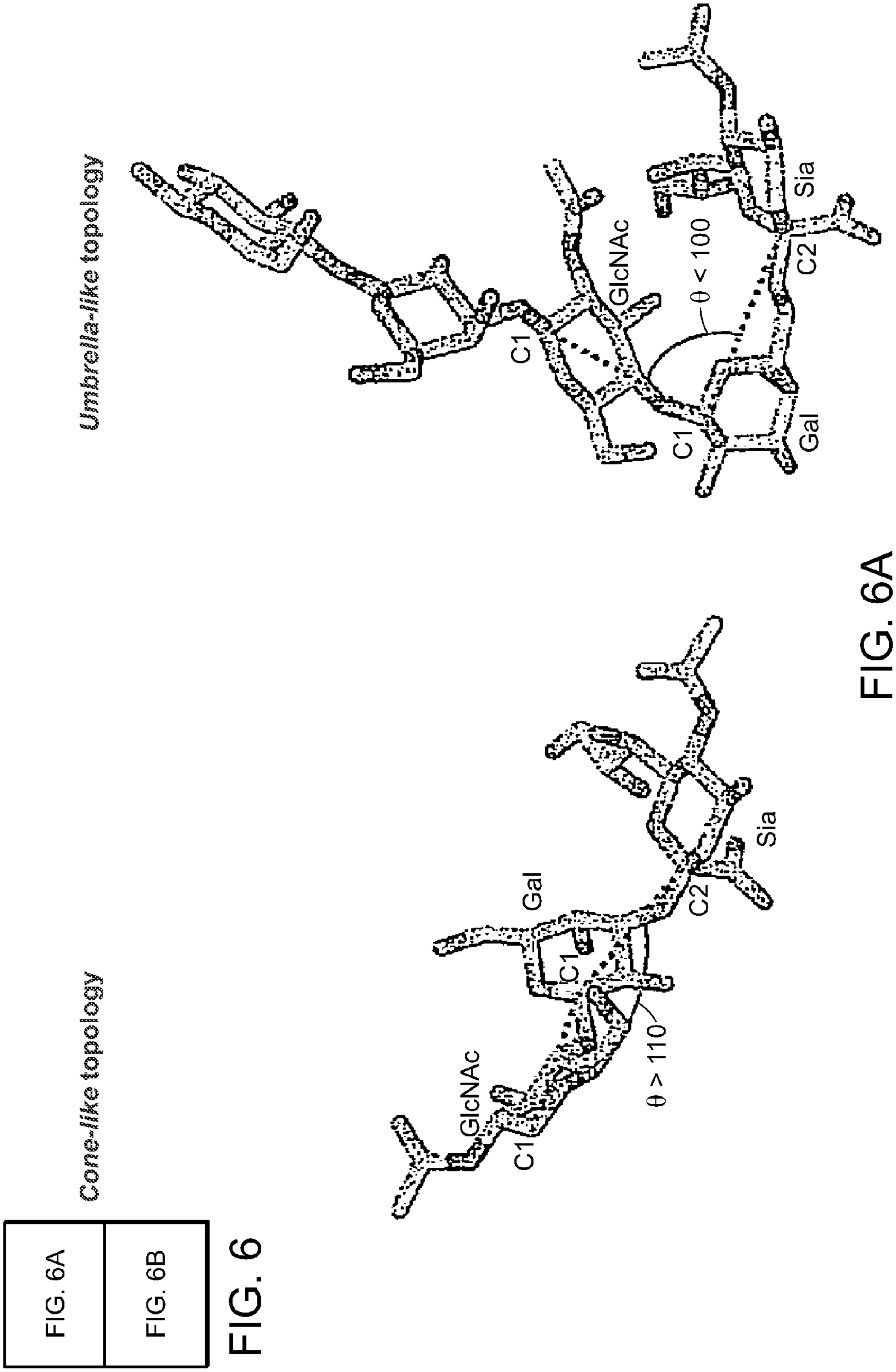
FIG. 6: Cone-topology vs. umbrella-topology of α2-3 and α2-6 siaylated glycans. The topology of α2-3 and α2-6 is governed by the glycosidic torsion angles of the trisaccharide motifs-Neu5Acα2-3Galβ1-3/4GlcNAc and Neu5Acα2-6Galβ1-4GlcNAc respectively (FIG. 7). A parameter (θ)—angle between C2 atom of Neu5Ac and C1 atoms of the subsequent Gal and GlcNAc sugars in these trisaccharide motifs was defined to characterize the topology. Superimposition of the θ contour and the conformational maps of the α2-3 and α2-6 motifs shows that α2-3 motifs adopt 100% cone-like topology and α2-6 motifs sampled both cone-like and umbrella-like topologies (FIG. 7). In the cone-like topology sampled by α2-3 and α2-6, GlcNAc and subsequent sugars are positioned along a region spanning a cone. Interactions of HA with cone-like topology primarily involve contacts of amino acids at the numbered positions (based on H3 HA numbering) with Neu5Ac and Gal sugars. On the other hand, in umbrella-like topology, which is unique to α2-6, \ GlcNAc and subsequent sugars bend towards the HA binding site (as observed in HA-α2-6 co-crystal structures). Longer α2-6 oligosaccharides (e.g. at least a tetrasaccharide) would favor this conformation since it is stabilized by intra-sugar van der Waals contact between acetyl groups of GlcNAc and Neu5Ac. HA interactions with umbrella-like topology involve contacts of amino acids at the numbered positions (based on H3 HA numbering) with GlcNAc and subsequent sugars in addition to contacts with Neu5Ac and Gal sugars.
Figure 6B:
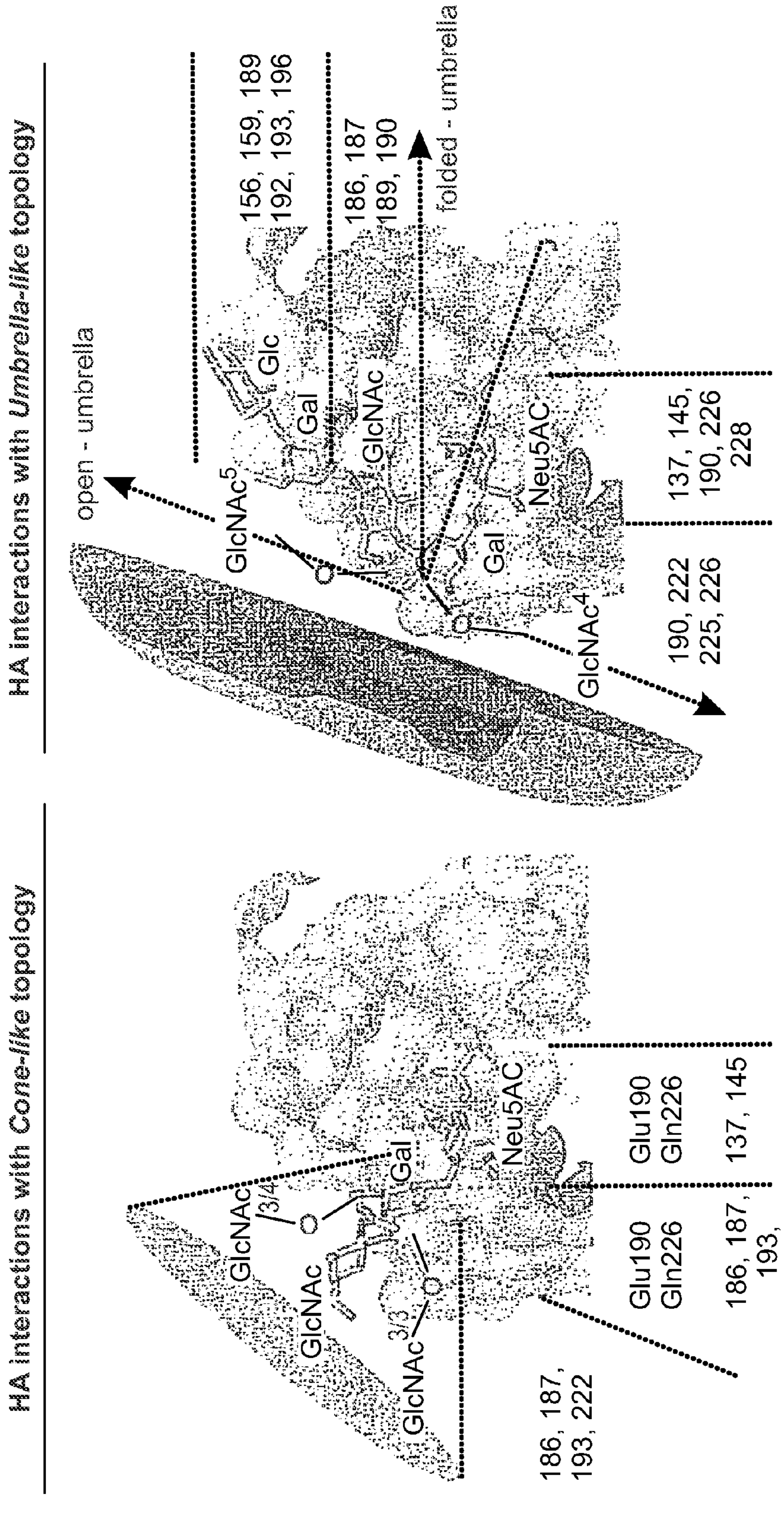
Figure 7B:
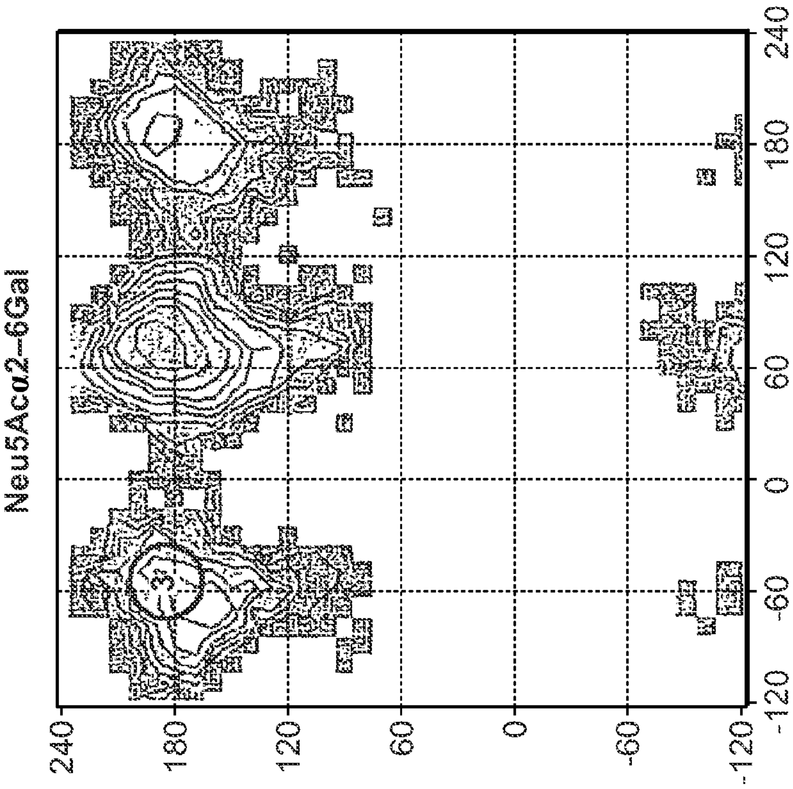
FIG. 7: Conformational sampling of cone- and umbrella-like topology by α2-3 and α2-6. (A)-(D) show the conformational (φ, ψ) maps of Neu5Acα2-3Gal, Neu5Acα2-6Gal, Galβ1-3GlcNAc, and Galβ1-4GlcNAc linkages, respectively. These maps obtained from GlycoMaps DB (http://www.glycosciences.de/modeling/glycomapsdb/) were generated using ab initio MD simulations using MM3 force field. Energy distribution is color coded starting from red (representing highest energy) to green representing lowest energy. Encircled regions 1-5 represent (φ,ψ) values observed for the α2-3 and α2-6 oligosaccharides in the HA-glycan co-crystal structures. The trans conformation (encircled region 1) of Neu5Acα2-3Gal predominates in HA binding pocket with the exception of the co-crystal structure of A/Aichi/2/68H3N2 HA with α2-3 where this conformation is gauche (encircled region 2). On the other hand, the cis conformation of Neu5Acα2-6Gal (encircled region 3) predominates in HA binding pocket. The cone-like topology is sampled by encircled regions 1 and 2 and the umbrella-like topology is sampled by encircled region 3. (E)-(F) show sampling of cone-like and umbrella-like topologies by α2-3 and α2-6 motifs, respectively. Regions marked in red in the conformational maps were used as the outer boundaries to calculate the θ parameter (angle between C2 atom of Neu5Ac and C1 atoms of subsequent Gal and GlcNAc sugars) for a given set of (φ,ψ) values. Based on the energy cutoff, the value of θ>110° was used to characterize cone-like topology and θ<100° was used to characterize umbrella-like topology. Superimposition of the θ contour with the conformational energy map indicated that α2-3 motif adopts 100% cone-like topology since it was energetically unfavorable to adopt umbrella-like topology. On the other hand, the α2-6 motif sampled both the cone-like and umbrella-like topologies and this sampling was classified based on the ω angle (O—C6-C5-H5) of Neu5Acα2-6Gal linkage.
Figure 7A:
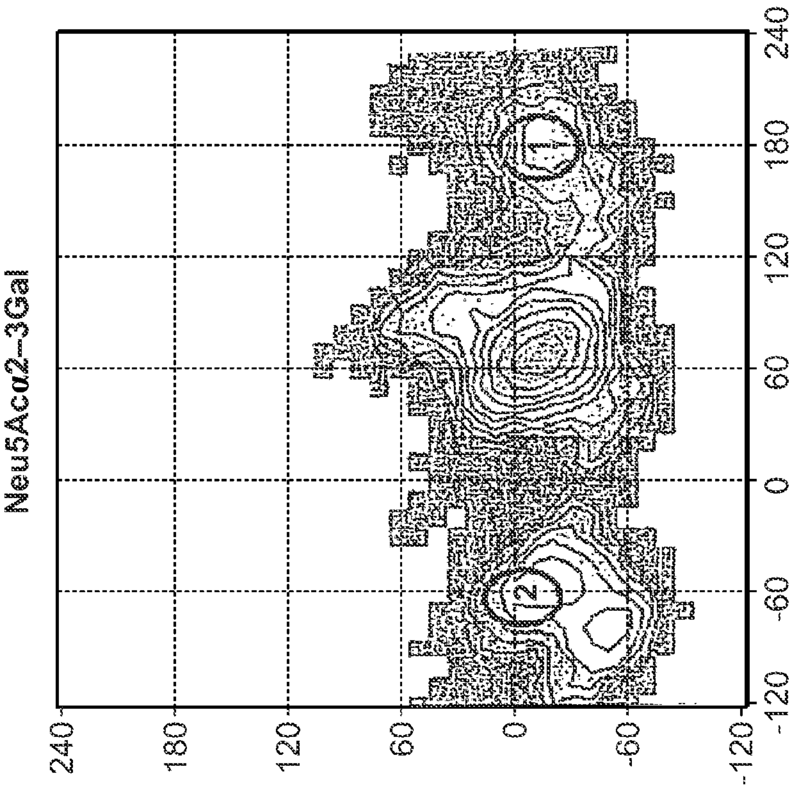
Figure 7C:
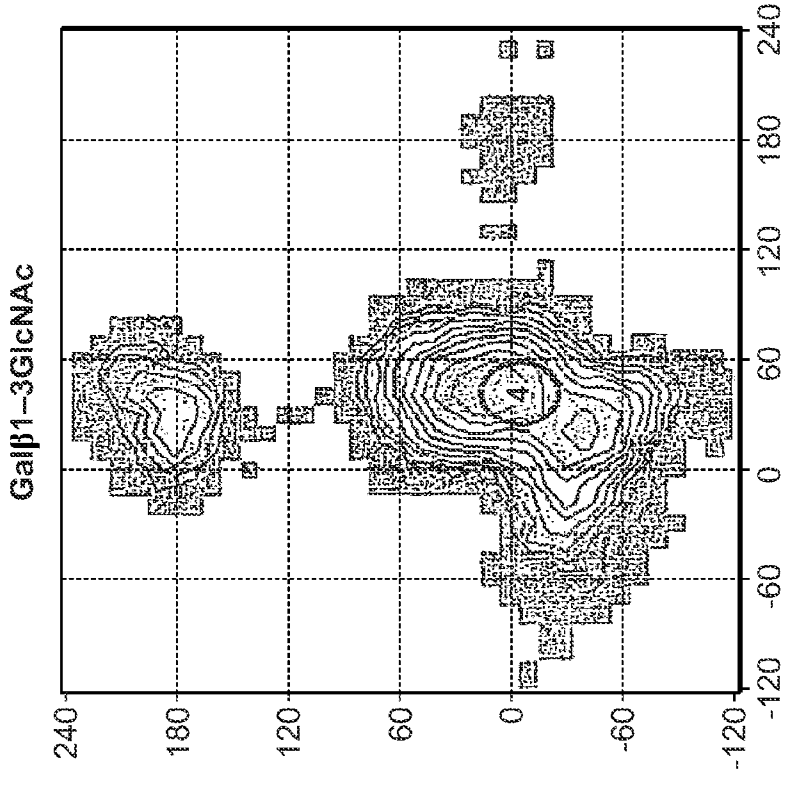
Figure 7D:
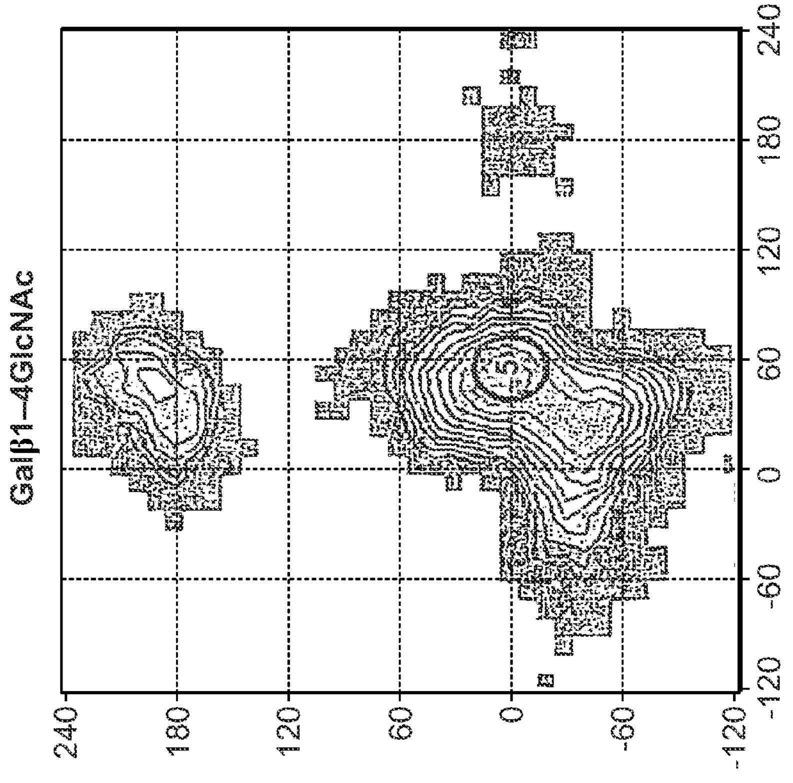
Figure 7:
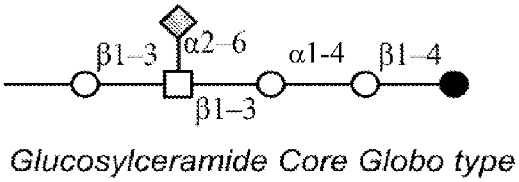
Figure 9B:
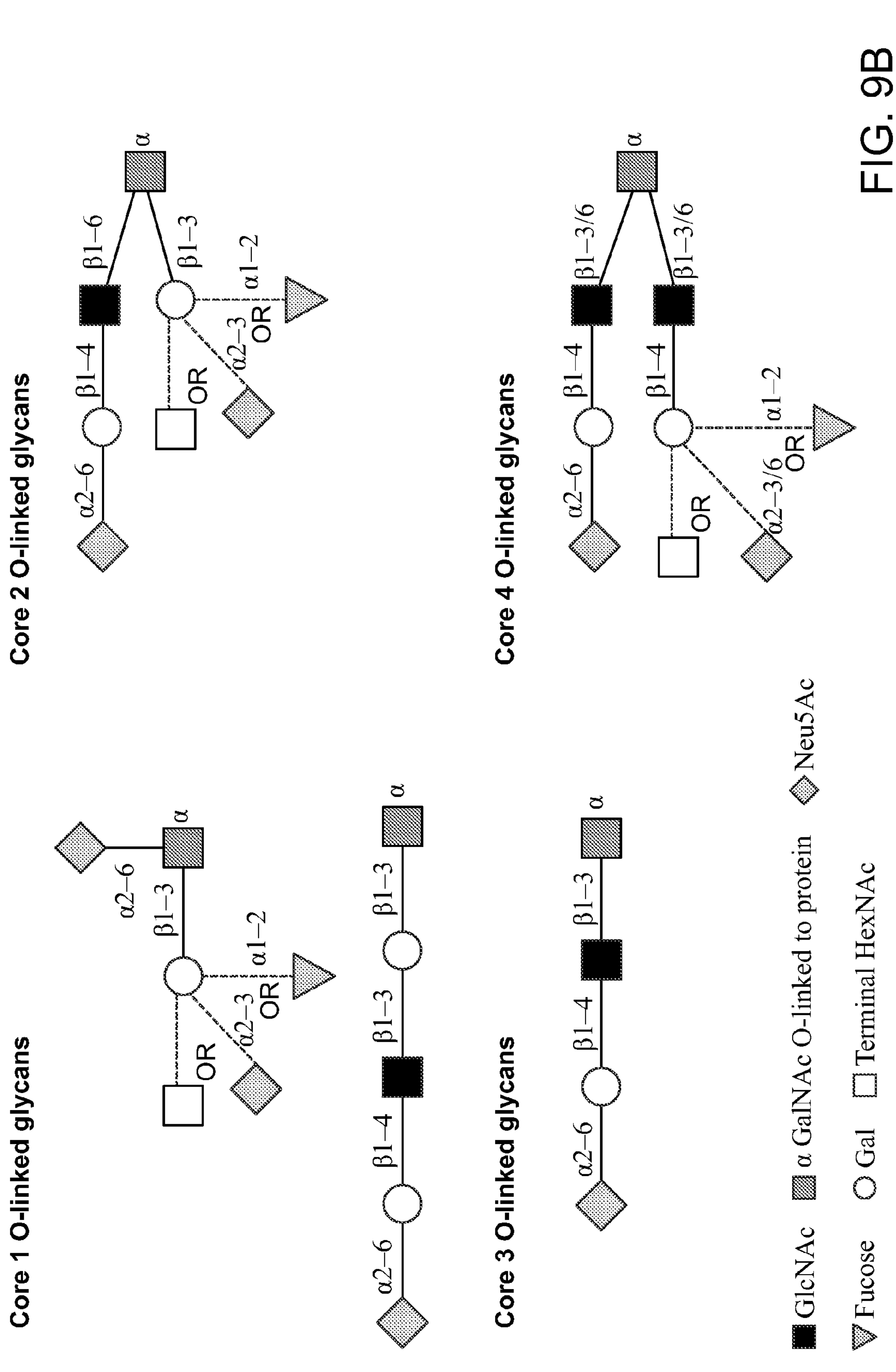

Cone-topology: The phrase "cone-topology" is used herein to refer to a 3-dimensional arrangement adopted by certain glycans and in particular by glycans on HA receptors. As illustrated in FIG. 6 (left panel), the cone-topology can be adopted by α2-3 sialylated glycans or by α2-6 sialylated glycans, and is typical of short oligonucleotide chains, though some long oligonucleotides can also adopt this conformation. The cone-topology is characterized by the glycosidic torsion angles of Neu5Acα2-3Gal linkage which samples three regions of minimum energy conformations given by ϕ ($C_1$-$C_2$—O—$C_3$/$C_6$) value of about −60, about 60, or about 180 and ψ ($C_2$—O—$C_3$/$C_6$—H3/$C_5$) samples −60 to 60 (FIG. 7). FIG. 8 presents certain representative (though not exhaustive) examples of glycans that adopt a cone-topology.

Corresponding to: As used herein, the term "corresponding to" is often used to designate the position/identity of an amino acid residue in an HA polypeptide. Those of ordinary skill will appreciate that, for purposes of simplicity, a canonical numbering system (based on wild type H3 HA) is utilized herein (as illustrated, for example, in FIGS. 1-5), so that an amino acid "corresponding to" a residue at position 190, for example, need not actually be the $190^{th}$ amino acid in a particular amino acid chain but rather corresponds to the residue found at 190 in wild type H3 HA; those of ordinary skill in the art readily appreciate how to identify corresponding amino acids.

Degree of separation removed: As used herein, amino acids that are a "degree of separation removed" are HA amino acids that have indirect effects on glycan binding. For example, one-degree-of-separation-removed amino acids may either: (1) interact with the direct-binding amino acids; and/or (2) otherwise affect the ability of direct-binding amino acids to interact with glycan that is associated with host cell HA receptors; such one-degree-of-separation-removed amino acids may or may not directly bind to glycan themselves. Two-degree-of-separation-removed amino acids either (1) interact with one-degree-of-separation-removed amino acids; and/or (2) otherwise affect the ability of the one-degree-of-separation-removed amino acids to interact with direct-binding amino acids, etc.

Direct-binding amino acids: As used herein, the phrase "direct-binding amino acids" refers to HA polypeptide amino acids which interact directly with one or more glycans that is associated with host cell HA receptors.

Engineered: The term "engineered," as used herein, describes a polypeptide whose amino acid sequence has been selected by man. For example, an engineered HA polypeptide has an amino acid sequence that differs from the amino acid sequences of HA polypeptides found in natural influenza isolates. In some embodiments, an engineered HA polypeptide has an amino acid sequence that differs from the amino acid sequence of HA polypeptides included in the NCBI database.

H1 polypeptide: An "H1 polypeptide," as that term is used herein, is an HA polypeptide whose amino acid sequence includes at least one sequence element that is characteristic of H1 and distinguishes H1 from other HA subtypes. Representative such sequence elements can be determined by alignments such as, for example, those illustrated in FIGS. 1-3 and include, for example, those described herein with regard to H1-specific embodiments of HA Sequence Elements.

H3 polypeptide: An "H3 polypeptide," as that term is used herein, is an HA polypeptide whose amino acid sequence includes at least one sequence element that is characteristic of H3 and distinguishes H3 from other HA subtypes. Representative such sequence elements can be determined by alignments such as, for example, those illustrated in FIGS. 1, 2, and 4 and include, for example, those described herein with regard to H3-specific embodiments of HA Sequence Elements.

H5 polypeptide: An "H5 polypeptide," as used herein, is an HA polypeptide whose amino acid sequence includes at least one sequence element that is characteristic of H5 and distinguishes H5 from other HA subtypes. Representative such sequence elements can be determined by alignments such as, for example, those illustrated in FIGS. 1, 2, and 5 and include, for example, those described herein with regard to H5-specific embodiments of HA Sequence Elements.

Hemagglutinin (HA) polypeptide: As used herein, the term "hemagglutinin polypeptide" (or "HA polypeptide") refers to a polypeptide whose amino acid sequence includes at least one characteristic sequence of HA. A wide variety of HA sequences from influenza isolates are known in the art; indeed, the National Center for Biotechnology Information (NCBI) maintains a database (www.ncbi.nlm.nih.gov/genomes/FLU/flu.html) that, as of the filing of the present application included 9796 HA sequences. Those of ordinary skill in the art, referring to this database, can readily identify sequences that are characteristic of HA polypeptides generally, and/or of particular HA polypeptides (e.g., H1, H2, H3, H4, H5, H6, H7, H8, H9, H10, H11, H12, H13, H14, H15, or H16 polypeptides); or of HAs that mediate infection of particular hosts, e.g., avian, camel, canine, cat, civet, environment, equine, human, leopard, mink, mouse, seal, stone martin, swine, tiger, whale, etc. For example, in some embodiments, an HA polypeptide includes one or more characteristic sequence elements found between about residues 97 and 185, 324 and 340, 96 and 100, and/or 130 and 230 of an HA protein found in a natural isolate of an influenza virus. In some embodiments, an HA polypeptide has an amino acid sequence comprising at least one of HA Sequence Elements 1 and 2, as defined herein. In some embodiments, an HA polypeptide has an amino acid sequence comprising HA Sequence Elements 1 and 2, in some embodiments separated from one another by about 100 to about 200, or by about 125 to about 175, or about 125 to about 160, or about 125 to about 150, or about 129 to about 139, or about 129, about 130, about 131, about 132, about 133, about 134, about 135, about 136, about 137, about 138, or about 139 amino acids. In some embodiments, an HA polypeptide has an amino acid sequence that includes residues at positions within the regions 96-100 and/or 130-230 that participate in glycan binding. For example, many HA polypeptides include one or more of the following residues: Tyr98, Ser/Thr136, Trp153, His183, and Leu/Ile194. In some embodiments, an HA polypeptide includes at least 2, 3, 4, or all 5 of these residues. As used herein, the term "HA polypeptide" encompasses amino acid chains of any length (i.e. amino acid chains comprising at least 2 amino acids or longer).

Isolated: The term "isolated," as used herein, refers to an agent or entity that has either (i) been separated from at least some of the components with which it was associated when initially produced (whether in nature or in an experimental setting); or (ii) produced by the hand of man. Isolated agents or entities may be separated from at least about 10%, about 20%, about 30%, about 40%, about 50%, about 60%, about 70%, about 80%, about 90%, or more of the other components with which they were initially associated. In some embodiments, isolated agents are more than 90%, 91%, 92%, 93%, 94%, 95%, 96%, 97%, 98%, or 99% pure.

Long oligosaccharide: For purposes of the present disclosure, an oligosaccharide is typically considered to be "long" if it includes at least one linear chain that has at least four saccharide residues.

Non-natural amino acid: The phrase "non-natural amino acid" refers to an entity having the chemical structure of an amino acid (i.e.:

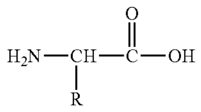

and therefore being capable of participating in at least two peptide bonds, but having an R group that differs from those found in nature. In some embodiments, non-natural amino acids may also have a second R group rather than a hydrogen, and/or may have one or more other substitutions on the amino or carboxylic acid moieties.

Polypeptide: A "polypeptide," generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, 92%, 93%, 94%, 95%, 96%, 97%, 98%, or 99% pure.

Short oligosaccharide: For purposes of the present disclosure, an oligosaccharide is typically considered to be "short" if it has fewer than 4, or certainly fewer than 3, residues in any linear chain.

Specificity: As is known in the art, "specificity" is a measure of the ability of a particular ligand (e.g., an HA polypeptide) to distinguish its binding partner (e.g., a human HA receptor, and particularly a human upper respiratory tract HA receptor) from other potential binding partners (e.g., an avian HA receptor).

Subject: As used herein, the term "subject" or "patient" refers to any organism to which a composition of this invention may be administered, e.g., for experimental, diagnostic, prophylactic, and/or therapeutic purposes. Typical subjects include animals (e.g., mammals such as mice, rats, rabbits, non-human primates, and humans; insects; worms; etc.).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" influenza infection has been diagnosed with or displays one or more symptoms of influenza infection.

Susceptible to: An individual who is "susceptible to" influenza infection has not been diagnosed with influenza infection and/or may not exhibit symptoms of influenza infection. In some embodiments, an individual who is susceptible to influenza infection will develop influenza infection. In some embodiments, an individual who is susceptible to influenza infection will not develop influenza infection.

Therapeutic agent: As used herein, the phrase "therapeutic agent" refers to any agent that elicits a desired biological or pharmacological effect when administered to a subject.

Therapeutically effective amount: As used herein, the term "therapeutically effective amount" means an amount of inventive glycan decoy that is sufficient, when administered to a subject suffering from or susceptible to influenza infection, to treat, diagnose, prevent, and/or delay the onset of influenza infection and/or symptom(s) thereof.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition (e.g., influenza infection). Treatment may be administered to a subject who does not exhibit signs of a disease and/or exhibits only early signs of the disease for the purpose of decreasing the risk of developing pathology associated with the disease.

Umbrella-topology: The phrase "umbrella-topology" is used herein to refer to a 3-dimensional arrangement adopted by certain glycans and in particular by certain glycans on HA receptors. The present invention encompasses the recognition that binding to umbrella-topology glycans is characteristic of HA proteins that mediate infection of human hosts. As illustrated in FIG. 6 (right panel), the umbrella-topology is typically adopted only by α2-6 sialylated glycans, and is typical of long (e.g., greater than tetrasaccharide) oligosaccharides. An example of umbrella-topology is given by ϕ angle of Neu5Acα2-6Gal linkage of around −60 (see, for example, FIG. 7). FIG. 9 presents certain representative (though not exhaustive) examples of glycans can adopt an umbrella topology. Umbrella topology glycans can be used as decoys to inhibit binding of influenza viruses to HA receptors having umbrella topology glycans. In certain embodiments, umbrella topology glycans are oligosaccharides of the following form:

Neu5Acα2-6Sug1-Sug2-Sug3 where:

(a) Neu5Ac α2-6 is typically (but not essentially) at the non-reducing end;

(b) Sug1:

- (i) is a hexose (frequently Gal or Glc) or hexosamine (GlcNAc or GalNAc) in α or β configuration (frequently β- for N- and O-linked extension and α- in the case of GalNAcα- that is O-linked to glycoprotein);
- (ii) no sugars other than Neu5Acα2-6 are attached to any of the non-reducing positions of Sug1 (except when Sug1 is GalNAcα- that is O-linked to the glycoprotein); and/or
- (iii) non-sugar moieties such as sulfate, phosphate, guanidium, amine, N-acetyl, etc. can be attached to non-reducing positions (typically 6 position) of Sug1 (e.g., to improve contacts with HA);

(c) Sug2 and/or Sug3 is/are:

- (i) hexose (frequently Gal or Glc) or hexosamine (GlcNAc or GalNAc) in a or β configuration (frequently β); and/or
- (ii) sugars (such as Fuc) or non-sugar moieties such as sulfate, phosphate, guanidium, amine, N-acetyl, etc. can be attached to non-reducing positions of Sug2, Sug3, and/or Sug4;

(d) Linkage between any two sugars in the oligosaccharide apart from Neu5Acα2-6 linkage can be 1-2, 1-3, 1-4, and/or 1-6 (typically 1-3 or 1-4); and/or (e) Structure where Neu5Acα2-6 is linked GalNAcα that is O-linked to the glycoprotein and additional sugars are linked to the non-reducing end of GalNAcα for example

- (i) Neu5Acα2-6(Neu5Acα2-3Galβ1-3)GalNAcα-
- (ii) Neu5Acα2-6(Galβ1-3)GalNAcα-

Vaccination: As used herein, the term "vaccination" refers to the administration of a composition intended to generate an immune response, for example to a disease-causing agent. For the purposes of the present invention, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition.

Variant: As used herein, the term "variant" is a relative term that describes the relationship between a particular HA polypeptide of interest and a "parent" HA polypeptide to which its sequence is being compared. An HA polypeptide of interest is considered to be a "variant" of a parent HA polypeptide if the HA polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue(s) as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent HA polypeptide is one found in a natural isolate of an influenza virus (e.g., a wild type HA).

Vector: As used herein, "vector" refers to a nucleic acid molecule capable of transporting another nucleic acid to which it has been linked. In some embodiment, vectors are capable of extra-chromosomal replication and/or expression of nucleic acids to which they are linked in a host cell such as a eukaryotic or prokaryotic cell. Vectors capable of directing the expression of operatively linked genes are referred to herein as "expression vectors."

Wild type: As is understood in the art, the phrase "wild type" generally refers to a normal form of a protein or nucleic acid, as is found in nature. For example, wild type HA polypeptides are found in natural isolates of influenza virus. A variety of different wild type HA sequences can be found in the NCBI influenza virus sequence database, http://www.ncbi.nlm.nih.gov/genomes/FLU/FLU.html.

DETAILED DESCRIPTION OF CERTAIN PARTICULAR EMBODIMENTS OF THE INVENTION

The present invention encompasses the recognition that interactions between influenza HA polypeptides and umbrella-topology glycans mediate influenza infections. The present further encompasses the recognition that agents that mimic umbrella-topology glycans can act as "receptor decoys" and can be useful as therapeutic agents in the treatment of influenza infections.

Among other things, the present invention provides systems for identifying agents that mimic umbrella-topology glycans and that compete interactions between HA polypeptides and HA receptors in subjects. The present invention further provides various agents and compositions containing them, as well as therapeutic strategies for the treatment of influenza infections. The present invention provides systems (e.g. detection assays) for characterizing HA-receptor interactions and agents that affect HA-receptor interactions.

HA Receptors

HA interacts with the surface of cells by binding to a glycoprotein receptor. Binding of HA to HA receptors is predominantly mediated by N-linked glycans on the HA receptors. Specifically, HA on the surface of flu virus particles recognizes sialylated glycans that are associated with HA receptors on the surface of the cellular host. After recognition and binding, the host cell engulfs the viral cell and the virus is able to replicate and produce many more virus particles to be distributed to neighboring cells. Some crystal structures of exemplary HA-glycan interactions have been identified and are presented in Table 1:

TABLE 1

Crystal Structures of HA-Glycan Complexes

| Abbreviation (PDB ID) | Virus Strain | Glycan (with assigned coordinates) |
| --- | --- | --- |
| ASI30_H1_23 (1RV0) | A/Swine/Iowa/30 (H1N1) | Neu5Ac |
| ASI30_H1_26 (1RVT) | A/Swine/Iowa/30 (H1N1) | Neu5Acα6Galβ4GlcNAcβ3Galβ4Glc |
| APR34_H1_23 (1RVX) | A/Puerto Rico/8/34 (H1N1) | Neu5Acα3Galβ4GlcNAc |
| APR34_H1_26 (1RVZ) | A/Puerto Rico/8/34 (H1N1) | Neu5Acα6Galβ4GlcNAc |
| ADU63_H3_23 (1MQM) | A/Duck/Ukraine/1/63 (H3N8) | Neu5Acα3Gal |
| ADU63_H3_26 (1MQN) | A/Duck/Ukraine/1/63 (H3N8) | Neu5Acα6Gal |
| AAI68_H3_23 (1HGG) | A/Aichi/2/68 (H3N2) | Neu5Acα3Galβ4Glc |
| ADS97_H5_23 (1JSN) | A/Duck/Singapore/3/97 (H5N3) | Neu5Acα3Galβ3GlcNAc |
| ADS97_H5_26(1JSO) | A/Duck/Singapore/3/97 (H5N3) | Neu5Ac |
| Viet04_H5 (2FK0) | A/Vietnam/1203/2004 (H5N1) | |

HA - α2-6 sialylated glycan complexes were generated by superimposition of the CA trace of the HA1 subunit of ADU63_H3 and ADS97_H5 and Viet04_H5 on ASI30_H1_26 and APR34_H1_26 (H1). Although the structural complexes of the human A/Aichi/2/68 (H3N2) with α2-6 sialylated glycans are published (Eisen et al., 1997, Virology, 232: 19), their coordinates were not available in the Protein Data Bank. The SARF2 (http://123d.ncifcrf.gov/sarf2.html) program was used to obtain the structural alignment of the different HA1 subunits for superimposition.

HA receptors are modified by either α2-3 or α2-6 sialylated glycans near the receptor's HA-binding site, and the type of linkage of the receptor-bound glycan can affect the conformation of the receptor's HA-binding site, thus affecting the receptor's specificity for different HAs.

For example, the glycan binding pocket of avian HA is narrow. According to the present invention, this pocket binds to the trans conformation of α2-3 sialylated glycans, and/or to cone-topology glycans, whether α2-3 or α2-6 linked.

HA receptors in avian tissues, and also in human deep lung and gastrointestinal (GI) tract tissues are characterized by α2-3 sialylated glycan linkages, and furthermore (according to the present invention), are characterized by glycans, including α2-3 sialylated and/or α2-6 sialylated glycans, which predominantly adopt cone topologies. HA receptors having such cone topology glycans may be referred to herein as CTHArs.

By contrast, human HA receptors in the bronchus and trachea of the upper respiratory tract are modified by α2-6 sialylated glycans. Unlike the α2-3 motif, the α2-6 motif has an additional degree of conformational freedom due to the $C_6$-$C_5$ bond (Russell et al., 2006, Glycoconj. J., 23:85; incorporated herein by reference). HAs that bind to such α2-6 sialylated glycans have a more open binding pocket to accommodate the diversity of structures arising from this conformational freedom. Moreover, according to the present invention, HAs may need to bind to glycans (e.g., α2-6 sialylated glycans) in an umbrella-topology, and particularly may need to bind to such umbrella-topology glycans with strong affinity and/or specificity, in order to effectively mediate infection of human upper respiratory tract tissues. HA receptors having such umbrella topology glycans may be referred to herein as UTHArs.

As a result of these spatially restricted glycosylation profiles, humans are not usually infected by viruses containing many wild type avian HAs (e.g., avian H5). Specifically, because the portions of the human respiratory tract that are most likely to encounter virus (i.e., the trachea and bronchi) lack receptors with cone-topology glycans (e.g., α2-3 sialylated glycans, and/or short glycans) and wild type avian HAs typically bind primarily or exclusively to receptors associated with cone-topology glycans (e.g., α2-3 sialylated glycans, and/or short glycans), humans rarely become infected with avian viruses. Only when in sufficiently close contact with virus that it can access the deep lung and/or gastrointestinal tract receptors having umbrella-topology glycans (e.g., long α2-6 sialylated glycans) do humans become infected.

Umbrella-Topology Glycans

As described in co-pending application Ser. No. 11/893,171, filed Aug. 14, 2007 (the entire contents of which are attached hereto as Appendix A), the present inventors have demonstrated that infection of mammalian (e.g., human) subjects by influenza viruses is mediated by interactions between viral HA polypeptides and umbrella-topology glycans on HA receptors in the subjects.

In some embodiments, umbrella-topology glycan preparations comprise a greater proportion of long (e.g. multiple lactosamine units) α2-6 oligosaccharide branches than short α2-6 (e.g. single lactosamine) branches. In some embodiments, umbrella-topology glycans comprise about 2-fold, about 3-fold, about 4-fold, about 5-fold, about 10-fold, about 20-fold, about 50-fold, or greater than about 50-fold more long α2-6 oligosaccharide branches than short α2-6 (e.g. single lactosamine) branches. FIG. 9 presents an exemplary, though not exhaustive, list of long α2-6 motifs. The long α2-6 motifs presented in FIG. 9 includes Neu5Acα2-6 linked at the non-reducing end to a long chain (e.g., at least a trisaccharide) found as a part of biological N-linked glycans, O-linked glycans, and glycolipids. The boxed inset shows examples of the umbrella-topology long α2-6 glycan moieties that are found as a part of biological glycans that bind to high affinity with HA.

In some embodiments, umbrella-topology glycans are glycans exhibiting a three-dimensional structure such as the structure presented in FIG. 6 (right panel). In some embodiments, umbrella-topology glycans are glycans exhibiting a three-dimensional structure substantially similar to the structure presented in FIG. 6 (right panel). In some embodiments, umbrella-topology glycans are glycans which contact HA polypeptides via the amino acid residues shown in FIG. 6 (right panel). In some embodiments, umbrella-topology glycans are glycans which are able to contact and/or specifically bind to the amino acid binding pocket shown in FIG. 6 (right panel).

In some embodiments, glycan structural topology is classified based on parameter θ defined as angle between $C_2$ of Sia, $C_1$ of Gal, and $C_1$ of GlcNAc. Values of θ>110° represent cone-like topology adopted by α2-3 and short α2-6 glycans. Values of θ<100° represent umbrella-like topology, such as topology adopted by long α2-6 glycans (FIG. 6).

In certain embodiments, the unique characteristic of HA interactions with umbrella-topology glycans and/or glycan decoys is the HA contact with a glycan comprising sialic acid (SA) and/or SA analogs at the non-reducing end. In some embodiments, chain length of the oligosaccharide is at least a trisaccharide (excluding the SA or SA analog). In some embodiments, a combination of the numbered residues shown in the right-hand panel of FIG. 6 is involved in contacts with umbrella-like topology.

In some embodiments, a sialic acid analog interacts with one or more of any highly conserved sialic acid-anchoring amino acid in HA, including, but not limited to, Tyr98, Ser136, Thr136, Trp153, Thr155, Val 155, Ser 155, His183, and Leu194. These interactions may include non-covalent interactions (e.g. ionic, van der Waals, hydrophobic, etc.) or covalent interactions with one or more of the above amino acids. Exemplary sialic acid analogs are shown in Table 2. Binding of HA to glycans containing some of these sialic acid analogs have been reported (Kelm et al., 1992 *Eur. J. Biochem.,* 205:146; incorporated herein by reference).

TABLE 2

Exemplary Sialic Acid Analogs

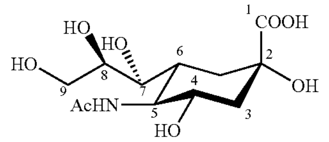

| Substituent Position | Substitutions |
|---|---|
| Naturally occurring sialic acid analogs | |
| 4 | OH, O-acetyl |
| 5 | N-acetyl, N-glycolyl, OH |
| 7 | OH, O-acetyl |
| 8 | OH, O-acetyl, O-sulfate, O-methyl |
| 9 | OH, O-acetyl, O-lactyl, O-phosphate |
| Common synthetic sialic acid analogs | |
| 1 | COO-Me, Bn, etc. |
| 2 | O-methyl, O-aryl, O-acyl, etc. |
| 4 | OH, O-acetyl, 4-oxo, etc. |
| 7 | OH, O-acyl (e.g., acetyl, benzoyl), O-methyl, 7-deoxy, 7-CHO (which means truncated side chain without 8 and 9), etc. |
| 8 | OH, O-methyl, O-acyl, 8-deoxy, 8-CHO (no 9), 8-$CH_2OH$ (no 9), etc. |
| 9 | OH, O-acyl (alkyl, aryl), O-ether (alkyl, aryl), SH, $NH_2$, N-amide (alkyl, aryl), Halogenate (Cl, Br, I), 9-carboxy, etc. |

In some embodiments, umbrella-topology glycans are glycans that are preferentially found on mammalian upper respiratory epithelial cells. In some embodiments, umbrella-topology glycans are glycans that are preferentially found on human upper respiratory epithelial cells. In some embodiments, umbrella-topology glycans are glycans that are about 2-fold, about 3-fold, about 4-fold, about 5-fold, about 10-fold, about 20-fold, about 50-fold, or greater than about 50-fold more likely to be found on human upper respiratory epithelial cells than on other cells.

In certain embodiments, structural features of umbrella-like topology glycans can be defined according to the following rules:

An oligosaccharide of the following form:

Neu5Acα2-6Sug1-Sug2-Sug3-Sug4 where:

1. Neu5Ac α2-6 is always or almost always at the non-reducing end;
2. Sug1:
   a. is a hexose (frequently Gal or Glc) or hexosamine (GlcNAc or GalNAc) in α or β configuration (frequently β);
   b. no sugars other than Neu5Acα2-6 should be attached to any of the non-reducing positions of Sug1; and/or
   c. non-sugar moieties such as sulfate, phosphate, guanidium, amine, N-acetyl, etc. can be attached to non-reducing positions (typically 6 position) of Sug1 to improve contacts with HA;
3. Sug2, Sug3, and/or Sug4:
   a. hexose (frequently Gal or Glc) or hexosamine (GlcNAc or GalNAc) in a or β configuration (frequently β); and/or
   b. sugars (such as Fuc) or non-sugar moieties such as sulfate, phosphate, guanidium, amine, N-acetyl, etc. can be attached to non-reducing positions of Sug2, Sug3, and/or Sug4;
4. Linkage between any two sugars in the oligosaccharide apart from Neu5Acα2-6 linkage can be 1-2, 1-3, 1-4, and/or 1-6 (typically 1-3 or 1-4); and/or
5. Structure without Sug4 such as 6'SLN attached to O-linked Core GalNAc (Neu5Acα2-6Galβ1-4GlcNAc) 131-3/6 (GalNAcα-O-Ser)

6'SLN O-Linked Core could potentially satisfy structural and HA contact constraints (FIG. 6) of umbrella-like topology glycan decoy.

In some embodiments, an umbrella-topology glycan has the structural form:

Neu5Acα2-6Sug1-Sug2-Sug3 where:

(a) Neu5Ac α2-6 is typically (but not essentially) at the non-reducing end;

(b) Sug1:

(i) is a hexose (frequently Gal or Glc) or hexosamine (GlcNAc or GalNAc) in α or β configuration (frequently β- for N- and O-linked extension and α- in the case of GalNAcα- that is O-linked to glycoprotein);

(ii) no sugars other than Neu5Acα2-6 are attached to any of the non-reducing positions of Sug1 (except when Sug1 is GalNAcα- that is O-linked to the glycoprotein); and/or (iii) non-sugar moieties such as sulfate, phosphate, guanidium, amine, N-acetyl, etc. can be attached to non-reducing positions (typically 6 position) of Sug1 (e.g., to improve contacts with HA);

(c) Sug2 and/or Sug3 is/are:

(i) hexose (frequently Gal or Glc) or hexosamine (GlcNAc or GalNAc) in a or β configuration (frequently β); and/or (ii) sugars (such as Fuc) or non-sugar moieties such as sulfate, phosphate, guanidium, amine, N-acetyl, etc. can be attached to non-reducing positions of Sug2, Sug3, and/or Sug4;

(d) Linkage between any two sugars in the oligosaccharide apart from Neu5Acα2-6 linkage can be 1-2, 1-3, 1-4, and/or 1-6 (typically 1-3 or 1-4); and/or (e) Structure where Neu5Acα2-6 is linked GalNAcα that is O-linked to the glycoprotein and additional sugars are linked to the non-reducing end of GalNAcα for example (i) Neu5Acα2-6(Neu5Acα2-3Galβ1-3)GalNAcα-

(ii) Neu5Acα2-6(Galβ1-3)GalNAcα

Examples of oligosaccharide motifs commonly found in physiological N-linked, O-linked glycans and glycolipids that comprise the structural features described above are shown in FIG. 9. The umbrella-topology glycan moieties presented in FIG. 9 is exemplary and is not comprehensive. Umbrella-topology glycan moieties can be any glycan moiety consistent with any or all of the characteristics of umbrella-topology glycan moieties described herein.

Figure 17C:
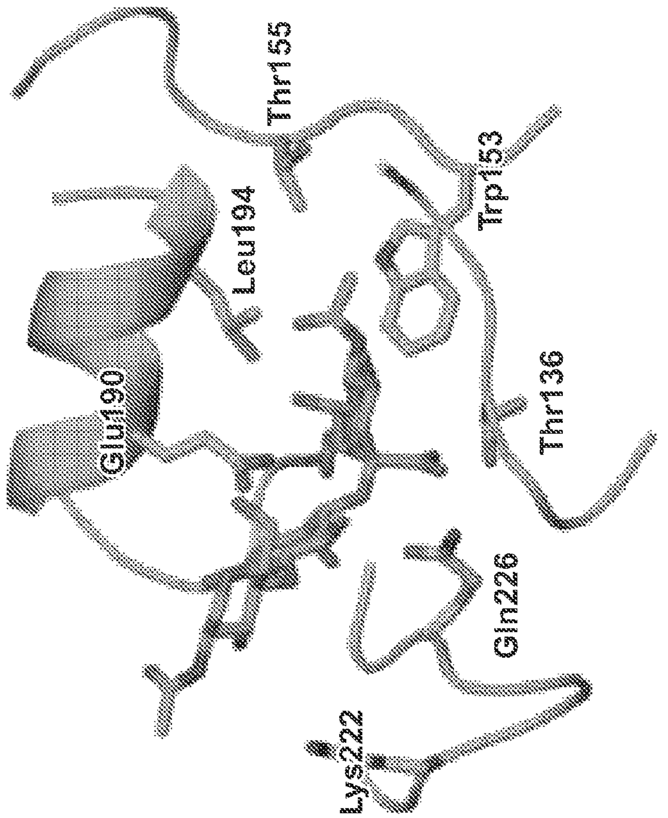
FIG. 17: Molecular interactions of SC18, NY18, and A V18 HAs with α2-3 and α2-6. The glycan binding site on HA is shown with amino acids involved in glycan binding, including the highly conserved Neu5Ac anchors (Thr136, Trp153, Thr155, and Leu194). Tyr95 and His183 are not shown for clarity. Amino acid positions are numbered based on H1N1 HA. (A) Shown is the interaction of the SC18 HA with long α2-6 in the umbrella-like topology. Lys222, Asp225, and Gln226 provide contacts with the base region, and Asp190, Gln192, and Ser193 provide contacts with the extension region. (B) Interaction of NY18 HA with long α2-6 shows the loss of contact of Asp225 with the base region (as observed in the case of SC18 HA in (A)). (C) Interaction of AV18 HA with α2-3 in cone-like topology shows that HA interactions with cone-like topology involve contacts only with the Neu5Ac and Gal sugars at the base, in contrast to that of the umbrella-like topology of long α2-6. Glu190 and Gln226 in AV18 are positioned to provide optimal contacts with these sugars. The side chain conformation of Glu190 in AV18 was assigned based on that of Glu190 in APR34HA-α2-3 co-crystal structure. (D) Shown are the differences in the key amino acid positions between SC18, NY18 and AV18 HAs, comparing them with the AST30 and APR34HAs.
Figure 17A:
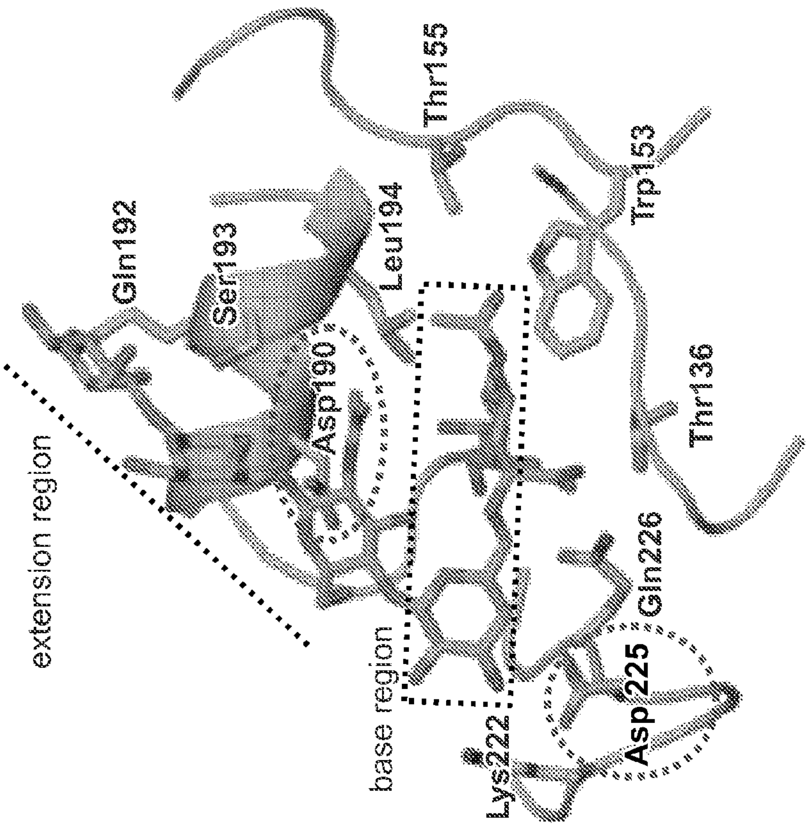
Figures 17B, 17D:
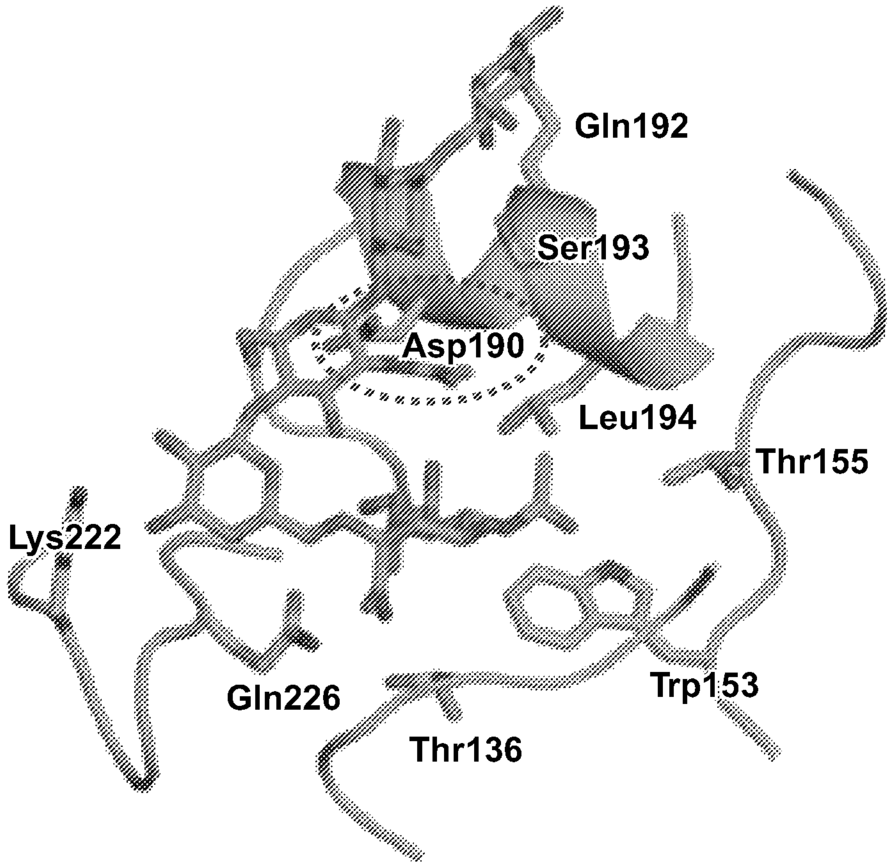

In some embodiments, glycan decoys may include the entire complex physiological N-linked, O-linked glycans (and glycoproteins) and glycolipids that comprise the above structural features. In some embodiments, three-dimensional structural topology of a decoy is classified using a parameter θ shown in FIG. 10. In some embodiments, residue positions of the glycan binding site of HA that interacts with an umbrella-like topology glycan decoy are shown in FIGS. 6 and 17. For example, in certain embodiments, an umbrella-like topology glycan is or comprises of any substance that is capable of interacting with HA amino acids in the 130-loop region (positions 130-139), 140-loop region (positions 140-146), 150-loop region (positions 153-160), 190-loop-helix region (positions 183-196) and the 220-loop region (positions 219-228). For example, in certain embodiments, an umbrella-topology glycan is or comprises any substance that is capable of interacting with HA amino acids 131, 133, 136, 137, 143, 144, 145, 153, 155, 156, 159, 186, 187, 189, 190, 192, 193, 194, 196, 222, 225, 226, 228, and/or combinations thereof. In certain embodiments, an umbrella-topology glycan is or comprises any substance that is capable of interacting with HA amino acids 156, 159, 189, 192, 193, 196, and/or combinations thereof. In certain embodiments, an umbrella-topology glycan is or comprises any substance that is capable of interacting with HA amino acids 186, 187, 189, 190, and/or combinations thereof. In certain embodiments, an umbrella-topology glycan is or comprises any substance that is capable of interacting with HA amino acids 137, 145, 190, 226, 228, and/or combinations thereof. In certain embodiments, an umbrella-topology glycan is or comprises any substance that is capable of interacting with HA amino acids 190, 222, 225, 226, and/or combinations thereof. In certain embodiments, an umbrella-topology glycan is or comprises any substance that is capable of interacting with HA amino acids 136, 153, 155, 194, and combinations thereof. In certain embodiments, an umbrella-topology glycan is or comprises any substance that is capable of interacting with HA amino acids 190 and 226. In certain embodiments, an umbrella-topology glycan is or comprises any substance that is capable of interacting with HA amino acids 222, 225, and 226. In certain embodiments, an umbrella-topology glycan is or comprises any substance that is capable of interacting with HA amino acids 190, 192, 193, and 225. In certain embodiments, an umbrella-topology glycan is or comprises any substance that is capable of interacting with HA amino acids 186, 193, and 222. Note that amino acid positions stated above are based on H3 HA numbering.

Analysis of HA-glycan co-crystals reveals that the position of Neu5Ac relative to the HA binding site is almost invariant. Contacts with Neu5Ac involve highly conserved residues such as Y98, S/T136, W153, H183 and L/I194. Contacts with other sugars involve different residues, depending on whether the sugar linkage is α2-3 or α2-6 and whether the glycan topology is cone or umbrella. For example, in the cone topology, the primary contacts are with Neu5Ac and with Gal sugars. E190 and Q226 play particularly important roles in this binding. Other positions (e.g., 137, 145, 186, 187, 193, 222) can participate in binding to cone structures. In some cases, different residues can make different contacts with different glycan structures. The type of amino acid in these positions can influence ability of an HA polypeptide to bind to receptors with different modification and/or branching patterns in the glycan structures. In the umbrella topology, contacts are made with sugars beyond Neu5Ac and Gal. In some embodiments, amino acid residues at one or more positions (e.g., 137, 145, 156, 159, 186, 187, 189, 190, 192, 193, 196, 222, 225, 226) can participate in binding to umbrella structures. In some cases, different residues can make different contacts with different glycan structures. The type of amino acid in these positions can influence ability of an HA polypeptide to bind to receptors with different modification and/or branching patterns in the glycan structures. In some embodiments, a D residue at position 190 and/or a D residue at position 225 contribute(s) to binding to umbrella topologies.

In some embodiments, umbrella-topology glycans are any substances that comprise an umbrella-topology glycan moiety. In some embodiments, an umbrella-topology glycan is or comprises an umbrella-topology glycan moiety (i.e. an umbrella-topology glycan moiety that is not associated with any other moiety). In some embodiments, the carrier moiety may comprise any type of substance, including, but not limited to, a peptide, polypeptide, protein, carbohydrate, lipid, nucleic acid, small molecule, cell, virus, etc. In some embodiments the ratio of umbrella glycan to carrier molecule (on a weight or number basis) is greater than the ratio of glycan to protein in a human HA receptor molecule, e.g., a naturally occurring human HA receptor which carries an umbrella topology glycan. For example, a carrier molecule can have more umbrella glycans than a naturally occurring HA receptor molecule, e.g., a naturally occurring human HA receptor which carries an umbrella topology glycan. In some embodiments the ratio of umbrella glycan to carrier molecule (on a weight or number basis) is less than the ratio of glycan to protein in a human HA receptor molecule, e.g., a naturally occurring human HA receptor which carries an umbrella topology glycan. In an embodiment the carrier molecule presents more than one umbrella glycan and the glycans, as presented, are spaced apart from one another similarly as is found on naturally occurring human HA receptors which carry an umbrella topology glycan. In other embodiments the glycans are more, or less, spaced apart, as compared to their presentation on naturally occurring human HA receptors which carry an umbrella topology glycan. In a preferred embodiment the decoy includes an umbrella glycan on an HA polypeptide that differs from a naturally occurring human HA by at least one amino acid residue.

In some embodiments, umbrella-topology glycans comprise a peptide or polypeptide moiety and at least one umbrella-topology glycan moiety. In certain embodiments, umbrella-topology glycans comprise an HA receptor and at least one umbrella-topology glycan moiety. In certain embodiments, umbrella-topology glycans comprise a characteristic portion of an HA receptor and at least one umbrella-topology glycan moiety. In certain embodiments, umbrella-topology glycans comprise an HA receptor derived and/or obtained from human upper respiratory tissues (e.g. trachea and/or bronchus) and at least one umbrella-topology glycan moiety. In certain embodiments, umbrella-topology glycans comprise a characteristic portion of an HA receptor derived and/or obtained from human upper respiratory tissues (e.g. trachea and/or bronchus) and at least one umbrella-topology glycan moiety.

Umbrella-Topology Glycan Decoys

In some embodiments, an "umbrella-topology glycan decoy" refers to any substance that shares sufficient structural similarity with umbrella-topology glycans to bind to HA polypeptides. In some embodiments, an "umbrella-topology glycan decoy" refers to any substance that is able to compete away the interaction between HA and umbrella-topology glycans. In some embodiments, an "umbrella-like topology glycan decoy" can be any substance that is able to contact any or all of the residues (including any combination of individual residues) in the glycan binding site of HA that are capable of interacting with umbrella-topology glycans (see, e.g., FIGS. 6 and 9).

In some embodiments, an umbrella-topology glycan decoy is or comprises an umbrella-topology glycan mimic. In some embodiments, an umbrella-topology glycan mimic is or comprises a glycan. In some embodiments, an umbrella-topology glycan decoy is or comprises an umbrella-topology glycan moiety. In some embodiments, an umbrella-topology glycan decoy is or comprises an isolated umbrella-topology glycan moiety (i.e. an umbrella-topology glycan moiety that is not associated with any other moiety). In some embodiments, an umbrella-topology glycan moiety has a structure that is or is substantially similar to any of the structures shown in FIGS. 6 and 9.

Figure 10C:
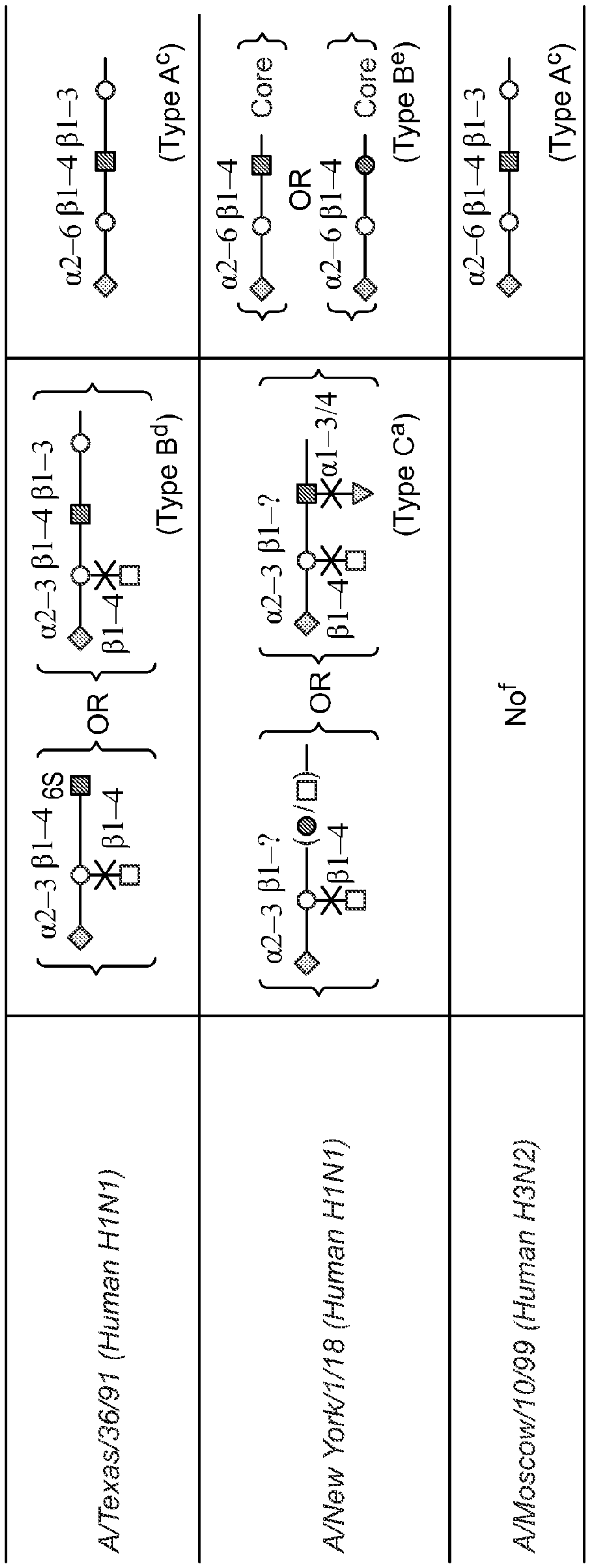
FIG. 10: Data mining analysis of HA binding glycan array data. Shown at the top are examples of types glycan features (e.g. pairs, triplets, quadruplets, etc.) abstracted from a representative complex glycan structure. A comprehensive set of these features was abstracted from glycans in the glycan array. Shown at the bottom is the graphical representation of the complex classifier rules for each HA analyzed using the glycan array. α2-3 Type A represents broadest specificity, whereas Type B and Type C classifiers represent constraints imposed by structural variations around the trisaccharide α2-3 motif. α2-6 Type A represents binding to long α2-6 (linear or branched), whereas Type B represents binding to short α2-6 (linear or branched). "Core" corresponds to either the spacer attached to the reducing end or the trimannosyl core in case of the single α2-6 biantennary glycan on the array. [a]: Binding signals observed for fucosylated α2-3 motif only if it has GlcNAc[6S]; [b]: Binding signals observed only for 6'-sialyl lactose; [c]: Binding signals also observed for short 6'-sialyl lactosamine (Type B); [d]: Binding signals are significantly lower than α2-3 Type B of H5N1 double mutant; [e]: Binding signals observed only for short α2-6 with GlcNAc [6S]; f: Binding signals just above background observed for α2-3 motif with GlcNAc[6S]; *: The origin of A/Vietnam/1203/04 is avian but this viral strain was isolated from an infected human. Keys: 6-O sulfated GlcNAc; Glc or GalNAc; Non-fucosylated GlcNAc; Gal without GalNAcβ1-4Gal linkage.

In some embodiments, glycan decoys may include entire complex physiological N-linked and/or O-linked glycans, glycoproteins, and/or glycolipids that are defined by any or all of the structural features described in the section, above, entitled "*Umbrella-Topology Glycans*." In some embodiments, three-dimensional structural topology of a decoy is classified using a parameter θ shown in FIG. 10. In some embodiments, residue positions of the glycan binding site of HA that interacts with an umbrella-like topology glycan decoy are shown in FIGS. 6 and 17.

In some embodiments, an umbrella-topology glycan decoy is or comprises a small molecule. In some embodiments, an umbrella-topology glycan decoy is or comprises a peptide (e.g., peptide, polypeptide, protein, etc.). In some embodiments, an umbrella-topology glycan decoy is or comprises a lipid. In some embodiments, an umbrella-topology glycan decoy is or comprises a nucleic acid.

An umbrella-topology glycan decoy can be any substance that is capable of interacting with HA amino acid residues that are involved in or are capable of binding to umbrella-topology glycans. In certain embodiments, an umbrella-topology glycan decoy is or comprises any substance that is capable of interacting with HA amino acids 136, 137, 145, 153, 155, 156, 159, 186, 187, 189, 190, 192, 193, 194, 196, 222, 225, 226, 228, and/or combinations thereof. In certain embodiments, an umbrella-topology glycan decoy is or comprises any substance that is capable of interacting with HA amino acids 156, 159, 189, 192, 193, 196, and/or combinations thereof. In certain embodiments, an umbrella-topology glycan decoy is or comprises any substance that is capable of interacting with HA amino acids 186, 187, 189, 190, and/or combinations thereof. In certain embodiments, an umbrella-topology glycan decoy is or comprises any substance that is capable of interacting with HA amino acids 137, 145, 190, 226, 228, and/or combinations thereof. In certain embodiments, an umbrella-topology glycan decoy is or comprises any substance that is capable of interacting with HA amino acids 190, 222, 225, 226, and/or combinations thereof. In certain embodiments, an umbrella-topology glycan is or comprises any substance that is capable of interacting with HA amino acids 136, 153, 155, 194, and combinations thereof. In certain embodiments, an umbrella-topology glycan decoy is or comprises any substance that is capable of interacting with HA amino acids 190 and 226. In certain embodiments, an umbrella-topology glycan decoy is or comprises any substance that is capable of interacting with HA amino acids 222, 225, and 226. In certain embodiments, an umbrella-topology glycan decoy is or comprises any substance that is capable of interacting with HA amino acids 190, 192, 193, and 225. In certain embodiments, an umbrella-topology glycan decoy is or comprises any substance that is capable of interacting with HA amino acids 186, 193, and 222. Note that amino acid positions stated above are based on H3 HA numbering.

In some embodiments, an umbrella-topology glycan decoy is or comprises an umbrella-topology glycan mimic (e.g. glycan, peptide, small molecule, etc.) that is physically associated with a carrier moiety. In some embodiments, a carrier will carry a plurality of individual glycan mimics. Without wishing to be bound by any particular theory, the present inventors propose that multiple points of contact between glycans and their binding partners (e.g., HA polypeptides) may facilitate, or even be required, for specific and/or stable interaction.

In some embodiments, the umbrella-topology glycan mimic is covalently associated with the carrier. In some embodiments, the covalent association is direct (e.g. the umbrella-topology glycan mimic is directly attached to the carrier). In some embodiments, the covalent association is indirect (e.g. mediated by a linker). In certain embodiments, the linker is a cleavable linker (e.g. a linker that can be cleaved by enzymatic activity, chemical cleavage, heat-induced cleavage, pH-induced cleavage, light-induced cleavage, etc.). In certain embodiments, the linker is a non-cleavable linker. In certain embodiments, the linker comprises proteins or peptides, nucleic acids, carbohydrates, lipids, small molecules, etc.

In some embodiments, the umbrella-topology glycan mimic is non-covalently associated with the carrier. In some embodiments, a non-covalent interaction includes electrostatic interactions, affinity interactions, metal coordination, physical adsorption, host-guest interactions, hydrophobic interactions, pi-stacking interactions, hydrogen bonding interactions, van der Waals interactions, magnetic interactions, dipole-dipole interactions, and combinations thereof.

In some embodiments, the umbrella-topology glycan mimic is associated with the surface of the carrier. In some embodiments, the umbrella-topology glycan mimic is associated with the interior surface of the carrier (e.g. the interior surface of a particle, cell, etc.). In some embodiments, the umbrella-topology glycan mimic is encapsulated within the carrier (e.g. within the interior of a particle, in the cytoplasm of a cell, within a polymeric matrix, etc.).

In some embodiments, the carrier moiety may comprise any type of substance, including, but not limited to, a peptide (including a polypeptide, a protein, an antibody, etc.), carbohydrate (e.g., mono-, di-, or polysaccharide, glycan, etc.), lipid, nucleic acid, polymer, small molecule, dendrimer (e.g., starburst dendrimers containing umbrella-topology glycans), cell, virus, particle (e.g. microparticle, nanoparticle, picoparticle, polymeric particle, quantum dot, metal particle, bone-derived particle, ceramic-derived particle, liposome, micelle, etc.), etc.

In certain embodiments, umbrella-topology glycan decoys comprise a peptide or polypeptide carrier and at least one umbrella-topology glycan moiety. In certain embodiments, umbrella-topology glycan decoys comprise an HA receptor and at least one umbrella-topology glycan moiety. In certain embodiments, umbrella-topology glycan decoys comprise a characteristic portion of an HA receptor and at least one umbrella-topology glycan moiety. In certain embodiments, umbrella-topology glycan decoys comprise an HA receptor derived and/or obtained from mammalian (e.g., human) upper respiratory tissues (e.g. trachea and/or bronchus) and at least one umbrella-topology glycan moiety. In certain embodiments, umbrella-topology glycan decoys comprise a fragment (e.g., a characteristic portion) of an HA receptor derived and/or obtained from human upper respiratory tissues (e.g. trachea and/or bronchus) and at least one umbrella-topology glycan moiety. In some embodiments, HA receptor fragments are obtained by protease treatment of membrane glycoproteins from upper respiratory cells of humans or other animals (e.g., ferrets). Examples of upper respiratory cells include ciliated tracheal epithelial, bronchial epithelial, goblet cells from tracheal or bronchial regions, non-ciliated epithelial cells, and combinations thereof.

In some embodiments, a peptide carrier moiety may comprise at least about 5 amino acids, at least about 10 amino acids, at least about 20 amino acids, at least about 50 amino acids, at least about 100 amino acids, at least about 200 amino acids, or more amino acids. In certain embodiments, peptides are proteins having fewer than about 100 amino acids. In some embodiments, peptides range from about 5 to about 100, from about 5 to about 50, from about 5 to about 40, from about 5 to about 35, from about 5 to about 30, from about 5 to about 25, or from about 20 to about 25 amino acids in length. In some embodiments, a peptide sequence can be based on the sequence of a protein. In some embodiments, a peptide sequence can be a random arrangement of amino acids. Peptides from panels of peptides comprising random sequences and/or sequences which have been varied consistently to provide a maximally diverse panel of peptides may be used.

In certain embodiments, umbrella-topology glycan decoys comprise a glycopeptide (e.g., HA receptor, mucin, fetuin, IgG, etc) carrier that then carries N- or O-linked umbrella-topology glycans. In certain embodiments, umbrella-topology glycan decoys comprise a neo-glycoprotein carrier in which glycans are linked to a polypeptide backbone via reductive amination to a core polypeptide (e.g., bovine serum albumin).

In some embodiments, umbrella-topology glycan decoys comprise carriers with artificial polypeptide backbones such as, for example, poly-L-glutamic acid. In some specific embodiments, one or more (and in some embodiments each) glutamic acid may have an umbrella topology glycan conjugated via the alpha carboxyl group.

In certain embodiments, umbrella-topology glycan decoys comprise a nucleic acid carrier and at least one umbrella-topology glycan moiety. Nucleic acid carriers include, but are not limited to, viral fragments, including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; functional nucleic acids (e.g. RNAi-inducing entities, ribozymes, etc.), etc.

In certain embodiments, umbrella-topology glycan decoys comprise a small molecule carrier and at least one umbrella-topology glycan moiety. In general, a "small molecule" is understood in the art to be an organic molecule that is less than about 5 kilodaltons (Kd) in size. In some embodiments, the small molecule is less than about 4 Kd, 3 Kd, about 2 Kd, or about 1 Kd. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, small molecules are non-polymeric.

In certain embodiments, umbrella-topology glycan decoys comprise a lipid carrier and at least one umbrella-topology glycan moiety. In some embodiments, exemplary lipids that may be used in accordance with the present invention include, but are not limited to, oils, fatty acids, saturated fatty acid, unsaturated fatty acids, essential fatty acids, cis fatty acids, trans fatty acids, glycerides, monoglycerides, diglycerides, triglycerides, hormones, steroids (e.g., cholesterol, bile acids), vitamins (e.g. vitamin E), phospholipids, sphingolipids, and lipoproteins.

In some embodiments, a lipid may comprise one or more fatty acid groups or salts thereof. In some embodiments, the fatty acid group may comprise digestible, long chain (e.g., $C_8$-$C_{50}$), substituted or unsubstituted hydrocarbons. In some embodiments, the fatty acid group may be a $C_{10}$-$C_{20}$ fatty acid or salt thereof. In some embodiments, the fatty acid group may be a $C_{15}$-$C_{20}$ fatty acid or salt thereof. In some embodiments, the fatty acid group may be a $C_{15}$-$C_{25}$ fatty acid or salt thereof. In some embodiments, the fatty acid group may be unsaturated. In some embodiments, the fatty acid group may be monounsaturated. In some embodiments, the fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, the fatty acid group may be one or more of butyric, caproic, caprylic, capric, lauric, myristic, palmitic, stearic, arachidic, behenic, or lignoceric acid. In some embodiments, the fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

In certain embodiments, umbrella-topology glycan decoys comprise a carbohydrate carrier and at least one umbrella-topology glycan moiety. In some embodiments, a carbohydrate may be natural or synthetic. A carbohydrate may also be a derivatized natural carbohydrate. In certain embodiments, a carbohydrate may be a simple or complex sugar. In certain embodiments, a carbohydrate is a monosaccharide, including but not limited to glucose, fructose, galactose, and ribose. In certain embodiments, a carbohydrate is a disaccharide, including but not limited to lactose, sucrose, maltose, trehalose, and cellobiose. In certain embodiments, a carbohydrate is a polysaccharide, including but not limited to cellulose, microcrystalline cellulose, hydroxypropyl methylcellulose (HPMC), methylcellulose (MC), dextrose, dextran, glycogen, xanthan gum, gellan gum, starch, and pullulan. In certain embodiments, a carbohydrate is a sugar alcohol, including but not limited to mannitol, sorbitol, xylitol, erythritol, malitol, and lactitol.

In certain embodiments, umbrella-topology glycan decoys comprise a particle carrier and at least one umbrella-topology glycan moiety. In some embodiments, carriers may be particles, including, but not limited to, microparticles, nanoparticles, picoparticles, polymeric particles, quantum dots, metal particles, bone-derived particles, ceramic-derived particles, liposomes, micelles, etc. In some embodiments, particles are biodegradable and biocompatible. In general, a biocompatible substance is not toxic to cells. In some embodiments, a substance is considered to be biocompatible if its addition to cells results in less than a certain threshold of cell death (e.g., less than 75%, less than 50%, less than 25%, or less than 10% cell death). In some embodiments, a substance is considered to be biocompatible if its addition to cells does not induce adverse effects. In general, a biodegradable substance is one that undergoes breakdown under physiological conditions over the course of a therapeutically relevant time period (e.g., weeks, months, or years). In some embodiments, a biodegradable substance is a substance that can be broken down by cellular machinery. In some embodiments, a biodegradable substance is a substance that can be broken down by chemical processes.

In general, a particle in accordance with the present invention is any entity having a greatest dimension (e.g. diameter) of less than 500 microns (μm). In some embodiments, inventive particles have a greatest dimension of less than 100 μm. In some embodiments, inventive particles have a greatest dimension of less than 10 μm. In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 300 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 5 nm and 1 μm. In some embodiments, inventive particles have a greatest dimension ranging between 25 nm and 200 nm.

In certain embodiments, particles can have a mean geometric diameter between about 1 μm and about 500 μm, between about 1 μm and about 200 μm, between about 1 μm and about 106 μm, between about 1 μm and about 100 μm, between about 1 μm and about 50 μm, between about 1 μm and about 53 μm, between about 5 μm and about 53 μm, between about 5 μm and about 50 μm, between about 53 μm and about 106 μm, between about 1 μm and about 5 μm, between about 1 μm and about 20 μm, between about 20 μm and about 53 μm, between about 53 μm and about 75 μm, between about 75 μm and about 106 μm, or about 30 μm.

In certain embodiments, particles can have a geometric size distribution between about 1 μm and about 250 μm, between about 1 μm and about 100 μm, between about 1 μm and about 50 μm, between about 5 μm and about 200 μm, between about 10 μm and about 500 μm, between about 10 μm and about 250 μm, between about 10 μm and about 100 μm, between about 100 μm and about 200 μm, between about 100 μm and about 150 μm, between about 53 μm and about 106 μm, between about 1 μm and about 5 μm, between about 1 μm and about 20 μm, between about 20 μm and about 53 μm, between about 53 μm and about 75 μm, or between about 75 μm and about 106 μm.

Aerodynamic diameter is a physical property of a particle in a viscous fluid such as air. In general, particles have irregular shapes with actual geometric diameters that can be difficult to measure. Aerodynamic diameter is an expression of a particle's aerodynamic behavior as if it were a perfect sphere with unit-density and diameter equal to the aerodynamic diameter. Such a model has the same terminal settling velocity. Aerodynamic diameter can be applied to particulate pollutants and inhaled drugs to predict where in the respiratory tract such particles will deposit. In some embodiments, drug particles for pulmonary delivery can be characterized by aerodynamic diameter instead of or in addition to geometric diameter. The velocity at which drug settles is proportional to the aerodynamic diameter, $d_a$:

$$d_a=(\rho/X)^{1/2}\times d_g$$

where ρ=density and X=shape factor. For spherical species, X=1. Aerodynamic diameter is the diameter of a sphere of unit density (1 g/ml) that has the same gravitational settling velocity as the particle in question. Aerodynamic diameter is given as:

$$dpa=dps\times sqrt(\text{density of particle})$$

where dps=Stoke's diameter. In certain embodiments, particles can have mean aerodynamic diameters between about 1 μm and about 5 μm, between about 1 μm and about 35 μm, between about 5 μm and about 35 μm, between about 1 μm and about 35 μm, between about 35 μm and about 70 μm, between about 1 μm and about 75 μm, between about 35 μm and about 75 μm, between about 1 μm and about 50 μm, or about 5 μm.

Bulk density a property of particulate materials. In general, bulk density is used to refer to the mass of a population of particles divided by the volume they occupy. Typically, the volume includes the space between particles as well as the space inside the pores of individual particles. Bulk density is not an intrinsic property of a material, but can change depending on how the material is handled. For example, grain poured in cylinder will have a particular bulk density; if the cylinder is disturbed, grain particles will move and settle closer together, resulting in a higher bulk density. For this reason, the bulk density of powders is usually reported both as "freely settled" and "tapped" density, where the tapped density refers to the bulk density of the powder after a compaction process. Typically, the compactation process may involve vibration of the container which holds the population of particles. In certain embodiments, particles can have tap density ranges between about 0.01 g/cm$^3$ and about 0.4 g/cm$^3$, greater than 0.4 g/cm$^3$, or less than 0.4 g/cm$^3$.

In some embodiments, particles have a diameter of approximately 1000 nm. In some embodiments, particles have a diameter of approximately 750 nm. In some embodiments, particles have a diameter of approximately 500 nm. In some embodiments, particles have a diameter of approximately 450 nm. In some embodiments, particles have a diameter of approximately 400 nm. In some embodiments, particles have a diameter of approximately 350 nm. In some embodiments, particles have a diameter of approximately 300 nm. In some embodiments, particles have a diameter of approximately 275 nm. In some embodiments, particles have a diameter of approximately 250 nm. In some embodiments, particles have a diameter of approximately 225 nm. In some embodiments, particles have a diameter of approximately 200 nm. In some embodiments, particles have a diameter of approximately 175 nm. In some embodiments, particles have a diameter of approximately 150 nm. In some embodiments, particles have a diameter of approximately 125 nm. In some embodiments, particles have a diameter of approximately 100 nm. In some embodiments, particles have a diameter of approximately 75 nm. In some embodiments, particles have a diameter of approximately 50 nm. In some embodiments, particles have a diameter of approximately 25 nm.

In certain embodiments, particles are greater in size than the renal excretion limit (e.g. particles having diameters of greater than 6 nm). In specific embodiments, particles have diameters greater than 5 nm, greater than 10 nm, greater than 15 nm, greater than 20 nm, greater than 50 nm, greater than 100 nm, greater than 250 nm, greater than 500 nm, greater than 1000 nm, or larger. In certain embodiments, particles are small enough to avoid clearance of particles from the bloodstream by the liver (e.g. particles having diameters of less than 1000 nm). In specific embodiments, particles have diameters less than 1500 nm, less than 1000 nm, less than 750 nm, less than 500 nm, less than 250 nm, less than 100 nm, or smaller. In general, physiochemical features of particles, including particle size, can be selected to allow a particle to circulate longer in plasma by decreasing renal excretion and/or liver clearance. In some embodiments, particles have diameters ranging from 5 nm to 1500 nm, from 5 nm to 1000 nm, from 5 nm to 750 nm, from 5 nm to 500 nm, from 5 nm to 250 nm, or from 5 nm to 100 nm. In some embodiments, particles have diameters ranging from 10 nm to 1500 nm, from 15 nm to 1500 nm, from 20 nm to 1500 nm, from 50 nm to 1500 nm, from 100 nm to 1500 nm, from 250 nm to 1500 nm, from 500 nm to 1500 nm, or from 1000 nm to 1500 nm.

It is often desirable to use a population of particles that is relatively uniform in terms of size, shape, and/or composition so that each particle has similar properties. For example, at least 80%, at least 90%, or at least 95% of the particles may have a diameter or greatest dimension that falls within 5%, 10%, or 20% of the average diameter or greatest dimension. In some embodiments, a population of particles may be heterogeneous with respect to size, shape, and/or composition.

Zeta potential is a measurement of surface potential of a particle. In some embodiments, particles have a zeta potential ranging between −50 mV and +50 mV. In some embodiments, particles have a zeta potential ranging between −25 mV and +25 mV. In some embodiments, particles have a zeta potential ranging between −10 mV and +10 mV. In some embodiments, particles have a zeta potential ranging between −5 mV and +5 mV. In some embodiments, particles have a substantially negative zeta potential. In some embodiments, particles have a substantially positive zeta potential. In some embodiments, particles have a substantially neutral zeta potential (i.e. approximately 0 mV).

Particles can have a variety of different shapes including spheres, oblate spheroids, cylinders, ovals, ellipses, shells, cubes, cuboids, cones, pyramids, rods (e.g., cylinders or elongated structures having a square or rectangular cross-section), tetrapods (particles having four leg-like appendages), triangles, prisms, etc.

In some embodiments, particles are microparticles (e.g. microspheres). In general, a "microparticle" refers to any particle having a diameter of less than 1000 μm. In some embodiments, particles are nanoparticles (e.g. nanospheres). In general, a "nanoparticle" refers to any particle having a diameter of less than 1000 nm. In some embodiments, particles are picoparticles (e.g. picospheres). In general, a "picoparticle" refers to any particle having a diameter of less than 1 nm. In some embodiments, particles are liposomes. In some embodiments, particles are micelles.

Particles can be solid or hollow and can comprise one or more layers (e.g., nanoshells, nanorings, etc.). Particles may have a core/shell structure, wherein the core(s) and shell(s) can be made of different materials. Particles may comprise gradient or homogeneous alloys. Particles may be composite particles made of two or more materials, of which one, more than one, or all of the materials possesses magnetic properties, electrically detectable properties, and/or optically detectable properties.

In some embodiments, particles may optionally comprise one or more dispersion media, surfactants, release-retarding ingredients, or other pharmaceutically acceptable excipient. In some embodiments, particles may optionally comprise one or more plasticizers or additives.

In some specific embodiments, particular carriers utilized in umbrella-topology decoys of the present invention are selected from the group consisting of HA receptor fragments, mucins, fetuins, IgG, bovine serum albumin, gamma poly glutamic acid, polyacrylamide, chitosan, gold nanoparticles (i.e., functionalized with umbrella topology glycans), and combinations thereof.

In certain embodiments, umbrella-topology glycan decoys comprise a cell or virus carrier and at least one umbrella-topology glycan moiety. For example, an umbrella-topology glycan moiety may be associated with (e.g. covalently or non-covalently bound to) the surface of a cell or virus. In some embodiments, an umbrella-topology glycan moiety may be encapsulated within a cell or virus.

The present invention encompasses the recognition that agents that mimic such umbrella-topology glycans can act as decoys and compete interactions between HA polypeptides and their receptors. In some embodiments, glycan mimics compete with endogenous glycans for binding to HA polypeptides. In some embodiments, glycan mimics compete with endogenous umbrella-type glycans for binding to HA polypeptides. In some embodiments, glycan mimics compete with upper-respiratory glycans for binding to HA polypeptides. In some embodiments, glycan mimics compete with umbrella-topology upper-respiratory glycans for binding to HA polypeptides.

In some embodiments, glycan mimics bind to HA polypeptides, but do not compete with endogenous glycans for binding to HA polypeptides.

In some embodiments, umbrella-topology glycan decoys are characterized by a three-dimensional structure that is capable of binding to and/or associating with one or more HA polypeptides. In some embodiments, umbrella-topology glycan decoys comprise a multivalent arrangement of individual glycan moieties associated with a carrier. For example, a glycan decoy may comprise 2, 3, 4, 5, 10, 20, 50, 100, 200, 500, 1000, or more individual glycan moieties associated with a carrier (covalently or non-covalently, as described above) in an arrangement and/or orientation that allows the glycan decoy to bind to and/or associate with one or more HA polypeptides. In some embodiments, an umbrella-topology glycan decoy comprising a multivalent arrangement of individual glycan moieties resembles and/or mimics the HA polypeptide-binding site of a wild-type HA receptor. In some embodiments, an umbrella-topology glycan decoy comprising a multivalent arrangement of individual glycan moieties resembles and/or mimics the HA polypeptide-binding site of a wild-type HA receptor in its natural context (e.g. in various lung tissues).

HA polypeptides are described in further detail below, in the section entitled "Hemagglutinin (HA)."

Hemagglutinin (HA)

Influenza viruses are RNA viruses which are characterized by a lipid membrane envelope containing two glycoproteins, hemagglutinin (HA) and neuraminidase (NA), embedded in the membrane of the virus particular. There are 16 known HA subtypes and 9 NA subtypes, and different influenza strains are named based on the number of the strain's HA and NA subtypes. Based on comparisons of amino acid sequence identity and of crystal structures, the HA subtypes have been divided into two main groups and four smaller clades. The different HA subtypes do not necessarily share strong amino acid sequence identity, but the overall 3D structures of the different HA subtypes are similar to one another, with several subtle differences that can be used for classification purposes. For example, the particular orientation of the membrane-distal subdomains in relation to a central α-helix is one structural characteristic commonly used to determine HA subtype (Russell et al., 2004, Virology, 325:287; incorporated herein by reference).

HA exists in the membrane as a homotrimer of one of 16 subtypes, termed H1-H16. Only three of these subtypes (H1, H2, and H3) have thus far become adapted for human infection. One reported characteristic of HAs that have adapted to infect humans (e.g., of HAs from the pandemic H1N1 (1918) and H3N2 (1967-68) influenza subtypes) is their ability to preferentially bind to α2-6 sialylated glycans in comparison with their avian progenitors that preferentially bind to α2-3 sialylated glycans (Skehel and Wiley, 2000, *Ann. Rev. Biochem.,* 69:531; Rogers and Paulson, 1983, *Virology,* 127:361; Rogers et al., 1983, *Nature,* 304:76; Sauter et al., 1992, *Biochemistry,* 31:9609; Connor et al., 1994, *Virology,* 205:17; and Tumpey et al., 2005, *Science,* 310:77; all of which are incorporated herein by reference). The present invention, however, encompasses the recognition that ability to infect human hosts correlates less with binding to glycans of a particular linkage, and more with binding to glycans of a particular topology. Thus, the present invention demonstrates that HAs that mediate infection of humans bind to umbrella-topology glycans, often showing preference for umbrella-topology glycans over cone-topology glycans (even though cone-topology glycans may be α2-6 sialylated glycans).

Several crystal structures of HAs from H1 (human and swine), H3 (avian) and H5 (avian) subtypes bound to sialylated oligosaccharides (of both α2-3 and α2-6 linkages) are available and provide molecular insights into the specific amino acids that are involved in distinct interactions of the HAs with these glycans (Eisen et al., 1997, Virology, 232:19; Ha et al., 2001, *Proc. Natl. Acad. Sci., USA,* 98:11181; Ha et al., 2003, Virology, 309:209; Gamblin et al., 2004, *Science,* 303:1838*; Stevens et al.,* 2004, *Science,* 303:1866*; Russell et al.,* 2006, *Glycoconj. J.,* 23:85; and Stevens et al., 2006, *Science,* 312:404; all of which are incorporated herein by reference).

For example, the crystal structures of H5 (A/duck/Singapore/3/97) alone or bound to an α2-3 or an α2-6 sialylated oligosaccharide identifies certain amino acids that interact directly with bound glycans, and also amino acids that are one or more degree of separation removed (Stevens et al., 2001, *Proc. Natl. Acad. Sci., USA,* 98:11181; incorporated herein by reference). In some cases, conformation of these residues is different in bound versus unbound states. For instance, Glu190, Lys193, and Gln226 all participate in direct-binding interactions and have different conformations in the bound versus the unbound state. The conformation of Asn186, which is proximal to Glu190, is also significantly different in the bound versus the unbound state.

Binding Characteristics of HA Polypeptides

In certain embodiments, HA polypeptides bind to umbrella-topology glycans with high affinity. In certain embodiments, HA polypeptides bind to a plurality of different umbrella-topology glycans, often with high affinity and/or specificity. In accordance with the present invention, HA polypeptides include peptides that are able to bind to receptors in human upper respiratory epithelial tissues.

In some embodiments, HA polypeptides bind to umbrella-topology glycans (e.g., long α2-6 sialylated glycans such as, for example, Neu5Acα2-6Galβ1-4GlcNAcβ1-3Galβ1-4GlcNAc-) with high affinity. For example, in some embodiments, HA polypeptides bind to umbrella-topology glycans with an affinity comparable to that observed for a wild type HA that mediates infection of a humans (e.g., H1N1 HA or H3N2 HA). In some embodiments, HA polypeptides bind to umbrella-topology glycans with an affinity that is at least 25%, 30%, 35%, 40%, 45%, 50%, 55%, 60%, 65%, 70%, 75%, 80%, 85%, 90%, 95%, 96%, 97%, 98%, 99%, or 100% of that observed under comparable conditions for a wild type HA that mediates infection of humans. In some embodiments, HA polypeptides bind to umbrella-topology glycans with an affinity that is greater than that observed under comparable conditions for a wild type HA that mediates infection of humans.

In certain embodiments, binding affinity of HA polypeptides is assessed over a range of concentrations. Such a strategy provides significantly more information, particularly in multivalent binding assays, than do single-concentration analyses. In some embodiments, for example, binding affinities of HA polypeptides are assessed over concentrations ranging over at least 2, 3, 4, 5, 6, 7, 8, 9, 10 or more fold.

In certain embodiments, HA polypeptides show high affinity if they show a saturating signal in a multivalent glycan array binding assay such as those described herein. In some embodiments, HA polypeptides show high affinity if they show a signal above about 400000 or more (e.g., above about 500000, 600000, 700000, 800000, etc.) in such studies. In some embodiments, HA polypeptides show saturating binding to umbrella-topology glycans over a concentration range of at least 2 fold, 3 fold, 4 fold, 5 fold or more, and in some embodiments over a concentration range as large as 10 fold or more.

Furthermore, in some embodiments, HA polypeptides bind to umbrella-topology glycans more strongly than they bind to cone-topology glycans. In some embodiments, HA polypeptides show a relative affinity for umbrella-topology glycans versus cone-topology glycans that is about 10, 9, 8, 7, 6, 5, 4, 3, or 2.

In some embodiments, HA polypeptides bind to α2-6 sialylated glycans; in some embodiments, HA polypeptides bind preferentially to α2-6 sialylated glycans. In certain embodiments, HA polypeptides bind to a plurality of different α2-6 sialylated glycans. In some embodiments, HA polypeptides are not able to bind to α2-3 sialylated glycans, and in other embodiments, HA polypeptides are able to bind to α2-3 sialylated glycans.

In some embodiments, HA polypeptides bind to receptors found on human upper respiratory epithelial cells. In certain embodiments, HA polypeptides bind to HA receptors in the bronchus and/or trachea. In some embodiments, HA polypeptides are not able to bind receptors in the deep lung, and in other embodiments, HA polypeptides are able to bind receptors in the deep lung.

In some embodiments, HA polypeptides bind to at least about 10%, about 15%, about 20%, about 25%, about 30% about 35%, about 40%, about 45%, about 50%, about 55%, about 60%, about 65%, about 70%, about 75%, about 80%, about 85%, about 90%, about 95%, or more of the glycans found on HA receptors in human upper respiratory tract tissues (e.g., epithelial cells).

In some embodiments, HA polypeptides bind to one or more of the glycans illustrated in FIGS. 6 (right panel) and 9. In some embodiments, HA polypeptides bind to multiple glycans illustrated in FIGS. 6 (right panel) and 9. In some embodiments, HA polypeptides bind with high affinity and/or specificity to glycans illustrated in FIGS. 6 (right panel) and 9. In some embodiments, HA polypeptides bind to glycans illustrated in FIGS. 6 (right panel) and 9 preferentially as compared with their binding to glycans illustrated in FIGS. 6 (left panel) and 8.

The present invention provides isolated HA polypeptides with designated binding specificity, and also provides engineered HA polypeptides with designated binding characteristics with respect to umbrella-topology glycans.

In some embodiments, HA polypeptides with designated binding characteristics are H1 polypeptides. In some embodiments, HA polypeptides with designated binding characteristics are H2 polypeptides. In some embodiments, HA polypeptides with designated binding characteristics are H3 polypeptides. In some embodiments, HA polypeptides with designated binding characteristics are H4 polypeptides. In some embodiments, HA polypeptides with designated binding characteristics are H5 polypeptides. In some embodiments, HA polypeptides with designated binding characteristics are H6 polypeptides. In some embodiments, HA polypeptides with designated binding characteristics are H7 polypeptides. In some embodiments, HA polypeptides with designated binding characteristics are H8 polypeptides. In some embodiments, HA polypeptides with designated binding characteristics are H9 polypeptides. In some embodiments, HA polypeptides with designated binding characteristics are H10 polypeptides. In some embodiments, HA polypeptides with designated binding characteristics are H11 polypeptides. In some embodiments, HA polypeptides with designated binding characteristics are H12 polypeptides. In some embodiments, HA polypeptides with designated binding characteristics are H13 polypeptides. In some embodiments, HA polypeptides with designated binding characteristics are H14 polypeptides. In some embodiments, HA polypeptides with designated binding characteristics are H15 polypeptides. In some embodiments, HA polypeptides with designated binding characteristics are H16 polypeptides.

In some embodiments, HA polypeptides with designated binding characteristics are not H1 polypeptides, are not H2 polypeptides, and/or are not H3 polypeptides.

In some embodiments, HA polypeptides do not include the H1 protein from any of the strains: A/South Carolina/1/1918; A/Puerto Rico/8/1934; A/Taiwan/i/1986; A/Texas/36/1991; A/Beijing/262/1995; A/Johannesburg/92/1996; A/New Calcdonia/20/1999; A/Solomon Islands/3/2006.

In some embodiments, HA polypeptides are not the H2 protein from any of the strains of the Asian flu epidemic of 1957-58). In some embodiments, HA polypeptides do not include the H2 protein from any of the strains: A/Japan/305+/1957; A/Singapore/i/1957; A/Taiwan/1/1964; A/Taiwan/1/1967.

In some embodiments, HA polypeptides do not include the H3 protein from any of the strains: A/Aichi/2/1968; A/Philipines/2/1982; A/Mississippi/i/1985; A/Leningrad/360/1986; A/Sichuan/2/1987; A/Shanghai/11/1987; A/Beijing/353/1989; A/Shandong/9/1993; A/Johannesburg/33/1994; A/Nanchang/813/1995; A/Sydney/5/1997; A/Moscow/10/1999; A/Panama/2007/1999; A/Wyoming/3/2003; A/Oklahoma/323/2003; A/California/7/2004; A/Wisconsin/65/2005.

Variant HA Polypeptides

In certain embodiments, an HA polypeptide is a variant of a parent HA polypeptide in that its amino acid sequence is identical to that of the parent HA but for a small number of particular sequence alterations. In some embodiments, the parent HA is an HA polypeptide found in a natural isolate of an influenza virus (e.g., a wild type HA polypeptide).

In some embodiments, HA polypeptide variants have different glycan binding characteristics than their corresponding parent HA polypeptides. In some embodiments, HA variant polypeptides have greater affinity and/or specificity for umbrella-topology glycans (e.g., as compared with for cone-topology glycans) than do their cognate parent HA polypeptides. In certain embodiments, such HA polypeptide variants are engineered variants.

In some embodiments, HA polypeptide variants with altered glycan binding characteristics have sequence alternations in residues within or affecting the glycan binding site. In some embodiments, such substitutions are of amino acids that interact directly with bound glycan; in other embodiments, such substitutions are of amino acids that are one degree of separation removed from those that interact with bound glycan, in that the one degree of separation removed-amino acids either (1) interact with the direct-binding amino acids; (2) otherwise affect the ability of the direct-binding amino acids to interact with glycan, but do not interact directly with glycan themselves; or (3) otherwise affect the ability of the direct-binding amino acids to interact with glycan, and also interact directly with glycan themselves. HA polypeptide variants contain substitutions of one or more direct-binding amino acids, one or more first degree of separation-amino acids, one or more second degree of separation-amino acids, or any combination of these. In some embodiments, HA polypeptide variants may contain substitutions of one or more amino acids with even higher degrees of separation.

In some embodiments, HA polypeptide variants with altered glycan binding characteristics have sequence alterations in residues that make contact with sugars beyond Neu5Ac and Gal (see, for example, FIG. 6).

In some embodiments, HA polypeptide variants have at least one amino acid substitution, as compared with a wild type parent HA. In certain embodiments, HA polypeptide variants have at least two, three, four, five or more amino acid substitutions as compared with a cognate wild type parent HA; in some embodiments HA polypeptide variants have two, three, or four amino acid substitutions. In some embodiments, all such amino acid substitutions are located within the glycan binding site.

In some embodiments, HA polypeptide variants have sequence substitutions at positions corresponding to one or more of residues 137, 145, 156, 159, 186, 187, 189, 190, 192, 193, 196, 222, 225, 226, and 228. In some embodiments, HA polypeptide variants have sequence substitutions at positions corresponding to one or more of residues 156, 159, 189, 192, 193, and 196; and/or at positions corresponding to one or more of residues 186, 187, 189, and 190; and/or at positions corresponding to one or more of residues 190, 222, 225, and 226; and/or at positions corresponding to one or more of residues 137, 145, 190, 226 and 228. In some embodiments, HA polypeptide variants have sequence substitutions at positions corresponding to one or more of residues 190, 225, 226, and 228.

In certain embodiments, HA polypeptide variants, and particularly H5 polypeptide variants, have one or more amino acid substitutions relative to a wild type parent HA (e.g., H5) at residues selected from the group consisting of residues 98, 136, 138, 153, 155, 159, 183, 186, 187, 190, 193, 194, 195, 222, 225, 226, 227, and 228. In some embodiments, HA polypeptide variants, and particularly H5 polypeptide variants, have one or more amino acid substitutions relative to a wild type parent HA at residues selected from amino acids located in the region of the receptor that directly binds to the glycan, including but not limited to residues 98, 136, 153, 155, 183, 190, 193, 194, 222, 225, 226, 227, and 228. In some embodiments, an HA polypeptide variant, and particularly an H5 polypeptide variant, has one or more amino acid substitutions relative to a wild type parent HA at residues selected from amino acids located adjacent to the region of the receptor that directly binds the glycan, including but not limited to residues 98, 138, 186, 187, 195, and 228.

In some embodiments, HA polypeptide variants, and particularly H5 polypeptide variants, have one or more amino acid substitutions relative to a wild type parent HA at residues selected from the group consisting of residues 138, 186, 187, 190, 193, 222, 225, 226, 227 and 228. In other embodiments, HA polypeptide variants, and particularly H5 polypeptide variants, have one or more amino acid substitutions relative to a wild type parent HA at residues selected from amino acids located in the region of the receptor that directly binds to the glycan, including but not limited to residues 190, 193, 222, 225, 226, 227, and 228. In further embodiments, HA polypeptide variants, and particularly H5 polypeptide variants, have one or more amino acid substitutions relative to a wild type parent HA at residues selected from amino acids located adjacent to the region of the receptor that directly binds the glycan, including but not limited to residues 138, 186, 187, and 228.

In further embodiments, HA polypeptide variants, and particularly H5 polypeptide variants, have one or more amino acid substitutions relative to a wild type parent HA at residues selected from the group consisting of residues 98, 136, 153, 155, 183, 194, and 195. In some embodiments, HA polypeptide variants, and particularly H5 polypeptide variants, have one or more amino acid substitutions relative to a wild type parent HA at residues selected from amino acids located in the region of the receptor that directly binds to the glycan, including but not limited to residues 98, 136, 153, 155, 183, and 194. In some embodiments, HA polypeptide variants, and particularly H5 polypeptide variants, have one or more amino acid substitutions relative to a wild type parent HA at residues selected from amino acids located adjacent to the region of the receptor that directly binds the glycan, including but not limited to residues 98 and 195.

In certain embodiments, HA polypeptide variants, and particularly H5 polypeptide variants, have one or more amino acid substitutions relative to a wild type parent HA at residues selected from amino acids that are one degree of separation removed from those that interact with bound glycan, in that the one degree of separation removed-amino acids either (1) interact with the direct-binding amino acids; (2) otherwise affect the ability of the direct-binding amino acids to interact with glycan, but do not interact directly with glycan themselves; or (3) otherwise affect the ability of the direct-binding amino acids to interact with glycan, and also interact directly with glycan themselves, including but not limited to residues 98, 138, 186, 187, 195, and 228.

In some embodiments, HA polypeptide variants, and particularly H5 polypeptide variants, have one or more amino acid substitutions relative to a wild type parent HA at residues selected from amino acids that are one degree of separation removed from those that interact with bound glycan, in that the one degree of separation removed-amino acids either (1) interact with the direct-binding amino acids; (2) otherwise affect the ability of the direct-binding amino acids to interact with glycan, but do not interact directly with glycan themselves; or (3) otherwise affect the ability of the direct-binding amino acids to interact with glycan, and also interact directly with glycan themselves, including but not limited to residues 138, 186, 187, and 228.

In some embodiments, HA polypeptide variants, and particularly H5 polypeptide variants, have one or more amino acid substitutions relative to a wild type parent HA at residues selected from amino acids that are one degree of separation removed from those that interact with bound glycan, in that the one degree of separation removed-amino acids either (1) interact with the direct-binding amino acids; (2) otherwise affect the ability of the direct-binding amino acids to interact with glycan, but do not interact directly with glycan themselves; or (3) otherwise affect the ability of the direct-binding amino acids to interact with glycan, and also interact directly with glycan themselves, including but not limited to residues 98 and 195.

In certain embodiments, HA polypeptide variants, and particularly H5 polypeptide variants, have an amino acid substitution relative to a wild type parent HA at residue 159.

In some embodiments, HA polypeptide variants, and particularly H5 polypeptide variant, have one or more amino acid substitutions relative to a wild type parent HA at residues selected from 190, 193, 225, and 226. In some embodiments, HA polypeptide variants, and particularly H5 polypeptide variants, have one or more amino acid substitutions relative to a wild type parent HA at residues selected from 190, 193, 226, and 228.

In some embodiments, HA polypeptide variants, and particularly H5 variants, have one or more of the following amino acid substitutions: Ser137Ala, Lys 156Glu, Asn186Pro, Asp187Ser, Asp187Thr, Ala189Gln, Ala189Lys, Ala189Thr, Glu190Asp, Glu190Thr, Lys193Arg, Lys193Asn, Lys193His, Lys193Ser, Gly225Asp, Gln226Ile, Gln226Leu, Gln226Val, Ser227Ala, Gly228Ser.

In some embodiments, HA polypeptide variants, and particularly H5 variants, have one or more of the following sets of amino acid substitutions:

Glu190Asp, Lys193Ser, Gly225Asp and Gln226Leu;

Glu190Asp, Lys193Ser, Gln226Leu and Gly228Ser;

Ala189Gln, Lys193Ser, Gln226Leu, Gly228Ser;

Ala189Gln, Lys193Ser, Gln226Leu, Gly228Ser;

Asp187Ser/Thr, Ala189Gln, Lys193Ser, Gln226Leu, Gly228Ser;

Ala189Lys, Lys193Asn, Gln226Leu, Gly228Ser;

Asp187Ser/Thr, Ala189Lys, Lys193Asn, Gln226Leu, Gly228Ser;

Lys156Glu, Ala189Lys, Lys193Asn, Gln226Leu, Gly228Ser;

Lys193His, Gln226Leu/Ile/Val, Gly228Ser;

Lys193Arg, Gln226Leu/Ile/Val, Gly228Ser;

Ala189Lys, Lys193Asn, Gly225Asp;

Lys156Glu, Ala189Lys, Lys193Asn, Gly225Asp;

Ser137Ala, Lys156Glu, Ala189Lys, Lys193Asn, Gly225Asp;

Glu190Thr, Lys193Ser, Gly225Asp;

Asp187Thr, Ala189Thr, Glu190Asp, Lys193Ser, Gly225Asp;

Asn186Pro, Asp187Thr, Ala189Thr, Glu190Asp, Lys193Ser, Gly225Asp;

Asn186Pro, Asp187Thr, Ala189Thr, Glu190Asp, Lys193Ser, Gly225Asp, Ser227Ala.

In some embodiments, an HA polypeptide has at least one further substitution as compared with a wild type HA, such that affinity and/or specificity of the variant for umbrella-topology glycans is increased.

In some embodiments, HA polypeptides (including HA polypeptide variants) have sequences that include D190, D225, L226, and/or S228. In some embodiments, HA polypeptides have sequences that include D190 and D225; in some embodiments, HA polypeptides have sequences that include L226 and S228.

In some embodiments, HA polypeptide variants have an open binding site as compared with a parent HA, and particularly with a parent wild type HAs.

Portions or Fragments of HA Polypeptides

The present invention further provides characteristic portions of HA polypeptides and nucleic acids that encode them. In general, a characteristic portion is one that contains a continuous stretch of amino acids, or a collection of continuous stretches of amino acids, that together are characteristic of the HA polypeptide. Each such continuous stretch generally will contain at least two amino acids. Furthermore, those of ordinary skill in the art will appreciate that typically at least 5, 10, 15, 20 or more amino acids are required to be characteristic of a H5 HA polypeptide. In general, a characteristic portion is one that, in addition to the sequence identity specified above, shares at least one functional characteristic with the relevant intact HA polypeptide. In some embodiments, inventive characteristic portions of HA polypeptides share glycan binding characteristics with the relevant full-length HA polypeptides.

While some of the particular examples and descriptions of HA polypeptides provided herein are specifically directed to H5 HA, one of ordinary skill in the art will readily recognize that the invention is not limited to H5 HA, but that the invention and its principles are generally applicable to any HA genotype, subtype, variant, portion, fragment, etc.

Identifying Glycan Decoys

In some embodiments, the present invention provides systems and methods for identifying glycan decoys. In general, such systems and methods involve contacting HA polypeptides with one or more candidate substances that mimic umbrella-topology glycans (referred to herein as "candidate decoys") and determine the ability of the agent(s) to bind to the HA polypeptide and/or to compete an interaction between the HA polypeptide and an HA receptor (or umbrella-topology glycans found on an HA receptor).

In some embodiments, glycan decoys are glycan mimics that bind to HA polypeptides. In some embodiments, glycan mimics compete with endogenous glycans for binding to HA polypeptides. In some embodiments, glycan mimics compete with endogenous umbrella-type glycans for binding to HA polypeptides. In some embodiments, glycan mimics compete with upper-respiratory glycans for binding to HA polypeptides. In some embodiments, glycan mimics compete with umbrella-topology upper-respiratory glycans for binding to HA polypeptides.

In some embodiments, peptide mimics bind to HA polypeptides, but do not compete with endogenous glycans for binding to HA polypeptides.

In some embodiments, a candidate decoy may be free in solution, fixed to a support, and/or expressed in and/or on the surface of a cell. The candidate decoy and/or the HA polypeptide may be labeled, thereby permitting detection of binding. The candidate decoy is frequently the labeled species, decreasing the chance that the labeling will interfere with and/or enhance binding. Competitive binding formats may be performed in which one of the substances is labeled, and one may measure the amount of free label versus bound label to determine the effect on binding.

In some embodiments, binding assays involve, for example, exposing a candidate decoy to an HA polypeptide and detecting binding between the candidate decoy and the HA polypeptide. A binding assay may be conducted in vitro (e.g., in a candidate tube, comprising substantially only the components mentioned; in cell-free extracts; and/or in substantially purified components). Alternatively or additionally, binding assays may be conducted in cyto and/or in vivo (e.g., within a cell, tissue, organ, and/or organism; described in further detail below).

In certain embodiments, at least one HA polypeptide is contacted with at least one candidate decoy and an effect detected. In some embodiments, for example, a HA polypeptide is contacted with a candidate decoy, and binding between the two entities is monitored. In some embodiments, an assay may involve contacting a candidate decoy with a characteristic portion of a HA polypeptide (including, but not limited to, the region of the HA polypeptide that contacts umbrella-topology glycans). Binding of the HA polypeptide to the candidate decoy is detected. It will be appreciated that fragments, portions, homologs, variants, and/or derivatives of HA polypeptides may be employed, provided that they comprise umbrella-topology glycan binding activity.

In some embodiments, assays may involve providing a candidate decoy (e.g. immobilized on a solid support, such as a glycan array, described in further detail below in the section entitled "*Glycan Arrays*"), and a non-immobilized HA polypeptide. The extent to which the candidate decoy and HA polypeptide bind to one another is determined. Alternatively, the HA polypeptide may be immobilized and the candidate decoy non-immobilized. Such assays may be used to identify candidate decoys capable of binding to HA polypeptides and/or fragments, portions, homologs, variants, and/or derivatives thereof.

In some embodiments, an antibody that recognizes an HA polypeptide (e.g. an α-HA antibody) is immobilized to a solid support (e.g. Protein-A beads). The antibody is contacted with the HA polypeptide, which binds to the immobilized antibody. The resulting complex is then brought into contact with the candidate decoy (purified proteins, cellular extract, combinatorial library, etc.). If the HA polypeptide interacts with the candidate decoy, the candidate decoy will become indirectly immobilized to the solid support. Presence of the candidate decoy on the solid support can be assayed by any standard technique known in the art (including, but not limited to, western blotting, mass spectrometry, etc.). This type of assay is known in the art as an "immunoprecipitation" assay.

In some embodiments, an HA polypeptide is immobilized on a solid support (e.g. agarose beads). In specific embodiments, the HA polypeptide is expressed as a GST-fusion protein in bacteria, yeast, insect cells, and/or higher eukaryotic cell line and/or purified from crude cell extracts using glutathione-agarose beads. As a control, binding of a candidate decoy, which is not a GST-fusion protein, to the glutathione-agarose beads is determined in the absence of HA polypeptide. The binding of the candidate decoy to the immobilized HA polypeptide is then determined. This type of assay is known in the art as a "GST pulldown" assay. Alternatively or additionally, the candidate substance may be immobilized and the HA polypeptide non-immobilized.

It is possible to perform this type of assay using different affinity purification systems for immobilizing one of the components, for example Ni-NTA agarose- and/or histidine-tagged components.

Binding of a HA polypeptide to the candidate decoy may be determined by a variety of methods well-known in the art. For example, the non-immobilized component may be labeled (with for example, a radioactive label, an epitope tag, an enzyme-antibody conjugate, etc.). Alternatively or additionally, binding may be determined by immunological detection techniques. For example, the reaction mixture may be subjected to Western blotting and the blot probed with an antibody that detects the non-immobilized component. Alternatively or additionally, enzyme linked immunosorbent assay (ELISA) may be utilized to assay for binding.

In some embodiments, screening methods of the present invention comprise: (1) obtaining a candidate substance; (2) contacting the candidate decoy with an HA polypeptide (and/or characteristic portion thereof) and an umbrella-topology glycan known to bind to the HA polypeptide; and (3) detecting inhibition of binding between the HA polypeptide and the known umbrella-topology glycan in the presence and/or absence of the candidate decoy.

In some embodiments, screening methods of the present invention comprise: (1) obtaining a candidate decoy; and (2) contacting the candidate decoy with a pre-formed HA polypeptide (and/or characteristic portion thereof)-umbrella-topology glycan complex; and (3) determining whether the candidate substance affects the HA polypeptide (and/or characteristic portion thereof)-umbrella-topology glycan complex.

In some embodiments, screening methods of the present invention comprise (1) obtaining a candidate decoy; (2) contacting the candidate decoy with HA polypeptide (and/or characteristic portion thereof) and an umbrella-topology glycan known to specifically bind to the HA polypeptide; and (3) detecting whether the candidate decoy can compete with the binding interaction between HA polypeptide (and/or characteristic portion thereof) and the known umbrella-topology glycan.

In some embodiments, a candidate decoy is determined to be an umbrella-topology glycan decoy if administering the candidate decoy to an HA polypeptide and an umbrella-topology glycan known to specifically bind to the HA polypeptide results in decreased binding between the HA polypeptide and the known umbrella-topology glycan. In some embodiments, a candidate decoy is determined to be an umbrella-topology glycan if administering the candidate decoy to an HA polypeptide and an umbrella-topology glycan known to specifically bind to the HA polypeptide results in an at least 2-fold decrease in binding between the HA polypeptide and the known umbrella-topology glycan. In some embodiments, a candidate decoy is determined to be an umbrella-topology glycan if administering the candidate decoy to an HA polypeptide and an umbrella-topology glycan known to specifically bind to the HA polypeptide results in an at least 3-fold, at least 4-fold, at least 5-fold, at least 10-fold, at least 20-fold, at least 50-fold, at least 100-fold, at least 200-fold, at least 500-fold, at least 1000-fold, at least 10,000-fold, or greater than 10,000-fold decrease in binding between the HA polypeptide and the known umbrella-topology glycan. In some embodiments, a candidate decoy is determined to be an HA polypeptide if administering the candidate decoy to the HA polypeptide and an umbrella-topology glycan known to specifically bind to the HA polypeptide results in an at least 25%, 50%, 75%, 100%, 200%, 500%, 1000%, or greater than 1000% decrease in binding between the HA polypeptide and the known umbrella-topology glycan.

In some embodiments, the present invention provides methods for screening for umbrella-topology glycan decoys wherein a candidate decoy is contacted with a cell (e.g. a cell that expresses or is bound to an HA polypeptide). The cell can then be assayed for the ability of an HA polypeptide to interact with one or more candidate umbrella-topology glycan decoys.

In certain embodiments, cells may be directly assayed for binding between HA polypeptides and candidate decoys. Immunohistochemical techniques, confocal techniques, and/or other techniques to assess binding are well known to those of skill in the art. Various cell lines may be utilized for such screening assays, including cells specifically engineered for this purpose. Examples of cells used in the screening assays include mammalian cells, fungal cells, bacterial cells, or viral cells. A cell may be a stimulated cell, such as a cell stimulated with a growth factor. One of skill in the art would understand that the invention disclosed herein contemplates a wide variety of in cyto assays for measuring the ability of HA polypeptides to bind to candidate decoys.

Depending on the assay, cell and/or tissue culture may be required. A cell may be examined using any of a number of different physiologic assays. Alternatively or additionally, molecular analysis may be performed, including, but not limited to, western blotting to monitor protein expression and/or test for protein-protein interactions; mass spectrometry to monitor other chemical modifications; etc.

The present invention provides methods for identifying substances that bind to HA polypeptides and, therefore, may be involved in influenza infection. One in cyto method of identifying substances that bind to HA polypeptides is the two-hybrid system assay (Fields et al., 1994, *Trends in Genetics,* 10:286; and Colas et al., 1998, *TIBTECH,* 16:355; both of which are incorporated herein by reference). In this assay, yeast cells express a first fusion protein comprising a test substance in accordance with the present invention (e.g. an HA polypeptide, gene encoding an HA polypeptide, and/or characteristic portions thereof) and a DNA-binding domain of a transcription factor such as Gal4 and/or LexA. The cells additionally contain a reporter gene whose promoter contains binding sites for the corresponding DNA-binding domain. By transforming the cells with a vector that expresses a second fusion protein comprising a candidate decoy fused to an activation domain (e.g. from Gal4 and/or herpes simplex virus VP16) expression of the reporter gene may be increased if the candidate decoy interacts with the HA polypeptide. In this way, it is possible rapidly to identify novel glycan decoys.

The present invention provides assays involving solid phase-bound HA polypeptides and detecting their interactions with one or more candidate decoys. Thus, an HA polypeptide may comprise a detectable marker, such as a radioactive, fluorescent, and/or luminescent label. Furthermore, candidate decoys can be coupled to substances which permit indirect detection (e.g. by means of employing an enzyme which uses a chromogenic substrate and/or by means of binding a detectable antibody). Changes in the conformation of HA polypeptides as the result of an interaction with a candidate decoys may be detected, for example, by the change in the emission of the detectable marker. Alternatively or additionally, solid phase-bound protein complexes may be analyzed by means of mass spectrometry.

In some embodiments, any of the binding assays described herein may be performed using a range of concentrations of HA polypeptide and/or candidate decoy. In some embodiments, the binding assays described herein are used to assess the ability of a candidate decoy to compete with a known umbrella-topology glycan over range of candidate decoy and known umbrella-topology glycan concentrations (e.g. candidate decoy: known umbrella-topology glycan ratios of less than about 1:1000, about 1:1000, about 1:100, about 1:50, about 1:20, about 1:10, about 1:5, about 1:3, about 1:2, about 1:1, about 2:1, about 3:1, about 5:1, about 10:1, about 20:1, about 50:1, about 100:1, about 1000:1, and/or greater than about 1000:1). In some embodiments, the binding assays described herein are used to assess the ability of a candidate decoy to compete with a known umbrella-topology glycan over range of HA polypeptide concentrations (e.g. greater than about 100 μg/ml, about 100 μg/ml, about 50 μg/ml, about 40 μg/ml, about 30 μg/ml, about 20 μg/ml, about 10 μg/ml, about 50 μg/ml, about 4 μg/ml, about 3 μg/ml, about 2 μg/ml, about 1.75 μg/ml, about 1.5 μg/ml, about 1.25 μg/ml, about 1.0 μg/ml, about 0.9 μg/ml, about 0.8 μg/ml, about 0.7 μg/ml, about 0.6 μg/ml, about 0.5 μg/ml, about 0.4 μg/ml, about 0.3 μg/ml, about 0.2 μg/ml, about 0.1 μg/ml, about 0.05 μg/ml, about 0.01 μg/ml, and/or less than about 0.01 μg/ml).

In some embodiments, any of the binding studies described herein can be executed in a high throughput fashion. Using high throughput assays, it is possible to screen up to several thousand candidate decoys in a single day. In some embodiments, each well of a microtiter plate can be used to run a separate assay against a selected candidate decoy, or, if concentration and/or incubation time effects are to be observed, every 5-10 wells can test a single candidate decoy. Thus, a single standard microtiter plate can assay up to 96 candidate decoy; if 1536 well plates are used, then a single plate can assay up to 1536 candidate decoys; and so forth. It is possible to assay many plates per day; assay screens for up to about 6,000, about 20,000, about 50,000, or more than about 100,000 different candidate decoys are possible using high throughput systems in accordance with the present invention.

Glycan Arrays

To rapidly expand the current knowledge of known specific glycan-glycan binding protein (GBP) interactions, the Consortium for Functional Glycomics (CFG; www.functionalglycomics.org), an international collaborative research initiative, has developed glycan arrays comprising several glycan structures that have enabled high throughput screening of GBPs for novel glycan ligand specificities. Glycan arrays comprise both monovalent and polyvalent glycan motifs (i.e., attached to polyacrylamide backbone), and each array comprises 264 glycans with low (10 μM) and high (100 μM) concentrations, and six spots for each concentration (see http://www.functionalglycomics.org/static/consortium/resources/resourcecoreh5.shtml).

Glycan arrays predominantly comprise synthetic glycans that capture the physiological diversity of N- and O-linked glycans. In addition to synthetic glycans, N-linked glycan mixtures derived from different mammalian glycoproteins may be also represented on the array.

As used herein, a glycan "array" refers to a set of one or more glycans, optionally immobilized on a solid support. In some embodiments, an "array" is a collection of glycans present as an organized arrangement or pattern at two or more locations that are physically separated in space. Typically, a glycan array will have at least 4, 8, 16, 24, 48, 96 or several hundred or thousand discrete locations. In general, glycan arrays may have any of a variety of formats. Various different array formats applicable to biomolecules are known in the art. For example, a huge number of protein and/or nucleic acid arrays are well known. Those of ordinary skill in the art will immediately appreciate standard array formats appropriate for glycan arrays of the present invention.

In some embodiments, glycan arrays are present in "microarray" formats. A microarray may typically have sample locations separated by a distance of 50 μm-200 μm or less and immobilized sample in the nano- to micro-molar range or nano- to pico-gram range. Array formats known in the art include, for example, those in which each discrete sample location has a scale of, for example, 10 μm.

In some embodiments, glycan arrays comprise a plurality of glycans spatially immobilized on a support. As used herein, "support" refers to any material that is suitable to be used to array glycan molecules. As will be appreciated by those of ordinary skill in the art, any of a wide variety of materials may be employed. To give but a few examples, support materials which may be of use in the invention include hydrophobic membranes, for example, nitrocellulose, PVDF or nylon membranes. Such membranes are well known in the art and can be obtained from, for example, Bio-Rad, Hemel Hempstead, UK.

In some embodiments, the support on which glycans are arrayed may comprise a metal oxide. Suitable metal oxides include, but are not limited to, titanium oxide, tantalum oxide, and aluminum oxide. Examples of such materials may be obtained from Sigma-Aldrich Company Ltd, Fancy Road, Poole, Dorset. BH12 4QH UK.

In some embodiments, such a support is or comprises a metal oxide gel. A metal oxide gel is considered to provide a large surface area within a given macroscopic area to aid immobilization of the carbohydrate-containing molecules.

Additional or alternative support materials which may be used in accordance with the present invention include gels, for example silica gels or aluminum oxide gels. Examples of such materials may be obtained from, for example, Merck KGaA, Darmstadt, Germany.

In some embodiments, glycan arrays are immobilized on a support that can resist change in size or shape during normal use. For example a support may be a glass slide coated with a component material suitable to be used to array glycans. Also, some composite materials can desirable provide solidity to a support.

As demonstrated herein, glycan arrays are useful for the characterization of HA-receptor interactions and/or agents (e.g. umbrella-topology glycan decoys) that affect HA-receptor interactions. In certain embodiments, HA polypeptides are tested on such arrays to assess their ability to bind to umbrella-topology glycans (e.g., to α2-6 sialylated glycans, and particularly to long α2-6 sialylated glycans arranged in an umbrella-topology), and/or to interact with umbrella-topology glycan decoys.

Indeed, the present invention provides arrays of α2-6 sialylated glycans, and optionally α2-3 sialylated glycans, that can be used to characterize HA polypeptide binding interactions and/or to identify and/or characterize umbrella-topology glycan decoys. In some embodiments, arrays contain glycans (e.g., α2-6 sialylated glycans, and particularly long α2-6 sialylated glycans) in an umbrella-topology. As will be clear to those of ordinary skill in the art, such arrays are useful for characterizing or detecting interaction with any HA polypeptides, including for example, those found in natural influenza isolates in addition to those designed and/or prepared by researchers.

In some embodiments, such arrays include glycans representative of about 10%, about 15%, about 20%, about 25%, about 30% about 35%, about 40%, about 45%, about 50%, about 55%, about 60%, about 65%, about 70%, about 75%, about 80%, about 85%, about 90%, about 95%, or more of the glycans (e.g., umbrella-topology glycans, which will often be α2-6 sialylated glycans, particularly long α2-6 sialylated glycans) found on human HA receptors, and particularly on human upper respiratory tract HA receptors. In some embodiments, arrays include some or all of the glycan structures depicted in FIGS. 9 and 13. In some embodiments, arrays include at least about 10%, about 15%, about 20%, about 25%, about 30% about 35%, about 40%, about 45%, about 50%, about 55%, about 60%, about 65%, about 70%, about 75%, about 80%, about 85%, about 90%, about 95%, or more of these depicted glycans.

The present invention provides methods for identifying or characterizing umbrella-topology glycan decoys using glycan arrays. In some embodiments, for example, such methods comprise steps of (1) providing a sample containing at least one HA polypeptide, (2) contacting the sample with a glycan array comprising candidate umbrella-topology glycan decoys, and (3) detecting binding of HA polypeptide(s) to one or more candidate decoys on the array.

In some embodiments, for example, the present invention provides for identifying or characterizing umbrella-topology glycan decoys using glycan arrays comprising steps of (1) providing a plurality of samples, each containing a different dilution of at least one HA polypeptide, (2) contacting the plurality of samples with a glycan array comprising candidate umbrella-topology glycan decoys, and (3) detecting binding of different dilutions of HA polypeptides to one or more candidate decoys on the array.

In some embodiments, for example, the present invention provides for identifying or characterizing umbrella-topology glycan decoys using glycan arrays comprising steps of (1) providing a sample containing at least one HA polypeptide, (2) contacting the sample with a glycan array comprising a plurality of dilutions of at least one candidate umbrella-topology glycan decoy, and (3) detecting binding of HA polypeptide(s) to one or more of the plurality of dilutions of candidate decoys on the array.

In some embodiments, for example, the present invention provides for identifying or characterizing umbrella-topology glycan decoys using glycan arrays comprising steps of (1) providing a plurality of samples, each containing a different dilution of at least one HA polypeptide, (2) contacting the plurality of samples with a glycan array comprising a plurality of dilutions of at least one candidate umbrella-topology glycan decoy, and (3) detecting binding of different dilutions of HA polypeptides to one or more of the plurality of dilutions of candidate decoys on the array.

In some embodiments, methods such as those described above are used to assess the ability of a candidate decoy to compete with a known umbrella-topology glycan over range of candidate decoy and known umbrella-topology glycan concentrations (e.g. candidate decoy: known umbrella-topology glycan ratios of less than about 1:1000, about 1:1000, about 1:100, about 1:50, about 1:20, about 1:10, about 1:5, about 1:3, about 1:2, about 1:1, about 2:1, about 3:1, about 5:1, about 10:1, about 20:1, about 50:1, about 100:1, about 1000:1, and/or greater than about 1000:1). In some embodiments, methods such as those described above are used to assess the ability of a candidate decoy to compete with a known umbrella-topology glycan over range of HA polypeptide concentrations (e.g. greater than about 100 μg/ml, about 100 μg/ml, about 50 μg/ml, about 40 μg/ml, about 30 μg/ml, about 20 μg/ml, about 10 μg/ml, about 50 μg/ml, about 4 μg/ml, about 3 μg/ml, about 2 μg/ml, about 1.75 μg/ml, about 1.5 μg/ml, about 1.25 μg/ml, about 1.0 μg/ml, about 0.9 μg/ml, about 0.8 μg/ml, about 0.7 μg/ml, about 0.6 μg/ml, about 0.5 μg/ml, about 0.4 μg/ml, about 0.3 μg/ml, about 0.2 μg/ml, about 0.1 μg/ml, about 0.05 μg/ml, about 0.01 μg/ml, and/or less than about 0.01 μg/ml).

Suitable sources for samples containing HA polypeptides to be contacted with glycan arrays according to the present invention include, but are not limited to, pathological samples, such as blood, serum/plasma, peripheral blood mononuclear cells/peripheral blood lymphocytes (PBMC/PBL), sputum, urine, feces, throat swabs, dermal lesion swabs, cerebrospinal fluids, cervical smears, pus samples, food matrices, and tissues from various parts of the body such as brain, spleen, and liver. Alternatively or additionally, other suitable sources for samples containing HA polypeptides include, but are not limited to, environmental samples such as soil, water, and flora. Yet other samples include laboratory samples, for example of engineered HA polypeptides designed and/or prepared by researchers. Other samples that have not been listed may also be applicable.

A wide variety of detection systems suitable for assaying HA polypeptide binding to glycan arrays are known in the art. For example, HA polypeptides can be detectably labeled (directly or indirectly) prior to or after being contacted with the array; binding can then be detected by detection of localized label. In some embodiments, scanning devices can be utilized to examine particular locations on an array.

Alternatively or additionally, binding to arrayed glycans can be measured using, for example, calorimetric, fluorescence, or radioactive detection systems, or other labeling methods, or other methods that do not require labeling. In general, fluorescent detection typically involves directly probing the array with a fluorescent molecule and monitoring fluorescent signals. Alternatively or additionally, arrays can be probed with a molecule that is tagged (for example, with biotin) for indirect fluorescence detection (in this case, by testing for binding of fluorescently-labeled streptavidin). Alternatively or additionally, fluorescence quenching methods can be utilized in which the arrayed glycans are fluorescently labeled and probed with a test molecule (which may or may not be labeled with a different fluorophore). In such embodiments, binding to the array acts to squelch the fluorescence emitted from the arrayed glycan, therefore binding is detected by loss of fluorescent emission. Alternatively or additionally, arrayed glycans can be probed with a live tissue sample that has been grown in the presence of a radioactive substance, yielding a radioactively labeled probe. Binding in such embodiments can be detected by measuring radioactive emission.

Such methods are useful to determine the fact of binding and/or the extent of binding by HA polypeptides to glycan arrays. In some embodiments of the invention, such methods can further be used to identify and/or characterize agents that interfere with or otherwise alter glycan-HA polypeptide interactions.

Methods described below may be of particular use in, for example, identifying whether a glycan (e.g. putative umbrella-topology glycan decoy) thought to be capable of interacting with an HA polypeptide can actually do so, or to identify whether a decoy unexpectedly has the capability of interacting with an HA polypeptide.

In some embodiments, binding to glycan arrays may be utilized, for example, to determine kinetics of interaction between an HA polypeptide and a glycan. For example, methods for determining interaction kinetics may include steps of (1) contacting a glycan array with the HA polypeptide being tested; and, (2) measuring kinetics of interaction between the HA polypeptide and arrayed glycan(s).

The kinetics of interaction of a binding agent with any of the glycans in an array can be measured by real time changes in, for example, colorimetric or fluorescent signals, as detailed above. Such methods may be of particular use in, for example, determining whether a particular binding agent is able to interact with a specific carbohydrate with a higher degree of binding than does a different binding agent interacting with the same glycan and/or set of glycans.

It will be appreciated, of course, that glycan binding by HA polypeptides can be evaluated on glycan samples or sources not present in an array format per se. For example, HA polypeptides can be bound to tissue samples and/or cell lines to assess their glycan binding characteristics. Appropriate cell lines include, for example, any of a variety of mammalian cell lines, particularly those expressing HA receptors containing umbrella-topology glycans (e.g., at least some of which may be α2-6 sialylated glycans, and particularly long α2-6 sialylated glycans). In some embodiments, utilized cell lines express individual glycans with umbrella-topology. In some embodiments, utilized cell lines express a diversity of glycans. In some embodiments, cell lines are obtained from clinical isolates; in some they are maintained or manipulated to have a desired glycan distribution and/or prevalence. In some embodiments, tissue samples and/or cell lines express glycans characteristic of mammalian upper respiratory epithelial cells.

Pharmaceutical Compositions

The present invention provides umbrella-topology glycan decoys used in the treatment of influenza infection. In some embodiments, the present invention provides pharmaceutical compositions comprising glycan decoys and at least one pharmaceutically acceptable excipient. The present invention provides pharmaceutical compositions comprising a therapeutically effective amount of inventive glycan decoy(s) appropriately formulated for administration to a subject suffering from and/or susceptible to influenza infection. Such pharmaceutical compositions may optionally comprise one or more additional therapeutically-active substances.

In accordance with some embodiments, methods of treating influenza infection are provided. In some embodiments, inventive methods comprise administering a pharmaceutical composition comprising at least one glycan decoy of the present invention to a subject in need thereof. Inventive glycan decoys may be administered with other medications used to treat the symptoms of influenza infection. In some embodiments, the compositions are administered to humans.

Figure 12:
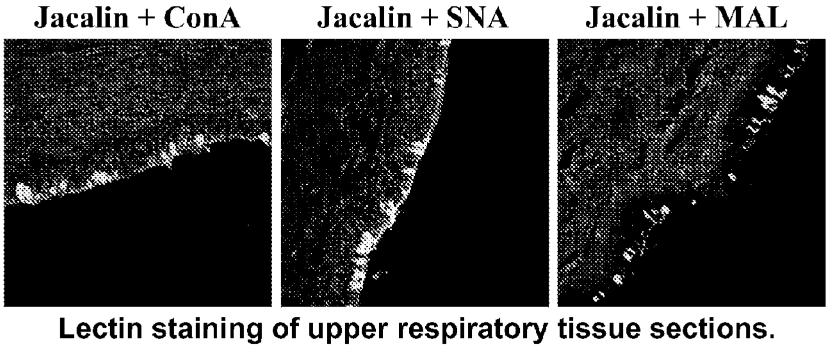
FIG. 12: Lectin staining of upper respiratory tissue sections. A co-stain of the tracheal tissue with Jacalin (green) and ConA (red) reveals a preferential binding of Jacalin (binds specifically to O-linked glycans) to goblet cells on the apical surface of the trachea and ConA (binds specifically to N-linked glycans) to the ciliated tracheal epithelial cells. Without wishing to be bound by any particular theory, the present inventors note that this finding suggests that goblet cells predominantly express O-linked glycans while ciliated epithelial cells predominantly express N-linked glycans. Co-staining of trachea with Jacalin and SNA (red; binds specifically to α2-6) shows binding of SNA to both goblet and ciliated cells. On the other hand, co-staining of Jacalin (green) and MAL (red), which specifically binds to α2-3 sialylated glycans, shows weak minimal to no binding of MAL to the pseudostratified tracheal epithelium but extensive binding to the underlying regions of the tissue. Together, the lectin staining data indicate predominant expression and extensive distribution of α2-6 sialylated glycans as a part of both N-linked and O-linked glycans respectively in ciliated and goblet cells on the apical side of the tracheal epithelium.

In some embodiments, inventive pharmaceutical compositions comprise a plurality of individual umbrella-topology glycan mimics. In some embodiments, such individual umbrella-topology glycan mimics are provided in ratios corresponding to those at which such umbrella-topology glycans are found on HA receptors in nature, and in particular in the human respiratory tract (e.g., the human upper respiratory tract). For example, human bronchial epithelial cells typically show glycan distributions as depicted in FIGS. 12 and 13; in some embodiments, inventive glycan decoy compositions include individual glycan mimics in ratios appropriate to such distributions. In some embodiments, the composition is enriched for umbrella topology glycans, e.g., the ratio of umbrella topology: cone topology glycans in the composition is greater than is found in the human respiratory tract (e.g., the human upper respiratory tract). In some embodiments umbrella topology glycans are at least 50, 60, 70, 80, 90, 95 or 99% (by number or weight) of the glycans in the composition.

In some embodiments, inventive pharmaceutical compositions are substantially free of agents that mimic glycans other than umbrella-topology glycans. For example, in some embodiments, inventive pharmaceutical compositions are substantially free of agents that mimic cone-topology glycans.

The invention encompasses the preparation and/or use of pharmaceutical compositions comprising at least one glycan decoy for treatment of influenza infection as an active ingredient. Such a pharmaceutical composition may consist of the active ingredient alone, in a form suitable for administration to a subject, or the pharmaceutical composition may comprise the active ingredient and one or more pharmaceutically acceptable excipients, one or more additional ingredients, and/or a combination of these. The active ingredient may be present in the pharmaceutical composition in the form of a physiologically acceptable ester and/or salt, such as in combination with a physiologically acceptable cation and/or anion, as is well known in the art.

Although the descriptions of pharmaceutical compositions provided herein are principally directed to pharmaceutical compositions that are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Patients to which administration of the pharmaceutical compositions of the invention is contemplated include, but are not limited to, humans and/or other primates; mammals, including commercially relevant mammals such as cattle, pigs, horses, sheep, cats, and/or dogs; and/or birds, including commercially relevant birds such as chickens, ducks, geese, and/or turkeys.

Pharmaceutical compositions as described herein may be prepared by any method known or hereafter developed in the art of pharmaceutics. In general, such preparatory methods include the step of bringing the active ingredient into association with one or more excipients and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable excipient(s), and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations of the present invention may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy,* $21^{st}$ Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWLEN 20], polyoxyethylene sorbitan [TWEEN®60], polyoxyethylene sorbitan monooleate [TWEEN®80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g. polyoxyethylene monostearate [MYRJ®45], polyoxyethylene hydrogenated castor oil, polyethoxylated castor oil, polyoxymethylene stearate, and SOLUTOL), sucrose fatty acid esters, polyethylene glycol fatty acid esters (e.g. CREMOPHOR), polyoxyethylene ethers, (e.g. polyoxyethylene lauryl ether [BRIJ®30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLURONIC®F 68, POLOXAMER 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS", PHENONIP", methylparaben, GERMALL® 115, GERMABEN®II, NEOLONE™, KATHON, and EUXYL. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredient(s), liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and perfuming agents. In certain embodiments for parenteral administration, an active ingredient can be mixed with solubilizing agents such as CREMOPHOR, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. A sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the active ingredients of this invention with suitable non-irritating excipients such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and/or (i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

Active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a composition of this invention may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1.0% to about 10% (w/w) active ingredient, although the concentration of the active ingredient may be as high as the solubility limit of the active ingredient in the solvent. Formulations for topical administration may further comprise one or more of the excipients and/or additional ingredients described herein.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 μm to about 7 μm or from about 1 μm to about 6 μm. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 μm and at least 95% of the particles by number have a diameter less than 7 μm. Alternatively, at least 95% of the particles by weight have a diameter greater than 1 μm and at least 90% of the particles by number have a diameter less than 6 μm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and the active ingredient may constitute 0.1% to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 m to about 200 μm.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 μm to 500 μm. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the excipients and/or additional ingredients described herein. A pharmaceutical composition of the invention may be prepared, packaged, and/or sold in a formulation suitable for buccal administration. Such formulations may, for example, be in the form of tablets and/or lozenges made using conventional methods, and may contain, for example, 0.1% to 20% (w/w) active ingredient, the balance comprising an orally dissolvable and/or degradable composition and, optionally, one or more of the excipients and/or additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 m to about 200 μm, and may further comprise one or more of the excipients and/or additional ingredients described herein.

A pharmaceutical composition of the invention may be prepared, packaged, and/or sold in a formulation suitable for ophthalmic administration. Such formulations may, for example, be in the form of eye drops including, for example, a 0.1%/1.0% (w/w) solution and/or suspension of the active ingredient in an aqueous or oily liquid excipient. Such drops may further comprise buffering agents, salts, and/or one or more other of the excipients and/or additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* $21^{st}$ ed., Lippincott Williams & Wilkins, 2005 (incorporated herein by reference).

Methods for Treating Influenza Infections

The present invention provides methods of treating influenza infection. In certain embodiments, such methods involve administering one or more inventive umbrella-topology glycan decoys to a subject in need thereof. In some embodiments, glycan decoys inhibit the ability of HA (e.g. HA expressed on the surface of influenza virus) to bind to umbrella-topology glycans (e.g. glycans associated with human upper respiratory epithelial tissues, such as trachea and bronchus).

In some embodiments, the invention provides pharmaceutical compositions comprising at least one glycan decoy and at least one pharmaceutically acceptable excipient. In other aspects, a pharmaceutical composition comprising a glycan decoy is administered to a cell, such as one in a patient suffering from and/or susceptible to influenza infection. In some embodiments, glycan decoys of the present invention are used in the treatment of influenza infection. In specific embodiments, inventive glycan decoys are used to inhibit the ability of influenza virus particles (e.g. comprising HA polypeptides) to bind to HA receptors (e.g. comprising umbrella-topology glycans).

In some embodiments, glycan decoys of the present invention are used in the treatment of one or more of the following symptoms: fever, sore throat, muscle pains, severe headache, coughing, weakness, general discomfort, pneumonia, nausea, and/or vomiting. In certain embodiments, these symptoms are caused by influenza infection.

In some embodiments, inventive pharmaceutical compositions are administered to a subject suffering from or susceptible to an influenza infection. In some embodiments, a subject is considered to be suffering from an influenza infection in the subject is displaying one or more symptoms commonly associated with influenza infection. In some embodiments, the subject is known or believed to have been exposed to the influenza virus. In some embodiments, a subject is considered to be susceptible to an influenza infection if the subject is known or believed to have been exposed to the influenza virus. In some embodiments, a subject is known or believed to have been exposed to the influenza virus if the subject has been in contact with other individuals known or suspected to have been infected with the influenza virus and/or if the subject is or has been present in a location in which influenza infection is known or thought to be prevalent.

In some embodiments, the present invention provides a method of treating influenza infection comprising steps of (1) providing a patient exhibiting symptoms of influenza infection, and (2) administering a therapeutic amount of one or more glycan decoys to the patient. In some embodiments, the present invention provides a method of treating influenza infection comprising steps of (1) providing a patient suffering from influenza infection, and (2) administering a therapeutic amount of one or more glycan decoys to the patient. In some embodiments, the present invention provides a method of treating influenza infection comprising steps of (1) providing a patient susceptible to influenza infection, and (2) administering a therapeutic amount of one or more glycan decoys to the patient.

In some embodiments, the present invention provides methods of treating influenza infection comprising steps of (1) providing a patient exhibiting symptoms of, suffering from, and/or susceptible to influenza infection, and (2) administering a substance that competes away the binding of HA polypeptides (e.g. HA polypeptides associated with influenza virus particles) with umbrella-topology glycans in human upper respiratory tissues.

In some embodiments, the present invention provides a method of preventing and/or delaying the onset of influenza infection comprising steps of (1) providing a patient susceptible to influenza infection, and (2) administering a therapeutic amount of one or more glycan decoys to the patient.

In some embodiments, the present invention provides methods of preventing and/or delaying the onset of influenza infection comprising steps of (1) providing a patient susceptible to influenza infection, and (2) administering a substance that competes away the binding of HA polypeptides (e.g. HA polypeptides associated with influenza virus particles) with umbrella-topology glycans in human upper respiratory tissues.

Administration

Inventive umbrella-topology glycan decoys are useful in the treatment of influenza infection. Thus, pharmaceutical compositions containing one or more inventive glycan decoys may be administered to one or more individuals suffering from, susceptible to, and/or exhibiting symptoms of influenza infection. The present invention therefore encompasses methods of inhibiting binding between HA polypeptides (e.g. HA polypeptides associated with influenza virus particles) and umbrella-topology glycans (e.g. glycans of human upper respiratory epithelial tissues), as well as methods of treating influenza infection in subjects.

In some embodiments, a therapeutically effective amount of a pharmaceutical composition comprising a glycan decoy is delivered to a subject and/or organism prior to, simultaneously with, and/or after diagnosis with influenza infection. In some embodiments, a therapeutic amount of a pharmaceutical composition is delivered to a patient and/or organism prior to, simultaneously with, and/or after onset of symptoms of influenza infection. In some embodiments, the amount of pharmaceutical composition is sufficient to treat, alleviate, ameliorate, relieve, delay onset of, inhibit progression of, reduce severity of, and/or reduce incidence of one or more symptoms or features of influenza infection.

Pharmaceutical compositions, according to the method of the present invention, may be administered using any amount and any route of administration effective for treatment. The exact amount required will vary from subject to subject, depending on the species, age, and general condition of the subject, the severity of the infection, the particular composition, its mode of administration, its mode of activity, and the like. Compositions of the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disorder being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

Pharmaceutical compositions of the present invention may be administered by any route. In some embodiments, pharmaceutical compositions of the present invention are administered by a variety of routes, including oral, intravenous, intramuscular, intra-arterial, intramedullary, intrathecal, parenteral, subcutaneous, intraventricular, transdermal, interdermal, rectal, intravaginal, intraperitoneal, topical (e.g. by powders, ointments, creams, gels, and/or drops), transdermal, mucosal, nasal, buccal, enteral, sublingual; by intratracheal instillation, bronchial instillation, and/or inhalation; and/or as an oral spray, nasal spray, and/or aerosol. In some embodiments, inventive compositions are administered intravenously. In some embodiments, inventive compositions are administered orally. In some embodiments, inventive compositions can be delivered using a pump (e.g., external pump or pump that is implanted within the body of a subject, such as a mechanical pump and/or an osmotic pump).

In general the most appropriate route of administration will depend upon a variety of factors including the nature of the composition (e.g., its stability in the environment of the gastrointestinal tract), the condition of the subject (e.g., whether the subject is able to tolerate oral administration), etc.

In certain embodiments, a composition may be administered in amounts ranging from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

It will be appreciated that therapeutic agents and pharmaceutical compositions of the present invention can be employed in combination therapies. In some embodiments, the present invention encompasses "therapeutic cocktails" comprising inventive compositions. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose. For example, a glycan decoy may be administered with another agent that is used to treat symptoms of influenza infection. In some embodiments, the therapies employed may achieve different effects (e.g., control of any adverse side effects).

Pharmaceutical compositions of the present invention may be administered either alone or in combination with one or more other therapeutic agents. By "in combination with," it is not intended to imply that the agents must be administered at the same time and/or formulated for delivery together, although these methods of delivery are within the scope of the invention. Compositions can be administered concurrently with, prior to, or subsequent to, one or more other desired therapeutics or medical procedures. In general, each agent will be administered at a dose and/or on a time schedule determined for that agent. Additionally, the invention encompasses the delivery of the inventive pharmaceutical compositions in combination with agents that may improve their bioavailability, reduce and/or modify their metabolism, inhibit their excretion, and/or modify their distribution within the body.

The particular combination of therapies (therapeutics and/or procedures) to employ in a combination regimen will take into account compatibility of the desired therapeutics and/or procedures and/or the desired therapeutic effect to be achieved. It will be appreciated that the therapies employed may achieve a desired effect for the same disorder (for example, an inventive agent may be administered concurrently with another therapeutic agent used to treat influenza infection), and/or they may achieve different effects (e.g., control of any adverse side effects). In some embodiments, compositions of the invention are administered with a second therapeutic agent that is approved by the U.S. Food and Drug Administration.

In will further be appreciated that therapeutically active agents utilized in combination may be administered together in a single composition or administered separately in different compositions.

In some embodiments, inventive glycan decoys may be administered in combination with one or more other glycan decoys.

In general, it is expected that agents utilized in combination with be utilized at levels that do not exceed the levels at which they are utilized individually. In some embodiments, the levels utilized in combination will be lower than those utilized individually.

The pharmaceutical compositions of the present invention may be administered alone and/or in combination with other agents that are used to treat influenza infection. In some embodiments, such agents interfere with expression or activity of an HA polypeptide. In certain embodiments, such agents comprise antibodies, such as antibodies that recognize virus particles containing a particular HA polypeptide (e.g., an HA polypeptide that binds to umbrella-topology glycans). In certain embodiments, such agents comprise nucleic acids (e.g., nucleic acid sequences complementary to HA sequences, which can be used for RNAi). In some embodiments, such agents may comprise TAMIFLU®.

In some embodiments, pharmaceutical compositions of the present invention may be administered alone and/or with other agents that are used to prevent and/or delay the onset of influenza infection. In some embodiments, such agents may comprise influenza vaccines. In certain embodiments, influenza vaccines are compositions comprising one or more of the following: (1) inactivated virus, (2) live attenuated influenza virus, for example, replication-defective virus, (3) HA polypeptide or characteristic or biologically active portion thereof, (4) nucleic acid encoding HA polypeptide or characteristic or biologically active portion thereof, (5) DNA vector that encodes HA polypeptide or characteristic or biologically active portion thereof, and/or (6) expression system, for example, cells expressing one or more influenza proteins to be used as antigens.

In certain embodiments, inactivated flu vaccines comprise one of three types of antigen preparation: inactivated whole virus, sub-virions where purified virus particles are disrupted with detergents or other reagents to solubilize the lipid envelope ("split" vaccine), or purified HA polypeptide ("subunit" vaccine). In certain embodiments, virus can be inactivated by treatment with formaldehyde, beta-propiolactone, ether, ether with detergent (such as Tween-80), cetyl trimethyl ammonium bromide (CTAB) and Triton N101, sodium deoxycholate and tri(n-butyl) phosphate. Inactivation can occur after or prior to clarification of allantoic fluid (from virus produced in eggs); the virions are isolated and purified by centrifugation (Nicholson et al., eds., *Textbook of Influenza*, Blackwell Science, Malden, M A, 1998). To assess the potency of the vaccine, the single radial immunodiffusion (SRD) test can be used (Schild et al., 1975, *Bull. World Health Organ.*, 52:43-50 & 223-31; and Mostow et al., 1975, *J. Clin. Microbiol.*, 2:531; both of which are incorporated herein by reference). In some embodiments, pharmaceutical compositions of the present invention may be administered in combination with live, attenuated flu vaccines. In some embodiments, vaccines comprise one or more adjuvants.

One of ordinary skill in the art will understand that the examples presented above are not meant to be limiting. The principles presented in the examples above can be generally applied to any combination therapies for treatment of influenza infection.

Diagnostics/Kits

The invention provides a variety of kits comprising one or more of umbrella-topology glycan decoys of the invention. For example, the invention provides kits comprising at least one glycan decoy and instructions for use. A kit may comprise multiple different glycan decoys. A kit may comprise any of a number of additional components or reagents in any combination. All of the various combinations are not set forth explicitly but each combination is included in the scope of the invention.

In some embodiments, novel glycan decoys to be utilized in inventive kits may be chemically synthesized in a laboratory. Alternatively or additionally, novel glycan decoys may be isolated from pathological samples, including, but not limited to, blood, serum/plasma, peripheral blood mononuclear cells/peripheral blood lymphocytes (PBMC/PBL), sputum, urine, feces, throat swabs, dermal lesion swabs, cerebrospinal fluids, cervical smears, pus samples, food matrices, and tissues from various parts of the body such as brain, spleen, and liver. In some embodiments, novel glycan decoys may be isolated from environmental samples, including, but not limited to, soil, water, and flora. Other samples that have not been listed may also be applicable.

According to certain embodiments of the invention, a kit may include, for example, (i) an umbrella-topology glycan decoy; (ii) instructions for administering the glycan decoy to a subject suffering from, susceptible to, and/or exhibiting symptoms of influenza infection.

According to certain embodiments of the invention, a kit for identifying glycan decoys may include, for example, (i) HA polypeptide; (ii) at least one candidate glycan decoy, such as a glycan array comprising a plurality of candidate glycan decoys; (iii) a positive control (e.g. umbrella-topology glycan known to bind to HA polypeptides); (iv) a negative control (e.g. cone-topology glycan); (v) instructions for determining whether the HA polypeptide is able to bind to a candidate decoy or whether a candidate decoy is able to compete away the binding between the HA polypeptide and the positive control.

Kits typically include instructions for use of inventive glycan decoys. Instructions may, for example, comprise protocols and/or describe conditions for identification of glycan decoys, administration of glycan decoys to a subject in need thereof, etc. Kits generally include one or more vessels or containers so that some or all of the individual components and reagents may be separately housed. Kits may also include a means for enclosing individual containers in relatively close confinement for commercial sale, e.g., a plastic box, in which instructions, packaging materials such as styrofoam, etc., may be enclosed. An identifier, e.g., a bar code, radio frequency identification (RFID) tag, etc., may be present in or on the kit or in or one or more of the vessels or containers included in the kit. An identifier can be used, e.g., to uniquely identify the kit for purposes of quality control, inventory control, tracking, movement between workstations, etc.

In certain embodiments, inventive glycan arrays and/or kits are used to perform dose response studies to assess binding of HA polypeptides to umbrella-topology glycans and/or glycan decoys (e.g. candidate umbrella-topology glycan decoys) at multiple doses (e.g., as described herein). Such studies give particularly valuable insight into the binding characteristics of tested HA polypeptides, and are particularly useful to assess specific binding. Dose response binding studies of this type find many useful applications. To give but one example, they can be helpful in tracking the evolution of binding characteristics in a related series of HA polypeptide variants, whether the series is generated through natural evolution, intentional engineering, or a combination of the two.

EXEMPLIFICATION

The representative Examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following Examples contain important additional information, exemplification and guidance that can be adapted to the practice of this invention in its various embodiments and the equivalents thereof. It will be appreciated, however, that these examples do not limit the invention. Variations of the invention, now known and/or further developed, are considered to fall within the scope of the present invention as described herein and as hereinafter claimed.

Example 1

Framework for Binding Specificity of H1, H3, and H5 HAs to α2-3 and α2-6 Sialylated Glycans Crystal structures of HAs from H1 (PDB IDS: 1RD8, 1RU7, 1RUY, 1RV0, 1RVT, 1RVX, 1RVZ), H3 (PDB IDs: 1MQL, 1MQM, 1MQN) and H5 (1JSN, 1JSO, 2FK0) and their complexes with α2-3 and/or α2-6 sialylated oligosaccharides have provided molecular insights into residues involved in specific HA-glycan interactions. Analyses of these HA-glycan co-crystal structures indicated that the orientation of the Neu5Ac sugar (SA) is fixed relative to the HA glycan binding site. A highly-conserved set of amino acids (including Tyr98, Ser/Thr136, Trp153, His183, Leu/Ile194, numbered based on H3 HA) across different HA subtypes are involved in anchoring the SA. The specificity of HA to α2-3 or α2-6 is therefore governed by interactions of the HA glycan binding site with the glycosidic oxygen atom and sugars beyond SA.

The conformation of the Neu5Acα2-3Gal linkage is such that Gal and sugars beyond Gal (at the reducing end, and in both linear and branched α2-3), occupy a "cone-like" region of space, and is governed by the glycosidic torsion angles at this linkage; hence, the present inventors define it as a "cone-like glycan topology" (FIGS. 6 and 7). In the cone-like topology, HA interactions with glycans primarily involve contacts with Neu5Ac and Gal sugars in a three sugar (or trisaccharide) α2-3 motif (Neu5Acα2-3Galβ1-3/4GlcNAc-), and this observation is corroborated by the co-crystal structures. In addition to amino acids Glu190 and Gln226 (FIG. 6), contacts with α2-3 motif and substitutions such as sulfation and fucosylation of this motif appear to involve key amino acid positions (FIG. 6). The variability of amino acids in these positions could potentially account for the differential binding specificity of HA to the diverse α2-3 sialylated glycans (see below). As against the Neu5Acα2-3Gal linkage, the presence of the $C_6$-$C_5$ bond provides additional glycan conformational flexibility in the case of Neu5Acα2-6Gal linkage (FIG. 7). This flexibility leads to the α2-6 motif adopting both a cone-like topology, as well as a wider region of space as in an "umbrella," hence the present inventors define it as an "umbrella-like glycan topology" (FIGS. 6 and 7). The umbrella-like topology, therefore spans a wider region on the HA surface than does the cone-like topology. In contrast to the cone-like topology, oligosaccharide length and degree of branching beyond a trisaccharide influence HA binding contacts in the umbrella-like topology. Therefore, the present invention encompasses the recognition that amino acids involved in interactions with the umbrella-like topology (key numbered positions shown in FIG. 6) are not conserved across the human adapted H1 and H3 HAs. Depending upon the HA subtype, a combination of amino acids at these positions are involved in interacting with a long α2-6, and this observation is corroborated by the co-crystal structures of H1 and H3 with α2-6 oligosaccharides. Cone-like topology is therefore characteristic of α2-3 as well as short α2-6 glycans such as single lactosamine branches (FIG. 8). On the other hand, umbrella-like topology is unique to α2-6 and is typically adopted by long glycans with multiple repeating lactosamine units (FIG. 9).

Interrogation of HA-glycan co-crystal structures highlights the fact that the human adapted H1 and H3 HAs have mutated from their presumed avian counterparts to gain additional contacts with α2-6 in the umbrella-like topology. Defining HA-glycan interactions based on trans and cis conformations (adopted by α2-3 and α2-6 linkages, respectively) is inadequate as this does not fully capture the structural features and conformational flexibility of the diverse sialylated glycans observed in human tissues. However, the "cone-like" and "umbrella-like" classification for HA binding fully captures the structural diversity and conformational plurality of sialylated glycans. Significantly, this classification is able to distinguish α2-3 and α2-6 binding of avian HAs from that of α2-6 binding of human adapted H1 and H3 HAs.

Characteristics of HA binding to cone-like and umbrella-like topologies were further corroborated using a novel data mining approach to analyze the extensive glycan array data available for H1, H3, and H5 HAs. Data mining analysis provided correlations between glycan features (Table 3 and FIG. 10) abstracted from glycans on the array and HA binding to these glycans. These correlations are given as rules or classifiers (Table 4 and FIG. 10) which verify the above structural constraints.

TABLE 3

Features Extracted from the Glycans on the Glycan Array

| Features Extracted | Feature Description |
|---|---|
| | Monosaccharide Level |
| Composition | Number of hex, hexNAcs, dHex, sialic acids, etc. Terminal composition is distinctly recorded. |
| Explicit Composition | Number of Glc, Gal, GlcNAc, Fuc, GalNAc, Neu5Ac, Neu5Gc, etc. Terminal explicit composition is explicitly recorded. |
| | Higher Order Features |
| Pairs | Pair refers to a pair of monosaccharide, connected covalently by a linkage. The pairs are classified into two categories, regular [B] and terminal [T] to distinguish between the pair with one monosaccharide that terminates in the non reducing end. The frequency of the pairs was extracted as features. |
| Triplets | Triplet refers to a set of three monosaccharides connected covalently by two linkages. We classify them into three categories namely regular [B], terminal [T], and surface [S]. The compositions of each category of triplets were extracted as features |
| Quadruplets | Similar to the triplet features, quadruplet features are also extracted, with four monosaccharides and their linkages. Quadruplets are classified into two varieties regular [B] and surface [S]. The frequencies of the different quadruplets were extracted as features. |
| Clusters | In the case of surface triplets and quadruplets above, if the linkage information is ignored, we get a set of monosaccharide clusters, and their frequency of occurrence (composition) is tabulated. These features were chosen to analyze the importance of types of linkages between the monosaccharides. |
| Average Leaf Depth | As an indicator of the effective length of the probes, average depth of the reducing end of the tree is extracted as a glycan feature. |
| Number of Leaves | As a measure of spread of the glycan tree, the number of non reducing monosaccharides is extracted as a feature. |

TABLE 3-continued

| Features Extracted from the Glycans on the Glycan Array | |
|---|---|
| Features Extracted | Feature Description |
| GBP Binding Features (obtained for all GBPs screened using the array) | |
| Mean signal per glycan | Raw signal value averaged over triplicate or quadruplicate [depending on array version] representation of the same glycan |
| Signal to Noise Ratio | Mean noise computed based on negative control [standardized method developed by CFG] to calculate signal to noise ratio [S/N] |

TABLE 4

| Classifier Rules | |
|---|---|
| Classifier ID | Classifier Rule |
| α2-3 Type A | Neu5Acα3Gal & !GalNAcβ4Gal |
| α2-3 Type B | Neu5Acα3Galβ4GlcNAc & !GalNAcβ4Gal & {GlcNAcβ3Gal or GlcNAc[6S]} |
| α2-3 Type C | Neu5Acα3Galβ & !GalNAcβ4Gal & !Fucα3/4GlcNAc |
| α2-6 Type A | Neu5Acα6Galβ4GlcNAcβ3Gal |
| α2-6 Type B | Neu5Acα6Galβ4GlcNAc-Core OR Neu5Acα6Galβ4Glc-Core |

Figure 11:
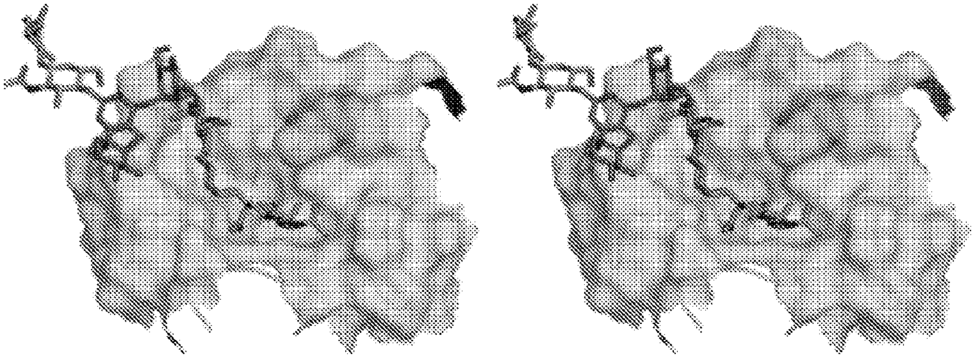
FIG. 11: Binding of Viet04-H5 HA to biantennary α2-6 sialylated glycan (cone-topology). Stereo view of surface rendered Viet04_H5 glycan binding site with Neu5Acα2-6Gal linkage in the extended conformation (obtained from the pertussis toxin co-crystal structure; PDB ID: 1PTO). Lys193 (orange) does not have any contacts with the glycan in this conformation. Additional amino acids potentially involved in binding to the glycan in this conformation include Asn186, Lys222, and Ser227. However, certain contacts observed in HA binding to a α2-6 sialylated oligosaccharide in the cis-conformation are absent in the extended conformation. Without wishing to be bound by any particular theory, we note that this suggests that the extended conformation may not bind to HA as optimally as the cis-conformation. Structures of branched N-linked glycans where the Neu5Acα2-6Galβ1-4GlcNAcb branch was attached to the Manα1-3Man (PDB ID: 1LGC) and Manal-6Man (PDB ID: IZAG) were superimposed on to the Neu5Acα2-6Gal linkage in the Viet04_H5 HA binding site for both the cis and the extended conformation of this linkage. The superimposition shows that the structure with Neu5Acα2-6Galβ1-4GlcNAc branch attached to Manα1-6Man of the core has unfavorable steric overlaps with the binding site (in both the conformations). On the other hand, the structure with this branch attached to Manα1-3Man of the core (shown in figure where trimannose core is colored in purple) has steric overlaps with Lys193 in the cis-conformation but can bind without any contact with Lys 193 in the extended conformation, albeit less optimally.

Classifier rules were obtained based on the features defined in FIG. 10 and in Table 4 that Consistent with these observations, distinct α2-3 classifiers (FIG. 10) indicated that variations around the trisaccharide α2-3 motif primarily influence the differential α2-3 binding of H1, H3, and H5 HAs. Among the different avian HAs analyzed on the glycan array, H5 HAs show the most diverse binding to α2-3 including sulfated and fucosylated α2-3. The highly conserved Asn186, Lys193, and Lys222 in avian H5 HAs are positioned to provide optimal contacts to different sulfate and fucose substitutions in the trisaccharide α2-3 motif. On the other hand, length-dependent α2-6 classifiers (FIG. 10) support the role of oligosaccharide length in HA binding to α2-6 in the umbrella-like topology. The α2-6 classifier common to the human adapted H1 and H3 HAs is consistent with their gain in ability to bind long α2-6. Glycan binding of wild type (WT) and mutant H5N1 HAs is, however, not supported by the long α2-6 classifier although it is supported by both α2-3 and short α2-6 classifiers (FIG. 10). The interaction between H5N1 HA with a biantennary short α2-6 glycan is illustrated in FIG. 11. Thus, the present invention encompasses the recognition that current avian viruses (such as H5N1, H7N7 and H9N1) will need to acquire HA mutations in order to make optimal contacts with α2-6 glycan in the umbrella-like topology (illustrated in FIGS. 6 and 9).

Example 2

HA Mutations Leading to Human Adaptation of H5N1 Viruses

In the following, H5 HA is used as an illustrative example to describe identification of mutations that could provide optimal contacts with long α2-6 adopting umbrella-like topology. Since H1, H2, and H5 HA belong to the same structural clade, they would have almost identical backbone structures and loop topologies. Based on this classification, mutations in H5 HA that would provide "H1-like" or "H2-like" contacts with long α2-6 glycans are defined.

H1-Like Mutations

Analysis of H1 HA-α2-6 glycan co-crystal structures showed that HA contacts can be divided into two regions—a base region involving contacts with Neu5Acα2-6Galβ1-motif and an extension region involving contacts with -GlcNAcβ1-3Galβ1-4Glcβ1- motif. In addition to highly conserved SA anchors (as described above), HA residues involved in base contacts are Lys222, Asp225 and Gln226. HA residues involved in extension contacts are Asp190, Gln192 and Ser193. Superimposition of the glycan binding sites of H1 and H5 HAs indicates that H5 HA already has a few residues such as Lys222 and Gln226 positioned to interact with base region. Lys193 (in H5 HA) could potentially have unfavorable steric contacts with the extension region when compared to Ser193 (in H1 HA). Consistent with this observation, the H5 HA double mutant Glu190Asp/Gly225Asp (which has Asp190 and Asp225, as observed in H1 HA) does not show any binding signal for α2-6 glycans in the glycan array due to possible steric interference from Lys193. Thus, the present invention encompasses the recognition that a combination of mutations at positions 190, 192, 193 and 225 would provide optimal "H1-like" contacts with long α2-6.

H2-Like Mutations

Given the high sequence similarity of H5 to H2 HA, this provides another perspective for defining H5 HA mutations for human receptor specificity. There are no crystal structures of H2 HA to date. Preliminary comparison of avian and human adapted H2 HA sequences indicates two primary amino acid changes (Gln226Leu and Gly228Ser) from avian to human H2 HA. Therefore, the present invention encompasses the recognition that a combination of these mutations taken together with other mutations at the above residue positions would provide optimal "H2-like" contacts with long α2-6.

Example 3

Glycan Diversity in Human Upper Respiratory Tissues

Since human upper respiratory epithelia are primary targets for influenza A virus human infection and human-human transmission, the present inventors set out to identify what the different types of sialylated glycans are in these tissues. The approach was to bridge lectin staining of different tissue sections with glycan profiling of representative human cell lines using MALDI-MS and MS/MS (TOF-TOF) analyses. To elaborate the diversity of the α2-6 glycans predominantly expressed in the upper respiratory tissues, representative human tracheal sections were co-stained with a panel of plant lectins. *Sambucus nigra* agglutinin (SNA-I) is a prototypic lectin that specifically binds to α2-6 glycans. Jacalin and Concanavalin A (Con A) bind to specific motifs in O-linked (-Galβ1-3GalNAcα- and -GlcNAcβ1-3GalNAcα-) and N-linked (trimannosyl core) glycans, respectively. Lectin binding studies showed diversity in the distribution of α2-3 and α2-6 in upper respiratory tissues. Staining studies indicate predominant distribution of α2-6 sialylated glycans as a part of both N-linked (ciliated cells) and O-linked glycans (in the goblet cells) on the apical side of the tracheal epithelium (FIGS. 12 and 13). On the other hand, the internal regions of the tracheal tissue predominantly comprises of α2-3 distributed on N-linked glycans.

MALDI-MS glycan profiling analyses showed a substantial diversity (FIG. 13) as well as predominant expression of α2-6 sialylated glycans on the human upper airways. Fragmentation of representative mass peaks using MALDI TOF-TOF supports glycan topologies where longer oligosaccharide branches with multiple lactosamine repeats are extensively distributed as compared to short oligosaccharide branches (FIG. 13).

Figure 13A:
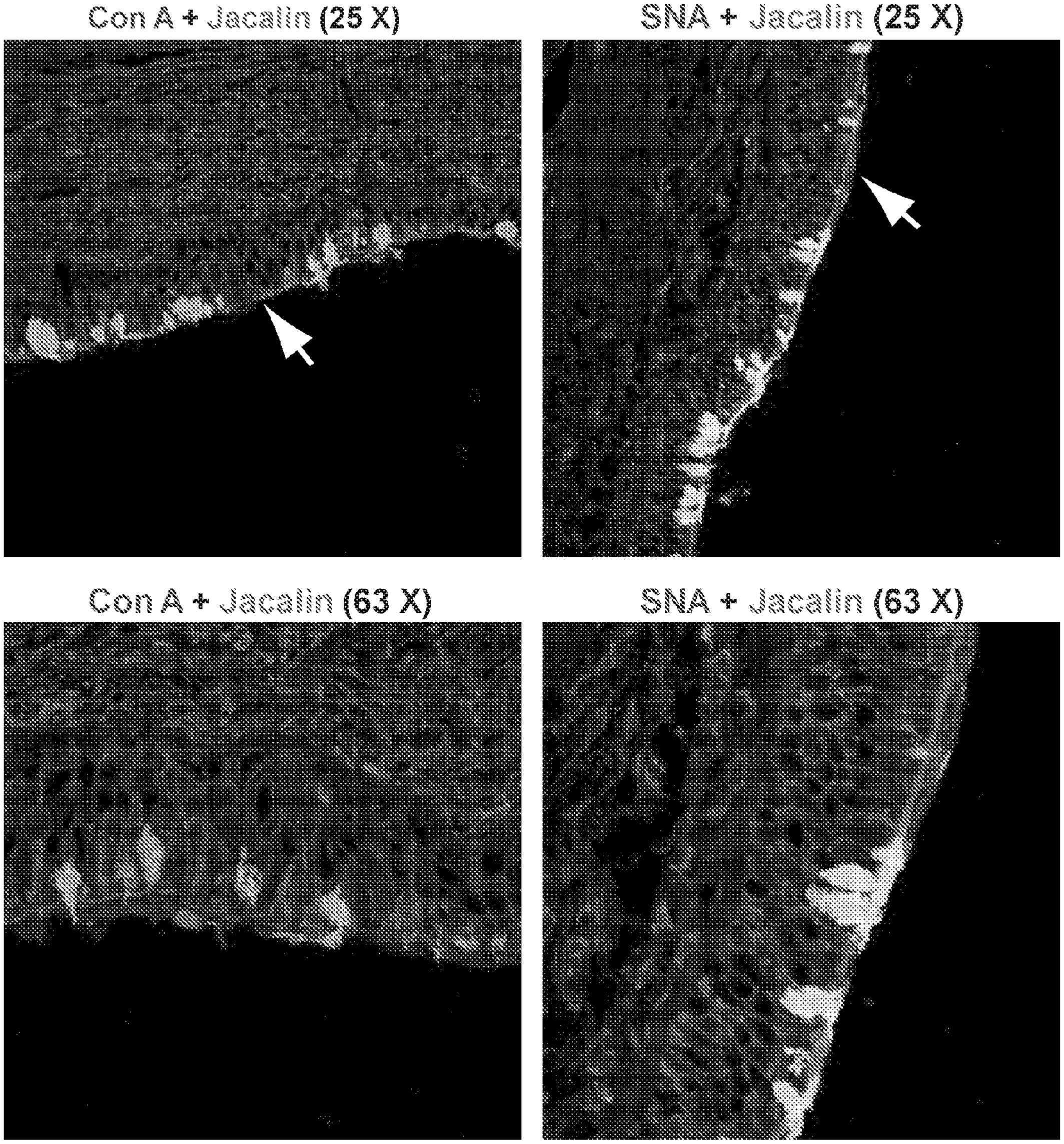
FIG. 13: Glycan diversity in human upper respiratory tissues. (A) Co-staining of tracheal tissue sections with ConA (red)/Jacalin (green) and SNA-1 (red)/Jacalin (green). Localized regions of Jacalin binding correspond to goblet cells expressing O-linked glycans, and regions of Con A binding correspond to ciliated cells expressing N-linked glycans (white arrow) on the apical side of the tracheal epithelium. The extensive binding of SNA-1 to both goblet cells (co-stain with Jacalin in yellow) and ciliated cells, respectively, shows predominant expression of O-linked and N-linked α2-6 on the apical side. Given that ciliated epithelia predominantly express N-linked α2-6, MALDI-MS analysis of N-linked glycans isolated from human bronchial epithelial (HBE) cells was performed. HBE cells were chosen as representative upper respiratory ciliated epithelial cells based on the extensive attachment of human adapted H1N1 and H3N2 viruses to these cells. (B) MALDI-MS glycan profile of HBE cells is shown using graphical representation (without explicit linkage assignment) of possible sialylated glycan structures that satisfy the mass peaks (within ±3.5 Daltons). HBEs predominantly express α2-6 (in comparison with α2-3) sialylated glycans. (C) Desialylation using Sialidase A and subsequent 2-AB labeling of the N-linked glycans observed in (B) to deconvolute the branching pattern from the number of sialic acids. Peaks highlighted in cyan in (B) and (C) were further analyzed using TOFTOF MS. (D) The MS-MS profile of a representative peak at m/z 2148 shows fragment ions at m/z 548 and 713 and their corresponding counter ions (shown in red) that support the long oligosaccharide branch (with multiple lactosamine repeats) over multiple short lactosamine branches. MS-MS profile of m/z 2660 also supports long oligosaccharide branch.
Figure 13B:
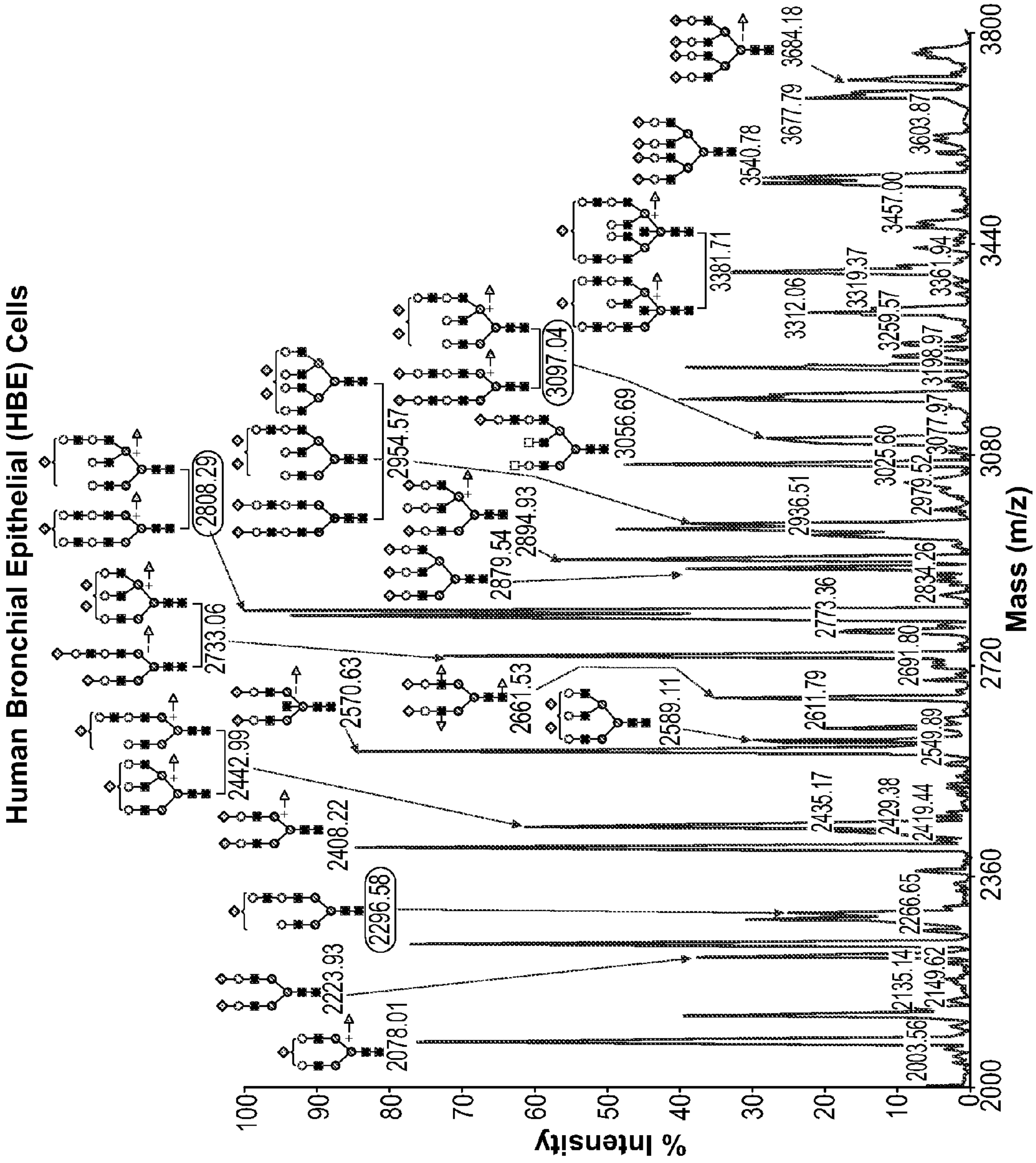
Figure 13C:
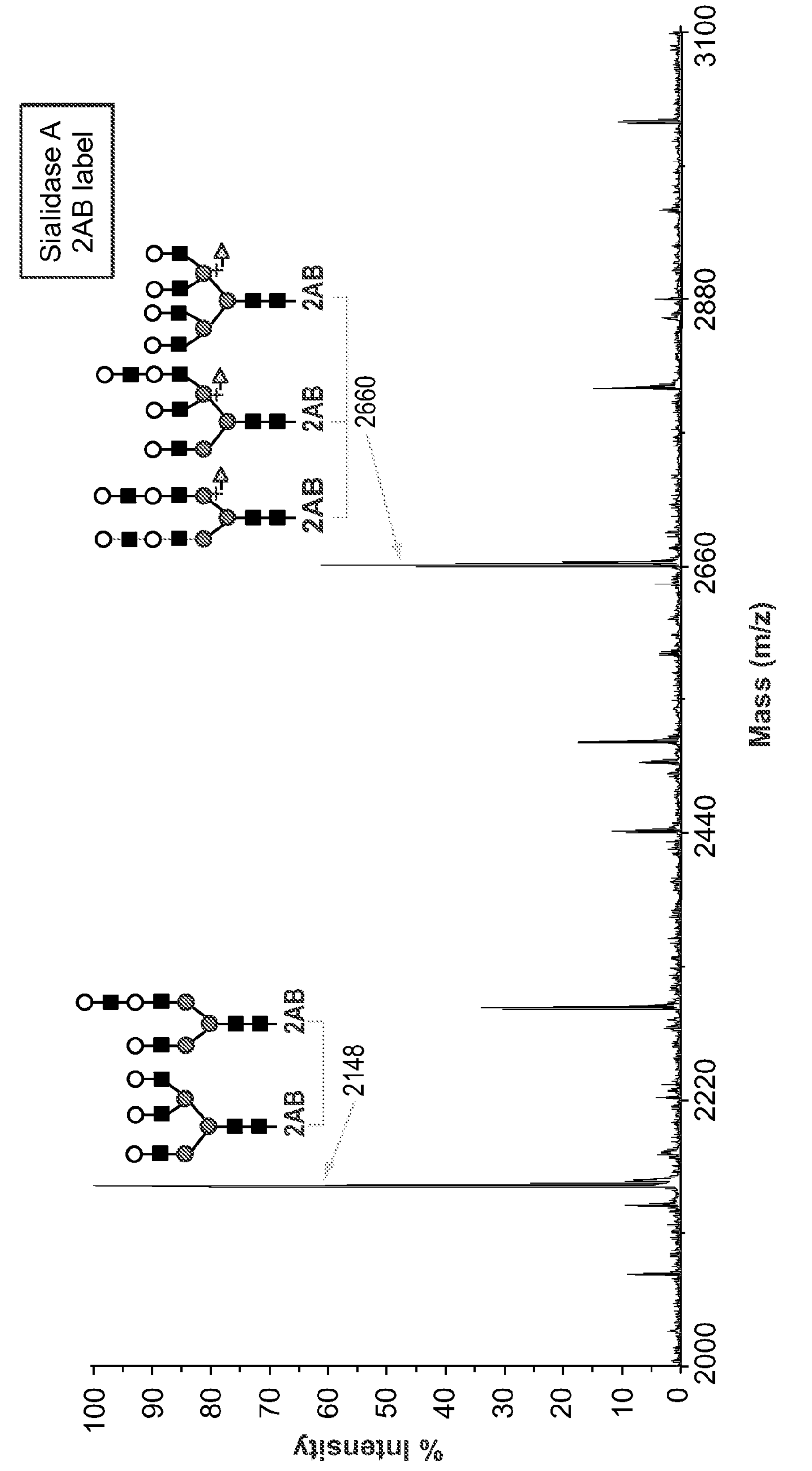
Figure 13D:
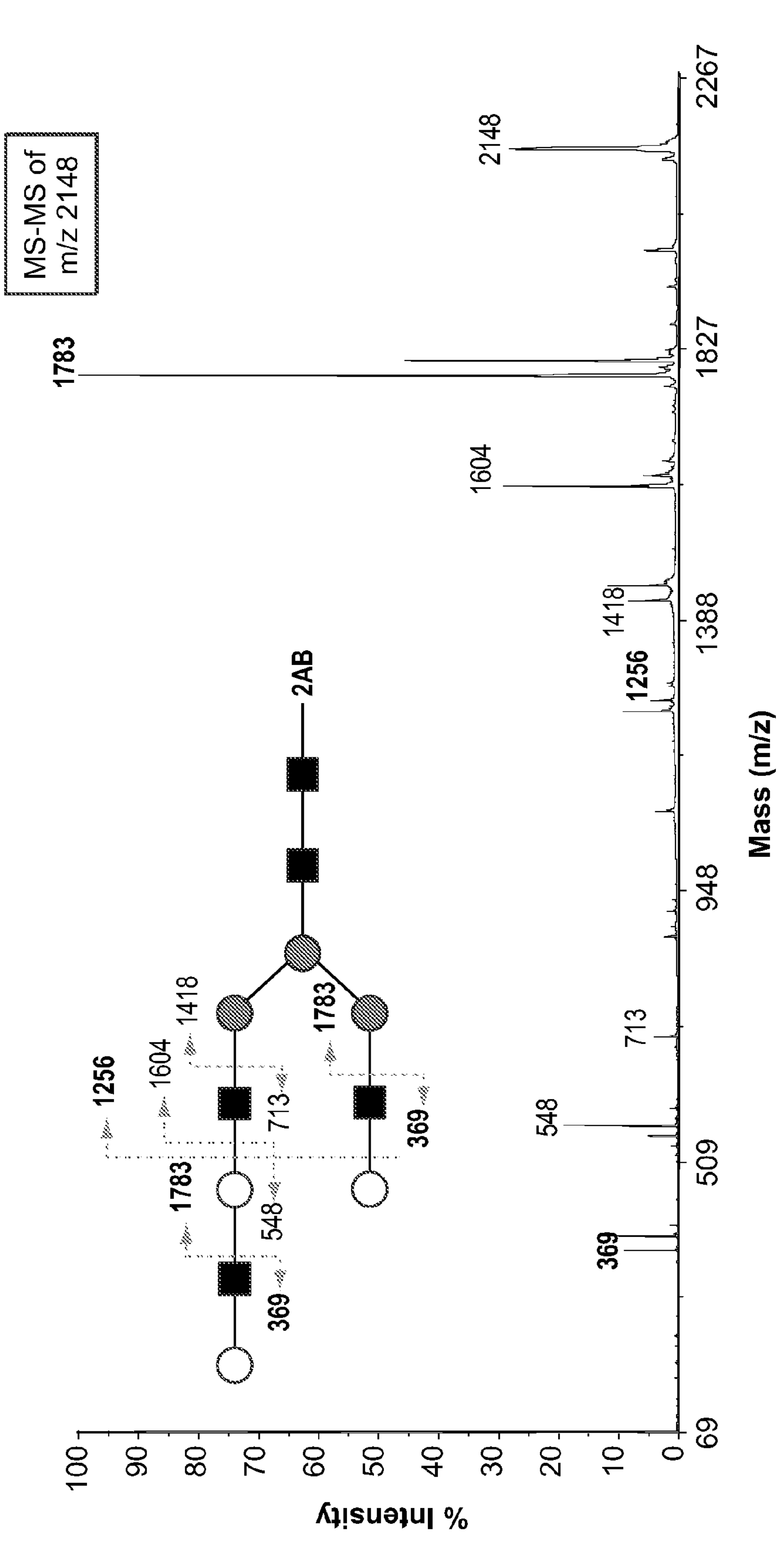

Data in FIGS. 12 and 13A were generated by the following method. Formalin-fixed and paraffin-embedded human tracheal tissue sections were purchased from US Biological. After the tissue sections were deparaffinized and rehydrated, endogenous biotin was blocked using the streptavidin/biotin blocking kit (Vector Labs). Sections were then incubated with FITC labeled Jacalin (specific for O-linked glycans), biotinylated Concanavalin A (Con A, specific for α-linked mannose residues, which are part of the core oligosaccharide structure that constitute N-linked glycans), biotinylated Maackia amurensis lectin (MAL, specific for SAα-2,3-Gal) and biotinylated Sambuccus nigra agglutinin (SNA, specific for SAα-2,6-Gal) (Vector labs; 10 μg/ml in PBS with 0.5% Tween-20) for 3 hours. After washing with TBST (Tris buffered saline with 1% Tween-20), sections were incubated with Alexa fluor 546 streptavidin (2 μg/ml in PBS with 0.5% Tween-20) for 1 hour. Slides were washed with TBST and viewed under a confocal microscope (Zeiss LSM510 laser scanning confocal microscopy). All incubations were performed at room temperature.

Data in FIG. 13 were generated using the following method. Human bronchial epithelial (HBE) cells (16HBE14o-; Gruenert, D. C., University of California, San Francisco) were chosen as representative upper respiratory ciliated epithelial cells based on the extensive attachment of human adapted H1N1 and H3N2 viruses to these cells. These cells (~$70\times10^6$) were harvested when they were >90% confluent with 100 mM citrate saline buffer and the cell membrane was isolated after treatment with protease inhibitor (Calbiochem) and homogenization. The cell membrane fraction was treated with PNGaseF (New England Biolabs) and the reaction mixture was incubated overnight at 37° C. The reaction mixture was boiled for 10 minutes to deactivate the enzyme and the deglycosylated peptides and proteins were removed using a Sep-Pak C18 SPE cartridge (Waters). Glycans were further desalted and purified into neutral (25% acetonitrile fraction) and acidic (50% acetonitrile containing 0.05% trifluoroacetic acid) fractions using graphitized carbon solid-phase extraction columns (Supelco). Acidic fractions were analyzed by MALDI-TOF MS in positive and negative modes respectively with soft ionization conditions (accelerating voltage 22 kV, grid voltage 93%, guide wire 0.3% and extraction delay time of 150 ns). Peaks were calibrated as non-sodiated species. The predominant expression of α2-6 sialylated glycans was confirmed by pretreatment of samples using Sialidase A and S. Isolated glycans were subsequently incubated with 0.1 U of *Arthrobacter ureafaciens* sialidase (Sialidase A, non-specific) or *Streptococcus pneumoniae* sialidase (Sialidase S, specific for α2-3 sialylated glycans) in a final volume of 100 ml of 50 mM sodium phosphate, pH 6.0 at 37° C. for 24 hours. The neutral and the acidic fractions were analyzed by MALDI-TOF MS in positive and negative modes, respectively. Sialidase A-treated glycans were 2-aminobenzamide (2-AB) derivatized and lyophilized. MS/MS mass spectra were acquired on an Applied Biosystems 4700 TOF/TOF Proteomics analyzer, equipped with delayed extraction and a UV laser (355 nm) controlled by AB 4700 Data Explorer software. 1 μl of a 5 mg/ml solution of α-cyano-4-hydroxycinnamic acid prepared in acetonitrile/water mixture (60:40, v/v) was seeded on a standard 192-well stainless steel MALDI sample plate and allowed to air dry. Subsequently, 1 μl of 2-AB labeled glycan sample was spotted on the matrix and allowed to dry. Typically, 1000-5000 shots/spectrum was collected in the positive reflector mode for MS/MS spectra. CID mode (with air as the collision gas) with a chamber pressure of $1\text{-}6\times10^{-6}$ Torr and acceleration voltage of 2 kV was used for glycan fragmentation and internal peptide standards were used for calibration.

Example 4

Dose-Response Binding of H1 and H3 HA to Human Lung Tissues

Figure 14:
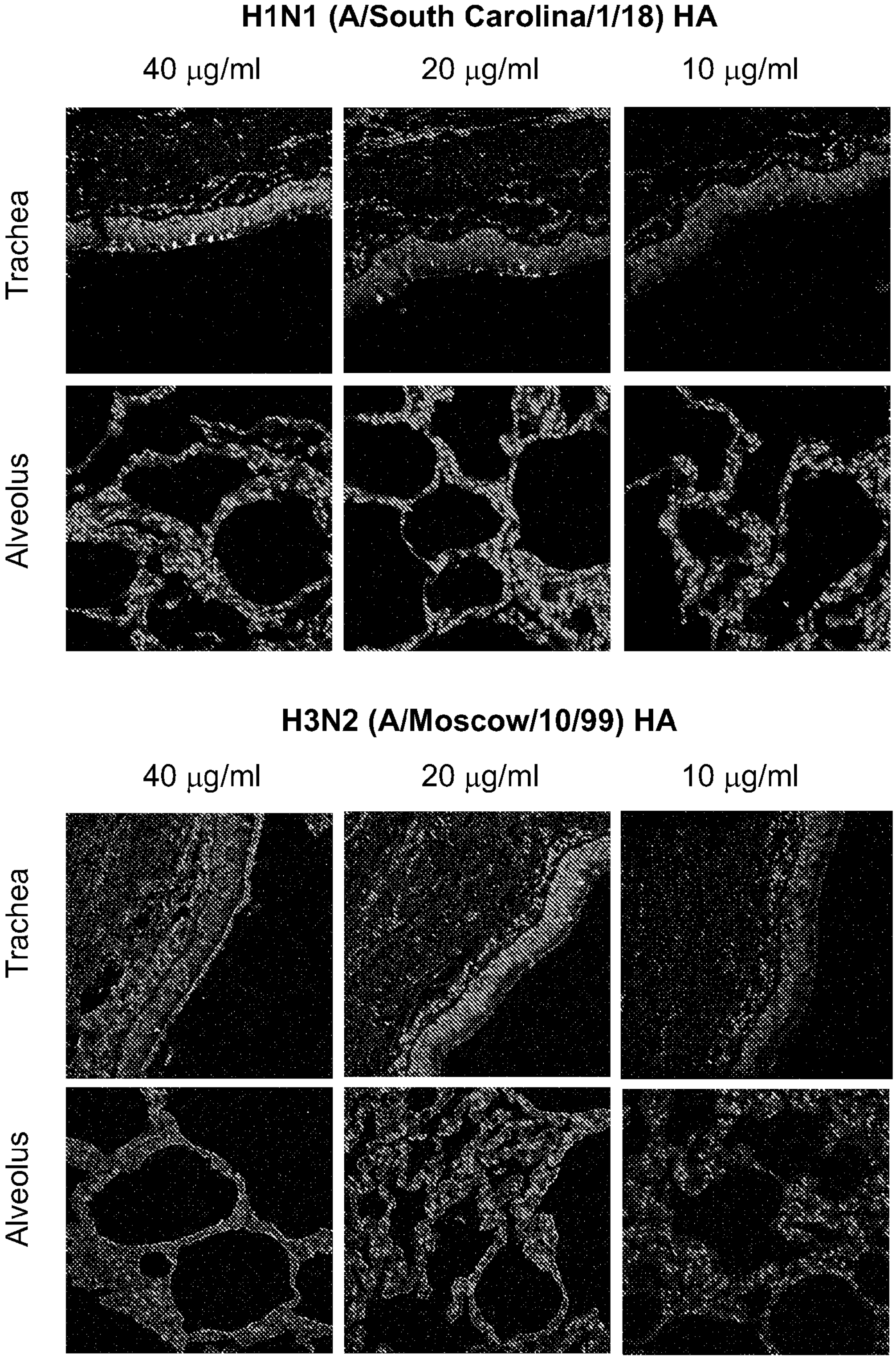
FIG. 14: Dose-response binding of recombinant H1, H3 WT HA to upper and lower respiratory tissue sections. HA binding is shown in green against propidium iodide staining (red). The apical side of tracheal tissue predominantly expresses α2-6 glycans with long branch topology. Alveolar tissue, on the other hand, predominantly expresses α2-3 glycans. H1 HA binds significantly to the apical surface of the trachea and its binding reduces gradually with dilution from 40 μg/ml to 10 μg/ml. H1 HA also shows some weak binding to the alveolar tissue only at the highest concentration. The binding pattern of H3 HA is different from that of H1 HA. For example, H3 HA shows significant binding to both tracheal and alveolar tissue sections at 40 μg/ml and 20 μg/ml. However, at a concentration of 10 μg/ml, H3 HA shows binding primarily to the apical side of the tracheal tissue and little or no binding to the alveolar tissue. Together, these tissue binding data highlight the importance of high affinity binding to the apical side of tracheal tissue. Furthermore, these data reveal that high specificity for α2-6 sialylated glycan (as demonstrated by H1 HA) is not absolutely required to mediate infection of humans, since H3 HA shows some affinity for α2-3 sialylated glycans.

The apical side of tracheal tissue predominantly expresses α2-6 glycans with long branch topology. The alveolar tissue on the other hand predominantly expresses α2-3 glycans. HAs from the hallmark pandemic SC18 and the human vaccine strain A/Moscow/10/99H3N2 (Mos99) were chosen as typical representative human adapted H1 and H3 candidates. H1 HA binds significantly to localized regions on the apical surface of the trachea and its binding reduces gradually with dilution from 40 μg/ml to 10 μg/ml (FIG. 14). H1 HA also shows some weak binding to the alveolar tissue only at the highest concentration. The binding pattern of H3 HA is different from that of H1 HA where in H3 HA shows significant binding to both tracheal and alveolar tissue sections at 40 μg/ml and 20 μg/ml (FIG. 14). However, at a concentration of 10 μg/ml, the HA shows binding primarily to the apical side of the tracheal tissue and little to no binding to the alveolar tissue. Furthermore, the apical side binding of H3 HA is well distributed in contrast with the localized binding of H1 HA. Together, the tissue binding data point to the high affinity binding of H1 and H3 HA to the apical side of the tracheal tissue and, while H3 HA shows affinity for α2-3 (relatively lower than α2-6), H1 HA is highly specific for α2-6.

The data in FIG. 14 were generated using the following methods. Formalin-fixed and paraffin-embedded human tissue lung and tracheal sections were purchased from US Biomax, Inc and from US Biological, respectively. Tissue sections were deparaffinized, rehydrated and incubated with 1% BSA in PBS for 30 minutes to prevent non-specific binding. H1N1 and H3N2 HA were pre-complexed with primary antibody (mouse-anti 6×His tag, Abcam) and secondary antibody (Alexa fluor 488 goat anti-mouse, Invitrogen) in a ratio of 4:2:1, respectively, for 20 minutes on ice. Formed complexes were diluted in 1% BSA (in PBS) to a final HA concentration of 40 μg/ml, 20 μg/ml, or 10 μg/ml. Tissue sections were then incubated with the HA-antibody complexes for 3 hours at room temperature. Sections were counterstained with propidium iodide (Invitrogen; 1:100 in TBST), washed extensively and then viewed under a confocal microscope (Zeiss LSM510 laser scanning confocal microscopy).

Example 5

Dose Response Direct Binding of Wild Type HA Polypeptides to Glycans of Different Topology As described herein, the present invention encompasses the recognition that binding by HA polypeptides to glycans having a particular topology, herein termed "umbrella" topology, correlates with ability of the HA polypeptides to mediate infection of human hosts. The present Example describes results of direct binding studies with different HA polypeptides that mediate infection of different hosts, and illustrates the correlation between human infection and umbrella-topology glycan binding.

Direct binding assays typically utilize glycan arrays in which defined glycan structures (e.g., monovalent or multivalent) are presented on a support (e.g., glass slides or well plates), often using a polymer backbone. In so-called "sequential" assays, trimeric HA polypeptide is bound to the array and then is detected, for example using labeled (e.g., with FITC or horseradish peroxidase) primary and secondary antibodies. In "multivalent" assays, trimeric HA is first complexed with primary and secondary antibodies (typically in a 4:2:1 HA:primary:secondary ratio), such that there are 12 glycan binding sites per pre-complexed HA, and is then contacted with the array. Binding assays are typically carried out over a range of HA concentrations, so that information is obtained regarding relative affinities for different glycans in the array.

For example, direct binding studies were performed with arrays having different glycans such as 3'SLN, 6'SLN, 3'SLN-LN, 6'SLN-LN, and 3'SLN-LN-LN, where LN represents Galβ1-4GlcNAc, 3' represents Neu5Acα2-3, and 6' represents Neu5Acα2-6). Specifically, biotinylated glycans (50 μl of 120 μmol/ml) were incubated overnight (in PBS at 4° C.) with a streptavidin-coated High Binding Capacity 384-well plate that was previously rinsed three times with PBS. The plate was then washed three times with PBS to remove excess glycan, and was used without further processing.

During the early stages of development of dose-dependent direct binding assays using the biotin-avidin glycan array plate, different concentrations of His-tagged HA protein, primary antibody (mouse anti-6×His tag) and secondary antibody (HRP conjugated goat anti-mouse IgG) were incubated to achieve the ratio of 4:2:1 HA:primary:secondary. However, in this assay, it was challenging to detect binding signals at low HA concentrations since the binding kinetics limit the formation of HA precomplex at these concentrations (below 2.5 μg/ml). In order to accurately quantify relative binding affinities, binding of the precomplex was measured at a lower concentration range (0.05 μg/ml to 5 μg/ml). Towards addressing this issue, the binding assay was modified subsequently by preparation of the precomplex at the highest HA concentration followed by serial dilution of the stock. Briefly, the mixture (i.e., precomplexed HA) was then made up to a final volume of 250 μl with 1% BSA in PBS. 50 μl of the precomplexed HA was then added to the glycan-coated wells in the 384-well plate, and was incubated at room temperature for 2 hours. The wells were subsequently washed three times with PBS containing 0.05% TWEEN-20, and then three times with PBS. Direct binding studies were also done for representative H5N1 viruses to compare their HA binding specificity with that of human adapted HAs. Virus stocks (from CDC) were propagated in the allantoic cavity of 10-day-old embryonated hens' eggs at 37° C. Allantoic fluids were harvested 24 hours post inoculation and inactivated by treatment with B-propiolactone (BPL; 1/1,000) for 3 days at 4° C. Virus binding to the glycan-coated wells was performed as described (Yamada et al, 2006, *Nature,* 444:378; incorporated herein by reference) by adding appropriate amount of virus to each well after diluting in PBS containing 1% bovine serum albumin and incubating overnight at 4° C. After rinsing excess virus with PBS containing 0.05% Tween-20 and PBS, wells were incubated with antibody against the virus (ferret-α-influenza A raised against A/Hong Kong/213/03H5N1) for 5 hours at 4° C. Following extensive washing of the antibody, the plate was incubated with HRP-linked goat-α-ferret antibody (Rockland Immunochemicals) for 2 hours at 4° C. After extensive washes with PBS containing 0.05% Tween-20 and PBS, in all cases, HRP activity was estimated using Amplex Red Peroxidase Kit (Invitrogen, CA) according to the manufacturer's instructions. Serial dilutions of HA precomplexes were studied. Appropriate negative (non-sialylated glycans) and background (no glycans or no HA) controls were included, and all assays were done in triplicate. Results are presented in FIGS. 15 and 16.

Figure 15:
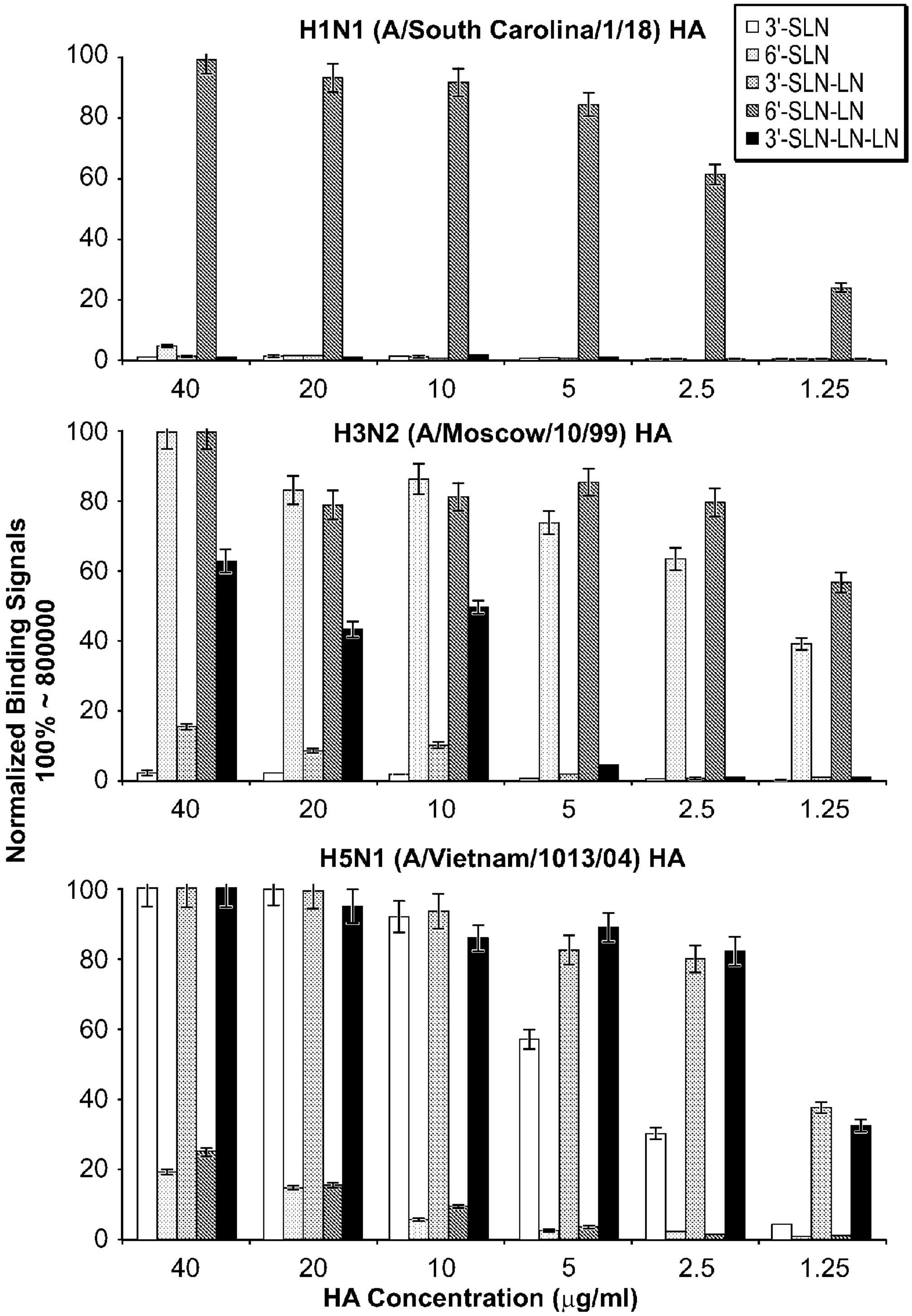
FIG. 15: Dose-Dependent Direct Binding of human adapted H1, H2, and H3 HAs. The characteristic binding pattern of human adapted H1, H2, and H3 HAs is their binding at saturating levels over a range of HA dilution from 40 μg/ml to 2.5 μg/ml. The narrow specificity of H1 HA (SC18) correlates with its restrictive tracheal tissue binding (FIG. 14). On the other hand, the ability of H3 HA (Mos99) to bind to diverse sialylated glycans is consistent with its more extensive binding to tracheal tissue sections as compared to that of H1 HA (FIG. 14).
Figures 16, 16A:
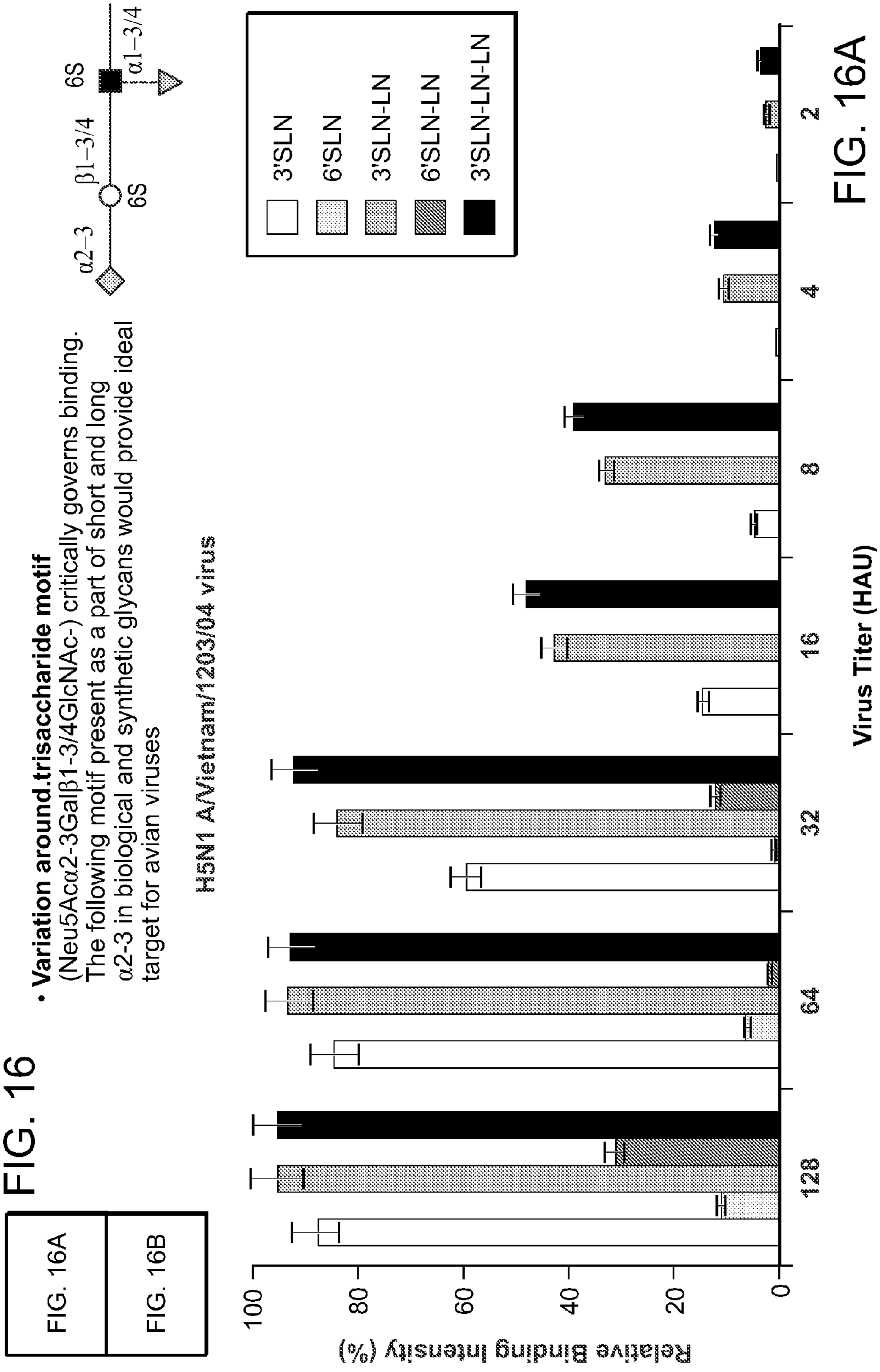
FIG. 16: Dose dependent direct glycan binding of H5N1 viruses. In contrast to the dose-dependent binding profile of the human adapted H1, H2, and H3 HAs, Viet034 and HK486 H5N1 viruses bind with high affinity to α2-3 (saturating signals from 128 down to 32 HAUs) and minimal affinity to long α2-6 oligosaccharides. Therefore, the present invention encompasses the recognition that a trisaccharide motif Neu5Acα2-3Galβ1-3/4GlcNAc- with sulfation/fucosylation substitutions (shown on right) as a part of physiological N-linked, O-linked glycans and glycolipids would be ideal targets for avian viruses.
Figure 16B:
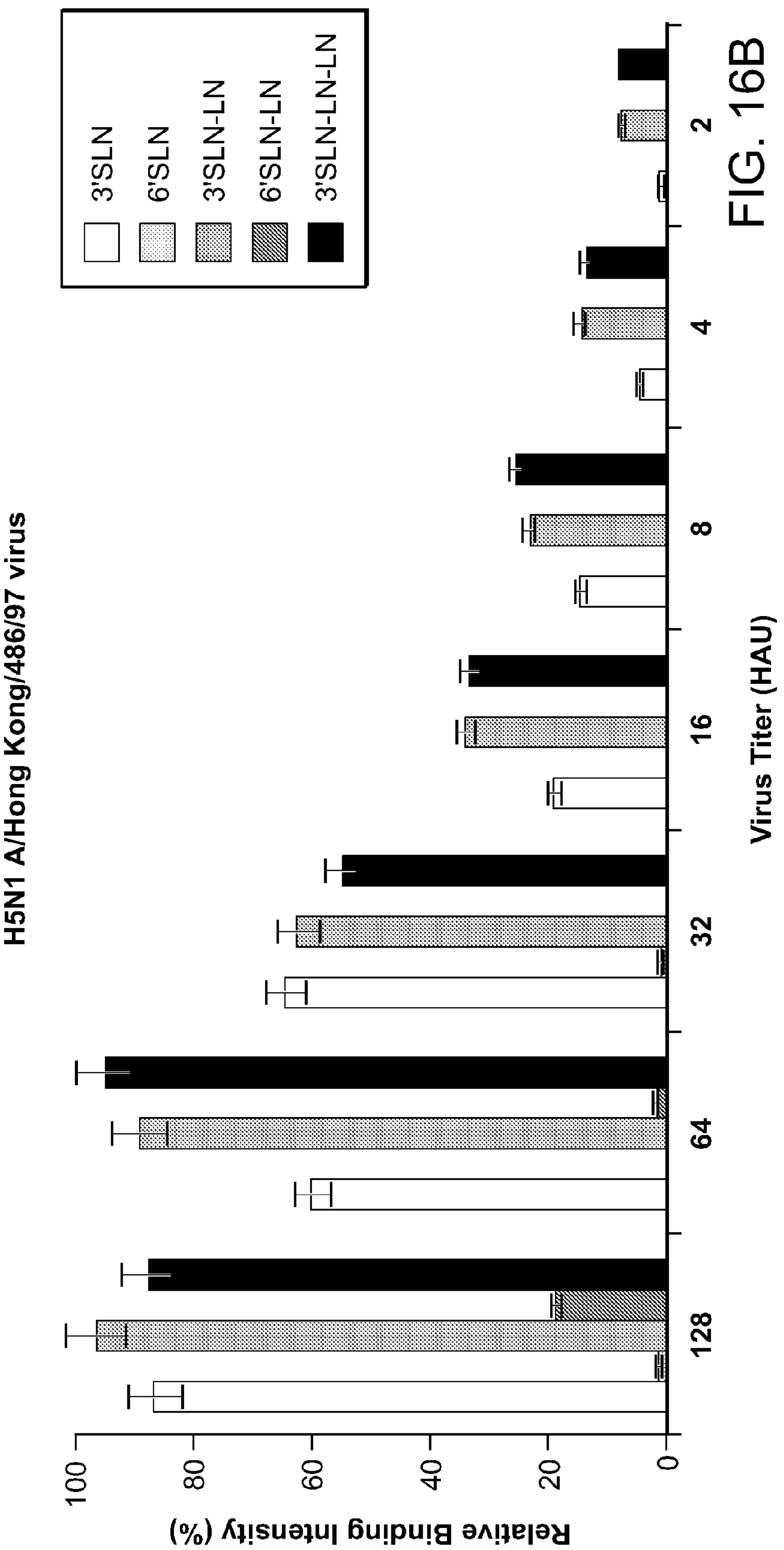

The present invention encompasses the recognition that one characteristic of the binding pattern of known human adapted H1, H2, and H3 HAs is their binding at saturating levels to the long α2-6 (6'SLN-LN) over a range of dilution from 40 μg/ml to 2.5 μg/ml (FIG. 15). While H1 HA is highly specific for binding to the long α2-6, H2 and H3 HA also bind to short α2-6 (6'SLN) with high affinity and to a long α2-3 with a lower affinity relative to α2-6 (FIG. 15). The direct binding dose response of H1 and H3 HA is consistent with the tissue-binding pattern. Furthermore, the high affinity binding of H1 and H3 HA to long α2-6 correlates with their extensive binding to apical side of the tracheal tissues which expresses α2-6 glycans with long branch topology. This correlation provides valuable insight into the upper respiratory tissue tropism of human adapted H1 and H3 HAs. α2-3 binding of H2 and H3 HAs further suggests that a switch in the glycan binding preference (i.e. losing ability to bind to α2-3) is not a necessary determinant for human adaptation of HA. Importantly, Tx91, also a mixed α2-6/α2-3 binding virus that shows HA binding to long α2-6 (FIG. 10), is able to efficiently transmit. On the other hand, NY 18 another mixed α2-3/α2-6 binding virus that does not have HA binding specificity to long α2-6 (FIG. 10), does not transmit efficiently (details of HA binding specificity correlating with transmissibility are further elaborated in Example 6 below). Thus, the present invention encompasses the recognition that efficient human adaptation of these viruses is therefore correlated to HA binding to sialylated glycans of a characteristic umbrella-like topology, going beyond the specific α2-3 or α2-6 linkage. The tested H5N1 viruses on the other hand show the opposite glycan-binding trend, wherein they bind with high affinity to α2-3 (saturating signals from 40 μg/ml down to 2.5 μg/ml) as compared to their relatively low affinity for α2-6 (significant signals seen only at 128 HAUs; FIG. 16). Without wishing to be bound by any one theory, the observed initiation of H5N1 infection to tissues predominantly expressing α2-6 could possibly be explained by the α2-6 binding at high viral loads (>128 HAUs shown in FIG. 16).

Example 6

1918 H1N1 Influenza A Pandemic Virus Hemagglutinin Binding Affinity to α2-6 Sialylated Glycans with Distinct Structural Topology is a Determinant for Virus Transmission Human infection of influenza viruses involves binding of viral surface hemagglutinin (HA) to α2-6 sialylated glycan (α2-6) receptors on the epithelial cell surface of the human upper respiratory tissues. The relationship between the glycan binding preference of HA and transmission efficiency has been demonstrated in a ferret model using the highly pathogenic and virulent 1918 H1N1 viruses (Tumpey et al., 2007, *Science,* 315:655; incorporated herein by reference). In this study, it was demonstrated that while the 1918 H1N1 pandemic virus (A/South Carolina/1/1918 (SC18) with α2-6 binding preference) transmitted efficiently, a single amino acid HA mutation (SC18+1 mutation) resulted in a mixed α2-3 sialylated glycan (α2-3)/α2-6 binding virus (NY18) that transmitted inefficiently. Furthermore, an additional HA mutation (NY18+1 mutation) that switched the glycan binding preference of from α2-6 to α2-3 resulted in a virus (AV18) that was unable to transmit in the ferrets. While A/New York/1/18 (NY18) H1N1 virus, which shows mixed α2-3/α2-6 binding, transmitted inefficiently; surprisingly, A/Texas/36/91 (Tx91; also a mixed α2-3/α2-6 binding H1N1 virus) was able to transmit efficiently. These differences in virus transmission as the result of single amino acid HA mutations, in turn raise important questions about HA-glycan specificity in the context of glycan topology not only for efficient human adaptation (as discussed in Examples 1-5) but also for efficient transmission. Building on the previous examples, a dose-dependent glycan binding assay that is able to quantitatively measure the binding affinity and establish specificity was developed. The following demonstrates that while the typical glycan array assay shows no qualitative difference between the long α2-6 binding of SC18 and NY18, the dose-dependent assay of the same shows significant quantitative differences between their binding affinities to long α2-6. Furthermore, these differences are reflected as well in the distinct binding pattern of SC18 and NY18 HA to physiological glycans present in human upper respiratory tissues. Together, the present inventors have demonstrated that transmission differences between SC18 and NY18 viruses correlates with their quantitative binding affinity to long α2-6 glycans with characteristic umbrella-like topology.

Materials and Methods

Cloning, Baculovirus Synthesis, Expression and Purification of HA

The soluble form of HA was expressed using the Baculovirus Expression Vector System (BEVS). SC18 (A/South Carolina/1/1918; SC18) baculovirus (generated from pAcGP67-SC18-HA plasmid; Stevens et al., 2004, Science, 303:1866; Stevens et al., 2006, *Nat. Rev. Microbiol.,* 4:857; both of which are incorporated herein by reference)) was a gift from Dr. James Stevens. pAcGp67-NY18-HA and pAcGp67-AV18-HA plasmids were generated from pAcGP67-SC18-HA by [Asp225Gly] and [Asp 190Glu, Asp225Gly] mutations respectively. Mutagenesis was carried out using QuikChange Multi Site-Directed Mutagenesis Kit (Stratagene). The primers used for mutagenesis were designed using the web based program, PrimerX (http://bioinformatics.org/primerx/), and synthesized by IDT DNA technologies (Coralville, Iowa). NY18 and AV18 baculoviruses were created from a pAcGP67-NY18-HA and pAcGP67-AV18-HA constructs using Baculogold system (BD Biosciences, San Jose, Calif.) according to manufacturer's instructions. The baculoviruses were used to infect 300 ml suspension cultures of Sf9 cells (BD Biosciences, San Jose, Calif.) cultured in BD BaculoGold Max-XP Insect Cell medium (BD Biosciences, San Jose, Calif.). These cultures were monitored for signs of infection and harvested 4-5 days post-infection. BEVS produces trimeric HA which provides multivalent binding to glycans. The soluble form of HA was purified from the supernatant of infected cells using the protocol described previously (Stevens et al., 2004, *Science,* 303:1866; incorporated herein by reference). Briefly, the supernatant was concentrated using Centricon Plus-70 centrifugal filters (Millipore, Billerica, Mass.) and the trimeric HA recovered from the concentrated cell supernatant using affinity chromatography with columns packed with Ni-NTA beads (Qiagen, Valencia, Calif.). Eluted fractions which contained HA were pooled and dialyzed overnight with a 10 mM Tris-HCl, 50 mM NaCl buffer (pH 8.0). Ion exchange chromatography was then performed on the dialyzed samples using a Mono-Q HR10/10 column (GE healthcare, Piscataway, N.J.). The fractions containing HA were pooled together and subjected to ultrafiltration using Amicon Ultra 100 K NMWL membrane filters (Millipore, Billerica, Mass.). The protein was then concentrated and reconstituted in PBS. The purified protein was quantified using Bio-Rad's protein assay (Bio-Rad, Hercules, Calif.).

Dose Dependent Direct Binding of H1N1 HA

To investigate the multivalent HA-glycan interactions, a streptavidin plate array comprising representative biotinylated α2-3 and α2-6 (short and long) was used. The spatial arrangement of the glycans in the wells of this plate array favors binding to only one of the three HA monomers in the HA unit. The glycan spacing and the HA unit size limit HA unit binding to a single glycan in the ELISA type binding assay which involved the sequential application of HA unit, primary antibody, and secondary antibody (see below). Conversely, the precomplexation of HA units (see below) with primary and secondary antibodies (HA:primary:secondary=4:2:1 ratio) facilitates a specific spatial arrangement of 4 HA units. This precomplex unit, therefore enabled the investigation of the effects of the relative spatial positioning of multiple HA units on the glycan binding affinity via multivalency (see FIG. 18).

Streptavidin-coated High Binding Capacity 384-well plates (Pierce) were loaded to the full capacity of each well by incubating the well with 50 μl of 2.4 μM of biotinylated glycans overnight at 4° C. The biotinylated glycans (3'SLN, 6'SLN, 3'SLN-LN, 6'SLN-LN and 3'SLN-LN-LN) were obtained from the Consortium of Functional Glycomics through their resource request program. LN corresponds to lactosamine (Galβ1-4GlcNAc) and 3'SLN and 6'SLN respectively correspond to Neu5Acα2-3 and Neu5Acα2-6 linked to LN. Excess glycans were removed through extensive washing with PBS and the plates then used without additional processing. For the ELISA-type sequential binding the glycan-coated wells were incubated for 2 hours with HA at a concentration of 40 μg/ml (typical high concentrations used in glycan array experiments) in PBS containing 1% BSA and subsequently washed extensively with PBS-Tween followed by PBS. This was followed by an incubation with the primary antibody (Mouse anti-6×His tag IgG) at a concentration of 5 μg/ml in PBS containing 1% BSA for 3 hours at room temperature and repeating the above wash steps. The wells were finally incubated with a 2 μg/ml solution of the secondary antibody (HRP conjugated goat anti-Mouse IgG) for 1 hour at room temperature. In the case of dose dependent precomplexed HA experiments, appropriate amounts of His-tagged HA protein, primary antibody (Mouse anti-6×His tag IgG), and secondary antibody (HRP conjugated goat anti-Mouse IgG (Santacruz Biotechnology)) in the ratio 4:2:1 and incubated on ice for 20 minutes. Precomplexed HA was made up to a final volume of 250 μl with 1% BSA in PBS buffer and 50 μl of this solution was added to each of the glycan-coated wells in the 384-well plate and incubated at room temperature for 2 hours. The wells were then extensively washed with PBS-Tween followed by PBS. The binding signal was determined based on HRP activity using Amplex Red Peroxidase Assay (Invitrogen, CA) according to the manufacturer instructions. Negative controls were included and all assays were performed in triplicate.

To quantify the binding affinity (for the above pre-complexation assay), binding parameter $K_d'$ is defined and calculated based on the following model. The typical form of the Hill equation is used to represent multivalent binding:

$$y = \frac{[HA]^n}{[HA]^n + K_d'}$$

which upon linearization becomes $$\log\left(\frac{y}{1-y}\right) = n * \log([HA]) - \log(K_d')$$

where y—fractional saturation of the glycan binding sites in the HA units; [HA]—concentration of HA (in M); n—cooperativity factor; $K_d'$—apparent binding constant for the multivalent HA-glycan interactions. The value of y is calculated by normalizing the binding signals to the saturating binding signal which represent 100% occupancy on all HA units. n and $K_d'$ were calculated based on the linearized Hill model (shown in Table 5). In the above model, it is assumed that glycans in each well of the plate are in excess of HA. To satisfy this assumption, binding signals for HA concentration range from 0.05 μg/ml to 5 μg/ml were used to calculate n and $K_d'$.

Binding of H1 HA to Human Upper Respiratory Tissues

Formalin-fixed and paraffin-embedded normal human tracheal tissue sections were purchased from US Biological. Tissue sections were deparaffinized, rehydrated, and pre-blocked with 1% BSA in PBS for 30 minutes at room temperature. HA-antibody pre-complexes were generated by incubating recombinant SC18 and NY18 proteins with primary (mouse anti-6×His tag, Abcam) and secondary (Alexa Fluor 488 goat anti-mouse IgG, Invitrogen) antibodies in a ratio of 4:2:1 respectively for 20 minutes on ice. The complexes formed were then diluted in 1% BSA-PBS to different final HA concentrations. Tissue binding studies were performed by incubating tissue sections with diluted HA-antibody complexes for 3 hours at room temperature. To visualize cell nuclei, sections were counterstained with propidium iodide (Invitrogen; 1:100 in TBST) for 20 minutes at RT. For co-staining assays, tissues were deparaffinized, rehydrated, and co-incubated with FITC labeled Jacalin (Vector labs; 10 μg/ml in PBS with 0.05% Tween 20 (PBST)) and HA-antibody precomplexes (generated as described above using Alexa Fluor 546 goat anti-mouse as secondary antibody and diluted in PBST) for 3 hours at room temperature. Sections were then washed and viewed under a Zeiss LSM510 laser scanning confocal microscope.

Results

Molecular Interactions of SC18, NY18 and AV18 HAs with α2-3 and α2-6

Based on analysis of HA-glycan co-crystal structures, HA-glycan interactions are characterized based on cone-like and umbrella-like glycan topology (Chandrasekharan et al., 2007, *Nat. Biotech*., in press). The x-ray crystal structure of SC18 HA has been solved (Stevens et al., 2004, *Science,* 303:1866; and Gamblin et al., 2004, *Science,* 303:1838; both of which are incorporated herein by reference) but the co-crystal structure of this HA with sialylated glycans remains unsolved. The structures of NY18 and AV18 HA were obtained by making the single Asp225Gly (for NY18 HA) and the additional NY18+Asp 190Glu mutation (for AV18) in silico. Co-crystal structures of the related A/Swine/Iowa/15/30 (ASI30) and A/Puerto Rico/8/34 (APR34) H1N1 HAs with α2-3 and α2-6 glycans (Gamblin et al., 2004, *Science,* 303:1838; incorporated herein by reference) enabled the investigation of molecular interactions between SC18, NY18, and AV18 with α2-3 and α2-6 oligosaccharides.

The umbrella-like topology is preferred by α2-6 longer oligosaccharides (e.g., tetrasaccharide and higher). The LSTc pentasaccharide (Neu5Acα2-6Galβ1-4GlcNAcβ1-3Galβ1-4Glc) used in the APR34 and AS130 HA-α2-6 co-crystal structures represents this long α2-6. Superimposition of these co-crystal structures and SC18 HA demonstrated that the contacts with long α2-6 oligosaccharide are divided into two regions. The base region involves contacts with Neu5Acα2-6Galβ1- motif and the extension region involves contacts with -GlcNAcβ1-3Galβ1-4Glcβ1- motif. A highly conserved set of amino acids (Tyr95, Ser/Thr136, Trp153, His183, Leu/Ile194) are involved in anchoring Neu5Ac (FIG. 17). Although both the backbone carbonyl oxygen and side chain of Asp225 in SC18 and APR34 HA are positioned to interact with Gal in the base region, only the carbonyl oxygen of Gly225 in AS130 interacts with this Gal (FIG. 17). Highly conserved Lys222 and Gln226 are also positioned to interact with the base region. Amino acids involved in contacts with the extension region include Asp 190 (in SC18 and AS130 HA), Gln192, and Ser193 (Asn193 in APR34 HA). NY18 HA (i.e., the Asp225Gly mutant of SC18) shares an almost identical glycan binding site with that of AS130 HA and therefore lacks the extra contact provided by the side chain of Asp225 with Gal in the base region. In contrast, AV18 (i.e., the Asp190Glu/Asp225Gly double mutant of SC18) lacks the contacts provided by both Asp225 and Asp 190 to the base and extension regions, respectively. Among SC18, NY18, and AV18 HAs, SC18 HA provides the best contacts with the long α2-6 in the umbrella-like topology followed by NY18 HA.

Distinct from the umbrella-like topology, the cone-like topology can be adopted both by α2-3 and α2-6 (preferentially by short trisaccharide units such as Neu5Acα2-6Galβ1-4Glc(NAc)). Unlike the two distinct regions of HA contacts found with the umbrella-like topology, the contacts with the cone-like topology primarily involve substitutions which center around a trisaccharide Neu5Acα2-3/6Galβ1-3/4Glc (NAc) motif as observed in the HA-α2-3 co-crystal structures. Specifically, Glu190 and Gln226, which are highly conserved across various avian HAs, are involved in making optimal contacts with the cone-like topology (FIG. 17). This observation is corroborated further by the disordered sugars beyond Neu5Ac in the AS130 HA-α2-3 co-crystal structure since Asp instead of Glu at 190 in this HA lacks the contact with the α2-3. Superimposition of AV18 and APR34 HA, which both contain these amino acids, shows that AV18 HA makes optimal contacts with the cone-like glycan topology. Both SC18 and NY18 HAs lack the Glu190 residue, and therefore their contacts with the cone-like glycan topology are less optimal when compared to AV18 HA.

Dose Dependent Direct HA Binding to Representative α2-3 and α2-6 Oligosaccharides Novel glycan array platforms have been developed to investigate HA-glycan interactions (Stevens et al., 2006, *Nat. Rev. Microbiol.,* 4:857; and Kumari et al., 2007, J. Virol., 4:42; both of which are incorporated herein by reference). These arrays have provided important insights into α2-3 versus α2-6 binding specificity of various wild type and mutant HAs. In these glycan array studies high and low binding signals to the glycans within a single assay using saturating HA concentration determine the glycan binding preference for a given HA. It is generally accepted that the glycan binding affinity for a single binding site on any glycan binding protein (e.g., a lectin) is low (e.g., in the high μM to mM range). Since each HA unit is a trimeric protein, there are three glycan binding sites per unit (Skehel and Wiley, 2000, *Ann. Rev. Biochem.,* 69:531; incorporated herein by reference). In addition, multiple HA units assemble on a virus surface. The glycan binding sites within a HA unit and the spatial arrangement of multiple HA units across a virus surface could play an important role in multivalent HA-glycan interactions. The present invention encompasses the recognition that the concentration of the HA units relative to the glycans consequently may govern HA-glycan binding specificity.

Figure 18:
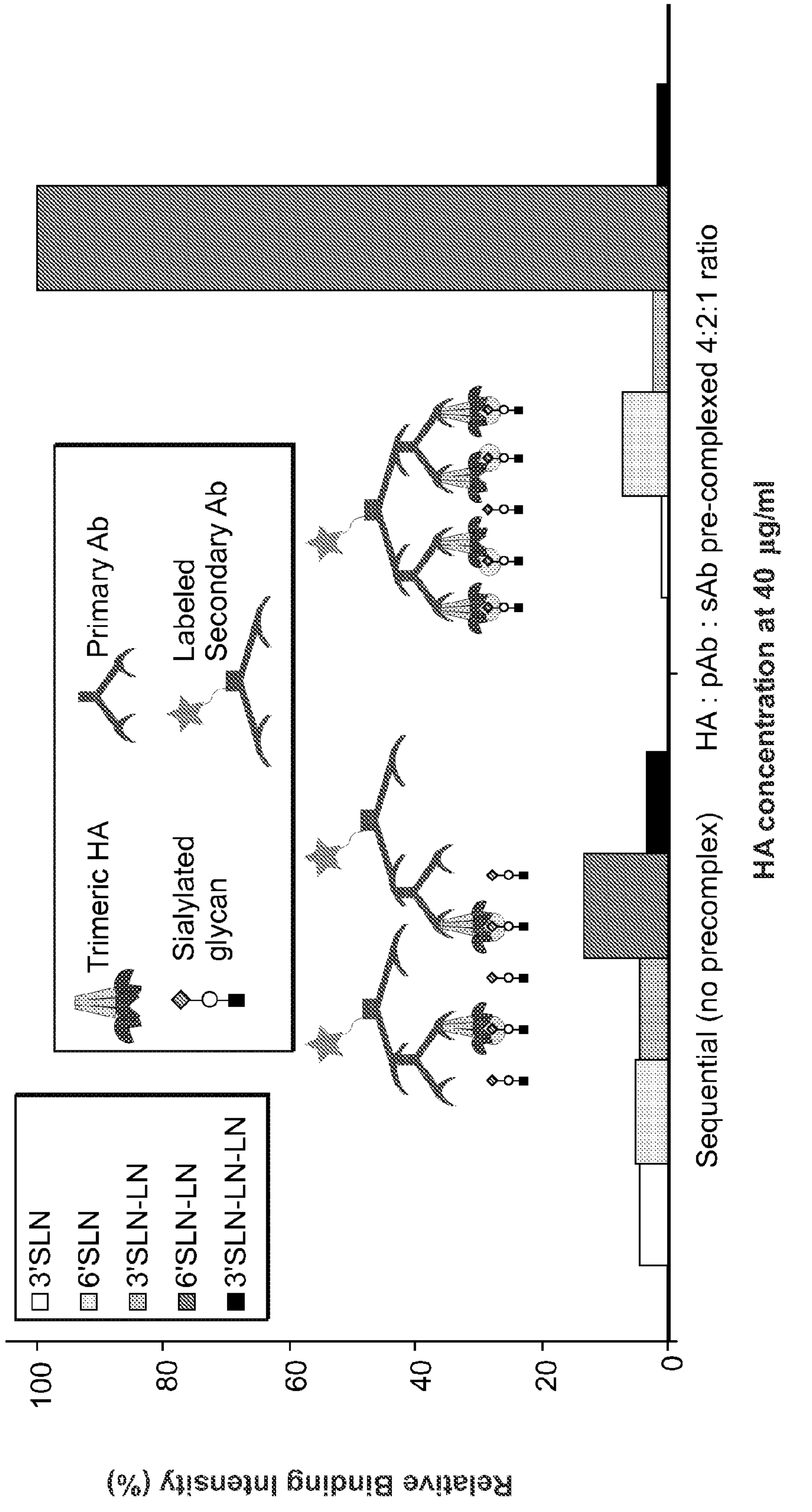
FIG. 18: Binding assay to capture multivalent HA-glycan interactions. Shown in the figure is comparison of binding signals between sequential binding assay and precomplexation of HA units with primary (pAb) and labeled secondary (sAb) antibodies. To investigate multivalent HA-glycan interactions, a streptavidin plate array comprising representative biotinylated α2-3 and α2-6 (short and long) glycans was used. Streptavidin-coated High Binding Capacity 384-well plates (Pierce) were loaded to the full capacity of each well with biotinylated glycans (3'SLN, 6'SLN, 3'SLN-LN, 6'SLN-LN, and 3'SLN-LN-LN). The spatial arrangement of the glycans in the wells of this plate array favors binding to only one of the three HA monomers in the HA unit. The glycan spacing and the HA unit size limit HA unit binding to a single glycan in the ELISA type binding assay which involves the sequential application of HA unit, primary and secondary antibodies. The conditions of the sequential assay favor the formation of HA:pAb:sAb in a 1:1:1 ratio. Despite the abundance of the labeled sAb (1 per HA unit) the minimal binding signals observed even at a high HA concentration of 40 μg/ml supports the low affinity binding of a single glycan to a HA unit (cyan circle). Conversely, precomplexation of HA units with primary and secondary antibodies (HA:primary:secondary=4:2:1 ratio) facilitates a specific spatial arrangement of 4 HA units. This precomplex unit, therefore enabled the investigation of the effects of the relative spatial positioning of multiple HA units on the glycan binding affinity via multivalency. This spatial arrangement enhances glycan binding signals via multivalency, as shown by 8 fold increase in binding to 6'SLN-LN given that there are 4 binding events (each event shown by a cyan circle) per precomplexed HA units. Binding signal was determined based on HRP activity. All assays were performed in triplicate. Legend for glycans: 3'SLN: Neu5Acα2-3Galβ1-4GlcNAc; 6'SLN (short α2-6): Neu5Acα2-6Galβ1-4GlcNAc; 3'SLN-LN: Neu5Acα2-3Galβ1-4GlcNAβ1-3Galβ1-4GlcNAc; 6'SLN-LN (long α2-6): Neu5Acα2-6Galβ1-4GlcNAcβ1-3Galβ1-4GlcNAc; 3'SLN-LN-LN: Neu5Acα2-3Galβ1-4GlcNAcβ11-3Galβ1-4GlcNAcβ1-3Galβ1-4GlcNAc
Figure 19A:
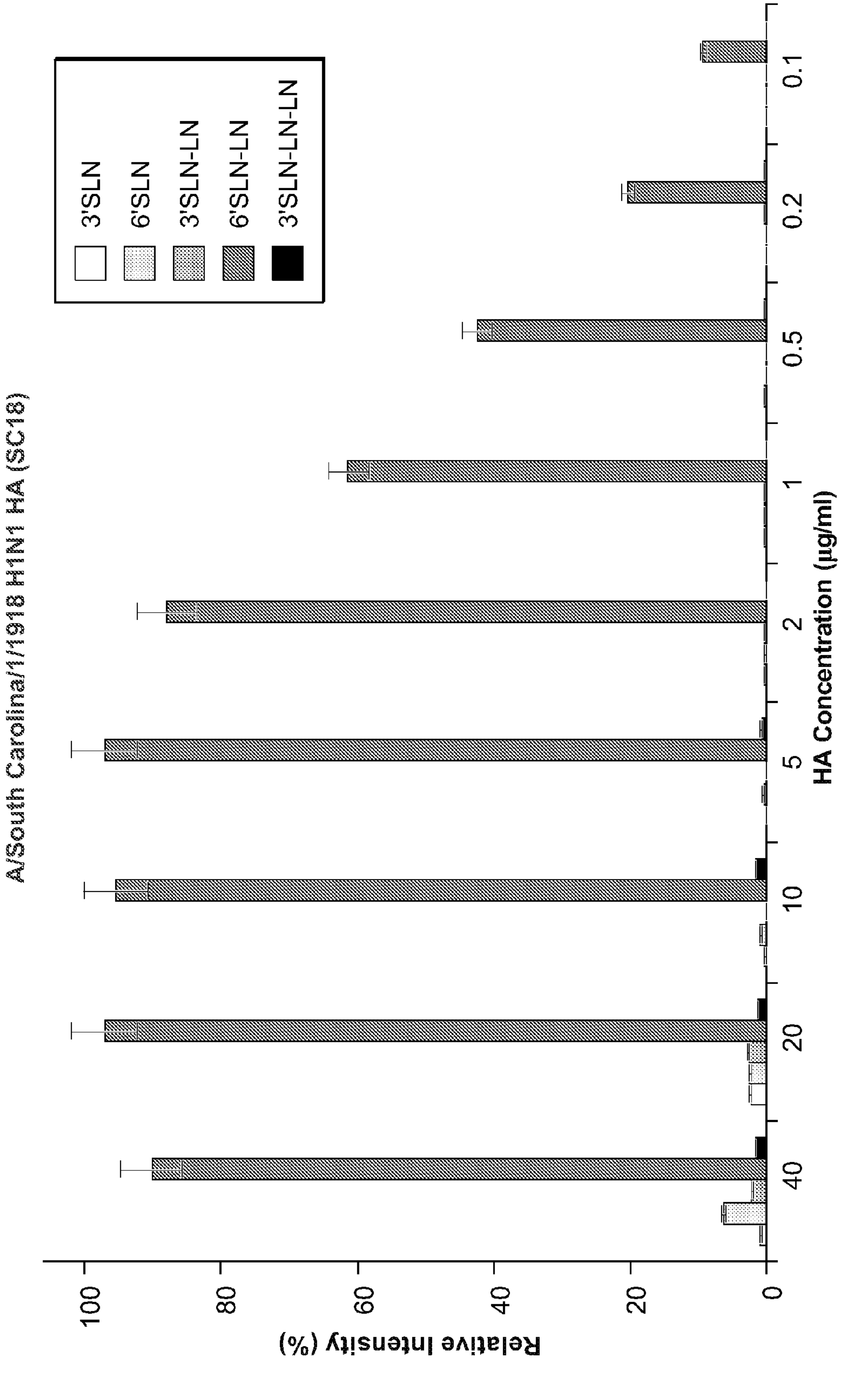
FIGS. 19-21: Dose-Dependent Direct Binding of H1N1 HAs. In the case of dose-dependent precomplexed HA experiments, a stock solution containing appropriate amounts of His-tagged HA protein, primary antibody (Mouse anti 6×His tag IgG), and secondary antibody (HRP conjugated goat anti Mouse IgG (Santacruz Biotechnology) in the ratio 4:2:1 was prepared and incubated on ice for 20 minutes. Appropriate amounts of precomplexed stock HA were diluted to 250 μl with 1% BSA in PBS buffer. 50 μl of precomplexed HA was added to each of the glycan-coated wells and incubated at room temperature for 2 hours followed by wash steps. To quantify the binding affinity, binding parameter $K_d'$ is defined and calculated based on the following model. The typical form of the Hill equation is used to represent the multivalent binding.
Figure 19B:
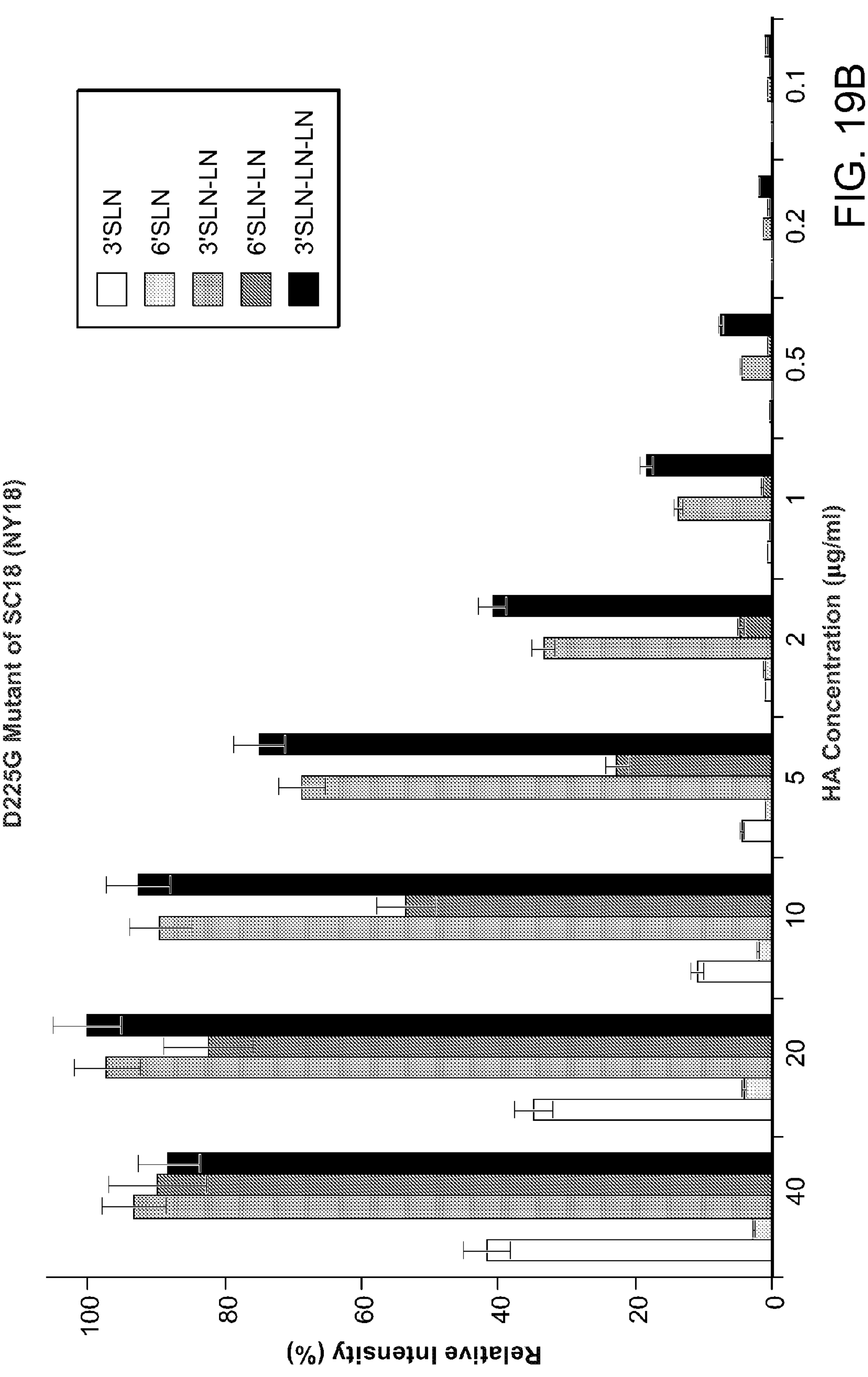
Figure 19C:
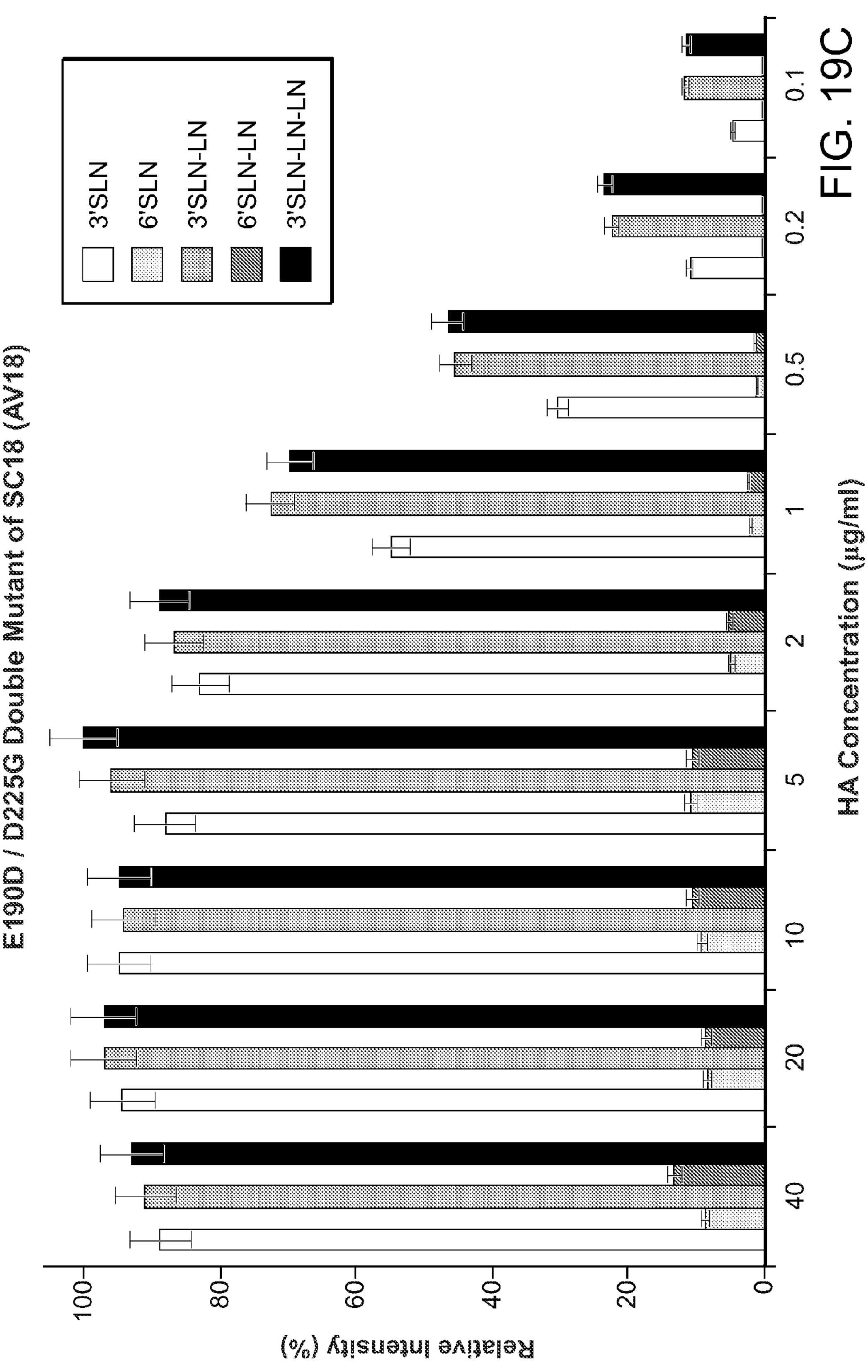
Figure 19D:
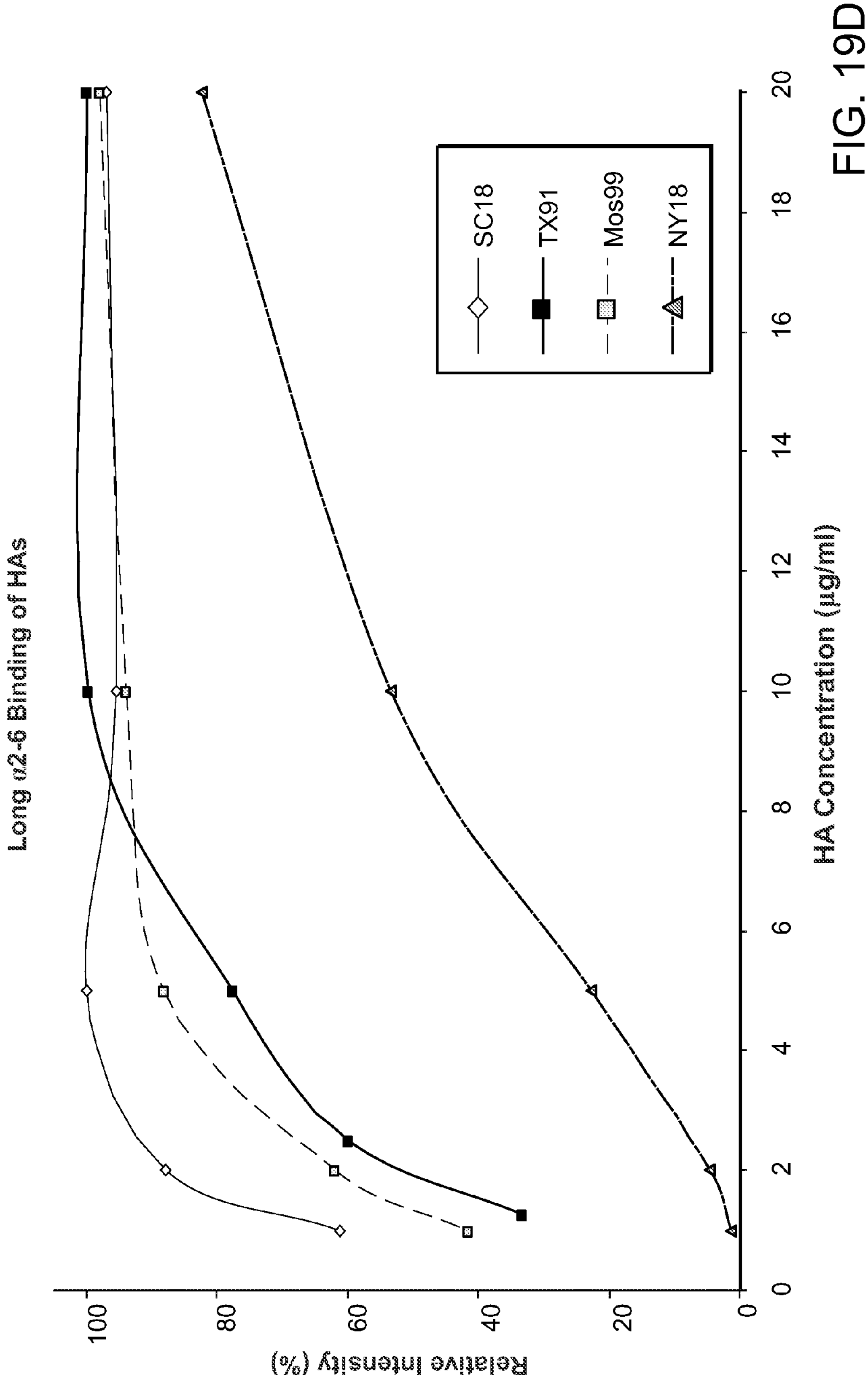

To understand differences in the glycan binding specificity of SC18, NY18, and AV18 HAs for a specific spatial arrangement of the HA units and the glycans, systematic direct HA binding studies on a plate array were performed (see Methods). Minimal binding signals were observed for SC18 HA in the sequential ELISA-type binding assay (FIG. 18). Granted that glycan spacing and HA unit size limits HA binding to only a single glycan in this assay, binding signals are consistent with the anticipated weak affinity of the HA unit to a single glycan. The precomplexation assay with SC18 HA—where 4 HA units are locked spatially-instead resulted in at least an 8-fold increase in the binding to the long α2-6 glycan (FIG. 18). This increase in the binding signal underscores the role that the spatial arrangement of multiple HA units play in enhancing glycan binding.

Figure 20B:
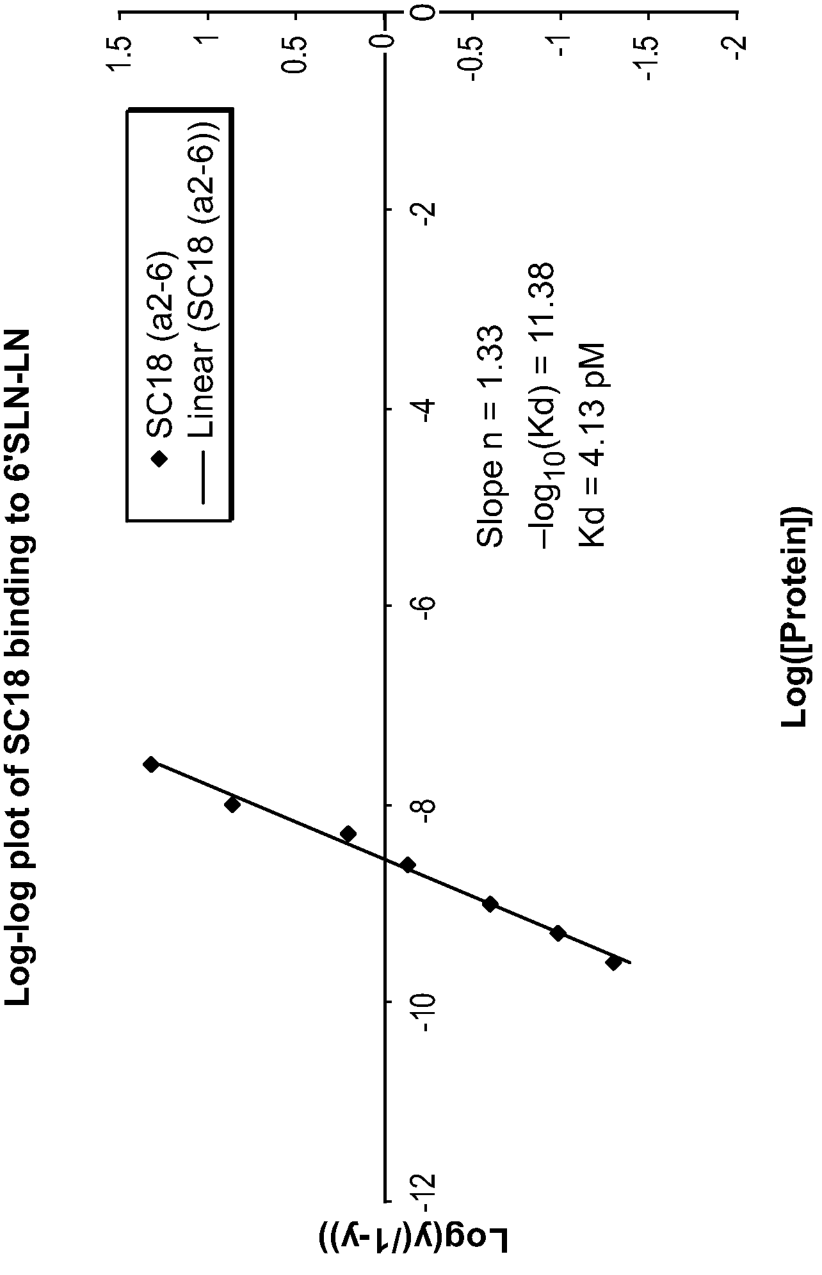
Figure 21A:
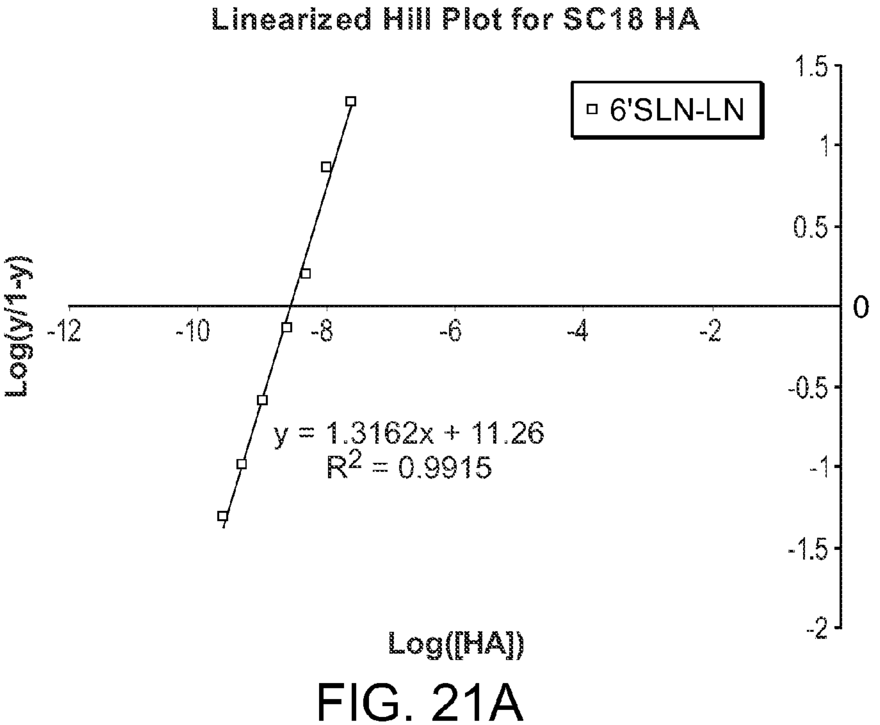
Figure 21B:
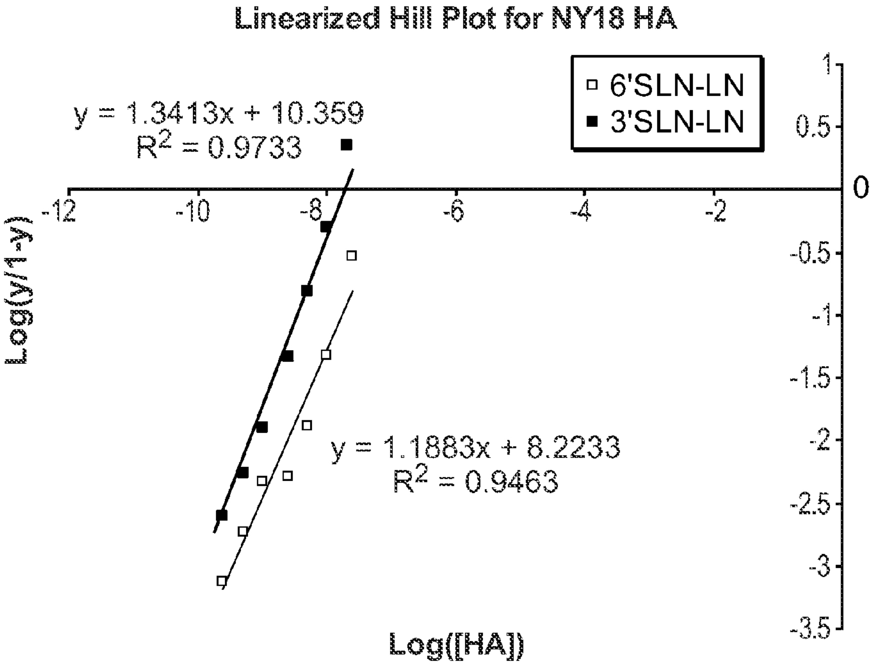
Figure 21C:
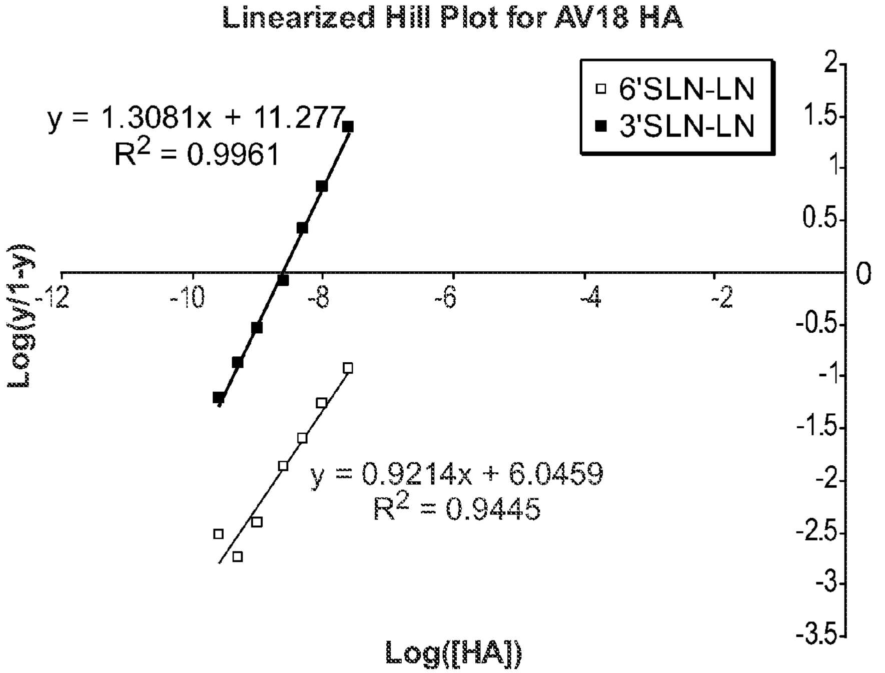

A dose-dependent direct binding assay by serial dilution of precomplexed SC18, NY18, and AV18 HAs was performed to establish their relative glycan binding affinities (FIG. 19). The cooperativity factor n and the apparent binding constant $K_d'$ were calculated based on the linearized Hill equation (see Methods and FIGS. 20 and 21) used to model the binding data (Table 5):

TABLE 5

Quantification of Relative α2-3 and α2-6 Binding Affinities of SC18, NY18, and AV18 HAs

| | 6' SLN-LN | | 3' SLN-LN | |
|---|---|---|---|---|
| | n | $K_d'$ | n | $K_d'$ |
| SC18 | 1.3 | 5.5 pM | n.b | n.b |
| NY18 | 1.2 | 6.3 nM | 1.3 | 50 pM |
| AV18 | 0.9 | 1 μM | 1.3 | 5 pM |

Table 5 shows the relative binding affinities of SC18, NY18, and AV18 HAs to representative long α2-3 and α2-6 glycans. The parameters n and $K_d'$ were determined as described in Methods and elaborated in FIGS. 20 and 21. These parameters were obtained to quantify the relative binding affinities of the HAs and hence their absolute values should be viewed in this context.

The R-square value >0.95 for all the glycan binding data indicates a good fit to the linearized Hill model. The value of n≥1 reflects the positive cooperativity in the HA-glycan interactions as a result of the spatial arrangement of multiple HA units and the binding of a HA unit to a single glycan. While SC18 HA showed high binding affinity to the single long α2-6 glycan ($K_d'$=5.5 pM), AV18 HA showed the reverse trend with almost no α2-6 binding and high α2-3 binding affinity ($K_d'$=5 pM). On the other hand, while the long α2-6 binding of NY18 HA was almost identical to that of SC18 HA at saturating HA concentrations (FIG. 19), the relative binding affinity to long α2-6 ($K_d'$=6 nM) was significantly lower than that of SC18 HA. These observations correlate with the differences in molecular interactions of SC18, NY18, and AV18 with α2-3 and α2-6 oligosaccharides.

Binding of SC18 and NY18 to Human Upper Respiratory Tissues

The present invention encompasses the recognition that differences in the binding affinities of α2-6 and α2-3 of SC18 and NY18 HA render them ideal lectin-like probes to investigate HA binding to diverse physiological glycans present in human upper respiratory tissues. Human tracheal sections were used to explore the binding pattern of SC18 and NY18 HA to physiological glycans. Although both SC18 and NY18 bind to the apical side of the trachea (FIG. 22), the pattern and distribution of the tissue binding of the two HAs differ. SC18 binding to the apical side of the trachea appears more restricted when compared to the well-distributed binding of NY18. NY18 HA also shown binding to the internal region of the trachea (that are known to express α2-3 glycans), consistent with its direct binding to α2-3 glycans (FIG. 19). In order to further investigate the differences in apical binding of SC18 and NY18 HAs, co-staining of tracheal tissues were performed using these HAs and Jacalin (a marker for goblet cells). This co-staining demonstrated that while SC18 HA predominantly binds to goblet cells, NY18 HA showed minimal binding to these cells (FIG. 23).

DISCUSSION

Glycan arrays comprising many distinct oligosaccharide motifs have been employed to investigate the glycan binding of wild type and mutant H1, H3, and H5 HAs (Stevens et al., 2006, *Nat. Rev. Microbiol.,* 4:857; Kumari et al., 2007, *J. Virol.,* 4:42; Stevens et al., 2006, *Science,* 312:404; all of which are incorporated herein by reference). In spite of these advances, interpretation of glycan receptor specificity which leads to human adaptation has remained challenging. This is due in large part to a general notion in the field that glycan-protein interactions are relatively weak and non-specific. Consequently, the glycan binding specificity for HA has largely been established using very high protein concentrations. High HA concentration may be useful to establish binders versus non-binders but the present invention encompasses the recognition that there are limitations in defining appropriate quantitative measurements to establish relative glycan binding affinities of HA. One example, at high concentrations, the typically used first order binding kinetics assumptions (pertaining to HA: glycan ratio) would not be satisfied. To accurately quantify the relative glycan binding affinities between HAs, the present invention encompasses the recognition that it is desirable to be at the "appropriate" HA concentration range. The present invention encompasses the recognition that several parameters (e.g., the spatial arrangement of multiple HA units, the surface glycan density, and the ratio of HA to glycan) should be taken into account when determining the "appropriate" HA concentration range for a given glycan array assay. Current approaches using high HA concentrations on glycan arrays do not account for these areas of concern. In this study, the specific spatial arrangement of the glycans (spacing imposed by biotin-avidin system) and the HA (imposed by precomplexation of HA units) in tandem with the dose-dependent glycan binding assay was able to overcome these challenges. The concentration range used to determine the binding affinity parameters (n and $K_d'$)

in this study is such that the glycan is in excess of the HA as would be expected in physiological conditions. The present invention encompasses the recognition that the approach described in this study can be readily extended to any glycan array platform employed to investigate protein-glycan interactions in general.

High or saturating HA concentrations display no differences between the binding signals of SC18 and NY18 to long α2-6 glycan. The only difference between SC18 and NY18 is the additional binding to α2-3 glycans for NY18 HA. As the α2-3 binding of SC18, NY18, and AV18 shows inverse correlation with the transmissibility, without wishing to be bound by any one theory, a possible conclusion from these data is that the loss of α2-3 binding specificity is a factor for transmission. However, A/Texas/36/91 (TX91; i.e., a mixed α2-6/α2-3 binding virus similar to NY18) transmitted efficiently in ferrets. The dose-dependent direct binding of TX91 and A/Moscow/10/99H3N2 (Mos99; i.e., a mixed α2-6/α2-3 binding human adapted H3 HA) compared to that of SC18 and NY18 shows that the high affinity binding to long α2-6 glycan is a common feature for SC18, Tx91, and Mos99, but not for NY18 (FIG. 19). This common feature of specificity to long α2-6 glycan is independent of specificity to α2-3 glycans. Thus, the present invention encompasses the recognition that high affinity binding to long α2-6 glycans, which are extensively expressed in the upper respiratory tissues, is a determinant not only for HA human adaptation, but also for influenza virus transmission in general.

Differential binding of SC18 and NY18 to the diverse physiological glycans present in the human upper respiratory tissues corroborates further these direct binding studies. The present invention encompasses the recognition that the narrow binding of SC18 to goblet cells should spark future investigations into the cellular tropism of human adapted viruses. This observation is consistent with Matrosovich et al. (Matrosovich et al., 2004, *Proc. Natl. Acad. Sci., USA,* 101: 4620; incorporated herein by reference), where they demonstrated that human adapted H1 and H3 virus strains preferentially infect non-ciliated cells and avian viruses preferentially infect ciliated cells. They also suggested that such differences in the cellular tropism of the viruses could explain the differences in their efficiency of human-human transmission.

EQUIVALENTS AND SCOPE

Those skilled in the art will recognize, or be able to ascertain using no more than routine experimentation, many equivalents to the specific embodiments of the invention, described herein. The scope of the present invention is not intended to be limited to the above Description, but rather is as set forth in the appended claims.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

In the claims articles such as “a,” “an,” and “the” may mean one or more than one unless indicated to the contrary or otherwise evident from the context. Thus, for example, reference to “a nanoparticle” includes a plurality of such nanoparticle, and reference to “the cell” includes reference to one or more cells known to those skilled in the art, and so forth. Claims or descriptions that include “or” between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term “comprising” is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any glycan decoy, any glycan mimic, any glycan moiety, any HA polypeptide, any amino acid position, any influenza strain, any method of identifying novel glycan decoys, any pharmaceutical composition, any method of administration, etc.) can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

We claim:

1. A method for identifying agents useful in the treatment of influenza infection, the method comprising steps of:

(a) providing an influenza hemagglutinin (HA), wherein the HA is characterized in that it preferentially binds to umbrella-topology glycans over cone-topology glycans such that it interacts with HA receptor glycans preferentially found in the human upper respiratory tract;

(b) providing a collection of candidate umbrella-topology decoys, which candidate umbrella-topology decoys comprise glycan moieties that share an oligosaccharide branch length characteristic with at least one umbrella-topology glycan selected from the group consisting of:

(i) those depicted in FIG. 6, (ii) those depicted in FIG. 7, (iii) those depicted in FIG. 9, (iv) α2-6 sialylated glycans with length of at least a tetrasaccharide and characterized by one or more of θ<100°, φ angle of Neu5Acα2-6Gal linkage of around −60, and multiple lactosamine units, and
(v) combinations thereof;
(c) contacting the influenza HA with one or more candidate umbrella-topology decoy from the collection;
(d) determining that at least one of the candidate umbrella-topology decoys from the collection competes the binding interaction between the influenza HA and one or more of the HA receptor glycans preferentially found on human upper respiratory tract, so that the candidate umbrella-topology decoy is useful in the treatment of influenza infection.

2. The method of claim 1, wherein the collection of candidate umbrella-topology decoys are sialylated glycans, wherein the sialylated glycans are provided as glycolipids or glycoproteins.

3. The method of claim 1, wherein the collection of candidate umbrella-topology decoys comprise one or more molecules physically associated with a carrier moiety.

4. The method of claim 3, wherein the one or more molecules physically associated with a carrier are physically associated by way of a covalent bond with the carrier moiety.

5. The method of claim 3, wherein the carrier moiety is selected from the group consisting of a peptide, glycopeptide, nucleic acid, small molecule, lipid, fatty acid group, carbohydrate, cell, virus, and particle.

6. The method of claim 1, wherein the at least one candidate decoy that mimics umbrella-topology glycans is characterized by a three-dimensional structure that interacts with one or more of HA amino acids at positions selected from the group consisting of 136, 137, 145, 153, 155, 156, 159, 186, 187, 189, 190, 192, 193, 194, 196, 222, 225, 226, 228, and combinations thereof, relative to a reference wild type H3 HA corresponding to the polypeptide of SEQ ID NO. 6.

7. The method of claim 1, wherein the at least one candidate decoy that mimics umbrella-topology glycans is characterized by a three-dimensional structure that interacts with one or more of HA amino acid acids at positions selected from the group consisting of 156, 159, 189, 192, 193, 196, and combinations thereof, relative to a reference wild type H3 HA corresponding to the polypeptide of SEQ ID NO. 6.

8. The method of claim 1, wherein the influenza HA is selected from the group consisting of: H1, H2, and H3 HA.

9. The method of claim 1, wherein the influenza HA is from a strain that is able to infect humans.

10. The method of claim 1, further comprising contacting the influenza HA with a positive control that is known to bind the influenza HA.

11. The method of claim 10, wherein the positive control is an umbrella-topology glycan.

12. The method of claim 1, wherein some or all of the candidate umbrella-topology decoys share one or more features with umbrella-topology glycans that are not shared with cone-topology glycans, such feature being selected from the group consisting of solvent accessibility, surface area, glycosidic torsion angles, conformational energy distribution, linkage, oligosaccharide branch length, amino acid residue contact sites, structural topology, binding characteristics, φ values, ψ values, θ values, ω angles, and combinations thereof.

13. The method of claim 1, wherein the HA receptor glycans preferentially found on human upper respiratory tract are at least 2-fold more likely to be found on human upper respiratory epithelial cells than on other cells.

14. The method of claim 1, wherein the HA receptor glycans preferentially found on human upper respiratory tract are at least 10-fold more likely to be found on human upper respiratory epithelial cells than on other cells.

15. The method of claim 1, wherein the HA receptor glycans preferentially found on human upper respiratory tract are at least 50-fold more likely to be found on human upper respiratory epithelial cells than on other cells.

16. The method of claim 1, wherein the at least one umbrella-topology glycan comprises at least one oligosaccharide of the following structure:
Neu5Acα2-6Sug1-Sug2-Sug3
where:
(a) Neu5Acα2-6 may be at the non-reducing end;
(b) Sug1:
(i) is or comprises hexose or hexosamine in α or β configuration;
(ii) does not include any sugars other than Neu5Acα2-6 attached to any of its non-reducing positions except when Sug1 is GalNAα2-6 that is O-linked to the glycoprotein; and
(iii) optionally comprises at least one non-sugar moiety attached to a non-reducing position;
(c) at least one of Sug2 and Sug3 is or comprises:
(i) hexose or hexosamine in a or 0 configuration; and
(ii) optionally one or more sugar or non-sugar moiety attached to a non-reducing position;
(d) linkage between any two sugars in the oligosaccharide apart from Neu5Acα2-6 linkage is selected from the group consisting of: 1-2, 1-3, 1-4, and 1-6.

17. The method of claim 1, wherein the at least one umbrella-topology glycan comprises at least one oligosaccharide of the following structure:
Neu5Acα2-6Sug1-Sug2-Sug3-Sug4-
where:
(a) Neu5Acα2-6 may be at the non-reducing end;
(b) Sug1:
(i) is or comprises hexose or hexosamine in a or 0 configuration;
(ii) does not include any sugars other than Neu5Acα2-6 attached to any of its non-reducing positions; and
(iii) optionally comprises at least one non-sugar moiety attached to a non-reducing position;
(c) at least one of Sug2, Sug3, and Sug4 is or comprises:
(i) hexose or hexosamine in α or β configuration; and
(ii) optionally one or more sugar or non-sugar moiety attached to a non-reducing position;
(d) linkage between any two sugars in the oligosaccharide apart from Neu5Acα2-6 linkage is selected from the group consisting of: 1-2, 1-3, 1-4, and 1-6.

18. The method of claim 16 or 17, wherein the hexose is selected from the group consisting of: Gal and Glc.

19. The method of claim 16 or 17, wherein the hexosamine is selected from the group consisting of: GlcNAc and GalNAc.

20. The method of claim 16 or 17, wherein the hexose or hexosamine is in the β configuration.

21. The method of claim 16, wherein one or more of Sug1, Sug2, and Sug3 comprises a non-sugar moiety attached to a non-reducing position.

22. The method of claim 17, wherein one or more of Sug1, Sug2, Sug3, and Sug4 comprises a non-sugar moiety attached to a non-reducing position.

23. The method of claim 21 or 22, wherein Sug1 comprises a non-sugar moiety attached to non-reducing position 6.

24. The method of claim 21 or 22, wherein the non-sugar moiety is selected from the group consisting of: sulfate, phosphate, guanidinium, amine, N-acetyl, and combinations thereof.

25. The method of claim 16, wherein the one or more of Sug2 and Sug3 comprises a sugar moiety attached to a non-reducing position.

26. The method of claim 17, wherein the one or more of Sug2, Sug3, and Sug4 comprises a sugar moiety attached to a non-reducing position.

27. The method of claim 24 or 26, wherein the one or more sugar moiety is Fuc.

28. The method of claim 16 or 17, wherein the at least one linkage between two sugars in the oligosaccharide apart from Neu5Acα2-6 linkage is selected from the group consisting of: 1-3 and 1-4.

29. The method of claim 16, wherein the at least one umbrella-topology glycan comprises Neu5Acα2-6 linked to GalNAcα that is O-linked to the glycoprotein and additional sugars are linked to the non-reducing end of GalNAcα.

30. The method of claim 28, wherein the at least one umbrella-topology glycan is Neu5Acα2-6(Neu5Acα2-3Galβ1-3)GalNAcα-.

31. The method of claim 29, wherein the at least one umbrella-topology glycan is Neu5Acα2-6(Galβ1-3)GalNAcα-.

32. The method of claim 17, wherein the at least one umbrella-topology glycan comprises a oligosaccharide structure without Sug4 such as 6'SLN that is attached to O-linked core GalNAc.

33. The method of claim 32, wherein the at least one umbrella-topology glycan is (Neu5Acα2-6Galβ1-4GlcNAc) β1-3/6(GalNAcα-O-Ser).

34. The method of claim 1, wherein the at least one umbrella-topology glycan is selected from the group consisting of: Neu5Acα2-6Galβ1-4GlcNAcβ1-3Galβ1-4GlcNAc-, Neu5Acα2-6GalNAcβ1-4GlcNAcβ1-3GalNAcβ1-4GlcNAc-, Neu5Acα2-6GlcNAcβ1-3Galβ1-3/4GlcNAc-, Neu5Acα2-6Galβ1-4GlcNAcβ1-3Galβ1-3GalNAcα, Neu5Acα2-6Galβ1-4GlcNAcβ1-3Galβ1-4GlcNAcβ1-3Galβ1-3GalNAcα, Neu5Acα2-6GalNAcβ1-4GlcNAcβ1-3Galβ1-3GalNAcα, Neu5Acα2-6GalNAcβ1-4GlcNAcβ1-3GalNAcβ1-4GlcNAcβ1-3Galβ1-3GalNAcα, Neu5Acα2-6 GalNAcα-β1-3Galα2-3Neu5Ac, Neu5Acα2-6Galβ1-4GlcNAcβ1-3/6GalNAcα, Neu5Acα2-6Galβ1-4GlcNAcβ1-3Galβ1-4GlcNAcβ1-3/6GalNAcα, Neu5Acα2-6GalNAcβ1-4GlcNAcβ1-3/6GalNAcα, Neu5Acα2-6GalNAcβ1-4GlcNAcβ1-3GalNAcβ1-4GlcNAcβ1-3/6GalNAcα, Neu5Acα2-6Galβ1-4GlcNAcβ1-6GalNAcα-β1-3Galα2-3Neu5Ac, Neu5Acα2-6Galβ1-4GlcNAcβ1-3/6GalNAcα-β1-3/6GlcNAcβ1-4Galα2-3/6Neu5Ac, Neu5Acα2-6GlcNAcβ1-3Galβ1-4GlcNAcβ1-3Galβ1-3GalNAc, Neu5Acα2-6GlcNAcβ1-3Galβ1-3GlcNAcβ1-3/6GalNAc, Neu5Acα2-6GlcNAcβ1-3Galβ1-4GlcNAcβ1-3/6GalNAc, Neu5Acα2-6Galβ1-3GalNAcβ1-4Galα1-3Galβ1-4Glc, Neu5Acα2-6Galβ1-4GlcNAcβ1-3Galβ1-4Glc, Neu5Acα2-6Galβ1-3GalNAcβ1-3Galα1-4Galβ1-4Glc, Neu5Acα2-6Galβ1-3GlcNAcβ1-3Galβ1-4Glc, Neu5α2-6Galβ1-4GlcNAcβ1-3GalNAcα, Neu5Acα2-6Galβ1-4GlcNAcβ1-3Galβ1-3GalNAcα, Neu5Acα2-6GalNAc(β1-3Gal-)β1-4Galβ1-4Glc, Neu5Acα2-6GalNAc(β1-3Gal-)β1-3Galα1-4Galβ1-4Glc, and combinations thereof.

35. The method of claim 1, wherein the cone-topology glycans are as set forth in FIG. 8.

36. The method of claim 1, wherein the cone-topology glycans are selected for the group consisting of: Neu5Acα2-3Galβ1-3GlcNAc, Neu5Acα2-3/6Galβ1-4GlcNAc, Neu5Acα2-3Galβ1-3GalNAc-, and combinations thereof.

* * * * *

SEQUENCE LISTING

```
<160> NUMBER OF SEQ ID NOS: 58

<210> SEQ ID NO 1
<211> LENGTH: 323
<212> TYPE: PRT
<213> ORGANISM: Artificial Sequence
<220> FEATURE:
<223> OTHER INFORMATION: NCBI influenza virus sequence

<400> SEQUENCE: 1

Glu Asn Gly Thr Cys Tyr Pro Gly Glu Phe Ile Asp Tyr Glu Glu Leu
1               5                   10                  15

Arg Glu Gln Leu Ser Ser Ile Ser Ser Phe Glu Lys Phe Glu Ile Phe
            20                  25                  30

Pro Lys Ala Ser Ser Trp Pro Asn His Glu Thr Thr Lys Gly Val Thr
        35                  40                  45

Ala Ala Cys Ser Tyr Ser Gly Ala Ser Ser Phe Tyr Arg Asn Leu Leu
    50                  55                  60

Trp Ile Thr Lys Lys Gly Thr Ser Tyr Pro Lys Leu Ser Lys Ser Tyr
65                  70                  75                  80

Thr Asn Asn Lys Gly Lys Glu Val Leu Val Leu Trp Gly Val His His
                85                  90                  95

Pro Pro Ser Val Ser Glu Gln Gln Ser Leu Tyr Gln Asn Ala Asp Ala
            100                 105                 110

Tyr Val Ser Val Gly Ser Ser Lys Tyr Asn Arg Arg Phe Ala Pro Glu
        115                 120                 125

Ile Ala Ala Arg Pro Glu Val Arg Gly Gln Ala Gly Arg Met Asn Tyr
    130                 135                 140

Tyr Trp Thr Leu Leu Asp Gln Gly Asp Thr Ile Thr Phe Glu Ala Thr
145                 150                 155                 160

Gly Asn Leu Ile Ala Pro Trp Tyr Ala Phe Ala Leu Asn Lys Gly Ser
                165                 170                 175

Asp Ser Gly Ile Ile Thr Ser Asp Ala Pro Val His Asn Cys Asp Thr
            180                 185                 190

Arg Cys Gln Thr Pro His Gly Ala Leu Asn Ser Ser Leu Pro Phe Gln
        195                 200                 205

Asn Val His Pro Ile Thr Ile Gly Glu Cys Pro Lys Tyr Val Lys Ser
    210                 215                 220

Thr Lys Leu Arg Met Ala Thr Gly Leu Arg Asn Val Pro Ser Ile Gln
225                 230                 235                 240

Ser Arg Gly Leu Phe Gly Ala Ile Ala Gly Phe Ile Glu Gly Gly Trp
                245                 250                 255

Thr Gly Met Ile Asp Gly Trp Tyr Gly Tyr His His Gln Asn Glu Gln
            260                 265                 270

Gly Ser Gly Tyr Ala Ala Asp Gln Lys Ser Thr Gln Asn Ala Ile Asp
        275                 280                 285

Gly Ile Thr Ser Lys Val Asn Ser Val Ile Glu Lys Met Asn Thr Gln
    290                 295                 300

Phe Thr Ala Val Gly Lys Glu Phe Asn Asn Leu Glu Arg Arg Ile Glu
305                 310                 315                 320

Asn Leu Asn


<210> SEQ ID NO 2
<211> LENGTH: 323
<212> TYPE: PRT
<213> ORGANISM: Artificial Sequence
```

<220> FEATURE:
<223> OTHER INFORMATION: NCBI influenza virus sequence

<400> SEQUENCE: 2

```
Glu Asn Gly Thr Cys Tyr Pro Gly Asp Phe Ile Asp Tyr Glu Glu Leu
1               5                   10                  15

Arg Glu Gln Leu Ser Ser Val Ser Ser Phe Glu Lys Phe Glu Ile Phe
            20                  25                  30

Pro Lys Thr Ser Ser Trp Pro Asn His Glu Thr Thr Lys Gly Val Thr
        35                  40                  45

Ala Ala Cys Ser Tyr Ala Gly Ala Ser Ser Phe Tyr Arg Asn Leu Leu
    50                  55                  60

Trp Leu Thr Lys Lys Gly Ser Ser Tyr Pro Lys Leu Ser Lys Ser Tyr
65                  70                  75                  80

Val Asn Asn Lys Gly Lys Glu Val Leu Val Leu Trp Gly Val His His
                85                  90                  95

Pro Pro Thr Gly Thr Asp Gln Gln Ser Leu Tyr Gln Asn Ala Asp Ala
            100                 105                 110

Tyr Val Ser Val Gly Ser Ser Lys Tyr Asn Arg Arg Phe Thr Pro Glu
        115                 120                 125

Ile Ala Ala Arg Pro Lys Val Arg Asp Gln Ala Gly Arg Met Asn Tyr
    130                 135                 140

Tyr Trp Thr Leu Leu Glu Pro Gly Asp Thr Ile Thr Phe Glu Ala Thr
145                 150                 155                 160

Gly Asn Leu Ile Ala Pro Trp Tyr Ala Phe Ala Leu Asn Arg Gly Ser
                165                 170                 175

Gly Ser Gly Ile Ile Thr Ser Asp Ala Pro Val His Asp Cys Asn Thr
            180                 185                 190

Lys Cys Gln Thr Pro His Gly Ala Ile Asn Ser Ser Leu Pro Phe Gln
        195                 200                 205

Asn Ile His Pro Val Thr Ile Gly Glu Cys Pro Lys Tyr Val Arg Ser
    210                 215                 220

Thr Lys Leu Arg Met Ala Thr Gly Leu Arg Asn Ile Pro Ser Ile Gln
225                 230                 235                 240

Ser Arg Gly Leu Phe Gly Ala Ile Ala Gly Phe Ile Glu Gly Gly Trp
                245                 250                 255

Thr Gly Met Ile Asp Gly Trp Tyr Gly Tyr His His Gln Asn Glu Gln
            260                 265                 270

Gly Ser Gly Tyr Ala Ala Asp Gln Lys Ser Thr Gln Asn Ala Ile Asp
        275                 280                 285

Gly Ile Thr Asn Lys Val Asn Ser Val Ile Glu Lys Met Asn Thr Gln
    290                 295                 300

Phe Thr Ala Val Gly Lys Glu Phe Asn Asn Leu Glu Arg Arg Ile Glu
305                 310                 315                 320

Asn Leu Asn
```

<210> SEQ ID NO 3
<211> LENGTH: 322
<212> TYPE: PRT
<213> ORGANISM: Artificial Sequence
<220> FEATURE:
<223> OTHER INFORMATION: NCBI influenza virus sequence

<400> SEQUENCE: 3

```
Glu Asn Gly Thr Cys Tyr Pro Gly Tyr Phe Ala Asp Tyr Glu Glu Leu
1               5                   10                  15
```

-continued

```
Arg Glu Gln Leu Ser Ser Val Ser Ser Phe Glu Arg Phe Glu Ile Phe
            20                  25                  30

Pro Lys Glu Ser Ser Trp Pro Asn His Thr Val Thr Gly Val Ser Ala
        35                  40                  45

Ser Cys Ser His Asn Gly Lys Ser Ser Phe Tyr Arg Asn Leu Leu Trp
    50                  55                  60

Leu Thr Gly Lys Asn Gly Leu Tyr Pro Asn Leu Ser Lys Ser Tyr Val
65                  70                  75                  80

Asn Asn Lys Glu Lys Glu Val Leu Val Leu Trp Gly Val His His Pro
                85                  90                  95

Pro Asn Ile Gly Asp Gln Arg Ala Leu Tyr His Thr Glu Asn Ala Tyr
            100                 105                 110

Val Ser Val Val Ser Ser His Tyr Ser Arg Arg Phe Thr Pro Glu Ile
        115                 120                 125

Ala Lys Arg Pro Lys Val Arg Asp Gln Glu Gly Arg Ile Asn Tyr Tyr
    130                 135                 140

Trp Thr Leu Leu Glu Pro Gly Asp Thr Ile Ile Phe Glu Ala Asn Gly
145                 150                 155                 160

Asn Leu Ile Ala Pro Trp Tyr Ala Phe Ala Leu Ser Arg Gly Phe Gly
                165                 170                 175

Ser Gly Ile Ile Thr Ser Asn Ala Pro Met Asp Glu Cys Asp Ala Lys
            180                 185                 190

Cys Gln Thr Pro Gln Gly Ala Ile Asn Ser Ser Leu Pro Phe Gln Asn
        195                 200                 205

Val His Pro Val Thr Ile Gly Glu Cys Pro Lys Tyr Val Arg Ser Ala
    210                 215                 220

Lys Leu Arg Met Val Thr Gly Leu Arg Asn Ile Pro Ser Ile Gln Ser
225                 230                 235                 240

Arg Gly Leu Phe Gly Ala Ile Ala Gly Phe Ile Glu Gly Gly Trp Thr
                245                 250                 255

Gly Met Val Asp Gly Trp Tyr Gly Tyr His His Gln Asn Glu Gln Gly
            260                 265                 270

Ser Gly Tyr Ala Ala Asp Gln Lys Ser Thr Gln Asn Ala Ile Asn Gly
        275                 280                 285

Ile Thr Asn Lys Val Asn Ser Val Ile Glu Lys Met Asn Thr Gln Phe
    290                 295                 300

Thr Ala Val Gly Lys Glu Phe Asn Lys Leu Glu Arg Arg Met Glu Asn
305                 310                 315                 320

Leu Asn


<210> SEQ ID NO 4
<211> LENGTH: 321
<212> TYPE: PRT
<213> ORGANISM: Artificial Sequence
<220> FEATURE:
<223> OTHER INFORMATION: NCBI influenza virus sequence

<400> SEQUENCE: 4

Ala Asn Gly Leu Cys Tyr Pro Gly Ser Phe Asn Asp Tyr Glu Glu Leu
1               5                   10                  15

Lys His Leu Leu Thr Ser Val Thr His Phe Glu Lys Val Lys Ile Leu
            20                  25                  30

Pro Arg Asp Gln Trp Thr Gln His Thr Thr Thr Gly Gly Ser Arg Ala
        35                  40                  45
```

```
Cys Ala Val Ser Gly Asn Pro Ser Phe Phe Arg Asn Met Val Trp Leu
    50                  55                  60

Thr Glu Lys Gly Ser Asn Tyr Pro Ile Ala Lys Arg Ser Tyr Asn Asn
65                  70                  75                  80

Thr Ser Gly Lys Gln Met Leu Val Ile Trp Gly Ile His His Pro Asn
                85                  90                  95

Asp Asp Thr Glu Gln Arg Thr Leu Tyr Gln Asn Val Gly Thr Tyr Val
            100                 105                 110

Ser Val Gly Thr Ser Thr Leu Asn Lys Arg Ser Ile Pro Glu Ile Ala
        115                 120                 125

Thr Arg Pro Lys Val Asn Gly Gln Gly Gly Arg Met Glu Phe Ser Trp
    130                 135                 140

Thr Leu Leu Glu Thr Trp Asp Val Ile Asn Phe Glu Ser Thr Gly Asn
145                 150                 155                 160

Leu Ile Ala Pro Glu Tyr Gly Phe Lys Ile Ser Lys Arg Gly Ser Ser
                165                 170                 175

Gly Ile Met Lys Thr Glu Lys Thr Leu Glu Asn Cys Glu Thr Lys Cys
            180                 185                 190

Gln Thr Pro Leu Gly Ala Ile Asn Thr Thr Leu Pro Phe His Asn Ile
        195                 200                 205

His Pro Leu Thr Ile Gly Glu Cys Pro Lys Tyr Val Lys Ser Asp Arg
    210                 215                 220

Leu Val Leu Ala Thr Gly Leu Arg Asn Val Pro Gln Ile Glu Ser Arg
225                 230                 235                 240

Gly Leu Phe Gly Ala Ile Ala Gly Phe Ile Glu Gly Gly Trp Gln Gly
                245                 250                 255

Met Val Asp Gly Trp Tyr Gly Tyr His His Ser Asn Asp Gln Gly Ser
            260                 265                 270

Gly Tyr Ala Ala Asp Lys Glu Ser Thr Gln Lys Ala Ile Asp Gly Ile
        275                 280                 285

Thr Asn Lys Val Asn Ser Val Ile Glu Lys Met Asn Thr Gln Phe Glu
    290                 295                 300

Ala Val Gly Lys Glu Phe Asn Asn Leu Glu Arg Arg Leu Glu Asn Leu
305                 310                 315                 320

Asn


<210> SEQ ID NO 5
<211> LENGTH: 321
<212> TYPE: PRT
<213> ORGANISM: Artificial Sequence
<220> FEATURE:
<223> OTHER INFORMATION: NCBI influenza virus sequence

<400> SEQUENCE: 5

Arg Asp Gly Leu Cys Tyr Pro Gly Ser Phe Asn Asp Tyr Glu Glu Leu
1               5                   10                  15

Lys His Leu Leu Ser Ser Val Lys His Phe Glu Lys Val Lys Ile Leu
            20                  25                  30

Pro Lys Asp Arg Trp Thr Gln His Thr Thr Thr Gly Gly Ser Arg Ala
        35                  40                  45

Cys Ala Val Ser Gly Asn Pro Ser Phe Phe Arg Asn Met Val Trp Leu
    50                  55                  60

Thr Glu Lys Gly Ser Asn Tyr Pro Val Ala Lys Gly Ser Tyr Asn Asn
65                  70                  75                  80

Thr Ser Gly Glu Gln Met Leu Ile Ile Trp Gly Val His His Pro Asn
```

```
                85                  90                  95

Asp Glu Lys Glu Gln Arg Thr Leu Tyr Gln Asn Val Gly Thr Tyr Val
            100                 105                 110

Ser Val Gly Thr Ser Thr Leu Asn Lys Arg Ser Thr Pro Asp Ile Ala
        115                 120                 125

Thr Arg Pro Lys Val Asn Gly Leu Gly Ser Arg Met Glu Phe Ser Trp
    130                 135                 140

Thr Leu Leu Asp Met Trp Asp Thr Ile Asn Phe Glu Ser Thr Gly Asn
145                 150                 155                 160

Leu Ile Ala Pro Glu Tyr Gly Phe Lys Ile Ser Lys Arg Gly Ser Ser
                165                 170                 175

Gly Ile Met Lys Thr Glu Gly Thr Leu Glu Asn Cys Glu Thr Lys Cys
            180                 185                 190

Gln Thr Pro Leu Gly Ala Ile Asn Thr Thr Leu Pro Phe His Asn Val
        195                 200                 205

His Pro Leu Thr Ile Gly Glu Cys Pro Lys Tyr Val Lys Ser Glu Lys
    210                 215                 220

Leu Val Leu Ala Thr Gly Leu Arg Asn Val Pro Gln Ile Glu Ser Arg
225                 230                 235                 240

Gly Leu Phe Gly Ala Ile Ala Gly Phe Ile Glu Gly Gly Trp Gln Gly
                245                 250                 255

Met Ile Asp Gly Trp Tyr Gly Tyr His His Ser Asn Asp Gln Gly Ser
            260                 265                 270

Gly Tyr Ala Ala Asp Lys Glu Ser Thr Gln Lys Ala Phe Asp Gly Ile
        275                 280                 285

Thr Asn Lys Val Asn Ser Val Ile Glu Lys Met Asn Thr Gln Phe Glu
    290                 295                 300

Ala Val Gly Lys Glu Phe Ser Asn Leu Glu Arg Arg Leu Glu Asn Leu
305                 310                 315                 320

Asn


<210> SEQ ID NO 6
<211> LENGTH: 316
<212> TYPE: PRT
<213> ORGANISM: Artificial Sequence
<220> FEATURE:
<223> OTHER INFORMATION: NCBI influenza virus sequence

<400> SEQUENCE: 6

Phe Ser Asn Cys Tyr Pro Tyr Asp Ile Pro Asp Tyr Ala Ser Leu Arg
1               5                   10                  15

Ser Leu Val Ala Ser Ser Gly Thr Leu Glu Phe Ile Thr Glu Gly Phe
            20                  25                  30

Thr Trp Thr Gly Val Thr Gln Asn Gly Gly Ser Ser Ala Cys Lys Arg
        35                  40                  45

Gly Pro Ala Asn Gly Phe Phe Ser Arg Leu Asn Trp Leu Thr Lys Ser
    50                  55                  60

Glu Ser Ala Tyr Pro Val Leu Asn Val Thr Met Pro Asn Asn Asp Asn
65                  70                  75                  80

Phe Asp Lys Leu Tyr Ile Trp Gly Val His His Pro Ser Thr Asn Gln
                85                  90                  95

Glu Gln Thr Asp Leu Tyr Val Gln Ala Ser Gly Arg Val Thr Val Ser
            100                 105                 110

Thr Arg Arg Ser Gln Gln Thr Ile Ile Pro Asn Ile Gly Ser Arg Pro
        115                 120                 125
```

```
Trp Val Arg Gly Gln Pro Gly Arg Ile Ser Ile Tyr Trp Thr Ile Val
    130                 135                 140

Lys Pro Gly Asp Val Leu Val Ile Asn Ser Asn Gly Asn Leu Ile Ala
145                 150                 155                 160

Pro Arg Gly Tyr Phe Lys Met Arg Thr Gly Lys Ser Ser Ile Met Arg
                165                 170                 175

Ser Asp Ala Pro Ile Asp Thr Cys Ile Ser Glu Cys Ile Thr Pro Asn
            180                 185                 190

Gly Ser Ile Pro Asn Asp Lys Pro Phe Gln Asn Val Asn Lys Ile Thr
        195                 200                 205

Tyr Gly Ala Cys Pro Lys Tyr Val Lys Asn Thr Leu Lys Leu Ala Thr
    210                 215                 220

Gly Met Arg Asn Val Pro Gly Lys Gln Thr Arg Gly Leu Phe Gly Ala
225                 230                 235                 240

Ile Ala Gly Phe Ile Glu Asn Gly Trp Glu Gly Met Ile Asp Gly Trp
                245                 250                 255

Tyr Gly Phe Arg His Gln Asn Ser Glu Gly Thr Gly Gln Ala Ala Asp
            260                 265                 270

Leu Lys Ser Thr Gln Ala Ala Ile Asp Gln Ile Asn Arg Lys Leu Asn
        275                 280                 285

Arg Val Ile Glu Lys Thr Asn Glu Lys Phe His Gln Ile Glu Lys Glu
    290                 295                 300

Phe Ser Glu Val Glu Gly Arg Ile Gln Asp Leu Glu
305                 310                 315


<210> SEQ ID NO 7
<211> LENGTH: 315
<212> TYPE: PRT
<213> ORGANISM: Artificial Sequence
<220> FEATURE:
<223> OTHER INFORMATION: NCBI influenza virus sequence

<400> SEQUENCE: 7

Phe Ser Asn Cys Tyr Pro Tyr Asp Val Pro Asp Tyr Ala Ser Leu Arg
1               5                   10                  15

Ser Leu Val Ala Ser Ser Gly Thr Leu Glu Phe Ile Thr Glu Gly Phe
            20                  25                  30

Thr Trp Thr Gly Val Thr Gln Asn Gly Gly Ser Asn Ala Cys Lys Arg
        35                  40                  45

Gly Pro Gly Ser Gly Phe Phe Ser Arg Leu Asn Trp Leu Thr Lys Ser
    50                  55                  60

Gly Ser Thr Tyr Pro Val Leu Asn Val Thr Met Pro Asn Asn Asp Asn
65                  70                  75                  80

Phe Asp Lys Leu Tyr Ile Trp Gly Ile His His Pro Ser Thr Asn Gln
                85                  90                  95

Glu Gln Thr Ser Leu Tyr Val Gln Ala Ser Gly Arg Val Thr Val Ser
            100                 105                 110

Thr Arg Arg Ser Gln Gln Thr Ile Ile Pro Asn Ile Gly Ser Arg Pro
        115                 120                 125

Trp Val Arg Gly Leu Ser Ser Arg Ile Ser Thr Tyr Trp Thr Ile Val
    130                 135                 140

Lys Pro Gly Asp Val Leu Val Ile Asn Ser Asn Gly Asn Leu Ile Ala
145                 150                 155                 160

Pro Arg Gly Tyr Phe Lys Met Arg Thr Gly Lys Ser Ser Ile Met Arg
                165                 170                 175
```

```
Ser Asp Ala Pro Ile Asp Thr Cys Ile Ser Glu Cys Ile Thr Pro Asn
            180                 185                 190

Gly Ser Ile Pro Asn Lys Pro Phe Gln Asn Val Asn Lys Ile Thr Tyr
        195                 200                 205

Gly Ala Cys Pro Lys Tyr Val Lys Gln Asn Thr Leu Lys Leu Ala Thr
    210                 215                 220

Gly Met Arg Asn Val Pro Glu Lys Gln Thr Arg Gly Leu Phe Gly Ala
225                 230                 235                 240

Ile Ala Gly Phe Ile Glu Asn Gly Trp Glu Gly Met Ile Asp Gly Trp
                245                 250                 255

Tyr Gly Phe Arg His Gln Asn Ser Glu Gly Thr Gly Gln Ala Ala Leu
            260                 265                 270

Lys Ser Thr Gln Ala Ala Thr Asp Gln Ile Asn Gly Lys Leu Asn Arg
        275                 280                 285

Val Ile Glu Lys Thr Asn Glu Lys Phe His Gln Ile Glu Lys Glu Phe
    290                 295                 300

Ser Glu Val Glu Gly Arg Ile Gln Asp Leu Glu
305                 310                 315


<210> SEQ ID NO 8
<211> LENGTH: 316
<212> TYPE: PRT
<213> ORGANISM: Artificial Sequence
<220> FEATURE:
<223> OTHER INFORMATION: NCBI influenza virus sequence

<400> SEQUENCE: 8

Phe Ser Asn Cys Tyr Pro Tyr Asp Val Pro Asp Tyr Ala Ser Leu Arg
1               5                   10                  15

Ser Leu Val Ala Ser Ser Gly Thr Leu Glu Phe Asn Asn Glu Ser Phe
            20                  25                  30

Asn Trp Ala Gly Val Thr Gln Asn Gly Thr Ser Ser Ala Cys Lys Arg
        35                  40                  45

Arg Ser Asn Lys Ser Phe Phe Ser Arg Leu Asn Trp Leu Thr His Leu
    50                  55                  60

Lys Tyr Lys Tyr Pro Ala Leu Asn Val Ile Met Pro Asn Asn Glu Lys
65                  70                  75                  80

Phe Asp Lys Leu Tyr Ile Trp Gly Val His His Pro Val Thr Asp Ser
                85                  90                  95

Asp Gln Ile Ser Leu Tyr Ala Gln Ala Ser Gly Arg Ile Thr Val Ser
            100                 105                 110

Thr Lys Arg Ser Gln Gln Thr Val Ile Pro Asn Ile Gly Tyr Arg Pro
        115                 120                 125

Arg Val Arg Asp Ile Ser Ser Arg Ile Ser Thr Tyr Trp Thr Ile Val
    130                 135                 140

Lys Pro Gly Asp Ile Leu Leu Ile Asn Ser Thr Gly Asn Leu Ile Ala
145                 150                 155                 160

Pro Arg Gly Tyr Phe Lys Ile Arg Ser Gly Lys Ser Ser Ile Met Arg
                165                 170                 175

Ser Asp Ala Pro Ile Gly Lys Cys Asn Ser Glu Cys Ile Thr Pro Asn
            180                 185                 190

Gly Ser Ile Pro Asn Asp Lys Pro Phe Gln Asn Val Asn Arg Ile Thr
        195                 200                 205

Tyr Gly Ala Cys Pro Arg Tyr Val Lys Gln Asn Thr Leu Lys Leu Ala
    210                 215                 220
```

Thr Gly Met Arg Asn Val Pro Glu Lys Gln Thr Arg Gly Ile Phe Gly
225 230 235 240

Ala Ile Ala Gly Phe Ile Glu Asn Gly Trp Glu Gly Met Val Asp Gly
245 250 255

Trp Tyr Gly Phe Arg His Gln Asn Ser Glu Gly Thr Gly Gln Ala Ala
260 265 270

Asp Leu Lys Ser Thr Gln Ala Ala Ile Asn Gln Ile Asn Gly Lys Leu
275 280 285

Arg Leu Ile Gly Lys Thr Asn Glu Lys Phe His Gln Ile Glu Lys Glu
290 295 300

Phe Ser Glu Val Glu Gly Arg Ile Gln Asp Leu Glu
305 310 315

<210> SEQ ID NO 9
<211> LENGTH: 319
<212> TYPE: PRT
<213> ORGANISM: Artificial Sequence
<220> FEATURE:
<223> OTHER INFORMATION: NCBI influenza virus sequence

<400> SEQUENCE: 9

Val Asp Thr Cys Tyr Pro Phe Asp Val Pro Asp Tyr Gln Ser Leu Arg
1 5 10 15

Ser Ile Leu Ala Asn Asn Gly Lys Phe Glu Phe Ile Ala Glu Glu Phe
20 25 30

Gln Trp Asn Thr Val Lys Gln Asn Gly Lys Ser Gly Ala Cys Lys Arg
35 40 45

Ala Asn Val Asn Asp Phe Phe Asn Arg Leu Asn Trp Leu Thr Lys Ser
50 55 60

Asn Gly Asp Ala Tyr Pro Leu Gln Asn Leu Thr Lys Val Asn Asn Gly
65 70 75 80

Asp Tyr Ala Arg Leu Tyr Ile Trp Gly Val His His Pro Ser Thr Asp
85 90 95

Thr Glu Gln Thr Asp Leu Tyr Lys Asn Asn Pro Gly Arg Val Thr Val
100 105 110

Ser Thr Lys Thr Ser Gln Thr Ser Val Val Pro Asn Ile Gly Ser Arg
115 120 125

Pro Trp Val Arg Gly Gln Ser Gly Arg Ile Ser Phe Tyr Trp Thr Ile
130 135 140

Val Asp Pro Gly Asp Ile Ile Val Phe Asn Thr Ile Gly Asn Leu Ile
145 150 155 160

Ala Pro Arg Cys His Tyr Lys Leu Asn Ser Gln Lys Lys Ser Thr Ile
165 170 175

Leu Asn Thr Ala Val Pro Ile Gly Ser Cys Val Ser Lys Cys His Thr
180 185 190

Asp Arg Gly Ser Ile Thr Thr Thr Lys Pro Phe Gln Asn Ile Ser Arg
195 200 205

Ile Ser Ile Gly Asp Cys Pro Lys Tyr Val Lys Gln Gly Ser Leu Lys
210 215 220

Leu Ala Thr Gly Met Arg Asn Ile Pro Glu Lys Ala Thr Arg Gly Leu
225 230 235 240

Phe Gly Ala Ile Ala Gly Phe Ile Glu Asn Gly Trp Gln Gly Leu Ile
245 250 255

Asp Gly Trp Tyr Gly Phe Arg His Gln Asn Ala Glu Gly Thr Gly Thr
260 265 270

```
Ala Ala Asp Leu Lys Ser Thr Gln Ala Ala Ile Asp Gln Ile Asn Gly
        275                 280                 285

Lys Leu Arg Asn Leu Ile Glu Lys Thr Asn Glu Lys Tyr His Gln Ile
    290                 295                 300

Glu Lys Glu Phe Glu Gln Val Glu Gly Arg Ile Gln Asp Leu Glu
305                 310                 315


<210> SEQ ID NO 10
<211> LENGTH: 324
<212> TYPE: PRT
<213> ORGANISM: Artificial Sequence
<220> FEATURE:
<223> OTHER INFORMATION: NCBI influenza virus sequence

<400> SEQUENCE: 10

Val Asn Asp Leu Cys Tyr Pro Gly Asp Phe Asn Tyr Glu Glu Leu Lys
1               5                   10                  15

His Leu Leu Ser Arg Ile Asn His Phe Glu Lys Ile Gln Ile Ile Pro
            20                  25                  30

Lys Ser Ser Trp Ser Ser His Glu Ala Ser Leu Gly Val Ser Ser Ala
        35                  40                  45

Cys Pro Tyr Gln Gly Lys Ser Ser Phe Phe Arg Asn Val Val Trp Leu
    50                  55                  60

Ile Lys Lys Asn Ser Thr Tyr Pro Thr Ile Lys Arg Ser Tyr Asn Asn
65                  70                  75                  80

Thr Asn Gln Glu Asp Leu Leu Val Leu Trp Gly Thr His His Pro Asn
                85                  90                  95

Asp Ala Ala Glu Gln Thr Lys Leu Tyr Gln Asn Pro Thr Thr Tyr Ile
            100                 105                 110

Ser Val Gly Thr Ser Thr Leu Asn Gln Arg Leu Val Pro Arg Ile Ala
        115                 120                 125

Thr Arg Ser Lys Val Asn Gly Gln Ser Gly Arg His Glu Phe Phe Trp
    130                 135                 140

Thr Ile Leu Lys Pro Asn Asp Ile Asn Phe Glu Ser Asn Gly Asn Phe
145                 150                 155                 160

Ile Ala Pro Glu Tyr Ala Tyr Lys Ile Val Lys Lys Gly Asp Ser Thr
                165                 170                 175

Ile Met Lys Ser Glu Leu Glu Tyr Gly Asn Cys Asn Thr Lys Cys Gln
            180                 185                 190

Thr Met Gly Ala Ile Asn Ser Ser Met Pro Phe His Asn Ile His Pro
        195                 200                 205

Leu Thr Ile Gly Glu Cys Pro Lys Tyr Val Lys Ser Asn Arg Leu Val
    210                 215                 220

Leu Ala Thr Gly Leu Arg Asn Ser Pro Gln Arg Glu Arg Arg Arg Arg
225                 230                 235                 240

Lys Lys Arg Gly Leu Phe Gly Ala Ile Ala Gly Phe Ile Glu Gly Gly
                245                 250                 255

Trp Gln Gly Met Val Asp Gly Trp Tyr Gly Tyr His His Ser Asn Glu
            260                 265                 270

Gln Gly Ser Gly Tyr Ala Ala Asp Lys Glu Ser Thr Gln Lys Ala Ile
        275                 280                 285

Asp Gly Val Thr Asn Lys Val Asn Ser Ile Ile Asp Lys Met Asn Thr
    290                 295                 300

Gln Phe Glu Ala Val Gly Arg Glu Phe Asn Trp Leu Glu Arg Arg Ile
305                 310                 315                 320
```

-continued

Glu Asn Leu Asn

<210> SEQ ID NO 11
<211> LENGTH: 326
<212> TYPE: PRT
<213> ORGANISM: Artificial Sequence
<220> FEATURE:
<223> OTHER INFORMATION: NCBI influenza virus sequence

<400> SEQUENCE: 11

```
Ala Asn Asp Leu Cys Tyr Pro Gly Asp Phe Asn Asp Tyr Glu Glu Leu
1               5                   10                  15

Lys His Leu Leu Ser Arg Ile Asn His Phe Glu Lys Ile Gln Ile Ile
            20                  25                  30

Pro Lys Asn Ser Trp Ser Ser His Glu Ala Ser Leu Gly Val Ser Ser
        35                  40                  45

Ala Cys Pro Tyr Gln Gly Lys Ser Ser Phe Phe Arg Asn Val Val Trp
    50                  55                  60

Leu Ile Lys Lys Asn Asn Ala Tyr Pro Thr Ile Lys Arg Ser Tyr Asn
65                  70                  75                  80

Asn Thr Asn Gln Glu Asp Leu Leu Val Leu Trp Gly Ile His His Pro
                85                  90                  95

Asn Asp Ala Ala Glu Gln Thr Arg Leu Tyr Gln Asn Pro Thr Thr Tyr
            100                 105                 110

Ile Ser Val Gly Thr Ser Thr Leu Asn Gln Arg Leu Val Pro Lys Ile
        115                 120                 125

Ala Thr Arg Ser Lys Val Asn Gly Gln Asn Gly Arg Met Glu Phe Phe
    130                 135                 140

Trp Thr Ile Leu Lys Pro Asn Asp Ala Ile Asn Phe Glu Ser Asn Gly
145                 150                 155                 160

Asn Phe Ile Ala Pro Glu Tyr Ala Tyr Lys Ile Val Lys Lys Gly Asp
                165                 170                 175

Ser Ala Ile Met Lys Ser Glu Leu Glu Tyr Gly Asn Cys Asn Thr Lys
            180                 185                 190

Cys Gln Thr Pro Met Gly Ala Ile Asn Ser Ser Met Pro Phe His Asn
        195                 200                 205

Ile His Pro Leu Thr Ile Gly Glu Cys Pro Lys Tyr Val Lys Asn Ser
    210                 215                 220

Arg Leu Val Leu Ala Thr Gly Leu Arg Asn Ser Pro Gln Arg Glu Arg
225                 230                 235                 240

Arg Arg Lys Lys Arg Gly Leu Phe Gly Ala Ile Ala Gly Phe Ile Glu
                245                 250                 255

Gly Gly Trp Gln Gly Met Val Asp Gly Trp Tyr Gly Tyr His His Ser
            260                 265                 270

Asn Glu Gln Gly Ser Gly Tyr Ala Ala Asp Lys Glu Ser Thr Gln Lys
        275                 280                 285

Ala Ile Asp Gly Val Thr Asn Lys Val Asn Ser Ile Ile Asp Lys Met
    290                 295                 300

Asn Thr Gln Phe Glu Ala Val Gly Arg Glu Phe Asn Asn Leu Glu Arg
305                 310                 315                 320

Arg Ile Glu Asn Leu Asn
                325
```

<210> SEQ ID NO 12
<211> LENGTH: 325

<212> TYPE: PRT
<213> ORGANISM: Artificial Sequence
<220> FEATURE:
<223> OTHER INFORMATION: NCBI influenza virus sequence

<400> SEQUENCE: 12

```
Gln Asn Gly Ile Cys Tyr Pro Gly Thr Leu Asn Glu Ile Glu Glu Leu
1               5                   10                  15

Lys Ala Leu Ile Gly Ser Gly Glu Arg Ile Glu Arg Phe Glu Met Phe
            20                  25                  30

Pro Lys Ser Thr Trp Ser Gly Val Asn Thr Asn Asn Gly Val Thr Arg
        35                  40                  45

Ala Cys Pro Asp Asn Ser Gly Ser Ser Phe Tyr Arg Asn Leu Leu Trp
    50                  55                  60

Ile Thr Lys Thr Asn Ser Ala Ala Tyr Pro Val Ile Lys Gly Thr Tyr
65                  70                  75                  80

Asn Asn Thr Gly Asn Gln Pro Ile Leu Tyr Phe Trp Gly Val His His
                85                  90                  95

Pro Pro Asp Thr Asn Ala Gln Asn Asn Leu Tyr Gly Ser Gly Asp Arg
            100                 105                 110

Tyr Val Arg Met Gly Thr Glu Ser Met Asn Phe Ala Lys Gly Pro Glu
        115                 120                 125

Ile Ser Ala Arg Pro Val Val Asn Gly Gln Arg Gly Arg Ile Asp Tyr
    130                 135                 140

Tyr Trp Ser Val Leu Lys Pro Gly Glu Thr Leu Asn Val Glu Ser Asn
145                 150                 155                 160

Gly Asn Leu Ile Ala Pro Trp Tyr Ala Tyr Lys Phe Val Ser Thr Asn
                165                 170                 175

Ser Lys Gly Ala Val Phe Lys Ser Asn Leu Pro Ile Glu Asn Cys Asp
            180                 185                 190

Ala Thr Cys Gln Thr Thr Ile Ala Gly Val Leu Arg Thr Asn Lys Thr
        195                 200                 205

Phe Gln Asn Val Ser Pro Leu Trp Ile Gly Lys Cys Pro Lys Tyr Val
    210                 215                 220

Lys Ser Glu Ser Leu Arg Leu Ala Thr Gly Leu Arg Asn Val Pro Gln
225                 230                 235                 240

Ile Ala Thr Arg Gly Leu Phe Gly Ala Ile Ala Gly Phe Ile Glu Gly
                245                 250                 255

Gly Trp Thr Gly Leu Val Asp Gly Trp Tyr Gly Tyr His His Glu Asn
            260                 265                 270

Ser Gln Gly Ser Gly Tyr Ala Ala Asp Arg Glu Ala Thr Gln Lys Ala
        275                 280                 285

Ile Asp Gly Ile Thr Asn Lys Val Asn Ser Ile Ile Asp Lys Met Asn
    290                 295                 300

Thr Gln Phe Glu Ala Val Asp His Glu Phe Ser Asn Leu Glu Arg Arg
305                 310                 315                 320

Ile Asp Asn Met Asn
                325
```

<210> SEQ ID NO 13
<211> LENGTH: 319
<212> TYPE: PRT
<213> ORGANISM: Artificial Sequence
<220> FEATURE:
<223> OTHER INFORMATION: NCBI influenza virus sequence

<400> SEQUENCE: 13

```
Ser Asp Val Cys Tyr Pro Gly Lys Phe Val Asn Glu Glu Ala Leu Arg
1               5                   10                  15

Gln Ile Leu Arg Glu Ser Gly Gly Ile Asn Lys Glu Thr Met Gly Phe
            20                  25                  30

Thr Tyr Ser Gly Ile Arg Thr Asn Gly Ala Thr Ser Thr Cys Arg Arg
        35                  40                  45

Ser Gly Ser Ser Phe Tyr Ala Glu Met Lys Trp Leu Leu Ser Asn Thr
    50                  55                  60

Asp Asn Ala Ala Phe Pro Gln Met Thr Lys Ser Tyr Lys Asn Thr Arg
65                  70                  75                  80

Lys Asp Pro Ala Leu Ile Ile Trp Gly Ile His His Ser Gly Ser Thr
                85                  90                  95

Thr Glu Gln Thr Lys Leu Tyr Gly Ser Gly Asn Lys Leu Ile Thr Val
            100                 105                 110

Glu Ser Ser Asn Tyr Gln Gln Ser Phe Val Pro Ser Pro Gly Ala Arg
        115                 120                 125

Pro Lys Val Asp Gly Gln Ser Gly Arg Ile Asp Phe His Trp Leu Met
    130                 135                 140

Leu Asn Pro Asn Asp Thr Ile Thr Phe Ser Phe Asn Gly Ala Phe Ile
145                 150                 155                 160

Ala Pro Asp Arg Ala Ser Phe Leu Arg Gly Lys Ser Met Gly Ile Gln
                165                 170                 175

Ser Gly Val Gln Val Asp Asp Asn Cys Glu Gly Asp Cys Tyr His Ser
            180                 185                 190

Gly Gly Thr Ile Ile Ser Asn Leu Pro Phe Gln Asn Ile Asn Ser Arg
        195                 200                 205

Ala Val Gly Lys Cys Pro Arg Tyr Val Lys Gln Glu Ser Leu Met Leu
    210                 215                 220

Ala Thr Gly Met Lys Asn Val Pro Glu Ile Pro Lys Gly Arg Gly Leu
225                 230                 235                 240

Phe Gly Ala Ile Ala Gly Phe Ile Glu Asn Gly Trp Glu Gly Leu Ile
                245                 250                 255

Asp Gly Trp Tyr Gly Phe Arg His Gln Asn Ala Gln Gly Glu Gly Thr
            260                 265                 270

Ala Ala Asp Tyr Lys Ser Thr Gln Ser Ala Ile Asp Gln Ile Thr Gly
        275                 280                 285

Lys Leu Asn Arg Leu Ile Glu Lys Thr Asn Gln Gln Phe Glu Leu Ile
    290                 295                 300

Asp Asn Glu Phe Thr Glu Val Glu Lys Gln Ile Gly Asn Val Ile
305                 310                 315


<210> SEQ ID NO 14
<211> LENGTH: 325
<212> TYPE: PRT
<213> ORGANISM: Artificial Sequence
<220> FEATURE:
<223> OTHER INFORMATION: NCBI influenza virus sequence

<400> SEQUENCE: 14

Pro Glu Gly Met Cys Tyr Pro Gly Ser Val Glu Asn Leu Glu Glu Leu
1               5                   10                  15

Arg Phe Val Phe Ser Ser Ala Ala Ser Tyr Lys Arg Ile Arg Leu Phe
            20                  25                  30

Asp Tyr Ser Arg Trp Asn Val Thr Arg Ser Gly Thr Ser Lys Ala Cys
        35                  40                  45
```

Asn Ala Ser Thr Gly Gly Gln Ser Phe Tyr Arg Ser Ile Asn Trp Leu
    50                  55                  60

Thr Lys Lys Lys Pro Asp Thr Tyr Asp Phe Asn Glu Gly Ala Tyr Val
65                  70                  75                  80

Asn Asn Glu Asp Gly Asp Ile Ile Phe Leu Trp Gly Ile His His Pro
                85                  90                  95

Pro Asp Thr Lys Glu Gln Thr Thr Leu Tyr Lys Asn Ala Asn Thr Leu
            100                 105                 110

Ser Ser Val Thr Thr Asn Thr Ile Asn Arg Ser Phe Gln Pro Asn Ile
        115                 120                 125

Gly Pro Arg Pro Leu Val Arg Gly Gln Gln Gly Arg Met Asp Tyr Tyr
    130                 135                 140

Trp Gly Ile Leu Lys Arg Gly Glu Thr Leu Lys Ile Arg Thr Asn Gly
145                 150                 155                 160

Asn Leu Ile Ala Pro Glu Phe Gly Tyr Leu Leu Lys Gly Glu Ser Tyr
                165                 170                 175

Gly Arg Ile Ile Gln Asn Glu Asp Ile Pro Ile Gly Asn Cys Asn Thr
            180                 185                 190

Lys Cys Gln Thr Tyr Ala Gly Ala Ile Asn Ser Ser Lys Pro Phe Gln
        195                 200                 205

Asn Ala Ser His Arg His Tyr Met Gly Glu Cys Pro Lys Tyr Val Lys
    210                 215                 220

Lys Ala Ser Leu Arg Leu Ala Val Gly Leu Arg Asn Thr Pro Ser Val
225                 230                 235                 240

Glu Pro Arg Gly Leu Phe Gly Ala Ile Ala Gly Phe Ile Glu Gly Gly
                245                 250                 255

Trp Ser Gly Met Ile Asp Gly Trp Tyr Gly Phe His His Ser Asn Glu
            260                 265                 270

Ser Glu Gly Thr Gly Met Ala Ala Asp Gln Lys Ser Thr Gln Glu Ala
        275                 280                 285

Ile Asp Lys Ile Thr Asn Lys Val Asn Asn Ile Val Asp Lys Met Asn
    290                 295                 300

Arg Glu Phe Glu Val Val Asn His Glu Phe Ser Glu Val Glu Lys Arg
305                 310                 315                 320

Ile Asn Met Ile Asn
                325

<210> SEQ ID NO 15
<211> LENGTH: 316
<212> TYPE: PRT
<213> ORGANISM: Artificial Sequence
<220> FEATURE:
<223> OTHER INFORMATION: NCBI influenza virus sequence

<400> SEQUENCE: 15

Val Asn Gly Thr Cys Tyr Pro Gly Asn Val Glu Asn Leu Glu Glu Leu
1               5                   10                  15

Arg Thr Leu Phe Ser Ser Ala Ser Ser Tyr Gln Arg Ile Gln Ile Phe
            20                  25                  30

Pro Asp Thr Ile Trp Asn Val Thr Val Thr Gly Thr Ser Lys Ala Cys
        35                  40                  45

Ser Gly Ser Phe Tyr Arg Ser Met Arg Trp Leu Thr Gln Lys Ser Gly
    50                  55                  60

Ser Tyr Pro Val Gln Asp Ala Gln Tyr Thr Asn Asn Arg Glu Lys Ser
65                  70                  75                  80

```
Ile Leu Phe Val Trp Gly Ile His His Pro Pro Thr Asp Thr Ala Trp
                85                  90                  95

Thr Asn Leu Tyr Ile Asn Thr Asp Thr Thr Thr Ser Val Thr Thr Glu
            100                 105                 110

Asp Leu Asn Arg Ile Phe Lys Pro Val Ile Gly Pro Arg Pro Leu Val
        115                 120                 125

Asn Gly Leu Gln Gly Arg Ile Asn Tyr Tyr Trp Ser Val Leu Lys Pro
    130                 135                 140

Gly Gln Thr Leu Arg Val Arg Ser Asn Gly Asn Leu Ile Ala Pro Trp
145                 150                 155                 160

Tyr Gly His Val Leu Ser Gly Gly Ser His Gly Arg Ile Leu Lys Thr
                165                 170                 175

Asp Leu Asn Ser Gly Asn Cys Val Val Gln Cys Gln Thr Glu Lys Gly
            180                 185                 190

Gly Leu Asn Ser Thr Leu Pro Phe His Asn Ile Ser Lys Tyr Ala Phe
        195                 200                 205

Gly Ile Cys Pro Lys Tyr Val Arg Val Lys Ser Leu Lys Leu Ala Val
    210                 215                 220

Gly Leu Arg Asn Val Pro Ala Arg Ser Asn Arg Gly Leu Phe Gly Ala
225                 230                 235                 240

Ile Ala Gly Phe Ile Glu Gly Gly Trp Pro Gly Leu Val Ala Gly Trp
                245                 250                 255

Tyr Gly Phe Gln His Ser Asn Asp Gln Gly Val Gly Met Ala Ala Asp
            260                 265                 270

Arg Asp Ser Thr Gln Arg Ala Ile Asp Lys Ile Thr Ser Lys Val Asn
        275                 280                 285

Asn Ile Val Asp Lys Met Asn Lys Gln Tyr Glu Ile Ile Asp His Glu
    290                 295                 300

Phe Ser Glu Val Glu Thr Arg Leu Asn Met Ile Asn
305                 310                 315


<210> SEQ ID NO 16
<211> LENGTH: 321
<212> TYPE: PRT
<213> ORGANISM: Artificial Sequence
<220> FEATURE:
<223> OTHER INFORMATION: NCBI influenza virus sequence

<400> SEQUENCE: 16

Ile Ala Tyr Cys Tyr Pro Gly Ala Thr Val Asn Glu Glu Ala Leu Arg
1               5                   10                  15

Gln Lys Ile Met Glu Ser Gly Gly Ile Asp Lys Ile Ser Thr Gly Phe
            20                  25                  30

Thr Tyr Gly Ser Ser Ile Asn Ser Ala Gly Thr Thr Arg Ser Cys Met
        35                  40                  45

Arg Ser Gly Gly Asn Ser Phe Tyr Ala Glu Leu Lys Trp Leu Val Ser
    50                  55                  60

Lys Asn Lys Gly Gln Asn Phe Pro Gln Thr Ala Asn Thr Tyr Arg Asn
65                  70                  75                  80

Thr Asp Ser Ala Glu His Leu Ile Ile Trp Gly Ile His His Pro Ser
                85                  90                  95

Ser Thr Gln Glu Lys Asn Asp Leu Tyr Gly Thr Gln Ser Leu Ser Ile
            100                 105                 110

Ser Val Gly Ser Ser Thr Tyr Gln Asn Asn Phe Val Pro Val Val Gly
        115                 120                 125
```

Ala Arg Pro Gln Val Asn Gly Gln Ser Gly Arg Ile Asp Phe His Trp
130 135 140

Thr Met Val Gln Pro Gly Asp Asn Ile Thr Phe Ser His Asn Gly Gly
145 150 155 160

Leu Ile Ala Pro Ser Arg Val Ser Lys Leu Lys Gly Arg Gly Leu Gly
165 170 175

Ile Gln Ser Gly Ala Ser Val Asp Asn Asp Cys Glu Ser Lys Cys Phe
180 185 190

Trp Lys Gly Gly Ser Ile Asn Thr Lys Leu Pro Phe Gln Asn Leu Ser
195 200 205

Pro Arg Thr Val Gly Gln Cys Pro Lys Tyr Val Asn Lys Lys Ser Leu
210 215 220

Leu Leu Ala Thr Gly Met Arg Asn Val Pro Glu Val Val Gln Gly Arg
225 230 235 240

Gly Leu Phe Gly Ala Ile Ala Gly Phe Ile Glu Asn Gly Trp Glu Gly
245 250 255

Met Val Asp Gly Trp Tyr Gly Phe Arg His Gln Asn Ala Gln Gly Thr
260 265 270

Gly Gln Ala Ala Asp Tyr Lys Ser Thr Gln Ala Ala Ile Asp Gln Ile
275 280 285

Thr Gly Lys Leu Asn Arg Leu Ile Glu Lys Thr Asn Thr Glu Phe Glu
290 295 300

Ser Ile Glu Ser Glu Phe Ser Glu Ile Glu His Gln Ile Gly Asn Val
305 310 315 320

Ile

<210> SEQ ID NO 17
<211> LENGTH: 321
<212> TYPE: PRT
<213> ORGANISM: Artificial Sequence
<220> FEATURE:
<223> OTHER INFORMATION: NCBI influenza virus sequence

<400> SEQUENCE: 17

Thr Asn Gly Ile Cys Tyr Pro Thr Leu Glu Asn Glu Glu Glu Leu Arg
1 5 10 15

Leu Lys Phe Ser Gly Val Leu Glu Phe Ser Lys Phe Glu Ala Phe Thr
20 25 30

Ser Asn Gly Trp Gly Ala Val Asn Ser Gly Ala Gly Val Thr Ala Ala
35 40 45

Cys Lys Phe Gly Ser Ser Asn Ser Phe Phe Arg Asn Met Ile Trp Leu
50 55 60

Ile His Gln Ser Gly Thr Tyr Pro Val Ile Arg Arg Thr Phe Asn Asn
65 70 75 80

Thr Lys Gly Arg Asp Val Leu Val Val Trp Gly Val His His Pro Ala
85 90 95

Thr Leu Lys Glu His Gln Asp Leu Tyr Lys Lys Asp Ser Ser Tyr Val
100 105 110

Ala Val Asp Ser Glu Ser Tyr Asn Arg Arg Phe Thr Pro Glu Ile Ser
115 120 125

Thr Arg Pro Lys Val Asn Gly Gln Ala Gly Arg Met Thr Phe Tyr Trp
130 135 140

Thr Ile Val Lys Pro Gly Glu Ala Ile Thr Glu Ser Asn Gly Ala Phe
145 150 155 160

-continued

```
Leu Ala Pro Arg Tyr Ala Phe Glu Leu Val Ser Leu Gly Asn Gly Lys
                165                 170                 175

Leu Phe Arg Ser Asp Leu Asn Ile Glu Ser Cys Ser Thr Lys Cys Gln
            180                 185                 190

Ser Glu Ile Gly Gly Ile Asn Thr Asn Arg Ser Phe His Asn Val His
        195                 200                 205

Arg Asn Thr Ile Gly Asp Cys Pro Lys Tyr Val Asn Val Lys Ser Leu
    210                 215                 220

Lys Leu Ala Thr Leu Gly Leu Arg Asn Val Pro Ala Ile Ala Thr Arg
225                 230                 235                 240

Gly Leu Phe Gly Ala Ile Ala Gly Phe Ile Glu Gly Gly Trp Pro Gly
                245                 250                 255

Leu Ile Asn Gly Trp Tyr Gly Phe Gln His Arg Asn Glu Glu Gly Thr
            260                 265                 270

Gly Ile Ala Ala Asp Lys Glu Ser Thr Gln Lys Ala Ile Asp Gln Ile
        275                 280                 285

Thr Ser Lys Val Asn Asn Ile Val Asp Arg Met Asn Thr Asn Phe Glu
    290                 295                 300

Ser Val Gln His Glu Phe Ser Glu Ile Glu Glu Arg Ile Asn Gln Leu
305                 310                 315                 320

Ser


<210> SEQ ID NO 18
<211> LENGTH: 320
<212> TYPE: PRT
<213> ORGANISM: Artificial Sequence
<220> FEATURE:
<223> OTHER INFORMATION: NCBI influenza virus sequence

<400> SEQUENCE: 18

Met Glu Gly Val Cys Tyr Pro Gly Ser Ile Glu Asn Gln Glu Glu Leu
1               5                   10                  15

Arg Ser Leu Phe Ser Ser Ile Lys Lys Tyr Glu Arg Val Lys Met Phe
            20                  25                  30

Asp Phe Thr Lys Trp Asn Val Thr Tyr Thr Gly Thr Ser Arg Ala Cys
        35                  40                  45

Asn Asn Thr Ser Asn Arg Gly Ser Phe Tyr Arg Ser Met Arg Trp Leu
    50                  55                  60

Thr Leu Lys Ser Gly Gln Phe Pro Val Gln Thr Asp Glu Tyr Lys Asn
65                  70                  75                  80

Thr Arg Asp Ser Asp Ile Leu Phe Thr Trp Ala Ile His His Pro Pro
                85                  90                  95

Thr Ser Ala Glu Gln Val Gln Leu Tyr Lys Asn Pro Asp Thr Leu Ser
            100                 105                 110

Ser Val Thr Thr Asp Glu Ile Asn Arg Ser Phe Lys Pro Asn Ile Gly
        115                 120                 125

Pro Arg Pro Leu Val Arg Gly Gln Gln Gly Arg Met Asp Tyr Tyr Trp
    130                 135                 140

Ala Val Leu Lys Pro Gly Gln Thr Lys Ile Gly Thr Asn Gly Asn Leu
145                 150                 155                 160

Ile Ala Pro Glu Tyr Gly His Leu Ile Thr Gly Lys Ser His Gly Arg
                165                 170                 175

Ile Leu Lys Asn Asn Leu Pro Val Gly Gln Cys Val Thr Glu Cys Gln
            180                 185                 190

Leu Asn Glu Gly Val Met Asn Thr Ser Lys Pro Phe Gln Asn Thr Ser
```

```
        195                 200                 205

Lys His Tyr Ile Gly Lys Cys Pro Lys Tyr Ile Pro Ser Gly Ser Leu
    210                 215                 220

Lys Leu Ala Ile Gly Leu Arg Asn Val Pro Gln Val Gln Asn Arg Gly
225                 230                 235                 240

Leu Phe Gly Ala Ile Ala Gly Phe Ile Glu Gly Gly Trp Pro Gly Leu
            245                 250                 255

Val Ala Gly Trp Tyr Gly Phe Gln His Gln Asn Ala Glu Gly Thr Gly
            260                 265                 270

Met Ala Ala Asp Arg Asp Ser Thr Gln Lys Ala Ile Asp Asn Met Gln
        275                 280                 285

Asn Lys Leu Asn Asn Val Ile Asp Lys Met Asn Lys Gln Phe Glu Val
    290                 295                 300

Val Asn His Glu Phe Ser Glu Val Glu Ser Arg Ile Asn Met Ile Asn
305                 310                 315                 320


<210> SEQ ID NO 19
<211> LENGTH: 318
<212> TYPE: PRT
<213> ORGANISM: Artificial Sequence
<220> FEATURE:
<223> OTHER INFORMATION: NCBI influenza virus sequence

<400> SEQUENCE: 19

Pro His Gly Leu Cys Tyr Pro Gly Glu Leu Asn Asn Asn Gly Glu Leu
1               5                   10                  15

Arg His Leu Phe Ser Gly Ile Arg Ser Phe Ser Arg Thr Glu Leu Ile
            20                  25                  30

Pro Pro Thr Ser Trp Gly Glu Val Leu Asp Gly Ala Thr Ser Ala Arg
        35                  40                  45

Asp Asp Lys Gly Thr Asn Ser Phe Tyr Arg Asn Leu Val Trp Phe Val
    50                  55                  60

Lys Lys Asn Asn Arg Tyr Pro Val Ile Ser Lys Thr Asn Asn Thr Thr
65                  70                  75                  80

Gly Arg Val Leu Val Leu Trp Gly Ile His His Pro Val Ser Val Glu
                85                  90                  95

Glu Thr Lys Thr Leu Tyr Val Asn Ser Asp Pro Tyr Thr Leu Val Ser
            100                 105                 110

Thr Lys Ser Trp Ser Glu Lys Tyr Lys Leu Glu Thr Gly Val Arg Pro
        115                 120                 125

Gly Tyr Asn Gly Gln Arg Ser Trp Met Lys Ile Tyr Trp Ser Leu Leu
    130                 135                 140

His Pro Gly Glu Met Ile Thr Phe Glu Ser Asn Gly Gly Leu Leu Ala
145                 150                 155                 160

Pro Arg Tyr Gly Tyr Ile Ile Glu Glu Tyr Gly Lys Gly Arg Ile Phe
                165                 170                 175

Gln Ser Arg Ile Arg Met Ser Lys Cys Asn Thr Lys Cys Gln Thr Ser
            180                 185                 190

Val Gly Gly Ile Asn Thr Asn Arg Thr Phe Gln Asn Ile Asp Lys Asn
        195                 200                 205

Ala Leu Gly Asp Cys Pro Lys Tyr Ile Lys Ser Gly Gln Leu Lys Leu
    210                 215                 220

Ala Thr Gly Leu Arg Asn Val Pro Ala Ile Asp Asn Arg Gly Leu Leu
225                 230                 235                 240

Gly Ala Ile Ala Gly Phe Ile Glu Gly Gly Trp Pro Gly Leu Ile Asn
```

-continued

```
                245                 250                 255

Gly Trp Tyr Gly Phe Gln His Gln Asn Glu Gln Gly Thr Gly Ile Ala
            260                 265                 270

Ala Asp Lys Glu Ser Thr Gln Lys Ala Ile Asp Gln Ile Thr Thr Lys
        275                 280                 285

Ile Asn Asn Ile Ile Asp Lys Met Asn Gly Asn Tyr Asp Ser Ile Arg
    290                 295                 300

Gly Glu Phe Asn Gln Val Glu Lys Arg Ile Asn Met Leu Ala
305                 310                 315


<210> SEQ ID NO 20
<211> LENGTH: 317
<212> TYPE: PRT
<213> ORGANISM: Artificial Sequence
<220> FEATURE:
<223> OTHER INFORMATION: NCBI influenza virus sequence

<400> SEQUENCE: 20

Val Asp Thr Cys Tyr Pro Phe Asp Val Pro Asp Tyr Gln Ser Leu Arg
1               5                   10                  15

Ser Ile Leu Ala Ser Ser Gly Ser Leu Glu Phe Ile Ala Glu Gln Phe
            20                  25                  30

Thr Trp Asn Gly Val Lys Val Asp Gly Ser Ser Ser Ala Cys Leu Arg
        35                  40                  45

Gly Gly Arg Asn Ser Phe Phe Ser Arg Leu Asn Trp Leu Thr Lys Glu
    50                  55                  60

Thr Asn Gly Asn Thr Gly Pro Ile Asn Val Thr Lys Glu Asn Thr Gly
65                  70                  75                  80

Ser Tyr Val Arg Leu Tyr Leu Trp Gly Val His His Pro Ser Ser Asp
                85                  90                  95

Asn Glu Gln Thr Asp Leu Tyr Lys Val Ala Thr Gly Arg Val Thr Val
            100                 105                 110

Ser Thr Arg Ser Asp Gln Ile Ser Ile Val Pro Asn Ile Gly Ser Arg
        115                 120                 125

Pro Arg Val Arg Asn Gln Ser Gly Arg Ile Ser Ile Tyr Trp Thr Leu
    130                 135                 140

Val Asn Pro Gly Asp Ser Ile Ile Phe Asn Ser Ile Gly Asn Leu Ile
145                 150                 155                 160

Ala Pro Arg Gly His Tyr Lys Ile Ser Lys Ser Thr Lys Ser Thr Val
                165                 170                 175

Leu Lys Ser Asp Lys Arg Ile Gly Ser Cys Thr Ser Pro Cys Leu Thr
            180                 185                 190

Asp Lys Gly Ser Ile Gln Ser Asp Lys Pro Phe Gln Asn Val Ser Arg
        195                 200                 205

Ile Ala Ile Gly Asn Cys Pro Lys Tyr Val Lys Gln Gly Ser Leu Met
    210                 215                 220

Leu Ala Thr Gly Met Arg Asn Ile Pro Gly Lys Gln Ala Lys Gly Leu
225                 230                 235                 240

Phe Gly Ala Ile Ala Gly Phe Ile Glu Asn Gly Trp Gln Gly Leu Ile
                245                 250                 255

Asp Trp Tyr Gly Phe Arg His Gln Asn Ala Glu Gly Thr Gly Thr Ala
            260                 265                 270

Ala Asp Leu Lys Ser Thr Gln Ala Ala Ile Asp Gln Ile Asn Lys Leu
        275                 280                 285

Asn Arg Leu Ile Glu Lys Thr Asn Glu Lys Tyr His Gln Ile Glu Lys
```

290 295 300

Glu Phe Glu Gln Val Glu Gly Arg Ile Gln Asp Leu Glu
305 310 315

<210> SEQ ID NO 21
<211> LENGTH: 327
<212> TYPE: PRT
<213> ORGANISM: Artificial Sequence
<220> FEATURE:
<223> OTHER INFORMATION: NCBI influenza virus sequence

<400> SEQUENCE: 21

Ser Asp Ile Cys Tyr Pro Gly Lys Phe Thr Asn Glu Glu Ala Leu Arg
1 5 10 15

Gln Ile Ile Arg Glu Ser Gly Gly Ile Asp Lys Glu Pro Met Gly Phe
20 25 30

Arg Tyr Ser Gly Ile Lys Thr Asp Gly Ala Thr Ser Ala Cys Lys Arg
35 40 45

Thr Val Ser Ser Phe Tyr Ser Glu Met Lys Trp Leu Leu Ser Ser Lys
50 55 60

Ala Asn Gln Val Phe Pro Gln Leu Gln Thr Tyr Arg Asn Asn Arg Lys
65 70 75 80

Glu Pro Ala Leu Ile Val Trp Gly Val His His Ser Ser Ser Leu Asp
85 90 95

Glu Gln Asn Lys Leu Tyr Gly Ala Gly Asn Lys Leu Ile Thr Val Gly
100 105 110

Ser Ser Lys Tyr Gln Gln Ser Phe Ser Pro Ser Pro Asp Arg Pro Lys
115 120 125

Val Asn Gly Gln Ala Gly Arg Ile Asp Phe His Trp Met Leu Leu Asp
130 135 140

Pro Gly Asp Thr Val Thr Phe Thr Phe Asn Gly Ala Phe Ile Ala Pro
145 150 155 160

Asp Arg Ala Thr Phe Leu Arg Ser Asn Ala Pro Ser Gly Val Glu Tyr
165 170 175

Asn Gly Lys Ser Leu Gly Ile Gln Ser Asp Ala Gln Ile Asp Glu Ser
180 185 190

Cys Glu Gly Glu Cys Phe Tyr Ser Gly Gly Thr Ile Asn Ser Pro Leu
195 200 205

Pro Phe Gln Asn Ile Asp Ser Trp Ala Val Gly Arg Cys Pro Arg Tyr
210 215 220

Val Lys Gln Ser Ser Leu Pro Leu Ala Leu Gly Met Lys Asn Val Pro
225 230 235 240

Glu Lys Ile His Thr Arg Gly Leu Phe Gly Ala Ile Ala Gly Phe Ile
245 250 255

Glu Asn Gly Trp Glu Gly Leu Ile Asp Gly Trp Tyr Gly Phe Arg His
260 265 270

Gln Asn Ala Gln Gly Gln Gly Thr Ala Ala Asp Tyr Lys Ser Thr Gln
275 280 285

Ala Ala Ile Asp Gln Ile Thr Gly Lys Leu Asn Arg Leu Ile Glu Lys
290 295 300

Thr Asn Thr Gln Phe Glu Leu Ile Asp Asn Glu Phe Thr Glu Val Glu
305 310 315 320

Gln Gln Ile Gly Asn Val Ile
325

```
<210> SEQ ID NO 22
<211> LENGTH: 320
<212> TYPE: PRT
<213> ORGANISM: Artificial Sequence
<220> FEATURE:
<223> OTHER INFORMATION: NCBI influenza virus sequence

<400> SEQUENCE: 22

Pro Asn Lys Leu Cys Phe Arg Gly Glu Leu Asp Asn Asn Gly Glu Leu
1               5                   10                  15

Arg His Leu Phe Ser Gly Val Asn Ser Phe Ser Arg Thr Glu Leu Ile
            20                  25                  30

Ser Pro Asn Lys Trp Gly Asp Ile Leu Asp Gly Val Thr Ala Ser Cys
        35                  40                  45

Arg Asp Asn Gly Ala Ser Ser Phe Tyr Arg Asn Leu Val Trp Ile Val
    50                  55                  60

Lys Asn Lys Asn Gly Lys Tyr Pro Val Ile Lys Gly Asp Tyr Asn Asn
65                  70                  75                  80

Thr Thr Gly Arg Asp Val Leu Val Leu Trp Gly Ile His His Pro Asp
                85                  90                  95

Thr Glu Thr Thr Ala Ile Asn Leu Tyr Ala Ser Lys Asn Pro Tyr Thr
            100                 105                 110

Leu Val Ser Thr Lys Glu Trp Ser Lys Arg Tyr Glu Leu Glu Ile Gly
        115                 120                 125

Thr Arg Ile Gly Asp Gly Gln Arg Ser Trp Met Lys Leu Tyr Trp His
    130                 135                 140

Leu Met Arg Pro Gly Glu Arg Ile Met Phe Glu Ser Asn Gly Gly Leu
145                 150                 155                 160

Ile Ala Pro Arg Tyr Gly Tyr Ile Ile Glu Lys Tyr Gly Thr Gly Arg
                165                 170                 175

Ile Phe Gln Ser Gly Val Arg Met Ala Lys Cys Asn Thr Lys Cys Gln
            180                 185                 190

Thr Ser Leu Gly Gly Ile Asn Thr Asn Lys Thr Phe Gln Asn Ile Glu
        195                 200                 205

Arg Asn Ala Leu Gly Asp Cys Pro Lys Tyr Ile Lys Ser Gly Gln Leu
    210                 215                 220

Lys Leu Ala Thr Gly Leu Arg Asn Val Pro Ser Val Gly Glu Arg Gly
225                 230                 235                 240

Leu Phe Gly Ala Ile Ala Gly Phe Ile Glu Gly Gly Trp Pro Gly Leu
                245                 250                 255

Ile Asn Gly Trp Tyr Gly Phe Gln His Gln Asn Glu Gln Gly Thr Gly
            260                 265                 270

Ile Ala Ala Asp Lys Ala Ser Thr Gln Lys Ala Ile Asp Glu Ile Thr
        275                 280                 285

Thr Lys Ile Asn Asn Ile Ile Glu Lys Met Asn Gly Asn Tyr Asp Ser
    290                 295                 300

Ile Arg Gly Glu Phe Asn Gln Val Glu Lys Arg Ile Asn Met Leu Ala
305                 310                 315                 320


<210> SEQ ID NO 23
<211> LENGTH: 164
<212> TYPE: PRT
<213> ORGANISM: Artificial Sequence
<220> FEATURE:
<223> OTHER INFORMATION: HA glycan binding domain sequence

<400> SEQUENCE: 23
```

Ser Tyr Ile Ile Glu Thr Ser Asn Ser Glu Asn Gly Thr Cys Tyr Pro
1 5 10 15

Gly Glu Phe Ile Asp Tyr Glu Glu Leu Arg Glu Gln Leu Ser Ser Ile
20 25 30

Ser Ser Phe Glu Lys Phe Glu Ile Phe Pro Lys Ala Ser Ser Trp Pro
35 40 45

Asn His Glu Thr Thr Lys Gly Val Thr Ala Ala Cys Ser Tyr Ser Gly
50 55 60

Ala Ser Ser Phe Tyr Arg Asn Leu Leu Trp Ile Thr Lys Lys Gly Thr
65 70 75 80

Ser Tyr Pro Lys Leu Ser Lys Ser Tyr Thr Asn Asn Lys Gly Lys Glu
85 90 95

Val Leu Val Leu Trp Gly Val His His Pro Pro Ser Val Ser Glu Gln
100 105 110

Gln Ser Leu Tyr Gln Asn Ala Asp Ala Tyr Val Ser Val Gly Ser Ser
115 120 125

Lys Tyr Asn Arg Arg Phe Ala Pro Glu Ile Ala Ala Arg Pro Glu Val
130 135 140

Arg Gly Gln Ala Gly Arg Met Asn Tyr Tyr Trp Thr Leu Leu Asp Gln
145 150 155 160

Gly Asp Thr Ile

<210> SEQ ID NO 24
<211> LENGTH: 164
<212> TYPE: PRT
<213> ORGANISM: Artificial Sequence
<220> FEATURE:
<223> OTHER INFORMATION: HA glycan binding domain sequence

<400> SEQUENCE: 24

Ser Tyr Ile Val Glu Thr Ser Asn Ser Asp Asn Gly Thr Cys Tyr Pro
1 5 10 15

Gly Asp Phe Ile Asp Tyr Glu Glu Leu Arg Glu Gln Leu Ser Ser Val
20 25 30

Ser Ser Phe Glu Lys Phe Glu Ile Phe Pro Lys Thr Ser Ser Trp Pro
35 40 45

Asn His Glu Thr Thr Arg Gly Val Thr Ala Ala Cys Pro Tyr Ala Gly
50 55 60

Ala Ser Ser Phe Tyr Arg Asn Leu Leu Trp Leu Val Lys Lys Gly Asn
65 70 75 80

Ser Tyr Pro Lys Leu Ser Lys Ser Tyr Val Asn Asn Lys Gly Lys Glu
85 90 95

Val Leu Val Leu Trp Gly Val His His Pro Pro Thr Ser Thr Asp Gln
100 105 110

Gln Ser Leu Tyr Gln Asn Ala Asp Ala Tyr Val Ser Val Gly Ser Ser
115 120 125

Lys Tyr Asp Arg Arg Phe Thr Pro Glu Ile Ala Ala Arg Pro Lys Val
130 135 140

Arg Gly Gln Ala Gly Arg Met Asn Tyr Tyr Trp Thr Leu Leu Glu Pro
145 150 155 160

Gly Asp Thr Ile

<210> SEQ ID NO 25
<211> LENGTH: 163
<212> TYPE: PRT
<213> ORGANISM: Artificial Sequence
<220> FEATURE:
<223> OTHER INFORMATION: HA glycan binding domain sequence

<400> SEQUENCE: 25

```
Ser Tyr Ile Val Glu Thr Pro Asn Ser Glu Asn Gly Ile Cys Tyr Pro
1               5                   10                  15

Gly Asp Phe Ile Asp Tyr Glu Glu Leu Arg Glu Gln Leu Ser Ser Val
            20                  25                  30

Ser Ser Phe Glu Arg Phe Glu Ile Phe Pro Lys Glu Ser Ser Trp Pro
        35                  40                  45

Asn His Asn Thr Asn Gly Val Thr Ala Ala Cys Ser His Glu Gly Lys
    50                  55                  60

Ser Ser Phe Tyr Arg Asn Leu Leu Trp Leu Thr Glu Lys Glu Gly Ser
65                  70                  75                  80

Tyr Pro Lys Leu Lys Asn Ser Tyr Val Asn Lys Lys Gly Lys Glu Val
                85                  90                  95

Leu Val Leu Trp Gly Ile His His Pro Pro Asn Ser Lys Glu Gln Gln
            100                 105                 110

Asn Leu Tyr Gln Asn Glu Asn Ala Tyr Val Ser Val Val Thr Ser Asn
        115                 120                 125

Tyr Asn Arg Arg Phe Thr Pro Glu Ile Ala Glu Arg Pro Lys Val Arg
    130                 135                 140

Asp Gln Ala Gly Arg Met Asn Tyr Tyr Trp Thr Leu Leu Lys Pro Gly
145                 150                 155                 160

Asp Thr Ile
```

<210> SEQ ID NO 26
<211> LENGTH: 164
<212> TYPE: PRT
<213> ORGANISM: Artificial Sequence
<220> FEATURE:
<223> OTHER INFORMATION: HA glycan binding domain sequence

<400> SEQUENCE: 26

```
Ser Tyr Ile Val Glu Thr Ser Asn Ser Glu Asn Gly Thr Cys Tyr Pro
1               5                   10                  15

Gly Asp Phe Ile Asp Tyr Glu Glu Leu Arg Glu Gln Leu Ser Ser Val
            20                  25                  30

Ser Ser Phe Glu Lys Phe Glu Ile Phe Pro Lys Thr Ser Ser Trp Pro
        35                  40                  45

Asn His Glu Thr Thr Lys Gly Val Thr Ala Ala Cys Ser Tyr Ala Gly
    50                  55                  60

Ala Ser Ser Phe Tyr Arg Asn Leu Leu Trp Leu Thr Lys Lys Gly Ser
65                  70                  75                  80

Ser Tyr Pro Lys Leu Ser Lys Ser Tyr Val Asn Asn Lys Gly Lys Glu
                85                  90                  95

Val Leu Val Leu Trp Gly Val His His Pro Pro Thr Gly Thr Asp Gln
            100                 105                 110

Gln Ser Leu Tyr Gln Asn Ala Asp Ala Tyr Val Ser Val Gly Ser Ser
        115                 120                 125

Lys Tyr Asn Arg Arg Phe Thr Pro Glu Ile Ala Ala Arg Pro Lys Val
    130                 135                 140

Arg Asp Gln Ala Gly Arg Met Asn Tyr Tyr Trp Thr Leu Leu Glu Pro
145                 150                 155                 160

Gly Asp Thr Ile
```

<210> SEQ ID NO 27
<211> LENGTH: 164
<212> TYPE: PRT
<213> ORGANISM: Artificial Sequence
<220> FEATURE:
<223> OTHER INFORMATION: HA glycan binding domain sequence

<400> SEQUENCE: 27

```
Ser Tyr Ile Ala Glu Thr Pro Asn Pro Glu Asn Gly Thr Cys Tyr Pro
1               5                   10                  15

Gly Tyr Phe Ala Asp Tyr Glu Glu Leu Arg Glu Gln Leu Ser Ser Val
            20                  25                  30

Ser Ser Phe Glu Arg Phe Glu Ile Phe Pro Lys Glu Ser Ser Trp Pro
        35                  40                  45

Asn His Thr Val Thr Lys Gly Val Thr Thr Ser Cys Ser His Asn Gly
    50                  55                  60

Lys Ser Ser Phe Tyr Arg Asn Leu Leu Trp Leu Thr Lys Lys Asn Gly
65                  70                  75                  80

Leu Tyr Pro Asn Val Ser Lys Ser Tyr Val Asn Asn Lys Glu Lys Glu
                85                  90                  95

Val Leu Val Leu Trp Gly Val His His Pro Ser Asn Ile Gly Asp Gln
            100                 105                 110

Arg Ala Ile Tyr His Thr Glu Asn Ala Tyr Val Ser Val Val Ser Ser
        115                 120                 125

His Tyr Ser Arg Arg Phe Thr Pro Glu Ile Ala Lys Arg Pro Lys Val
    130                 135                 140

Arg Asp Gln Glu Gly Arg Ile Asn Tyr Tyr Trp Thr Leu Leu Glu Pro
145                 150                 155                 160

Gly Asp Thr Ile
```

<210> SEQ ID NO 28
<211> LENGTH: 164
<212> TYPE: PRT
<213> ORGANISM: Artificial Sequence
<220> FEATURE:
<223> OTHER INFORMATION: HA glycan binding domain sequence

<400> SEQUENCE: 28

```
Ser Tyr Ile Val Glu Thr Ser Asn Ser Glu Asn Gly Thr Cys Tyr Pro
1               5                   10                  15

Gly Asp Phe Ile Asp Tyr Glu Glu Leu Arg Glu Gln Leu Ser Ser Val
            20                  25                  30

Ser Ser Phe Glu Lys Phe Glu Ile Phe Pro Lys Thr Ser Ser Trp Pro
        35                  40                  45

Asn His Glu Thr Thr Lys Gly Val Thr Ala Ala Cys Ser Tyr Ala Gly
    50                  55                  60

Ala Ser Ser Phe Tyr Arg Asn Leu Leu Trp Leu Thr Lys Lys Gly Ser
65                  70                  75                  80

Ser Tyr Pro Lys Leu Ser Lys Ser Tyr Val Asn Asn Lys Gly Lys Glu
                85                  90                  95

Val Leu Val Leu Trp Gly Val His His Pro Pro Thr Gly Thr Asp Gln
            100                 105                 110

Gln Ser Leu Tyr Gln Asn Ala Asp Ala Tyr Val Ser Val Gly Ser Ser
        115                 120                 125

Lys Tyr Asn Arg Arg Phe Thr Pro Glu Ile Ala Ala Arg Pro Lys Val
    130                 135                 140
```

Arg Gly Gln Ala Gly Arg Met Asn Tyr Tyr Trp Thr Leu Leu Glu Pro
145 150 155 160

Gly Asp Thr Ile

<210> SEQ ID NO 29
<211> LENGTH: 158
<212> TYPE: PRT
<213> ORGANISM: Artificial Sequence
<220> FEATURE:
<223> OTHER INFORMATION: HA glycan binding domain sequence

<400> SEQUENCE: 29

Asp Leu Phe Val Glu Arg Ser Asn Ala Phe Ser Asn Cys Tyr Pro Tyr
1 5 10 15

Asp Ile Pro Asp Tyr Ala Ser Arg Ser Leu Val Ala Ser Ser Gly Thr
20 25 30

Leu Glu Phe Ile Thr Glu Gly Phe Thr Trp Thr Gly Val Thr Gln Asn
35 40 45

Gly Gly Ser Ser Ala Cys Lys Arg Gly Pro Ala Asn Gly Phe Phe Ser
50 55 60

Arg Leu Asn Trp Leu Thr Lys Ser Glu Ser Ala Tyr Pro Val Leu Asn
65 70 75 80

Val Thr Met Pro Asn Asn Asp Asn Phe Asp Lys Leu Tyr Ile Trp Gly
85 90 95

Val His His Pro Ser Thr Asn Gln Glu Gln Thr Asn Leu Tyr Val Gln
100 105 110

Ala Ser Gly Arg Val Thr Val Ser Thr Arg Arg Ser Gln Gln Thr Ile
115 120 125

Ile Pro Asn Ile Gly Ser Arg Pro Trp Val Arg Gly Gln Pro Gly Arg
130 135 140

Ile Ser Ile Tyr Trp Thr Ile Val Lys Pro Gly Asp Val Leu
145 150 155

<210> SEQ ID NO 30
<211> LENGTH: 159
<212> TYPE: PRT
<213> ORGANISM: Artificial Sequence
<220> FEATURE:
<223> OTHER INFORMATION: HA glycan binding domain sequence

<400> SEQUENCE: 30

Asp Leu Phe Val Glu Arg Ser Lys Ala Phe Ser Asn Cys Tyr Pro Tyr
1 5 10 15

Asp Val Pro Asp Tyr Ala Ser Leu Arg Ser Leu Val Ala Ser Ser Gly
20 25 30

Thr Leu Glu Phe Ile Thr Glu Gly Phe Thr Trp Thr Gly Val Thr Gln
35 40 45

Asn Gly Gly Ser Asn Ala Cys Lys Arg Gly Pro Gly Ser Gly Phe Phe
50 55 60

Ser Arg Leu Asn Trp Leu Thr Lys Ser Gly Ser Thr Tyr Pro Val Leu
65 70 75 80

Asn Val Thr Met Pro Asn Asn Asp Asn Phe Asp Lys Leu Tyr Ile Trp
85 90 95

Gly Ile His His Pro Ser Thr Asn Gln Glu Gln Thr Ser Leu Tyr Val
100 105 110

Gln Ala Ser Gly Arg Val Thr Val Ser Thr Arg Arg Ser Gln Gln Thr
115 120 125

```
Ile Ile Pro Asn Ile Gly Ser Arg Pro Trp Val Arg Gly Leu Ser Ser
    130                 135                 140

Arg Ile Ser Ile Tyr Trp Thr Ile Val Lys Pro Gly Asp Val Leu
145                 150                 155
```

<210> SEQ ID NO 31
<211> LENGTH: 157
<212> TYPE: PRT
<213> ORGANISM: Artificial Sequence
<220> FEATURE:
<223> OTHER INFORMATION: HA glycan binding domain sequence

<400> SEQUENCE: 31

```
Asp Leu Phe Val Glu Arg Ser Lys Ala Tyr Ser Asn Cys Tyr Pro Tyr
1               5                   10                  15

Asp Val Pro Asp Tyr Ala Ser Leu Arg Ser Leu Val Ala Ser Ser Gly
            20                  25                  30

Thr Leu Glu Phe Asn Asn Glu Ser Phe Asn Trp Thr Gly Val Ala Asn
        35                  40                  45

Gly Thr Ser Ser Ser Cys Lys Arg Arg Ser Ile Lys Ser Phe Phe Ser
    50                  55                  60

Arg Leu Asn Trp Leu His Leu Lys Tyr Arg Tyr Pro Ala Leu Asn Val
65                  70                  75                  80

Thr Met Pro Asn Asn Asp Lys Phe Asp Lys Leu Tyr Ile Trp Gly Val
                85                  90                  95

His His Pro Ser Thr Asp Ser Asp Gln Thr Ser Leu Tyr Thr Gln Ala
            100                 105                 110

Ser Gly Arg Val Thr Val Ser Thr Lys Arg Ser Gln Gln Thr Val Ile
        115                 120                 125

Pro Asn Ile Gly Ser Arg Pro Trp Val Arg Gly Ile Ser Ser Arg Ile
    130                 135                 140

Ser Ile Tyr Trp Thr Ile Val Lys Pro Gly Asp Leu Leu
145                 150                 155
```

<210> SEQ ID NO 32
<211> LENGTH: 163
<212> TYPE: PRT
<213> ORGANISM: Artificial Sequence
<220> FEATURE:
<223> OTHER INFORMATION: HA glycan binding domain sequence

<400> SEQUENCE: 32

```
Ser Tyr Ile Val Glu Lys Asp Asn Pro Val Asn Gly Leu Cys Tyr Pro
1               5                   10                  15

Glu Asn Phe Asn Asp Tyr Glu Glu Leu Lys His Leu Leu Ser Ser Thr
            20                  25                  30

Asn His Phe Glu Lys Ile Arg Ile Ile Pro Arg Ser Ser Trp Ser Asn
        35                  40                  45

His Asp Ala Ser Ser Gly Val Ser Ser Ala Cys Pro Tyr Asn Gly Arg
    50                  55                  60

Ser Ser Phe Phe Arg Asn Val Val Trp Leu Ile Lys Lys Asn Asn Ala
65                  70                  75                  80

Tyr Pro Thr Ile Lys Arg Ser Tyr Asn Asn Thr Asn Gln Glu Asp Leu
                85                  90                  95

Leu Ile Leu Trp Gly Ile His His Pro Asn Asp Ala Ala Glu Gln Thr
            100                 105                 110

Lys Leu Tyr Gln Asn Pro Thr Thr Tyr Val Ser Val Gly Thr Ser Thr
        115                 120                 125
```

Leu Asn Gln Arg Ser Val Pro Glu Ile Ala Thr Arg Pro Lys Val Asn
    130                 135                 140

Gly Gln Ser Gly Arg Met Glu Phe Phe Trp Thr Ile Leu Lys Pro Asn
145                 150                 155                 160

Asp Ala Ile

<210> SEQ ID NO 33
<211> LENGTH: 163
<212> TYPE: PRT
<213> ORGANISM: Artificial Sequence
<220> FEATURE:
<223> OTHER INFORMATION: HA glycan binding domain sequence

<400> SEQUENCE: 33

Ser Tyr Ile Val Glu Lys Ala Asn Pro Val Asn Asp Leu Cys Tyr Pro
1               5                   10                  15

Gly Asp Phe Asn Asp Tyr Glu Glu Leu Lys His Leu Leu Ser Arg Ile
            20                  25                  30

Asn His Phe Glu Lys Ile Gln Ile Ile Pro Lys Ser Ser Trp Ser Ser
        35                  40                  45

His Glu Ala Ser Leu Gly Val Ser Ser Ala Cys Pro Tyr Gln Gly Lys
    50                  55                  60

Ser Ser Phe Phe Arg Asn Val Val Trp Leu Ile Lys Lys Asn Ser Thr
65                  70                  75                  80

Tyr Pro Thr Ile Lys Arg Ser Tyr Asn Asn Thr Asn Gln Glu Asp Leu
                85                  90                  95

Leu Val Leu Trp Gly Ile His His Pro Asn Asp Ala Ala Glu Gln Thr
            100                 105                 110

Lys Leu Tyr Gln Asn Pro Thr Thr Tyr Ile Ser Val Gly Thr Ser Thr
        115                 120                 125

Leu Asn Gln Arg Leu Val Pro Arg Ile Ala Thr Arg Ser Lys Val Asn
    130                 135                 140

Gly Gln Ser Gly Arg Met Glu Phe Phe Trp Thr Ile Ile Lys Pro Asn
145                 150                 155                 160

Asp Ala Ile

<210> SEQ ID NO 34
<211> LENGTH: 570
<212> TYPE: PRT
<213> ORGANISM: Artificial Sequence
<220> FEATURE:
<223> OTHER INFORMATION: Sequence alignment illustrating conserved
      subsequences characteristic of H5 HA.

<400> SEQUENCE: 34

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

-continued

```
Glu Lys Ala Asn Pro Ala Asn Asp Leu Tyr Cys Tyr Pro Gly Asp Phe
            100                 105                 110

Asn Asp Tyr Glu Glu Leu Lys His Leu Leu Ser Arg Ile Asn His Phe
        115                 120                 125

Glu Lys Ile Gln Ile Ile Pro Lys Ser Ser Trp Ser Asp His Glu Ala
    130                 135                 140

Ser Ser Gly Val Ser Ser Ala Cys Pro Tyr Gln Gly Lys Ser Ser Phe
145                 150                 155                 160

Phe Arg Asn Val Val Trp Leu Ile Lys Lys Asn Ser Ala Tyr Pro Thr
                165                 170                 175

Ile Lys Lys Arg Ser Tyr Asn Asn Thr Asn Gln Glu Asp Leu Leu Val
            180                 185                 190

Leu Trp Gly Ile His His Pro Asn Asp Ala Ala Glu Gln Thr Lys Leu
        195                 200                 205

Tyr Gln Asn Pro Thr Thr Tyr Ile Ser Val Gly Thr Ser Thr Leu Asn
    210                 215                 220

Gln Arg Leu Val Pro Lys Ile Ala Thr Arg Ser Lys Val Asn Gly Gln
225                 230                 235                 240

Ser Gly Arg Met Glu Phe Phe Trp Thr Ile Leu Lys Pro Asn Asp Ala
                245                 250                 255

Ile Asn Phe Glu Ser Asn Gly Asn Phe Ile Ala Pro Glu Tyr Ala Tyr
            260                 265                 270

Lys Ile Val Lys Lys Gly Asp Ser Thr Ile Met Lys Ser Glu Leu Glu
        275                 280                 285

Tyr Gly Asn Cys Asn Thr Lys Cys Gln Thr Pro Met Gly Ala Ile Asn
    290                 295                 300

Ser Ser Met Pro Phe His Asn Ile His Pro Leu Thr Ile Gly Glu Cys
305                 310                 315                 320

Pro Lys Tyr Val Lys Ser Asn Arg Leu Val Leu Ala Thr Gly Leu Arg
                325                 330                 335

Asn Ser Pro Gln Arg Glu Arg Arg Arg Lys Lys Arg Gly Leu Phe Gly
            340                 345                 350

Ala Ile Ala Gly Phe Ile Glu Gly Gly Trp Gln Gly Met Val Asp Gly
        355                 360                 365

Trp Tyr Gly Tyr His His Ser Asn Glu Gln Gly Ser Gly Tyr Ala Ala
    370                 375                 380

Asp Lys Glu Ser Thr Gln Lys Ala Ile Asp Gly Val Thr Asn Lys Val
385                 390                 395                 400

Asn Ser Ile Ile Asp Lys Met Asn Thr Gln Phe Glu Ala Val Gly Arg
                405                 410                 415

Glu Phe Asn Asn Leu Glu Arg Arg Ile Glu Asn Leu Asn Lys Lys Met
            420                 425                 430

Glu Asp Gly Phe Leu Asp Val Trp Thr Tyr Asn Ala Glu Leu Leu Val
        435                 440                 445

Leu Met Glu Asn Glu Arg Thr Leu Asp Phe His Asp Ser Asn Val Lys
    450                 455                 460

Asn Leu Tyr Asp Lys Val Arg Leu Gln Leu Arg Asp Asn Ala Lys Glu
465                 470                 475                 480

Leu Gly Asn Gly Cys Phe Glu Phe Tyr His Lys Cys Asp Asn Glu Cys
                485                 490                 495

Met Glu Ser Val Arg Asn Gly Thr Tyr Asp Tyr Pro Gln Tyr Ser Glu
            500                 505                 510
```

```
Glu Ala Arg Leu Lys Arg Glu Glu Ile Ser Gly Val Lys Leu Glu Ser
        515                 520                 525

Ile Gly Thr Tyr Gln Ile Leu Ser Ile Tyr Ser Thr Val Ala Ser Ser
    530                 535                 540

Leu Ala Leu Ala Ile Met Val Ala Gly Leu Ser Leu Trp Met Cys Ser
545                 550                 555                 560

Asn Gly Ser Leu Gln Cys Arg Ile Cys Ile
                565                 570


<210> SEQ ID NO 35
<211> LENGTH: 570
<212> TYPE: PRT
<213> ORGANISM: Artificial Sequence
<220> FEATURE:
<223> OTHER INFORMATION: Sequence alignment illustrating conserved
      subsequences characteristic of H5 HA.

<400> SEQUENCE: 35

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Ser Pro Asp Asn Asp Leu Tyr Cys Tyr Pro Gly Asp Phe
            100                 105                 110

Asn Asp Tyr Glu Glu Leu Lys His Leu Leu Ser Arg Ile Asn His Phe
        115                 120                 125

Glu Lys Ile Gln Ile Ile Pro Lys Ser Ser Trp Ser Asn His Glu Ala
    130                 135                 140

Ser Ser Gly Val Ser Ser Ala Cys Pro Tyr His Gly Lys Ser Ser Phe
145                 150                 155                 160

Phe Arg Asn Val Val Trp Leu Ile Lys Lys Asn Ser Ala Tyr Pro Thr
                165                 170                 175

Ile Lys Lys Arg Ser Tyr Asn Asn Thr Asn Gln Glu Asp Leu Leu Val
            180                 185                 190

Leu Trp Gly Ile His His Pro Asn Asp Ala Ala Glu Gln Thr Lys Leu
        195                 200                 205

Tyr Gln Asn Pro Thr Thr Tyr Ile Ser Val Gly Thr Ser Thr Leu Asn
    210                 215                 220

Gln Arg Leu Val Pro Lys Ile Ala Thr Arg Ser Lys Val Asn Gly Gln
225                 230                 235                 240

Ser Gly Arg Met Glu Phe Phe Trp Thr Ile Leu Lys Pro Asn Asp Ala
                245                 250                 255

Ile Asn Phe Glu Ser Asn Gly Asn Phe Ile Ala Pro Glu Tyr Ala Tyr
            260                 265                 270

Lys Ile Val Lys Lys Gly Asp Ser Ala Ile Met Lys Ser Glu Leu Glu
        275                 280                 285

Tyr Gly Asn Cys Asn Thr Lys Cys Gln Thr Pro Met Gly Ala Ile Asn
    290                 295                 300
```

-continued

```
Ser Ser Met Pro Phe His Asn Ile His Pro Leu Thr Ile Gly Glu Cys
305                 310                 315                 320

Pro Lys Tyr Val Lys Ser Asn Arg Leu Val Leu Ala Thr Gly Leu Arg
                325                 330                 335

Asn Thr Pro Gln Arg Glu Gly Arg Arg Lys Lys Arg Gly Leu Phe Gly
            340                 345                 350

Ala Ile Ala Gly Phe Ile Glu Gly Gly Trp Gln Gly Met Val Asp Gly
        355                 360                 365

Trp Tyr Gly Tyr His His Ser Asn Glu Gln Gly Ser Gly Tyr Ala Ala
    370                 375                 380

Asp Lys Glu Ser Thr Gln Lys Ala Ile Asp Gly Val Thr Asn Lys Val
385                 390                 395                 400

Asn Ser Ile Ile Asp Lys Met Asn Thr Gln Phe Glu Ala Val Gly Arg
                405                 410                 415

Glu Phe Asn Lys Leu Glu Arg Arg Ile Glu Asn Leu Asn Lys Lys Met
            420                 425                 430

Glu Asp Gly Phe Leu Asp Val Trp Thr Tyr Asn Ala Glu Leu Leu Val
        435                 440                 445

Leu Met Glu Asn Glu Arg Thr Leu Asp Phe His Asp Ser Asn Val Lys
    450                 455                 460

Asn Leu Tyr Asp Lys Val Arg Leu Gln Leu Arg Asp Asn Ala Lys Glu
465                 470                 475                 480

Leu Gly Asn Gly Cys Phe Glu Phe Tyr His Lys Cys Asp Asn Glu Cys
                485                 490                 495

Met Glu Ser Val Lys Asn Gly Thr Tyr Asp Tyr Pro Gln Tyr Ser Glu
            500                 505                 510

Glu Ala Arg Leu Asn Arg Glu Glu Ile Ser Gly Val Lys Leu Glu Ser
        515                 520                 525

Met Gly Thr Tyr Gln Ile Leu Ser Ile Tyr Ser Thr Val Ala Ser Ser
    530                 535                 540

Leu Ala Leu Ala Ile Met Val Ala Gly Leu Ser Leu Trp Met Cys Ser
545                 550                 555                 560

Asn Gly Ser Leu Gln Cys Arg Ile Cys Ile
                565                 570


<210> SEQ ID NO 36
<211> LENGTH: 558
<212> TYPE: PRT
<213> ORGANISM: Artificial Sequence
<220> FEATURE:
<223> OTHER INFORMATION: Sequence alignment illustrating conserved
      subsequences characteristic of H5 HA.

<400> SEQUENCE: 36

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
```

-continued

```
                85                  90                  95

Glu Lys Ala Asn Pro Val Asn Asp Leu Tyr Cys Tyr Pro Gly Asp Phe
            100                 105                 110

Asn Asp Tyr Glu Glu Leu Lys His Leu Leu Ser Arg Ile Asn His Phe
        115                 120                 125

Glu Lys Ile Gln Ile Ile Pro Lys Ser Ser Trp Ser Ser His Glu Ala
    130                 135                 140

Ser Leu Gly Val Ser Ser Ala Cys Pro Tyr Gln Gly Lys Ser Ser Phe
145                 150                 155                 160

Phe Arg Asn Val Val Trp Leu Ile Lys Lys Asn Ser Thr Tyr Pro Thr
                165                 170                 175

Ile Lys Lys Arg Ser Tyr Asn Asn Thr Asn Gln Glu Asp Leu Leu Val
            180                 185                 190

Leu Trp Gly Ile His His Pro Asn Asp Ala Ala Glu Gln Thr Lys Leu
        195                 200                 205

Tyr Gln Asn Pro Thr Thr Tyr Ile Ser Val Gly Thr Ser Thr Leu Asn
    210                 215                 220

Gln Arg Leu Val Pro Arg Ile Ala Thr Arg Ser Lys Val Asn Gly Gln
225                 230                 235                 240

Ser Gly Arg Met Glu Phe Phe Trp Thr Ile Leu Lys Pro Asn Asp Ala
                245                 250                 255

Ile Asn Phe Glu Ser Asn Gly Asn Phe Ile Ala Pro Glu Tyr Ala Tyr
            260                 265                 270

Lys Ile Val Lys Lys Gly Asp Ser Thr Ile Met Lys Ser Glu Leu Glu
        275                 280                 285

Tyr Gly Asn Cys Asn Thr Lys Cys Gln Thr Pro Met Gly Ala Ile Asn
    290                 295                 300

Ser Ser Met Pro Phe His Asn Ile His Pro Leu Thr Ile Gly Glu Cys
305                 310                 315                 320

Pro Lys Tyr Val Lys Ser Asn Arg Leu Val Leu Ala Thr Gly Leu Arg
                325                 330                 335

Asn Ser Pro Gln Arg Glu Arg Arg Arg Lys Lys Arg Gly Leu Phe Gly
            340                 345                 350

Ala Ile Ala Gly Phe Ile Glu Gly Gly Trp Gln Gly Met Val Asp Gly
        355                 360                 365

Trp Tyr Gly Tyr His His Ser Asn Glu Gln Gly Ser Gly Tyr Ala Ala
    370                 375                 380

Asp Lys Glu Ser Thr Gln Lys Ala Ile Asp Gly Val Thr Asn Lys Val
385                 390                 395                 400

Asn Ser Ile Ile Asp Lys Met Asn Thr Gln Phe Glu Ala Val Gly Arg
                405                 410                 415

Glu Phe Asn Asn Leu Glu Arg Arg Ile Glu Asn Leu Asn Lys Lys Met
            420                 425                 430

Glu Asp Gly Phe Leu Asp Val Trp Thr Tyr Asn Ala Glu Leu Leu Val
        435                 440                 445

Leu Met Glu Asn Glu Arg Thr Leu Asp Phe His Asp Ser Asn Val Lys
    450                 455                 460

Asn Leu Tyr Asp Lys Val Arg Leu Gln Leu Arg Asp Asn Ala Lys Glu
465                 470                 475                 480

Leu Gly Asn Gly Cys Phe Glu Phe Tyr His Lys Cys Asp Asn Glu Cys
                485                 490                 495

Met Glu Ser Val Arg Asn Gly Thr Tyr Asp Tyr Pro Gln Tyr Ser Glu
            500                 505                 510
```

```
Glu Ala Arg Leu Lys Arg Glu Glu Ile Ser Gly Val Lys Leu Glu Ser
        515                 520                 525

Ile Gly Ile Tyr Gln Ile Leu Ser Ile Tyr Ser Thr Val Ala Ser Ser
    530                 535                 540

Leu Ala Leu Ala Ile Met Val Ala Gly Leu Ser Leu Trp Met
545                 550                 555


<210> SEQ ID NO 37
<211> LENGTH: 570
<212> TYPE: PRT
<213> ORGANISM: Artificial Sequence
<220> FEATURE:
<223> OTHER INFORMATION: Sequence alignment illustrating conserved
      subsequences characteristic of H5 HA.

<400> SEQUENCE: 37

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Tyr Cys Tyr Pro Gly Asp Phe
            100                 105                 110

Asn Asp Tyr Glu Glu Leu Lys His Leu Leu Ser Arg Ile Asn His Phe
        115                 120                 125

Glu Lys Ile Gln Ile Ile Pro Lys Ser Ser Trp Ser Ser His Glu Ala
    130                 135                 140

Ser Leu Gly Val Ser Ser Ala Cys Pro Tyr Gln Gly Lys Pro Ser Phe
145                 150                 155                 160

Phe Arg Asn Val Val Trp Leu Ile Lys Lys Asn Ser Thr Tyr Pro Thr
                165                 170                 175

Ile Lys Lys Arg Ser Tyr Asn Asn Thr Asn Ile Glu Asp Leu Leu Ile
            180                 185                 190

Leu Trp Gly Ile His His Pro Asn Asp Ala Ala Glu Gln Thr Lys Leu
        195                 200                 205

Tyr Gln Asn Ser Asn Thr Tyr Val Ser Val Gly Thr Ser Thr Leu Asn
    210                 215                 220

Gln Arg Ser Ile Pro Glu Ile Ala Thr Arg Pro Lys Val Asn Gly Gln
225                 230                 235                 240

Ser Gly Arg Met Glu Phe Phe Trp Thr Ile Leu Lys Pro Asn Asp Ala
                245                 250                 255

Ile Asn Phe Glu Ser Asn Gly Asn Phe Ile Ala Pro Glu Tyr Ala Tyr
            260                 265                 270

Lys Ile Val Lys Lys Gly Asp Ser Thr Ile Met Lys Ser Glu Leu Glu
        275                 280                 285

Tyr Gly Asn Cys Asn Thr Lys Cys Gln Thr Pro Met Gly Ala Ile Asn
    290                 295                 300

Ser Ser Met Pro Phe His Asn Ile His Pro Leu Thr Ile Gly Glu Cys
```

-continued 305 310 315 320

Pro Lys Tyr Val Lys Ser Asn Arg Leu Val Leu Ala Thr Gly Leu Arg
325 330 335

Asn Ser Pro Gln Arg Glu Arg Arg Arg Lys Lys Arg Gly Leu Phe Gly
340 345 350

Ala Ile Ala Gly Phe Ile Glu Gly Gly Trp Gln Gly Met Val Asp Gly
355 360 365

Trp Tyr Gly Tyr His His Ser Asn Lys Gln Gly Ser Gly Tyr Ala Ala
370 375 380

Asp Lys Glu Ser Thr Gln Lys Ala Ile Asp Gly Val Thr Asn Lys Val
385 390 395 400

Asn Ser Ile Ile Asp Lys Met Asn Thr Gln Phe Glu Ala Val Gly Arg
405 410 415

Glu Phe Asn Asn Leu Glu Arg Arg Ile Glu Asn Leu Asn Lys Lys Met
420 425 430

Glu Asp Gly Phe Leu Asp Val Trp Thr Tyr Asn Ala Glu Leu Leu Val
435 440 445

Leu Met Glu Asn Glu Arg Thr Leu Asp Phe His Asp Ser Asn Val Lys
450 455 460

Asn Leu Tyr Asp Lys Val Arg Leu Gln Leu Arg Asp Asn Ala Lys Glu
465 470 475 480

Leu Gly Asn Gly Cys Phe Glu Phe Tyr His Lys Cys Asp Asn Glu Cys
485 490 495

Met Glu Ser Val Arg Asn Gly Thr Tyr Asp Tyr Pro Gln Tyr Ser Glu
500 505 510

Glu Ala Arg Leu Lys Arg Glu Glu Ile Ser Gly Val Lys Leu Glu Ser
515 520 525

Ile Gly Ile Tyr Gln Ile Leu Ser Ile Tyr Ser Thr Val Ala Ser Ser
530 535 540

Leu Ala Leu Ala Ile Met Val Ala Gly Leu Ser Leu Trp Met Cys Ser
545 550 555 560

Asn Gly Ser Leu Gln Cys Arg Ile Cys Ile
565 570

<210> SEQ ID NO 38
<211> LENGTH: 566
<212> TYPE: PRT
<213> ORGANISM: Artificial Sequence
<220> FEATURE:
<223> OTHER INFORMATION: Sequence alignment illustrating conserved subsequences characteristic of H5 HA.

<400> SEQUENCE: 38

Met Glu Arg Ile Val Ile Ala Leu Ala Ile Ile Ser Ile Val Lys Gly
1 5 10 15

Asp Gln Ile Cys Ile Gly Tyr His Ala Asn Asn Ser Thr Lys Gln Val
20 25 30

Asp Thr Ile Met Glu Lys Asn Val Thr Val Thr His Ala Gln Asp Ile
35 40 45

Leu Glu Lys Glu His Asn Gly Lys Leu Cys Ser Leu Lys Gly Val Arg
50 55 60

Pro Leu Ile Leu Lys Asp Cys Ser Val Ala Gly Trp Leu Leu Gly Asn
65 70 75 80

Pro Met Cys Asp Glu Phe Leu Asn Val Pro Glu Trp Ser Tyr Ile Val
85 90 95

```
Glu Lys Asp Asn Pro Ile Asn Gly Leu Tyr Cys Tyr Pro Gly Asp Phe
            100                 105                 110

Asn Asp Tyr Glu Glu Leu Lys His Leu Met Ser Ser Thr Asn His Phe
        115                 120                 125

Glu Lys Ile Gln Ile Ile Pro Arg Ser Ser Trp Ser Asn His Asp Ala
    130                 135                 140

Ser Ser Gly Val Ser Ser Ala Cys Pro Tyr Asn Gly Arg Ser Ser Phe
145                 150                 155                 160

Phe Arg Asn Val Val Trp Leu Ile Lys Lys Asn Asn Ala Tyr Pro Thr
                165                 170                 175

Ile Lys Lys Arg Thr Tyr Asn Asn Thr Asn Ile Glu Asp Leu Leu Ile
            180                 185                 190

Leu Trp Gly Ile His His Pro Asn Asp Ala Ala Glu Gln Thr Lys Leu
        195                 200                 205

Tyr Gln Asn Ser Asn Thr Tyr Val Ser Val Gly Thr Ser Thr Leu Asn
    210                 215                 220

Gln Arg Ser Ile Pro Glu Ile Ala Thr Arg Pro Lys Val Asn Gly Gln
225                 230                 235                 240

Ser Gly Arg Met Glu Phe Phe Trp Thr Ile Leu Lys Pro Asn Asp Ala
                245                 250                 255

Ile Ser Phe Glu Ser Asn Gly Asn Phe Ile Ala Pro Glu Tyr Ala Tyr
            260                 265                 270

Lys Ile Val Lys Lys Gly Asp Ser Ala Ile Met Lys Ser Glu Leu Glu
        275                 280                 285

Tyr Gly Asn Cys Asp Thr Lys Cys Gln Thr Pro Val Gly Ala Ile Asn
    290                 295                 300

Ser Ser Met Pro Phe His Asn Val His Pro Leu Thr Ile Gly Glu Cys
305                 310                 315                 320

Pro Lys Tyr Val Lys Ser Asp Lys Leu Val Leu Ala Thr Gly Leu Arg
                325                 330                 335

Asn Val Pro Gln Arg Glu Thr Arg Gly Leu Phe Gly Ala Ile Ala Gly
            340                 345                 350

Phe Ile Glu Gly Gly Trp Gln Gly Met Val Asp Gly Trp Tyr Gly Tyr
        355                 360                 365

His His Ser Asn Glu Gln Gly Ser Gly Tyr Ala Ala Asp Lys Glu Ser
    370                 375                 380

Thr Gln Lys Ala Ile Asp Gly Ile Thr Asn Lys Val Asn Ser Ile Ile
385                 390                 395                 400

Asp Lys Met Asn Thr Gln Phe Glu Thr Val Gly Lys Glu Phe Asn Asn
                405                 410                 415

Leu Glu Arg Arg Ile Glu Asn Leu Asn Lys Lys Met Glu Asp Gly Phe
            420                 425                 430

Leu Asp Val Trp Thr Tyr Asn Ala Glu Leu Leu Val Leu Met Glu Asn
        435                 440                 445

Glu Arg Thr Leu Asp Phe His Asp Ser Asn Val Lys Asn Leu Tyr Asp
    450                 455                 460

Lys Val Arg Leu Gln Leu Arg Asp Asn Ala Lys Glu Leu Gly Asn Gly
465                 470                 475                 480

Cys Phe Glu Phe Tyr His Lys Cys Asp Asn Glu Cys Met Glu Ser Val
                485                 490                 495

Arg Asn Gly Thr Tyr Asp Tyr Pro Gln Tyr Ser Glu Glu Ser Arg Leu
            500                 505                 510

Asn Arg Glu Glu Ile Asp Gly Val Lys Leu Glu Ser Met Gly Thr Tyr
```

-continued

```
        515                 520                 525

Gln Ile Leu Ser Ile Tyr Ser Thr Val Ala Ser Ser Leu Ala Leu Ala
    530                 535                 540

Ile Met Val Ala Gly Leu Ser Phe Trp Met Cys Ser Asn Gly Ser Leu
545                 550                 555                 560

Gln Cys Arg Ile Cys Ile
                565


<210> SEQ ID NO 39
<211> LENGTH: 569
<212> TYPE: PRT
<213> ORGANISM: Artificial Sequence
<220> FEATURE:
<223> OTHER INFORMATION: Sequence alignment illustrating conserved
      subsequences characteristic of H5 HA.

<400> SEQUENCE: 39

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Lys Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Tyr Cys Tyr Pro Gly Ile Phe
            100                 105                 110

Asn Asp Tyr Glu Glu Leu Lys His Leu Leu Ser Arg Ile Asn His Phe
        115                 120                 125

Glu Lys Ile Gln Ile Ile Pro Lys Ser Ser Trp Ser Asp His Glu Ala
    130                 135                 140

Ser Ser Gly Val Ser Ser Ala Cys Pro Tyr Gln Gly Lys Ser Ser Phe
145                 150                 155                 160

Phe Arg Asn Val Val Trp Leu Ile Lys Lys Asn Ser Ala Tyr Pro Thr
                165                 170                 175

Ile Lys Lys Ile Ser Tyr Asn Asn Thr Asn Gln Glu Asp Leu Leu Val
            180                 185                 190

Leu Trp Gly Ile His His Pro Asn Asp Ala Ala Glu Gln Thr Arg Leu
        195                 200                 205

Tyr Gln Asn Pro Thr Thr Tyr Ile Ser Val Gly Thr Ser Thr Leu Asn
    210                 215                 220

Gln Arg Leu Val Pro Lys Ile Ala Thr Arg Ser Lys Val Asn Gly Gln
225                 230                 235                 240

Ser Gly Arg Met Glu Phe Phe Trp Thr Ile Leu Lys Pro Asn Asp Ala
                245                 250                 255

Val Asn Phe Glu Ser Asn Gly Asn Phe Ile Ala Pro Glu Tyr Ala Tyr
            260                 265                 270

Lys Ile Val Lys Lys Gly Asp Ser Thr Ile Met Lys Ser Glu Leu Glu
        275                 280                 285

Tyr Gly Asp Cys Asn Thr Lys Cys Gln Thr Pro Met Gly Ala Ile Asn
    290                 295                 300
```

-continued

```
Ser Ser Met Pro Phe His Asn Ile His Pro Leu Thr Ile Gly Glu Cys
305                 310                 315                 320

Pro Lys Tyr Val Lys Ser Asn Arg Leu Val Leu Ala Thr Gly Leu Arg
                325                 330                 335

Asn Ser Pro Gln Arg Glu Arg Arg Lys Lys Arg Gly Leu Phe Gly Ala
            340                 345                 350

Ile Ala Gly Phe Ile Glu Gly Gly Trp Gln Gly Met Val Asp Gly Trp
        355                 360                 365

Tyr Gly Tyr His His Ser Asn Glu Gln Gly Ser Gly Tyr Ala Ala Asp
    370                 375                 380

Lys Glu Ser Thr Gln Lys Ala Ile Asp Gly Val Thr Asn Lys Val Asn
385                 390                 395                 400

Ser Ile Ile Asp Lys Met Asn Thr Gln Phe Glu Ala Val Gly Arg Glu
                405                 410                 415

Phe Asn Asn Leu Glu Arg Arg Ile Glu Asn Leu Asn Lys Lys Met Glu
            420                 425                 430

Asp Gly Phe Leu Asp Val Trp Thr Tyr Asn Ala Glu Leu Leu Val Leu
        435                 440                 445

Met Glu Asn Glu Arg Thr Leu Asp Phe His Asp Ser Asn Val Lys Asn
    450                 455                 460

Leu Tyr Asp Lys Val Arg Leu Gln Leu Arg Asp Asn Ala Lys Glu Leu
465                 470                 475                 480

Gly Asn Gly Cys Phe Glu Phe Tyr His Lys Cys Asp Asn Glu Cys Met
                485                 490                 495

Glu Ser Val Arg Asn Gly Thr Tyr Asp Tyr Pro Gln Tyr Ser Glu Glu
            500                 505                 510

Ala Arg Leu Lys Arg Glu Glu Ile Ser Gly Val Lys Leu Glu Ser Ile
        515                 520                 525

Gly Thr Tyr Gln Ile Leu Ser Ile Tyr Ser Thr Val Ala Ser Ser Leu
    530                 535                 540

Ala Leu Ala Ile Met Val Ala Gly Leu Ser Leu Trp Met Cys Ser Asn
545                 550                 555                 560

Gly Ser Leu Gln Cys Arg Ile Cys Ile
                565


<210> SEQ ID NO 40
<211> LENGTH: 566
<212> TYPE: PRT
<213> ORGANISM: Artificial Sequence
<220> FEATURE:
<223> OTHER INFORMATION: Sequence alignment illustrating conserved
      subsequences characteristic of H5 HA.

<400> SEQUENCE: 40

Val Leu Leu Leu Ala Ile Val Ser Leu Val Lys Ser Asp Gln Ile Cys
1               5                   10                  15

Ile Gly Tyr His Ala Asn Asn Ser Thr Glu Gln Val Asp Thr Ile Met
            20                  25                  30

Glu Lys Asn Val Thr Val Thr His Ala Gln Asp Ile Leu Glu Lys Thr
        35                  40                  45

His Asn Gly Lys Leu Cys Asp Leu Asp Gly Val Lys Pro Leu Ile Leu
    50                  55                  60

Arg Asp Cys Ser Val Ala Gly Trp Leu Leu Gly Asn Pro Met Cys Asp
65                  70                  75                  80

Glu Phe Leu Asn Val Pro Glu Trp Ser Tyr Ile Val Glu Lys Ile Asn
                85                  90                  95
```

```
Pro Ala Asn Asp Leu Tyr Cys Tyr Pro Gly Asn Phe Asn Asp Tyr Glu
            100                 105                 110

Glu Leu Lys His Leu Leu Ser Arg Ile Asn His Phe Glu Lys Ile Gln
        115                 120                 125

Ile Ile Pro Lys Ser Ser Trp Ser Asp His Glu Ala Ser Ser Gly Val
    130                 135                 140

Ser Ser Ala Cys Pro Tyr Gln Gly Arg Ser Ser Phe Phe Arg Asn Val
145                 150                 155                 160

Val Trp Leu Ile Lys Lys Asp Asn Ala Tyr Pro Thr Ile Lys Lys Arg
                165                 170                 175

Ser Tyr Asn Asn Thr Asn Gln Glu Asp Leu Leu Val Leu Trp Gly Ile
            180                 185                 190

His His Pro Asn Asp Ala Ala Glu Gln Thr Arg Leu Tyr Gln Asn Pro
        195                 200                 205

Thr Thr Tyr Ile Ser Val Gly Thr Ser Thr Leu Asn Gln Arg Leu Val
    210                 215                 220

Pro Lys Ile Ala Thr Arg Ser Lys Val Asn Gly Gln Ser Gly Arg Met
225                 230                 235                 240

Glu Phe Phe Trp Thr Ile Leu Lys Pro Asn Asp Ala Ile Asn Phe Glu
                245                 250                 255

Ser Asn Gly Asn Phe Ile Ala Pro Glu Asn Ala Tyr Lys Ile Val Lys
            260                 265                 270

Lys Gly Asp Ser Thr Ile Met Lys Ser Glu Leu Glu Tyr Gly Asn Cys
        275                 280                 285

Asn Thr Lys Cys Gln Thr Pro Ile Gly Ala Ile Asn Ser Ser Met Pro
    290                 295                 300

Phe His Asn Ile His Pro Leu Thr Ile Gly Glu Cys Pro Lys Tyr Val
305                 310                 315                 320

Lys Ser Asn Arg Leu Val Leu Ala Thr Gly Leu Arg Asn Ser Pro Gln
                325                 330                 335

Arg Glu Gly Arg Arg Lys Lys Arg Gly Leu Phe Gly Ala Ile Ala Gly
            340                 345                 350

Phe Ile Glu Gly Gly Trp Gln Gly Met Val Asp Gly Trp Tyr Gly Tyr
        355                 360                 365

His His Ser Asn Glu Gln Gly Ser Gly Tyr Ala Ala Asp Lys Glu Ser
    370                 375                 380

Thr Gln Lys Ala Ile Asp Gly Val Thr Asn Lys Val Asn Ser Ile Ile
385                 390                 395                 400

Asp Lys Met Asn Thr Gln Phe Glu Ala Val Gly Arg Glu Phe Asn Asn
                405                 410                 415

Leu Glu Arg Arg Ile Glu Asn Leu Asn Lys Lys Met Glu Asp Gly Phe
            420                 425                 430

Leu Asp Val Trp Thr Tyr Asn Ala Glu Leu Leu Val Leu Met Glu Asn
        435                 440                 445

Glu Arg Thr Leu Asp Phe His Asp Ser Asn Val Lys Asn Leu Tyr Asp
    450                 455                 460

Lys Val Arg Leu Gln Leu Arg Asp Asn Ala Lys Glu Leu Gly Asn Gly
465                 470                 475                 480

Cys Phe Glu Phe Tyr His Arg Cys Asp Asn Glu Cys Met Glu Ser Val
                485                 490                 495

Arg Asn Gly Thr Tyr Asp Tyr Pro Gln Tyr Ser Glu Glu Ala Arg Leu
            500                 505                 510
```

```
Lys Arg Glu Glu Ile Ser Gly Val Lys Leu Glu Ser Ile Gly Thr Tyr
        515                 520                 525

Gln Ile Leu Ser Ile Tyr Ser Thr Val Ala Ser Ser Leu Ala Leu Ala
    530                 535                 540

Ile Met Val Ala Gly Leu Ser Leu Trp Met Cys Ser Asn Gly Ser Leu
545                 550                 555                 560

Gln Cys Arg Ile Cys Ile
                565
```

<210> SEQ ID NO 41
<211> LENGTH: 570
<212> TYPE: PRT
<213> ORGANISM: Artificial Sequence
<220> FEATURE:
<223> OTHER INFORMATION: Sequence alignment illustrating conserved subsequences characteristic of H5 HA.

<400> SEQUENCE: 41

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Tyr Cys Tyr Pro Gly Asp Phe
            100                 105                 110

Asn Asp Tyr Glu Glu Leu Lys His Leu Leu Ser Arg Ile Asn His Phe
        115                 120                 125

Glu Lys Ile Gln Ile Ile Pro Lys Ser Ser Trp Ser Asp His Glu Ala
    130                 135                 140

Ser Ser Gly Val Ser Ser Ala Cys Pro Tyr Gln Gly Lys Ser Ser Phe
145                 150                 155                 160

Phe Arg Asn Val Val Trp Leu Ile Lys Lys Asn Ser Ala Tyr Pro Thr
                165                 170                 175

Ile Lys Lys Arg Ser Tyr Asn Asn Thr Asn Gln Glu Asp Leu Leu Val
            180                 185                 190

Leu Trp Gly Ile His His Pro Asn Asp Ala Ala Glu Gln Thr Lys Leu
        195                 200                 205

Tyr Gln Asn Pro Thr Thr Tyr Ile Ser Val Gly Thr Ser Thr Leu Asn
    210                 215                 220

Gln Arg Leu Val Pro Lys Ile Ala Thr Arg Ser Lys Val Asn Gly Gln
225                 230                 235                 240

Ser Gly Arg Met Glu Phe Phe Trp Thr Ile Leu Lys Pro Asn Asp Ala
                245                 250                 255

Ile Asn Phe Glu Ser Asn Gly Asn Phe Ile Ala Pro Glu Tyr Ala Tyr
            260                 265                 270

Lys Ile Val Lys Lys Gly Asp Ser Thr Ile Met Lys Ser Glu Leu Glu
        275                 280                 285

Tyr Gly Asn Cys Asn Thr Lys Cys Gln Thr Pro Met Gly Ala Ile Asn
    290                 295                 300
```

```
Ser Ser Met Pro Phe His Asn Ile His Pro Leu Thr Ile Gly Glu Cys
305                 310                 315                 320

Pro Lys Tyr Val Lys Ser Asn Arg Leu Val Leu Ala Thr Gly Leu Arg
                325                 330                 335

Asn Ser Pro Gln Arg Glu Arg Arg Arg Lys Lys Arg Gly Leu Phe Gly
            340                 345                 350

Ala Ile Ala Gly Phe Ile Glu Gly Gly Trp Gln Gly Met Val Asp Gly
        355                 360                 365

Trp Tyr Gly Tyr His His Ser Asn Glu Gln Gly Ser Gly Tyr Ala Ala
    370                 375                 380

Asp Lys Glu Ser Thr Gln Lys Ala Ile Asp Gly Val Thr Asn Lys Val
385                 390                 395                 400

Asn Ser Ile Ile Asp Lys Met Asn Thr Gln Phe Glu Ala Val Gly Arg
                405                 410                 415

Glu Phe Asn Asn Leu Glu Arg Arg Ile Glu Asn Leu Asn Lys Lys Met
            420                 425                 430

Glu Asp Gly Phe Leu Asp Val Trp Thr Tyr Asn Ala Glu Leu Leu Val
        435                 440                 445

Leu Met Glu Asn Glu Arg Thr Leu Asp Phe His Asp Ser Asn Val Lys
    450                 455                 460

Asn Leu Tyr Asp Lys Val Arg Leu Gln Leu Arg Asp Asn Ala Lys Glu
465                 470                 475                 480

Leu Gly Asn Gly Cys Phe Glu Phe Tyr His Lys Cys Asp Asn Glu Cys
                485                 490                 495

Met Glu Ser Val Arg Asn Gly Thr Tyr Asp Tyr Pro Gln Tyr Ser Glu
            500                 505                 510

Glu Ala Arg Leu Lys Arg Glu Glu Ile Ser Gly Val Lys Leu Glu Ser
        515                 520                 525

Ile Gly Thr Tyr Gln Ile Leu Ser Ile Tyr Ser Thr Val Ala Ser Ser
    530                 535                 540

Leu Ala Leu Ala Ile Met Val Ala Gly Leu Ser Leu Trp Met Cys Ser
545                 550                 555                 560

Asn Gly Ser Leu Gln Cys Arg Ile Cys Ile
                565                 570


<210> SEQ ID NO 42
<211> LENGTH: 555
<212> TYPE: PRT
<213> ORGANISM: Artificial Sequence
<220> FEATURE:
<223> OTHER INFORMATION: Sequence alignment illustrating conserved
      subsequences characteristic of H5 HA.

<400> SEQUENCE: 42

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
```

-continued

```
                85                  90                  95

Glu Lys Ala Asn Pro Ala Asn Asp Leu Tyr Cys Tyr Pro Gly Asn Phe
            100                 105                 110

Asn Asp Tyr Glu Glu Leu Lys His Leu Leu Ser Arg Ile Asn His Phe
        115                 120                 125

Glu Lys Ile Gln Ile Ile Pro Lys Ser Ser Trp Ser Asp His Glu Ala
    130                 135                 140

Ser Ser Gly Val Ser Ser Ala Cys Pro Tyr Leu Gly Lys Ser Ser Phe
145                 150                 155                 160

Phe Arg Asn Val Val Trp Leu Ile Lys Lys Asn Ser Ala Tyr Pro Thr
                165                 170                 175

Ile Lys Lys Arg Ser Tyr Asn Asn Thr Asn Gln Glu Asp Leu Leu Val
            180                 185                 190

Leu Trp Gly Ile His His Pro Asn Asp Ala Ala Glu Gln Thr Arg Leu
        195                 200                 205

Tyr Gln Asn Pro Thr Thr Tyr Ile Ser Val Gly Thr Ser Thr Leu Asn
    210                 215                 220

Gln Arg Leu Val Pro Lys Ile Ala Thr Arg Ser Lys Val Asn Gly Gln
225                 230                 235                 240

Ser Gly Arg Met Glu Phe Phe Trp Thr Ile Leu Lys Pro Asn Asp Ala
                245                 250                 255

Ile Asn Phe Glu Ser Asn Gly Asn Phe Ile Ala Pro Glu Tyr Ala Tyr
            260                 265                 270

Lys Ile Val Lys Lys Gly Asp Ser Ala Ile Met Lys Ser Glu Leu Glu
        275                 280                 285

Tyr Gly Asn Cys Asn Thr Lys Cys Gln Thr Pro Met Gly Ala Ile Asn
    290                 295                 300

Ser Ser Met Pro Phe His Asn Ile His Pro Leu Thr Ile Gly Glu Cys
305                 310                 315                 320

Pro Lys Tyr Val Lys Ser Asn Arg Leu Val Leu Ala Thr Gly Leu Arg
                325                 330                 335

Asn Ser Pro Gln Arg Glu Arg Arg Arg Lys Lys Arg Gly Leu Phe Gly
            340                 345                 350

Ala Ile Ala Gly Phe Ile Glu Gly Gly Trp Gln Gly Met Val Asp Gly
        355                 360                 365

Trp Tyr Gly Tyr His His Ser Asn Glu Gln Gly Ser Gly Tyr Ala Ala
    370                 375                 380

Asp Lys Glu Ser Thr Gln Lys Ala Ile Asp Gly Val Thr Asn Lys Val
385                 390                 395                 400

Asn Ser Ile Ile Asp Lys Met Asn Thr Gln Phe Glu Ala Val Gly Arg
                405                 410                 415

Glu Phe Asn Asn Leu Glu Arg Arg Ile Glu Asn Leu Asn Lys Lys Met
            420                 425                 430

Glu Asp Gly Phe Leu Asp Val Trp Thr Tyr Asn Ala Glu Leu Leu Val
        435                 440                 445

Leu Met Glu Asn Glu Arg Thr Leu Asp Phe His Asp Ser Asn Val Lys
    450                 455                 460

Asn Leu Tyr Asp Lys Val Arg Leu Gln Leu Arg Asp Asn Ala Lys Glu
465                 470                 475                 480

Leu Gly Asn Gly Cys Phe Glu Phe Tyr His Lys Cys Asp Asn Glu Cys
                485                 490                 495

Met Glu Ser Ile Arg Asn Gly Thr Tyr Asn Tyr Pro Gln Tyr Ser Glu
            500                 505                 510
```

-continued

```
Glu Ala Arg Leu Lys Arg Glu Glu Ile Ser Gly Val Lys Leu Glu Ser
        515                 520                 525

Ile Gly Ile Tyr Gln Ile Leu Ser Ile Tyr Ser Thr Val Ala Ser Ser
    530                 535                 540

Leu Ala Leu Ala Ile Met Met Ala Gly Leu Ser
545                 550                 555


<210> SEQ ID NO 43
<211> LENGTH: 13
<212> TYPE: PRT
<213> ORGANISM: Artificial Sequence
<220> FEATURE:
<223> OTHER INFORMATION: HA sequence element consensus sequence element
<220> FEATURE:
<221> NAME/KEY: MISC_FEATURE
<222> LOCATION: (2)..(2)
<223> OTHER INFORMATION: X= Tyr or Phe
<220> FEATURE:
<221> NAME/KEY: MISC_FEATURE
<222> LOCATION: (4)..(4)
<223> OTHER INFORMATION: X= 30-45 of any amino acid
<220> FEATURE:
<221> NAME/KEY: MISC_FEATURE
<222> LOCATION: (6)..(6)
<223> OTHER INFORMATION: X= 5-20 of any amino acid
<220> FEATURE:
<221> NAME/KEY: MISC_FEATURE
<222> LOCATION: (8)..(8)
<223> OTHER INFORMATION: X= 25-30 of any amino acid
<220> FEATURE:
<221> NAME/KEY: MISC_FEATURE
<222> LOCATION: (10)..(10)
<223> OTHER INFORMATION: X= 2 of any amino acid

<400> SEQUENCE: 43

Cys Xaa Pro Xaa Cys Xaa Trp Xaa Trp Xaa His His Pro
1               5                   10


<210> SEQ ID NO 44
<211> LENGTH: 15
<212> TYPE: PRT
<213> ORGANISM: Artificial Sequence
<220> FEATURE:
<223> OTHER INFORMATION: HA sequence element consensus sequence element
<220> FEATURE:
<221> NAME/KEY: MISC_FEATURE
<222> LOCATION: (4)..(4)
<223> OTHER INFORMATION: X= 27-42 of any amino acid
<220> FEATURE:
<221> NAME/KEY: MISC_FEATURE
<222> LOCATION: (6)..(6)
<223> OTHER INFORMATION: X= Ala or Thr
<220> FEATURE:
<221> NAME/KEY: MISC_FEATURE
<222> LOCATION: (7)..(7)
<223> OTHER INFORMATION: X= Ala or Ser
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: X= 5-20 of any amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X= 25-30 of any amino acid
<220> FEATURE:
```

```
<221> NAME/KEY: misc_feature
<222> LOCATION: (12)..(12)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: X= 2 of any amino acid

<400> SEQUENCE: 44

Cys Tyr Pro Xaa Thr Xaa Cys Xaa Trp Xaa Trp Xaa His His Pro
1               5                   10                  15


<210> SEQ ID NO 45
<211> LENGTH: 18
<212> TYPE: PRT
<213> ORGANISM: Artificial Sequence
<220> FEATURE:
<223> OTHER INFORMATION: HA sequence element consensus sequence element
<220> FEATURE:
<221> NAME/KEY: MISC_FEATURE
<222> LOCATION: (4)..(4)
<223> OTHER INFORMATION: X= 27-42 of any amino acid
<220> FEATURE:
<221> NAME/KEY: MISC_FEATURE
<222> LOCATION: (6)..(6)
<223> OTHER INFORMATION: X= Ala or Thr
<220> FEATURE:
<221> NAME/KEY: MISC_FEATURE
<222> LOCATION: (7)..(7)
<223> OTHER INFORMATION: X= Ala or Ser
<220> FEATURE:
<221> NAME/KEY: MISC_FEATURE
<222> LOCATION: (9)..(9)
<223> OTHER INFORMATION: X= 5-20 of any amino acid
<220> FEATURE:
<221> NAME/KEY: MISC_FEATURE
<222> LOCATION: (11)..(11)
<223> OTHER INFORMATION: X= Ile or Leu
<220> FEATURE:
<221> NAME/KEY: MISC_FEATURE
<222> LOCATION: (12)..(12)
<223> OTHER INFORMATION: X=Thr or Val
<220> FEATURE:
<221> NAME/KEY: MISC_FEATURE
<222> LOCATION: (13)..(13)
<223> OTHER INFORMATION: X= 23-28 of any amino acid
<220> FEATURE:
<221> NAME/KEY: MISC_FEATURE
<222> LOCATION: (15)..(15)
<223> OTHER INFORMATION: X= 2 of any amino acid

<400> SEQUENCE: 45

Cys Tyr Pro Xaa Thr Xaa Xaa Cys Xaa Trp Xaa Xaa Xaa Trp Xaa His
1               5                   10                  15

His Pro


<210> SEQ ID NO 46
<211> LENGTH: 10
<212> TYPE: PRT
<213> ORGANISM: Artificial Sequence
<220> FEATURE:
<223> OTHER INFORMATION: HA sequence element consensus sequence element

<400> SEQUENCE: 46

Gln Leu Ser Ser Ile Ser Ser Phe Glu Lys
1               5                   10


<210> SEQ ID NO 47
<211> LENGTH: 16
<212> TYPE: PRT
<213> ORGANISM: Artificial Sequence
<220> FEATURE:
```

<223> OTHER INFORMATION: HA sequence element consensus sequence element
<220> FEATURE:
<221> NAME/KEY: MISC_FEATURE
<222> LOCATION: (4)..(4)
<223> OTHER INFORMATION: X = 27-42 of any amino acid
<220> FEATURE:
<221> NAME/KEY: MISC_FEATURE
<222> LOCATION: (6)..(6)
<223> OTHER INFORMATION: X = Ser or Asn
<220> FEATURE:
<221> NAME/KEY: MISC_FEATURE
<222> LOCATION: (7)..(7)
<223> OTHER INFORMATION: X = Ala or Ser
<220> FEATURE:
<221> NAME/KEY: MISC_FEATURE
<222> LOCATION: (9)..(9)
<223> OTHER INFORMATION: X = 5-20 of any amino acid
<220> FEATURE:
<221> NAME/KEY: MISC_FEATURE
<222> LOCATION: (11)..(11)
<223> OTHER INFORMATION: X = 25-30 of any amino acid
<220> FEATURE:
<221> NAME/KEY: MISC_FEATURE
<222> LOCATION: (13)..(13)
<223> OTHER INFORMATION: X = 2 of any amino acid

<400> SEQUENCE: 47

```
Cys Tyr Pro Xaa Ser Xaa Xaa Cys Xaa Trp Xaa Trp Xaa His His Pro
1               5                   10                  15
```

<210> SEQ ID NO 48
<211> LENGTH: 18
<212> TYPE: PRT
<213> ORGANISM: Artificial Sequence
<220> FEATURE:
<223> OTHER INFORMATION: HA sequence element consensus sequence element
<220> FEATURE:
<221> NAME/KEY: MISC_FEATURE
<222> LOCATION: (4)..(4)
<223> OTHER INFORMATION: X = 27-42 of any amino acid
<220> FEATURE:
<221> NAME/KEY: MISC_FEATURE
<222> LOCATION: (6)..(6)
<223> OTHER INFORMATION: X = Ser or Asn
<220> FEATURE:
<221> NAME/KEY: MISC_FEATURE
<222> LOCATION: (7)..(7)
<223> OTHER INFORMATION: X = Ala or Ser
<220> FEATURE:
<221> NAME/KEY: MISC_FEATURE
<222> LOCATION: (9)..(9)
<223> OTHER INFORMATION: X = 5-20 of any amino acid
<220> FEATURE:
<221> NAME/KEY: MISC_FEATURE
<222> LOCATION: (12)..(12)
<223> OTHER INFORMATION: X = Thr or His
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: X = 2 of any amino acid

<400> SEQUENCE: 48

```
Cys Tyr Pro Xaa Ser Xaa Xaa Cys Xaa Trp Leu Xaa Xaa Trp Xaa His
1               5                   10                  15

His Pro
```

<210> SEQ ID NO 49
<211> LENGTH: 10
<212> TYPE: PRT
<213> ORGANISM: Artificial Sequence
<220> FEATURE:
<223> OTHER INFORMATION: HA sequence element consensus sequence element
<220> FEATURE:
<221> NAME/KEY: MISC_FEATURE
<222> LOCATION: (1)..(1)
<223> OTHER INFORMATION: X = Leu or Ile
<220> FEATURE:
<221> NAME/KEY: MISC_FEATURE
<222> LOCATION: (2)..(2)
<223> OTHER INFORMATION: X = Val or Ile

<400> SEQUENCE: 49

Xaa Xaa Ala Ser Ser Gly Thr Leu Glu Phe
1 5 10

<210> SEQ ID NO 50
<211> LENGTH: 16
<212> TYPE: PRT
<213> ORGANISM: Artificial Sequence
<220> FEATURE:
<223> OTHER INFORMATION: HA sequence element consensus sequence element
<220> FEATURE:
<221> NAME/KEY: MISC_FEATURE
<222> LOCATION: (4)..(4)
<223> OTHER INFORMATION: X = 27-42 of any amino acid
<220> FEATURE:
<221> NAME/KEY: MISC_FEATURE
<222> LOCATION: (9)..(9)
<223> OTHER INFORMATION: X = 5-20 of any amino acid
<220> FEATURE:
<221> NAME/KEY: MISC_FEATURE
<222> LOCATION: (11)..(11)
<223> OTHER INFORMATION: X = 25-30 of any amino acid
<220> FEATURE:
<221> NAME/KEY: MISC_FEATURE
<222> LOCATION: (13)..(13)
<223> OTHER INFORMATION: X = 2 of any amino acid

<400> SEQUENCE: 50

Cys Tyr Pro Xaa Ser Ser Ala Cys Xaa Trp Xaa Trp Xaa His His Pro
1 5 10 15

<210> SEQ ID NO 51
<211> LENGTH: 18
<212> TYPE: PRT
<213> ORGANISM: Artificial Sequence
<220> FEATURE:
<223> OTHER INFORMATION: HA sequence element consensus sequence element
<220> FEATURE:
<221> NAME/KEY: MISC_FEATURE
<222> LOCATION: (4)..(4)
<223> OTHER INFORMATION: X = 27-42 of any amino acid
<220> FEATURE:
<221> NAME/KEY: MISC_FEATURE
<222> LOCATION: (9)..(9)
<223> OTHER INFORMATION: X = 5-20 of any amino acid
<220> FEATURE:
<221> NAME/KEY: MISC_FEATURE
<222> LOCATION: (11)..(11)
<223> OTHER INFORMATION: X = 23-28 of any amino acid
<220> FEATURE:
<221> NAME/KEY: MISC_FEATURE
<222> LOCATION: (13)..(13)
<223> OTHER INFORMATION: X = 2 of any amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 51

Cys Tyr Pro Xaa Ser Ser Ala Cys Xaa Trp Leu Ile Xaa Trp Xaa His
1 5 10 15

His Pro

```
<210> SEQ ID NO 52
<211> LENGTH: 8
<212> TYPE: PRT
<213> ORGANISM: Artificial Sequence
<220> FEATURE:
<223> OTHER INFORMATION: HA sequence element consensus sequence element
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X = Lys or Arg

<400> SEQUENCE: 52

Asn Asp Ala Ala Glu Xaa Xaa Xaa
1               5


<210> SEQ ID NO 53
<211> LENGTH: 16
<212> TYPE: PRT
<213> ORGANISM: Artificial Sequence
<220> FEATURE:
<223> OTHER INFORMATION: HA sequence element consensus sequence element
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 53

Tyr Glu Glu Leu Lys His Leu Xaa Ser Xaa Xaa Asn His Phe Glu Lys
1               5                   10                  15


<210> SEQ ID NO 54
<211> LENGTH: 8
<212> TYPE: PRT
<213> ORGANISM: Artificial Sequence
<220> FEATURE:
<223> OTHER INFORMATION: HA sequence element consensus sequence element

<400> SEQUENCE: 54

Gly Ala Ile Ala Gly Phe Ile Glu
1               5


<210> SEQ ID NO 55
<211> LENGTH: 10
<212> TYPE: PRT
<213> ORGANISM: Artificial Sequence
<220> FEATURE:
<223> OTHER INFORMATION: HA sequence element consensus sequence element
<220> FEATURE:
<221> NAME/KEY: MISC_FEATURE
<222> LOCATION: (2)..(2)
<223> OTHER INFORMATION: X = 4-14 of any amino acid

<400> SEQUENCE: 55

Pro Xaa Gly Ala Ile Ala Gly Phe Ile Glu
1               5                   10


<210> SEQ ID NO 56
<211> LENGTH: 15
<212> TYPE: PRT
<213> ORGANISM: Artificial Sequence
<220> FEATURE:
```

-continued

```
<223> OTHER INFORMATION: HA sequence element consensus sequence element
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: X = 3 of any amino acid

<400> SEQUENCE: 56

Pro Ser Xaa Gln Ser Arg Xaa Gly Ala Ile Ala Gly Phe Ile Glu
1               5                   10                  15


<210> SEQ ID NO 57
<211> LENGTH: 15
<212> TYPE: PRT
<213> ORGANISM: Artificial Sequence
<220> FEATURE:
<223> OTHER INFORMATION: HA sequence element consensus sequence element
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: X = 3 of any amino acid

<400> SEQUENCE: 57

Pro Xaa Lys Xaa Thr Arg Xaa Gly Ala Ile Ala Gly Phe Ile Glu
1               5                   10                  15


<210> SEQ ID NO 58
<211> LENGTH: 19
<212> TYPE: PRT
<213> ORGANISM: Artificial Sequence
<220> FEATURE:
<223> OTHER INFORMATION: HA sequence element consensus sequence element
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X = 3 of any amino acid

<400> SEQUENCE: 58

Pro Gln Arg Xaa Xaa Xaa Arg Xaa Xaa Arg Xaa Gly Ala Ile Ala Gly
1               5                   10                  15

Phe Ile Glu
```